US012545739B2

(12) United States Patent
Tushir-Singh et al.

(10) Patent No.: US 12,545,739 B2
(45) Date of Patent: Feb. 10, 2026

(54) COMPOSITIONS AND METHODS FOR MAKING AND USING BISPECIFIC ANTIBODIES

(71) Applicant: University of Virginia Patent Foundation, Charlottesville, VA (US)

(72) Inventors: Jogender Tushir-Singh, Free Union, VA (US); Sanchita Bhatnagar, Free Union, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 91 days.

(21) Appl. No.: 16/764,331

(22) PCT Filed: Nov. 13, 2018

(86) PCT No.: PCT/US2018/060735
§ 371 (c)(1),
(2) Date: May 14, 2020

(87) PCT Pub. No.: WO2019/099374
PCT Pub. Date: May 23, 2019

(65) Prior Publication Data

US 2020/0283537 A1 Sep. 10, 2020

Related U.S. Application Data

(60) Provisional application No. 62/585,647, filed on Nov. 14, 2017.

(51) Int. Cl.

| | |
|---|---|
| ***C07K 16/28*** | (2006.01) |
| ***A61P 35/00*** | (2006.01) |
| *A61K 9/00* | (2006.01) |
| *A61K 39/00* | (2006.01) |

(52) U.S. Cl.
CPC .......... *C07K 16/2878* (2013.01); *A61P 35/00* (2018.01); *A61K 9/0019* (2013.01); *A61K 2039/505* (2013.01); *A61K 2039/545* (2013.01); *C07K 2317/24* (2013.01); *C07K 2317/526* (2013.01); *C07K 2317/56* (2013.01); *C07K 2317/92* (2013.01)

(58) Field of Classification Search
CPC .................................................. C07K 2317/31
USPC ....................................................... 424/136.1
See application file for complete search history.

(56) References Cited

U.S. PATENT DOCUMENTS

| | | | |
|---|---|---|---|
| 4,816,567 | A | 3/1989 | Cabilly et al. |
| 4,946,778 | A | 8/1990 | Ladner et al. |
| 4,975,369 | A | 12/1990 | Beavers et al. |
| 5,001,065 | A | 3/1991 | Larrick et al. |
| 5,075,431 | A | 12/1991 | Shively et al. |
| 5,081,235 | A | 1/1992 | Shively et al. |
| 5,169,939 | A | 12/1992 | Gefter et al. |
| 5,202,238 | A | 4/1993 | Fell, Jr. et al. |
| 5,204,244 | A | 4/1993 | Fell et al. |
| 5,231,026 | A | 7/1993 | Chang |
| 5,292,867 | A | 3/1994 | Chang |
| 5,354,847 | A | 10/1994 | Liu et al. |
| 5,472,693 | A | 12/1995 | Gourlie et al. |
| 5,482,856 | A | 1/1996 | Fell, Jr. et al. |
| 5,491,088 | A | 2/1996 | Hellstrom et al. |
| 5,500,362 | A | 3/1996 | Robinson et al. |
| 5,502,167 | A | 3/1996 | Waldmann et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,622,425 | A | 4/1997 | Lin |
| 5,625,126 | A | 4/1997 | Lonberg et al. |
| 5,633,425 | A | 5/1997 | Nils et al. |
| 5,661,016 | A | 8/1997 | Lonberg et al. |
| 5,731,168 | A | 3/1998 | Carter et al. |
| 6,927,286 | B1 * | 8/2005 | Shen ..................... C12N 15/52 435/252.35 |
| 7,695,936 | B2 | 4/2010 | Carter et al. |
| 9,862,778 | B2 | 1/2018 | Glen et al. |
| 10,626,189 | B2 | 4/2020 | Glen et al. |

(Continued)

FOREIGN PATENT DOCUMENTS

| | | | |
|---|---|---|---|
| EP | 3710482 | A4 | 9/2020 |
| WO | WO 2011/039126 | A1 | 4/2011 |

(Continued)

OTHER PUBLICATIONS

Shivange et al (Cancer Cell. Aug. 13, 2018; 34(2): 331-345).*
Vajda et al., Current Opinion in Structural Biology, 67 pp. 226-231 (2021).*
Marks et al., J. Biol. Chem. 295(29) 9823-9837 (2020).*
Akbar et al., Cell Reports 34, 108856, Mar. 16, 2021 ).*
Lo et al., BMC Genomics vol. 22, Article No. 116 (2021).*
Tushir-Singh (FASEB Journal, (Apr. 2019) vol. 33, No. Suppl. 1, pp. 647.44. Meeting Info.: Experimental Biology Meeting (EB). Orlando, FL, USA. Apr. 6 -9, 2019. Amer Assoc Anat; Amer Physiol Soc; Amer Soc Biochem & Mol Biol; Amer Soc Investigat Pathol; Amer Soc Pharmacol & Expt Therapeut).*

(Continued)

*Primary Examiner* — Lynn A Bristol
(74) *Attorney, Agent, or Firm* — Jenkins, Taylor & Hunt, P.A.

(57) ABSTRACT

A bispecific antibody that includes a first antigen binding site that is specific for a death receptor 5 (DR5) polypeptide and a second antigen binding site that is specific for a folate receptor alpha-1 (FOLR1) polypeptide, wherein the bispecific antibody includes: (i) a heavy chain amino acid sequence that includes SEQ ID NO:1 and a light chain amino acid sequence that includes SEQ ID NO:2; (ii) a heavy chain amino acid sequence that includes SEQ ID NO:11 and a light chain amino acid sequence that includes SEQ ID NO:2; (iii) a heavy chain amino acid sequence that includes SEQ ID NO:5 and a light chain amino acid sequence that includes SEQ ID NO: 6; or (iv) an scFv fragment that includes a knob-into-hole structure comprising SEQ ID NOs: 3 and 4.

35 Claims, 75 Drawing Sheets
(66 of 75 Drawing Sheet(s) Filed in Color)

Specification includes a Sequence Listing.

(56) References Cited

U.S. PATENT DOCUMENTS

| | | | | |
|---|---|---|---|---|
| 10,781,259 | B2 * | 9/2020 | Jackson | A61K 47/545 |
| 11,229,711 | B2 * | 1/2022 | Jackson | A61K 47/6803 |
| 11,285,207 | B2 | 3/2022 | Laura et al. | |
| 2013/0259878 | A1 | 10/2013 | Terrett | |
| 2014/0363454 | A1 * | 12/2014 | Jackson | A61K 47/6803 546/256 |
| 2014/0370019 | A1 * | 12/2014 | Bruenker | C07K 16/2878 435/69.6 |
| 2015/0093392 | A1 | 4/2015 | Terrett et al. | |
| 2015/0352230 | A1 * | 12/2015 | Mullen | C07K 17/08 424/9.6 |
| 2016/0311921 | A1 | 10/2016 | Schweizer et al. | |
| 2016/0367699 | A1 * | 12/2016 | Jackson | A61K 47/6817 |
| 2018/0147294 | A1 * | 5/2018 | Jackson | A61K 47/6851 |
| 2019/0209704 | A1 * | 7/2019 | Jackson | A61K 47/6867 |
| 2020/0405813 | A1 * | 12/2020 | Yam | A61K 47/6855 |
| 2023/0270881 | A1 | 8/2023 | Bhatnagar et al. | |

FOREIGN PATENT DOCUMENTS

| | | | |
|---|---|---|---|
| WO | WO 2012/061759 | A2 | 5/2012 |
| WO | WO2013055958 | A1 | 4/2013 |
| WO | WO2014161845 | A1 | 10/2014 |
| WO | 2014191578 | * | 12/2014 |
| WO | WO 2016/079050 | * | 5/2016 |
| WO | WO 2017/093447 | A1 | 6/2017 |
| WO | 2018052556 | * | 3/2018 |
| WO | 2023023677 | * | 2/2023 |

OTHER PUBLICATIONS

Tushir-Singh (FASEB Journal, (Apr. 2019) vol. 33, No. SUPPL 1, pp. 647.44. Meeting Info: Experimental Biology, EB 2019. Orlando, FL, United States. Apr. 6, 2019-Apr. 9, 2019).*

Armstrong et al., "Farletuzumab (a monoclonal antibody against folate receptor alpha) in relapsed platinum-sensitive ovarian cancer." Gynecol Oncol, vol. 129, pp. 452-458 (2013).

Ashkenazi et al., "To kill a tumor cell: the potential of proapoptotic receptor agonists." J Clin Invest, vol. 118, pp. 1979-1990 (2008).

Ashkenazi, "Directing cancer cells to self-destruct with pro-apoptotic receptor agonists." Nat Rev Drug Discov, vol. 7, pp. 1001-1012 (2008).

Ashkenazi, "Targeting the extrinsic apoptotic pathway in cancer: lessons learned and future directions." J Clin Invest, vol. 125, pp. 487-489 (2015).

Barbas et al., "Synthetic human antibodies." Nature Medicine, vol. 1, pp. 837-839 (1995).

Bauer et al., "Fibroblast activation protein is expressed by rheumatoid myofibroblast-like synoviocytes." Arthritis Res Ther vol. 8, Article ID R171 (2006).

Berek et al., "Oregovomab maintenance monoimmunotherapy does not improve outcomes in advanced ovarian cancer." J Clin Oncol, vol. 27, pp. 418-425 (2009).

Boerner et al., "Production of antigen-specific human monoclonal antibodies from in vitro-primed human splenocytes." J Immunol, vol. 147, pp. 86-95 (1991).

Brinkmann et al., "The making of bispecific antibodies." MAbs, vol. 9, pp. 182-212 (2017).

Brunker et al., "RG7386, a Novel Tetravalent FAP-DR5 Antibody, Effectively Triggers FAP- Dependent, Avidity-Driven DR5 Hyperclustering and Tumor Cell Apoptosis." Mol Cancer Ther, vol. 15, pp. 946-957 (2016).

Chen et al., "Single nucleotide polymorphisms in the CDH17 gene of colorectal carcinoma." World J Gastroenterol, vol. 18, pp. 7251-7261 (2012).

Chou et al., "Prediction of beta-turns." Biophys J, vol. 26, pp. 367-384 (1979).

Cole et al., "Human monoclonal antibodies." Mol Cell Biol, vol. 62, pp. 109-120 (1984).

Conrad et al., "In vitro selection methodologies to probe RNA function and structure." Mol Div, vol. 1, pp. 69-78 (1995).

Cote et al., "Generation of human monoclonal antibodies reactive with cellular antigens." Proc Natl Acad Sci USA, vol. 80, pp. 2026-2030 (1983).

Day et al., "Does High-Dose Antimicrobial Chemotherapy Prevent the Evolution of Resistance?" PLoS Comput Biol, vol. 12, Article ID e1004689 (2016).

De Kruif et al., "Selection and Application of Human Single Chain Fv Antibody Fragments from a Semi-synthetic Phage Antibody Display Library with Designed CDR3 Regions." J Mol Biol, vol. 248, pp. 97-105 (1995).

Devereux et al., "A comprehensive set of sequence analysis programs for the VAX." Nucleic Acids Res, vol. 12, pp. 387-395 (1984).

Domcke et al., "Evaluating cell lines as tumour models by comparison of genomic profiles." Nat Commun, vol. 4, Article ID 2126 (2013).

Durocher et al., "Expression systems for therapeutic glycoprotein production." Curr Opin Biotechnol, vol. 20, pp. 700-707 (2009).

Ellington, "RNA Selection: Aptamers achieve the desired recognition." Curr Biol, vol. 4, pp. 427-429 (1994).

European Search Report corresponding to European Patent Application No. 18879754.2 dated Jul. 15, 2021.

Fishwild et al., "High-avidity human IgGK monoclonal antibodies from a novel strain of minilocus transgenic mice." Nature Biotechnology, vol. 14, pp. 845-851 (1996).

Glund et al., "Restarting Dabigatran Etexilate 24 h After Reversal With Idarucizumab and Redosing Idarucizumab in Healthy Volunteers." J Am Coll Cardiol, vol. 67, pp. 1654-1656 (2016).

Godwin et al., "Targeting nuclear factor-kappa B to overcome resistance to chemotherapy." Front Oncol, vol. 3, p. 120 (2013).

Graves et al., "Apo2L/TRAIL and the death receptor 5 agonist antibody AMG 655 cooperate to promote receptor clustering and antitumor activity." Cancer Cell, vol. 26, pp. 177-189 (2014).

Gu et al., "Generation of dual-variable-domain immunoglobulin molecules for dual-specific targeting." Methods Enzymol, vol. 502, pp. 25-41 (2012).

Hoogenboom et al., "By-passing immunisation: Human antibodies from synthetic repertoires of germline VH gene segments rearranged in vitro." J Mol Biol, vol. 227, pp. 381-388 (1992).

Houston, Methods in Enzymol, vol. 203, pp. 46-88 (1991).

Huse et al., "Generation of a large combinatorial library of the immunoglobulin repertoire in phage lambda." Science, vol. 246, pp. 1275-1281 (1989).

Hutt et al., "Plasma half-life extension of small recombinant antibodies by fusion to immunoglobulin-binding domains." J Biol Chem, vol. 287, pp. 4462-4469 (2012).

International Preliminary Report on Patentability Corresponding to International application No. PCT/US 2018/060735 dated May 19, 2020.

International Search Report Corresponding to International application No. PCT/US 2018/060735 dated Apr. 19, 2019.

Jakob et al., "Structure reveals function of the dual variable domain immunoglobulin (DVD-Ig) molecule." MAbs, vol. 5, pp. 358-363 (2013).

Jin et al., "Deficient tumor necrosis factor-related apoptosis-inducing ligand (TRAIL) death receptor transport to the cell surface in human colon cancer cells selected for resistance to TRAIL-induced apoptosis." J Biol Chem, vol. 279, pp. 35829-35839 (2004).

Jones et al., "Replacing the complementarity-determining regions in a human antibody with those from a mouse." Nature, vol. 321, pp. 522-525 (1986).

Karlin et al., "Applications and statistics for multiple high-scoring segments in molecular sequences." Proc Natl Acad Sci USA, vol. 90, pp. 5873-5877 (1993).

Karlin et al., "Methods for assessing the statistical significance of molecular sequence features by using general scoring schemes." Proc Natl Acad Sci USA, vol. 87, pp. 2264-2268 (1990).

Kline et al., "Tumor antigen CA125 suppresses antibody-dependent cellular cytotoxicity (ADCC) via direct antibody binding and suppressed Fc-gamma receptor engagement." Oncotarget, vol. 8, pp. 52045-52060 (2017).

Klug et al., "All you wanted to know about SELEX." Mol Biol Reports, vol. 20, pp. 97-107 (1994).

(56) References Cited

OTHER PUBLICATIONS

Kohler et al., "Continuous cultures of fused cells secreting antibody of predefined specificity." Nature, vol. 256, pp. 495-497 (1975).
Kozbor et al., "Specific immunoglobulin production and enhanced tumorigenicity following ascites growth of human hybridomas." J Immunol Methods, vol. 81, pp. 31-42 (1985).
Kozbor et al., "The production of monoclonal antibodies from human lymphocytes." Immunology Today, vol. 4, pp. 72-78 (1983).
Kyte et al., "A simple method for displaying the hydropathic character of a protein." J Mol Biol, vol. 157, pp. 105-132 (1982).
Lato et al., "In vitro selection of RNA lectins: using combinatorial chemistry to interpret ribozyme evolution." Chem Biol, vol. 2, pp. 291-303 (1995).
Leabman et al., "Effects of altered FcgammaR binding on antibody pharmacokinetics in cynomolgus monkeys." MAbs, vol. 5, pp. 896-903 (2013).
LeBlanc et al., "Tumor-cell resistance to death receptor—induced apoptosis through mutational inactivation of the proapoptotic Bcl-2 homolog Bax." Nat Med, vol. 8, pp. 274-281 (2002).
Levett et al., "Use of immunoglobulin G avidity assays for differentiation of primary from previous infections with West Nile virus." J Clin Microbiol, vol. 43, pp. 5873-5875 (2005).
Li et al., "Apoptotic and antitumor activity of death receptor antibodies require inhibitory Fcgamma receptor engagement." Proc Natl Acad Sci USA, vol. 109, pp. 10966-10971 (2012).
Lin et al., "The antitumor activity of the human FOLR1-specific monoclonal antibody, farletuzumab, in an ovarian cancer mouse model is mediated by antibody-dependent cellular cytotoxicity." Cancer Biol Ther, vol. 14, pp. 1032-1038 (2013).
Lonberg et al., "Antigen-specific human antibodies from mice comprising four distinct genetic modifications." Nature, vol. 368, pp. 856-859 (1994).
Marks et al., "By-Passing Immunization: Building High Affinity Human Antibodies by Chain Shuffling." Bio/Technology, vol. 10, pp. 779-783 (1992).
Marks et al., "By-passing immunization: Human antibodies from V-gene libraries displayed on phage." J Mol Biol, vol. 222, pp. 581-597 (1991).
Merchant et al., "Phase I trial and pharmacokinetic study of lexatumumab in pediatric patients with solid tumors." J Clin Oncol, vol. 30, pp. 4141-4147 (2012).
Mongkolsapaya et al., "Structure of the TRAIL-DR5 complex reveals mechanisms conferring specificity in apoptotic initiation." Nat Struct Biol, vol. 6, pp. 1048-1053 (1999).
Morrison et al., "Chimeric human antibody molecules: Mouse antigen-binding domains with human constant region domains." Proc Natl Acad Sci USA, vol. 81, pp. 6851-6855 (1984).
Morrison, "Success in specification." Nature, vol. 368, pp. 812-813 (1994).
Neuberger et al., "Recombinant antibodies possessing novel effector functions." Nature, vol. 312, pp. 604-608 (1984).
Neuberger, "Generating high-avidity human Mabs in mice." Nature Biotechnology, vol. 14, p. 826 (1996).
Niyazi et al., "Efficacy of triple therapies including ionising radiation, agonistic TRAIL antibodies and cisplatin." Oncol Rep, vol. 21, pp. 1455-1460 (2009).
Notice of Publication corresponding to European Patent Application No. 18879754.2 dated Aug. 26, 2020.
Orlandi et al., "Cloning immunoglobulin variable domains for expression by the polymerase chain reaction." Proc Natl Acad Sci USA, vol. 86, pp. 3833-3837 (1989).
Ouellet et al., "An Apoptotic Molecular Network Identified by Microarray: On the TRAIL to New Insights in Epithelial Ovarian Cancer." Cancer, vol. 110(2), pp. 297-308 (2007).
Paz-Ares et al., "A randomized phase 2 study of paclitaxel and carboplatin with or without conatumumab for first-line treatment of advanced non-small-cell lung cancer." J Thorac Oncol, vol. 8, pp. 329-337 (2013).
Presta, "Antibody engineering." Curr Op Struct Biol, vol. 2, pp. 593-596 (1992).
Printz, "Cancer drug safety presents challenges: oncologists, researchers, and government balance risks with benefits." Cancer, vol. 117, pp. 5023-5025 (2011).
Ridgway et al., "'Knobs-into-holes' engineering of antibody CH3 domains for heavy chain heterodimerization." Protein Eng, vol. 9, pp. 617-621 (1996).
Riechmann et al., "Reshaping human antibodies for therapy." Nature, vol. 332, pp. 323-329 (1988).
Sasaki et al., "A phase I study of farletuzumab, a humanized anti-folate receptor alpha monoclonal antibody, in patients with solid tumors." Invest New Drugs, vol. 33, pp. 332-340 (2015).
Saunders et al., "Role of intratumoural heterogeneity in cancer drug resistance: molecular and clinical perspectives." EMBO Mol Med, vol. 4, pp. 675-684 (2012).
Schaefer et al., "A two-in-one antibody against HER3 and EGFR has superior inhibitory activity compared with monospecific antibodies." Cancer Cell, vol. 20, pp. 472-486 (2011).
Soria et al., "Phase 1b study of dulanermin (recombinant human Apo2L/TRAIL) in combination with paclitaxel, carboplatin, and bevacizumab in patients with advanced non-squamous non-small-cell lung cancer." J Clin Oncol vol. 28, pp. 1527-1533 (2010).
Spiess et al., "Alternative molecular formats and therapeutic applications for bispecific antibodies." Mol Immunol, vol. 67, pp. 95-106 (2015).
Takeda et al., "Construction of Chimaeric processed immunoglobulin genes containing mouse variable and human constant region sequences." Nature, vol. 314, pp. 452-454 (1985).
Takeda et al., "Death receptor 5 mediated-apoptosis contributes to cholestatic liver disease." Proc Natl Acad Sci USA, vol. 105, pp. 10895-10900 (2008).
Tran et al., "Immune targeting of fibroblast activation protein triggers recognition of multipotent bone marrow stromal cells and cachexia." J Exp Med, vol. 210, pp. 1125-1135 (2013).
Tuszynski et al., "Thrombospondin Promotes Platelet Aggregation." Blood, vol. 72, pp. 109-115 (1988).
Uphoff et al., "In vitro selection of aptamers: the dearth of pure reason." Curr Opin Struct Biol, vol. 6, pp. 281-287 (1996).
Vergote et al., "A Randomized, Double-Blind, Placebo-Controlled, Phase III Study to Assess Efficacy and Safety of Weekly Farletuzumab in Combination With Carboplatin and Taxane in Patients With Ovarian Cancer in First Platinum-Sensitive Relapse." J Clin Oncol, vol. 34, pp. 2271-2278 (2016).
Verhoeyen et al., "Reshaping human antibodies: grafting an antilysozyme activity." Science, vol. 239, pp. 1534-1536 (1988).
Vincenzi et al., "Drug-induced hepatotoxicity in cancer patients—implication for treatment." Expert Opin Drug Saf, vol. 15, pp. 1219-1238 (2016).
Wagner et al., "Death-receptor O-glycosylation controls tumor-cell sensitivity to the proapoptotic ligand Apo2L/TRAIL." Nat Med vol. 13, pp. 1070-1077 (2007).
Wakelee et al., "Phase I and pharmacokinetic study of lexatumumab (HGS-ETR2) given every 2 weeks in patients with advanced solid tumors." Ann Oncol, vol. 21, pp. 376-381 (2010).
Wallis et al., "A novel RNA motif for neomycin recognition." Chem Biol, vol. 2, pp. 543-552 (1995).
Wang et al., "The molecular mechanisms of TRAIL resistance in cancer cells: help in designing new drugs." Curr Pharm Des, vol. 20, pp. 6714-6722 (2014).
Wilson et al., "An Fcgamma receptor-dependent mechanism drives antibody-mediated target-receptor signaling in cancer cells." Cancer Cell, vol. 19, pp. 101-113 (2011).
Winter et al., "Man-made antibodies." Nature, vol. 349, pp. 293-299 (1991).
Written Opinion of the International Searching Authority Corresponding to International application No. PCT/US 2018/060735 dated Apr. 19, 2019.
Zhang et al., "3D Structural Fluctuation of IgG1 Antibody Revealed by Individual Particle Electron Tomography." Sci Rep, vol. 5, pp. Article No. 9803 (2015).
Zuch de Zafra et al., "Antitherapeutic antibody-mediated hepatotoxicity of recombinant human Apo2L/TRAIL in the cynomolgus monkey." Cell Death Dis, vol. 7, Article ID e2338 (2016).

(56) References Cited

OTHER PUBLICATIONS

Digiammarino, E., et al., "Design and generation of DVD-Ig molecules for dual-specific targeting", in Methods Mol Biol, vol. 899, 2012, pp. 145-156.
Ecker, D. M., et al., (2015). "The therapeutic monoclonal antibody market", in Mabs, vol. 7,2015, pp. 9-14.
Frolova, O., et al. "Regulation of HIF-lalpha signaling and chemoresistance in acute lymphocytic leukemia under hypoxic conditions of the bone marrow microenvironment", in Cancer Biol Ther, vol. 13, 2012, pp. 858-870.
Garber, K., "Bispecific antibodies rise again" in Nat Rev Drug Discov, 2014, pp. 799-801.
Herbst, R. S., et al., "A first-in-human study 30 of conatumumab in adult patients with advanced solid tumors", in Clin Cancer Res, vol. 16, 2010 b, pp. 5883-5891.
Herbst, R. S., et al., "Phase I dose-escalation study of recombinant human Apo2L/TRAIL, a dual proapoptotic receptor agonist, in patients with advanced cancer", in J Clin Oncol 28, 2010a, pp. 2839-2846.
Kang, J., et al., "Chemical sensitization and regulation of TRAIL-induced apoptosis in a panel of B-lymphocytic leukaemia cell lines", in Br J Haematol, vol. 123, pp. 921-932.
Kindler, H. L., et al. , "A randomized, placebo-controlled phase 2 study of ganitumab (AMG 479) or conatumumab (AMG 655) in combination with gemcitabine in patients with metastatic pancreatic cancer", in Ann Oncol, vol. 23, 2012, pp. 2834-2842.
Kohrt, H. E., et al., "Combination strategies to enhance antitumor ADCC", Immunotherapy, vol. 4, 2012, pp. 511-527.
Kontermann, R. E. "Dual targeting strategies with bispecific antibodies", in MAbs , vol. 4, 2012, pp. 182-197.
Lacy, S. E., et al., "Generation and characterization of ABT-981, a dual variable domain immunoglobulin (DVD-Ig(TM)) molecule that specifically and potently neutralizes both IL-lalpha and IL-lbeta", in Mabs, vol. 7, 2015, pp. 605-619.
Lu, M., et al., "E-cadherin couples death receptors to the cytoskeleton to regulate apoptosis", in Mol Cell, vol. 54, 2014, pp. 987-998.
Mahalingam, D., et al., "Targeting TRAIL towards the clinic", in Curr Drug Targets, vol. 12, 2011, pp. 2079-2090.
O'shannessy, D. J., et al., "Expression of folate receptor-alpha (FRA) in gynecologic malignancies and its relationship to the tumor type", in Int J Gynecol Pathol 32, 2013, pp. 258-268.
Office Action corresponding to European Patent Application No. 18879754.2 dated Feb. 8, 2024.
Plummer, R., et al., "Phase 1 and pharmacokinetic study of lexatumumab in patients with advanced cancers", in Clin Cancer Res, vol. 13, 2007, pp. 6187-6194.
Sabbatini, P., et al., "Abagovomab as maintenance therapy in patients with epithelial ovarian cancer: a phase III trial of the AGO OVAR, COGI, Gineco, and GEICO—the MIMOSA study", J Clin Oncol, 2013, vol. 31, pp. 1554-1561.
Sandilands, G. P., et al., (2010). "Were monocytes responsible for initiating the cytokine storm in the TGN1412 clinical trial tragedy", in Clin Exp Immunol, vol. 162, 2010, pp. 516-527.
Shanker, A., et al., "Treating metastatic solid tumors with bortezomib and a tumor necrosis factor-related apoptosis-inducing ligand receptor agonist antibody", In J Natl Cancer Inst , vol. 100, 2008, pp. 649-662.
Shimizu, A., et al., "H NMR studies of the Fc region of human IgG1 and IgG3 immunoglobulins: assignment of histidine resonances in the CH3 domain and identification of IgG3 protein carrying G3m(st) allotypes", in Mol Immunol, vol. 20, 1983, pp. 141-148.
Silacci, M., et al., "Discovery and characterization of COVA322, a clinical-stage bispecific TNF/IL-17A inhibitor for the treatment of inflammatory diseases", in Mabs, vol. 8, 2016, pp. 141-149.
Stevenson, G. T. "Three major uncertainties in the antibody therapy of cancer", in Haematologica 99, 2014, pp. 1538-1546.
Swiech, K., et al., "Transient transfection of serum-free suspension HEK 293 cell culture for efficient production of human rFVIII", in BMC Biotechnol 11, 2011, pp114.
Takeda, K., et al.,"Induction of tumor-specific T cell immunity by anti-DRS antibody therapy", In J Exp Med 199, 2004, pp. 437-448.
Topalian, S. L., et al., "Safety, activity, and immune correlates of anti-PD-1 antibody in cancer", in N Engl J Med, vol. 366, 2012, pp. 2443-2454.
Topp, M. S., et al., "Safety and activity of blinatumomab for adult patients with relapsed or refractory B-precursor acute lymphoblastic leukaemia: a multicentre, single-arm, phase 2 study", Lancet Oncol, vol. 16, 2015, pp. 57-66.
Uno, T., et al.,"Eradication of established tumors in mice by a combination antibody-based therapy", In Nat Med, vol. 12, 2006, pp. 693-698.
Walter, R. B. " Biting back: BiTE antibodies as a promising therapy for acute myeloid leukemia", In Expert Rev Hematol , vol. 7 , 2014, pp. 317-319.
Wickramasinghe, D. "Tumor and T cell engagement by BITE", in Discov Med 16, 2013, pp. 149-152.
Williams, K. A., et al., "Polymorphisms of MUC16 (CA125) and MUC1 (CA15.3) in relation to ovarian cancer risk and survival", in PLoS One 9, 2014, e88334.
Xin, L., et al., "Human monoclonal antibodies in cancer therapy: a review of recent developments", In Front Biosci (Landmark Ed) vol. 18, 2013, pp. 765-772.
Carter, P., "Bispecific Human IgG by Design," Journal of Immunological Methods, vol. 248, Issue. (1-2), Feb. 1, 2001, pp. 7-15.
Teleb et al., "Idarucizumab: Clinical Role of a Novel Reversal Agent for Dabigatran." Cardiovasc Hematol Disord Drug Targets, vol. 16, pp. 25-29 (2016).
Tushir-Singh, "Antibody-siRNA conjugates: drugging the undruggable for anti-leukemic therapy." Expert Opin Biol Ther, vol. 17, pp. 325-338 (2017).

* cited by examiner

| Properties | BaCa-1 | BaCa-2 | BaCa-3 | Parental IgG1 |
|---|---|---|---|---|
| Yield (mg/L) | (8-10 mg/L) | (4-6 mg/L) | (2-4 mg/L) | (>10 mg/L)*** |
| % monomer (1-Step purification)* mg/L | (90-95%) | (75-90%) | (50-75%) | (95-100%)*** |
| % Recovery (2-Step)** mg/L | (>90%) | (>60%) | (<50%) | (>95%)*** |
| Binding affinity (Kd), rDR5 (nM) | 0.73±0.03 | 1.077±0.06 | 0.538±0.023 | 0.518±0.028 (Lexatumumab) |
| Binding affinity (Kd), rFOLR1 (nM) | 0.61±0.026 | 0.0887±0.032 | 0.392±0.026 | 0.42±0.014 (Farletuzumab) |
| $IC_{50}$ (nM) OVCAR-4 cells | 0.046±0.066 | 1.18±2.69 | 9.95±2.24 | 23±3.20 (Lexatumumab) |

FIG. 1B

| Antibody | BaCa-1 | BaCa-2 | BaCa-3 | Lexatumumab |
|---|---|---|---|---|
| $IC_{50}$ (nM) | 0.278±1.10 | 2.889±1.69 | 16.15±1.04 | 36.36±1.05 |

| | Lexatumumab | BaCa |
|---|---|---|
| Kd (nM) | 3.3 ± 0.24 | 3.1 ± 0.25 |
| $K_{on}$ (1/Ms) | 6.06E+05 | 1.02E+06 |
| $K_{off}$ (1/Ms) | 2.22E-03 | 2.64E-03 |

| | Farletuzumab | BaCa |
|---|---|---|
| Kd (nM) | 15 ± 3.3 | 12 ± 1.1 |
| $K_{on}$ (1/Ms) | 1.91E+06 | 2.41E+06 |
| $K_{off}$ (1/Ms) | 3.57E-02 | 3.89E-02 |

| | BaCa | NBaCa | Lexatumumab |
|---|---|---|---|
| OVCAR-3: $IC_{50}$ (nM) | 0.170±1.12 | 30.29±1.06 | 33.30±1.09 |
| OVCAR-4: $IC_{50}$ (nM) | 0.051±0.51 | 21.98±1.12 | 22.65±2.05 |

| | Apo2L | Lexatu-mumab | Lexatumu-mab+Apo2L | Lexatumu-mab BaCa | Lexatumumab BaCa+Apo2L |
|---|---|---|---|---|---|
| $IC_{50}$ (nM) | 2.709 | 25.66 | 11.14 | 0.183 | 0.186 |

| | Apo2L | AMG-655 | AMG-655 +Apo2L | AMG-655 BaCa | AMG-655 BaCa+Apo2L |
|---|---|---|---|---|---|
| $IC_{50}$ (nM) | 2.975 | | 0.550 | 0.172 | 0.165 |

| Cell type | Antibody | $IC_{50}$ (nM) |
|---|---|---|
| OVCAR-4 | Lexatumumab | 33.30 |
| Colo-205 | Lexatumumab | 36.32 |
| OVCAR-4 | BaCa | 0.048 |
| Colo-205 | BaCa | 3.07 |

OVARIAN CANCER CELLS
(DR5+, DR5++, Responsive to DR5 Agonist
FOLR1++, FOLR1+++, FOLR1++++)

Tumor anchor receptor (FOLR1)
selective apoptosis (*in vitro*)

| | | Lexatumumab | BaCa |
|---|---|---|---|
| Biotinylated rDR5 | Kd (nM) | 3.3 ± 0.24 | 3.1 ± 0.25 |
| | $K_{on}$ (1/Ms) | 6.06E+05 | 1.02E+06 |
| | $K_{off}$ (1/Ms) | 2.22E-03 | 2.64E-03 |
| | | Farletuzumab | BaCa |
| Biotinylated rFOLR1 | Kd (nM) | 15 ± 3.3 | 12 ± 1.1 |
| | $K_{on}$ (1/Ms) | 1.91E+06 | 2.41E+06 |
| | $K_{off}$ (1/Ms) | 3.57E-02 | 3.89E-02 |

| Antibody | BaCa, (37°C) 10 days | BaCa, (25°C) 10 days | BaCa-Freeze thaw (12 cycles) | BaCa (4°C) 1 day |
|---|---|---|---|---|
| $IC_{50}$ (nM) | 0.72±0.1 | 0.49±0.15 | 0.44±0.16 | 0.397±.015 |

| Antibody | $T_{1/2}$ (Days) |
|---|---|
| BaCa-1 | 15.24 |
| BaCa-2 | 8.5 |
| Farletuzumab | 17.49 |

| Antibody | $T_{1/2}$ (Days) |
|---|---|
| BaCa-1 | 14.90 |
| BaCa-2 | 8.9 |
| Farletuzumab | 12.56 |

| Antibody | BaCa | Lexatumumab | BaCa-IR800 | Lexatumumab-IR800 |
|---|---|---|---|---|
| Kd (nM) | 0.65±0.2 | 0.42±0.11 | 0.58±0.18 | 0.85±0.21 |

| Antibody | Farletu -zumab | BaCa-KO-Fc (LALA) | BaCa-WT-Fc (LL) | BaCa-KO-Fc (LALA)-S267E | BaCa-WT-Fc (LL)-S267E |
|---|---|---|---|---|---|
| Kd (nM) | 0.9849 | 0.9044 | 1.209 | 0.801 | 0.596 |

| Antibody | Lexatu -mumab | BaCa-KO-Fc (LALA) | BaCa-WT-Fc (LL) | BaCa-KO-Fc (LALA)-S267E | BaCa-WT-Fc (LL)-S267E |
|---|---|---|---|---|---|
| Kd (nM) | 1.257 | 1.649 | 1.411 | 1.692 | 1.39 |

| Antibody | BaCa-KO-Fc (LALA) | BaCa-WT-Fc (LL) | BaCa-KO-Fc (LALA)-S267E | BaCa-WT-Fc (LL)-S267E |
|---|---|---|---|---|
| $IC_{50}$ (nM) | 0.5326 | 0.4982 | 0.6587 | 0.6859 |

| Antibody | Lexatumumab-KO-Fc (LALA) | Lexatumumab-WT-Fc (LL) | Lexatumumab-KO-Fc (LALA)-S267E | Lexatumumab-WT-Fc (LL)-S267E |
|---|---|---|---|---|
| $IC_{50}$ (nM) | 26.5205 | 30.1910 | 25.5620 | 31.0150 |

SEQUENCE LISTING

<160> NUMBER OF SEQ ID NOS: 12

<210> SEQ ID NO 1
<211> LENGTH: 710
<212> TYPE: PRT
<213> ORGANISM: Artificial Sequence
<220> FEATURE:
<223> OTHER INFORMATION: Artificially synthesized sequence

<400> SEQUENCE: 1

Glu Val Gln Leu Val Glu Ser Gly Gly Gly Val Val Gln Pro Gly Arg
1 5 10 15

Ser Leu Arg Leu Ser Cys Ser Ala Ser Gly Phe Thr Phe Ser Gly Tyr
20 25 30

Gly Leu Ser Trp Val Arg Gln Ala Pro Gly Lys Gly Leu Glu Trp Val
35 40 45

Ala Met Ile Ser Ser Gly Gly Ser Tyr Thr Tyr Tyr Ala Asp Ser Val
50 55 60

Lys Gly Arg Phe Ala Ile Ser Arg Asp Asn Ala Lys Asn Thr Leu Phe
65 70 75 80

Leu Gln Met Asp Ser Leu Arg Pro Glu Asp Thr Gly Val Tyr Phe Cys
85 90 95

Ala Arg His Gly Asp Asp Pro Ala Trp Phe Ala Tyr Trp Gly Gln Gly
100 105 110

Thr Pro Val Thr Val Ser Ser Ala Ser Thr Lys Gly Pro Ser Val Phe
115 120 125

-continued

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Glu His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Gly Gly Gly Ser Gly Gly Gly Ser Gly Gly Gly Ser Ser Ser Glu
    450                 455                 460

Leu Thr Gln Asp Pro Ala Val Ser Val Ala Leu Gly Gln Thr Val Arg
465                 470                 475                 480

Ile Thr Cys Gln Gly Asp Ser Leu Arg Ser Tyr Tyr Ala Ser Trp Tyr
                485                 490                 495

Gln Gln Lys Pro Gly Gln Ala Pro Val Leu Val Ile Tyr Gly Lys Asn
            500                 505                 510

Asn Arg Pro Ser Gly Ile Pro Asp Arg Phe Ser Gly Ser Ser Ser Gly
        515                 520                 525

Asn Thr Ala Ser Leu Thr Ile Thr Gly Ala Gln Ala Glu Asp Glu Ala
    530                 535                 540

Asp Tyr Tyr Cys Asn Ser Arg Asp Ser Ser Gly Asn His Val Val Phe
```

545 550 555 560

Gly Gly Gly Thr Lys Leu Thr Val Leu Gly Gly Gly Gly Ser Gly Gly
565 570 575

Gly Asp Ser Gly Gly Gly Gly Ser Gly Gly Gly Gly Ser Glu Val Gln
580 585 590

Leu Val Gln Ser Gly Gly Gly Val Glu Arg Pro Gly Gly Ser Leu Arg
595 600 605

Leu Ser Cys Ala Ala Ser Gly Phe Thr Phe Asp Asp Tyr Gly Met Ser
610 615 620

Trp Val Arg Gln Ala Pro Gly Lys Gly Leu Glu Trp Val Ser Gly Ile
625 630 635 640

Asn Trp Asn Gly Gly Ser Thr Gly Tyr Ala Asp Ser Val Lys Gly Arg
645 650 655

Val Thr Ile Ser Arg Asp Asn Ala Lys Asn Ser Leu Tyr Leu Gln Met
660 665 670

Asn Ser Leu Arg Ala Glu Asp Thr Ala Val Tyr Tyr Cys Ala Lys Ile
675 680 685

Leu Gly Ala Gly Arg Gly Trp Tyr Phe Asp Leu Trp Gly Lys Gly Thr
690 695 700

Thr Val Thr Val Ser Ser
705 710

<210> SEQ ID NO 2
<211> LENGTH: 217
<212> TYPE: PRT
<213> ORGANISM: Artificial Sequence
<220> FEATURE:
<223> OTHER INFORMATION: Artificially synthesized sequence

<400> SEQUENCE: 2

Asp Ile Gln Leu Thr Gln Ser Pro Ser Ser Leu Ser Ala Ser Val Gly
1 5 10 15

Asp Arg Val Thr Ile Thr Cys Ser Val Ser Ser Ser Ile Ser Ser Asn
20 25 30

Asn Leu His Trp Tyr Gln Gln Lys Pro Gly Lys Ala Pro Lys Pro Trp
35 40 45

Ile Tyr Gly Thr Ser Asn Leu Ala Ser Gly Val Pro Ser Arg Phe Ser
50 55 60

Gly Ser Gly Ser Gly Thr Asp Tyr Thr Phe Thr Ile Ser Ser Leu Gln
65 70 75 80

Pro Glu Asp Ile Ala Thr Tyr Tyr Cys Gln Gln Trp Ser Ser Tyr Pro
85 90 95

Tyr Met Tyr Thr Phe Gly Gln Gly Thr Lys Val Glu Ile Lys Arg Thr
100 105 110

Val Ala Ala Pro Ser Val Phe Ile Phe Pro Pro Ser Asp Glu Gln Leu
115 120 125

Lys Ser Gly Thr Ala Ser Val Val Cys Leu Leu Asn Asn Phe Tyr Pro
130 135 140

Arg Glu Ala Lys Val Gln Trp Lys Val Asp Asn Ala Leu Gln Ser Gly
145 150 155 160

Asn Ser Gln Glu Ser Val Thr Glu Gln Asp Ser Lys Asp Ser Thr Tyr
165 170 175

Ser Leu Ser Ser Thr Leu Thr Leu Ser Lys Ala Asp Tyr Glu Lys His
180 185 190

Lys Val Tyr Ala Cys Glu Val Thr His Gln Gly Leu Ser Ser Pro Val

```
        195                 200                 205

Thr Lys Ser Phe Asn Arg Gly Glu Cys
    210                 215


<210> SEQ ID NO 3
<211> LENGTH: 715
<212> TYPE: PRT
<213> ORGANISM: Artificial Sequence
<220> FEATURE:
<223> OTHER INFORMATION: Artificially synthesized sequence

<400> SEQUENCE: 3

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Gly Gly Gly Gly Ser Gly Gly Gly Gly Ser Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Val Val Gln Pro Gly Arg Ser Leu Arg Leu Ser
        275                 280                 285

Cys Ser Ala Ser Gly Phe Thr Phe Ser Gly Tyr Gly Leu Ser Trp Val
    290                 295                 300

Arg Gln Ala Pro Gly Lys Gly Leu Glu Trp Val Ala Met Ile Ser Ser
305                 310                 315                 320

Gly Gly Ser Tyr Thr Tyr Tyr Ala Asp Ser Val Lys Gly Arg Phe Ala
                325                 330                 335

Ile Ser Arg Asp Asn Ala Lys Asn Thr Leu Phe Leu Gln Met Asp Ser
```

-continued

```
            340                 345                 350

Leu Arg Pro Glu Asp Thr Gly Val Tyr Phe Cys Ala Arg His Gly Asp
        355                 360                 365

Asp Pro Ala Trp Phe Ala Tyr Trp Gly Gln Gly Thr Pro Val Thr Val
    370                 375                 380

Ser Ser Ala Ser Thr Lys Gly Pro Ser Val Phe Pro Leu Ala Pro Ser
385                 390                 395                 400

Ser Lys Ser Thr Ser Gly Gly Thr Ala Ala Leu Gly Cys Leu Val Lys
                405                 410                 415

Asp Tyr Phe Pro Glu Pro Val Thr Val Ser Trp Asn Ser Gly Ala Leu
            420                 425                 430

Thr Ser Gly Val His Thr Phe Pro Ala Val Leu Gln Ser Ser Gly Leu
        435                 440                 445

Tyr Ser Leu Ser Ser Val Val Thr Val Pro Ser Ser Ser Leu Gly Thr
    450                 455                 460

Gln Thr Tyr Ile Cys Asn Val Asn His Lys Pro Ser Asn Thr Lys Val
465                 470                 475                 480

Asp Lys Arg Val Glu Pro Lys Ser Cys Asp Lys Thr His Thr Cys Pro
                485                 490                 495

Pro Cys Pro Ala Pro Glu Leu Leu Gly Gly Pro Ser Val Phe Leu Phe
            500                 505                 510

Pro Pro Lys Pro Lys Asp Thr Leu Met Ile Ser Arg Thr Pro Glu Val
        515                 520                 525

Thr Cys Val Val Val Asp Val Ser His Glu Asp Pro Glu Val Lys Phe
    530                 535                 540

Asn Trp Tyr Val Asp Gly Val Glu Val His Asn Ala Lys Thr Lys Pro
545                 550                 555                 560

Arg Glu Glu Gln Tyr Asn Ser Thr Tyr Arg Val Val Ser Val Leu Thr
                565                 570                 575

Val Leu His Gln Asp Trp Leu Asn Gly Lys Glu Tyr Lys Cys Lys Val
            580                 585                 590

Ser Asn Lys Ala Leu Pro Ala Pro Ile Glu Lys Thr Ile Ser Lys Ala
        595                 600                 605

Lys Gly Gln Pro Arg Glu Pro Gln Val Tyr Thr Leu Pro Pro Ser Arg
    610                 615                 620

Glu Glu Met Thr Lys Asn Gln Val Ser Leu Tyr Cys Leu Val Lys Gly
625                 630                 635                 640

Phe Tyr Pro Ser Asp Ile Ala Val Glu Trp Glu Ser Asn Gly Gln Pro
                645                 650                 655

Glu Asn Asn Tyr Lys Thr Thr Pro Pro Val Leu Asp Ser Asp Gly Ser
            660                 665                 670

Phe Phe Leu Tyr Ser Lys Leu Thr Val Asp Lys Ser Arg Trp Gln Gln
        675                 680                 685

Gly Asn Val Phe Ser Cys Ser Val Met His Glu Ala Leu His Asn His
    690                 695                 700

Tyr Thr Gln Lys Ser Leu Ser Leu Ser Pro Gly
705                 710                 715
```

<210> SEQ ID NO 4
<211> LENGTH: 715
<212> TYPE: PRT
<213> ORGANISM: Artificial Sequence
<220> FEATURE:
<223> OTHER INFORMATION: Artificially synthesized sequence

<400> SEQUENCE: 4

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser Gly Gly Gly Gly Ser Gly
                245                 250                 255

Gly Gly Gly Ser Gly Gly Gly Gly Ser Glu Val Gln Leu Val Gln Ser
            260                 265                 270

Gly Gly Gly Val Glu Arg Pro Gly Gly Ser Leu Arg Leu Ser Cys Ala
        275                 280                 285

Ala Ser Gly Phe Thr Phe Asp Asp Tyr Gly Met Ser Trp Val Arg Gln
    290                 295                 300

Ala Pro Gly Lys Gly Leu Glu Trp Val Ser Gly Ile Asn Trp Asn Gly
305                 310                 315                 320

Gly Ser Thr Gly Tyr Ala Asp Ser Val Lys Gly Arg Val Thr Ile Ser
                325                 330                 335

Arg Asp Asn Ala Lys Asn Ser Leu Tyr Leu Gln Met Asn Ser Leu Arg
            340                 345                 350

Ala Glu Asp Thr Ala Val Tyr Tyr Cys Ala Lys Ile Leu Gly Ala Gly
        355                 360                 365

Arg Gly Trp Tyr Phe Asp Leu Trp Gly Lys Gly Thr Thr Val Thr Val
    370                 375                 380

Ser Ser Ala Ser Thr Lys Gly Pro Ser Val Phe Pro Leu Ala Pro Ser
385                 390                 395                 400

Ser Lys Ser Thr Ser Gly Gly Thr Ala Ala Leu Gly Cys Leu Val Lys
                405                 410                 415
```

Asp Tyr Phe Pro Glu Pro Val Thr Val Ser Trp Asn Ser Gly Ala Leu
420 425 430

Thr Ser Gly Val His Thr Phe Pro Ala Val Leu Gln Ser Ser Gly Leu
435 440 445

Tyr Ser Leu Ser Ser Val Val Thr Val Pro Ser Ser Ser Leu Gly Thr
450 455 460

Gln Thr Tyr Ile Cys Asn Val Asn His Lys Pro Ser Asn Thr Lys Val
465 470 475 480

Asp Lys Arg Val Glu Pro Lys Ser Cys Asp Lys Thr His Thr Cys Pro
485 490 495

Pro Cys Pro Ala Pro Glu Leu Leu Gly Gly Pro Ser Val Phe Leu Phe
500 505 510

Pro Pro Lys Pro Lys Asp Thr Leu Met Ile Ser Arg Thr Pro Glu Val
515 520 525

Thr Cys Val Val Val Asp Val Ser His Glu Asp Pro Glu Val Lys Phe
530 535 540

Asn Trp Tyr Val Asp Gly Val Glu Val His Asn Ala Lys Thr Lys Pro
545 550 555 560

Arg Glu Glu Gln Tyr Asn Ser Thr Tyr Arg Val Val Ser Val Leu Thr
565 570 575

Val Leu His Gln Asp Trp Leu Asn Gly Lys Glu Tyr Lys Cys Lys Val
580 585 590

Ser Asn Lys Ala Leu Pro Ala Pro Ile Glu Lys Thr Ile Ser Lys Ala
595 600 605

Lys Gly Gln Pro Arg Glu Pro Gln Val Tyr Thr Leu Pro Pro Ser Arg
610 615 620

Glu Glu Met Thr Lys Asn Gln Val Ser Leu Thr Cys Leu Val Lys Gly
625 630 635 640

Phe Tyr Pro Ser Asp Ile Ala Val Glu Trp Glu Ser Asn Gly Gln Pro
645 650 655

Glu Asn Asn Tyr Lys Thr Thr Pro Pro Val Leu Asp Ser Asp Gly Ser
660 665 670

Phe Phe Leu Thr Ser Lys Leu Thr Val Asp Lys Ser Arg Trp Gln Gln
675 680 685

Gly Asn Val Phe Ser Cys Ser Val Met His Glu Ala Leu His Asn Arg
690 695 700

Phe Thr Gln Lys Ser Leu Ser Leu Ser Pro Gly
705 710 715

<210> SEQ ID NO 5
<211> LENGTH: 581
<212> TYPE: PRT
<213> ORGANISM: Artificial Sequence
<220> FEATURE:
<223> OTHER INFORMATION: Artificially synthesized sequence

<400> SEQUENCE: 5

Glu Val Gln Leu Val Gln Ser Gly Gly Gly Val Glu Arg Pro Gly Gly
1 5 10 15

Ser Leu Arg Leu Ser Cys Ala Ala Ser Gly Phe Thr Phe Asp Asp Tyr
20 25 30

Gly Met Ser Trp Val Arg Gln Ala Pro Gly Lys Gly Leu Glu Trp Val
35 40 45

Ser Gly Ile Asn Trp Asn Gly Gly Ser Thr Gly Tyr Ala Asp Ser Val
50 55 60

```
Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Leu Trp Gly
            100                 105                 110

Lys Gly Thr Thr Val Thr Val Ser Ser Gly Gly Ser Gly Gly Ser Gly
        115                 120                 125

Gly Ser Gly Gly Ser Glu Val Gln Leu Val Glu Ser Gly Gly Gly Val
    130                 135                 140

Val Gln Pro Gly Arg Ser Leu Arg Leu Ser Cys Ser Ala Ser Gly Phe
145                 150                 155                 160

Thr Phe Ser Gly Tyr Gly Leu Ser Trp Val Arg Gln Ala Pro Gly Lys
                165                 170                 175

Gly Leu Glu Trp Val Ala Met Ile Ser Ser Gly Gly Ser Tyr Thr Tyr
            180                 185                 190

Tyr Ala Asp Ser Val Lys Gly Arg Phe Ala Ile Ser Arg Asp Asn Ala
        195                 200                 205

Lys Asn Thr Leu Phe Leu Gln Met Asp Ser Leu Arg Pro Glu Asp Thr
    210                 215                 220

Gly Val Tyr Phe Cys Ala Arg His Gly Asp Asp Pro Ala Trp Phe Ala
225                 230                 235                 240

Tyr Trp Gly Gln Gly Thr Pro Val Thr Val Ser Ser Ala Ser Thr Lys
                245                 250                 255

Gly Pro Ser Val Phe Pro Leu Ala Pro Ser Ser Lys Ser Thr Ser Gly
            260                 265                 270

Gly Thr Ala Ala Leu Gly Cys Leu Val Lys Asp Tyr Phe Pro Glu Pro
        275                 280                 285

Val Thr Val Ser Trp Asn Ser Gly Ala Leu Thr Ser Gly Val His Thr
    290                 295                 300

Phe Pro Ala Val Leu Gln Ser Ser Gly Leu Tyr Ser Leu Ser Ser Val
305                 310                 315                 320

Val Thr Val Pro Ser Ser Ser Leu Gly Thr Gln Thr Tyr Ile Cys Asn
                325                 330                 335

Val Asn His Lys Pro Ser Asn Thr Lys Val Asp Lys Lys Val Glu Pro
            340                 345                 350

Lys Ser Cys Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
385                 390                 395                 400

Val Glu His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
            420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Ala Leu Pro
    450                 455                 460

Ala Pro Ile Glu Lys Thr Ile Ser Lys Ala Lys Gly Gln Pro Arg Glu
465                 470                 475                 480
```

-continued

Pro Gln Val Tyr Thr Leu Pro Pro Ser Arg Glu Glu Met Thr Lys Asn
485 490 495

Gln Val Ser Leu Thr Cys Leu Val Lys Gly Phe Tyr Pro Ser Asp Ile
500 505 510

Ala Val Glu Trp Glu Ser Asn Gly Gln Pro Glu Asn Asn Tyr Lys Thr
515 520 525

Thr Pro Pro Val Leu Asp Ser Asp Gly Ser Phe Phe Leu Tyr Ser Lys
530 535 540

Leu Thr Val Asp Lys Ser Arg Trp Gln Gln Gly Asn Val Phe Ser Cys
545 550 555 560

Ser Val Met His Glu Ala Leu His Asn His Tyr Thr Gln Lys Ser Leu
565 570 575

Ser Leu Ser Leu Gly
580

<210> SEQ ID NO 6
<211> LENGTH: 337
<212> TYPE: PRT
<213> ORGANISM: Artificial Sequence
<220> FEATURE:
<223> OTHER INFORMATION: Artificially synthesized sequence

<400> SEQUENCE: 6

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ser Ser Gly Asn His
85 90 95

Val Val Phe Gly Gly Gly Thr Lys Leu Thr Val Leu Gly Gly Ser Gly
100 105 110

Gly Ser Gly Gly Ser Gly Gly Ser Asp Ile Gln Leu Thr Gln Ser Pro
115 120 125

Ser Ser Leu Ser Ala Ser Val Gly Asp Arg Val Thr Ile Thr Cys Ser
130 135 140

Val Ser Ser Ser Ile Ser Ser Asn Asn Leu His Trp Tyr Gln Gln Lys
145 150 155 160

Pro Gly Lys Ala Pro Lys Pro Trp Ile Tyr Gly Thr Ser Asn Leu Ala
165 170 175

Ser Gly Val Pro Ser Arg Phe Ser Gly Ser Gly Ser Gly Thr Asp Tyr
180 185 190

Thr Phe Thr Ile Ser Ser Leu Gln Pro Glu Asp Ile Ala Thr Tyr Tyr
195 200 205

Cys Gln Gln Trp Ser Ser Tyr Pro Tyr Met Tyr Thr Phe Gly Gln Gly
210 215 220

Thr Lys Val Glu Ile Lys Arg Thr Val Ala Ala Pro Ser Val Phe Ile
225 230 235 240

Phe Pro Pro Ser Asp Glu Gln Leu Lys Ser Gly Thr Ala Ser Val Val
245 250 255

```
Cys Leu Leu Asn Asn Phe Tyr Pro Arg Glu Ala Lys Val Gln Trp Lys
            260                 265                 270

Val Asp Asn Ala Leu Gln Ser Gly Asn Ser Gln Glu Ser Val Thr Glu
        275                 280                 285

Gln Asp Ser Lys Asp Ser Thr Tyr Ser Leu Ser Ser Thr Leu Thr Leu
    290                 295                 300

Ser Lys Ala Asp Tyr Glu Lys His Lys Val Tyr Ala Cys Glu Val Thr
305                 310                 315                 320

His Gln Gly Leu Ser Ser Pro Val Thr Lys Ser Phe Asn Arg Gly Glu
                325                 330                 335

Cys


<210> SEQ ID NO 7
<211> LENGTH: 363
<212> TYPE: PRT
<213> ORGANISM: Artificial Sequence
<220> FEATURE:
<223> OTHER INFORMATION: Artificially synthesized sequence

<400> SEQUENCE: 7

Ile Thr Gln Gln Asp Leu Ala Pro Gln Gln Arg Ala Ala Pro Gln Gln
1               5                   10                  15

Lys Arg Ser Ser Pro Ser Glu Gly Leu Cys Pro Pro Gly His His Ile
            20                  25                  30

Ser Glu Asp Gly Arg Asp Cys Ile Ser Cys Lys Tyr Gly Gln Asp Tyr
        35                  40                  45

Ser Thr His Trp Asn Asp Leu Leu Phe Cys Leu Arg Cys Thr Arg Cys
    50                  55                  60

Asp Ser Gly Glu Val Glu Leu Ser Pro Cys Thr Thr Thr Arg Asn Thr
65                  70                  75                  80

Val Cys Gln Cys Glu Glu Gly Thr Phe Arg Glu Glu Asp Ser Pro Glu
                85                  90                  95

Met Cys Arg Lys Cys Arg Thr Gly Cys Pro Arg Gly Met Val Lys Val
            100                 105                 110

Gly Asp Cys Thr Pro Trp Ser Asp Ile Glu Cys Val His Lys Glu Ser
        115                 120                 125

Gly Gly Gly Ser Gly Gly Ser Glu Ser Lys Tyr Gly Pro Pro Cys Pro
    130                 135                 140

Pro Cys Pro Ala Pro Glu Phe Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser Gln Glu Asp Pro Glu Val Gln Phe
            180                 185                 190

Asn Trp Tyr Val Asp Gly Val Glu Val His Asn Ala Lys Thr Lys Pro
        195                 200                 205

Arg Glu Glu Gln Phe Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Gly Leu Pro Ser Ser Ile Glu Lys Thr Ile Ser Lys Ala
                245                 250                 255

Lys Gly Gln Pro Arg Glu Pro Gln Val Tyr Thr Leu Pro Pro Ser Gln
            260                 265                 270

Glu Glu Met Thr Lys Asn Gln Val Ser Leu Thr Cys Leu Val Lys Gly
```

```
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Glu
                325                 330                 335

Gly Asn Val Phe Ser Cys Ser Val Met His Glu Ala Leu His Asn His
            340                 345                 350

Tyr Thr Gln Lys Ser Leu Ser Leu Ser Leu Gly
        355                 360


<210> SEQ ID NO 8
<211> LENGTH: 465
<212> TYPE: PRT
<213> ORGANISM: Artificial Sequence
<220> FEATURE:
<223> OTHER INFORMATION: Artificially synthesized sequence

<400> SEQUENCE: 8

Ala Gln Arg Met Thr Thr Gln Leu Leu Leu Leu Leu Val Trp Val Ala
1               5                   10                  15

Val Val Gly Glu Ala Gln Thr Arg Ile Ala Trp Ala Arg Thr Glu Leu
            20                  25                  30

Leu Asn Val Cys Met Asn Ala Lys His His Lys Glu Lys Pro Gly Pro
        35                  40                  45

Glu Asp Lys Leu His Glu Gln Cys Arg Pro Trp Arg Lys Asn Ala Cys
    50                  55                  60

Cys Ser Thr Asn Thr Ser Gln Glu Ala His Lys Asp Val Ser Tyr Leu
65                  70                  75                  80

Tyr Arg Phe Asn Trp Asn His Cys Gly Glu Met Ala Pro Ala Cys Lys
                85                  90                  95

Arg His Phe Ile Gln Asp Thr Cys Leu Tyr Glu Cys Ser Pro Asn Leu
            100                 105                 110

Gly Pro Trp Ile Gln Gln Val Asp Gln Ser Trp Arg Lys Glu Arg Val
        115                 120                 125

Leu Asn Val Pro Leu Cys Lys Glu Asp Cys Glu Gln Trp Trp Glu Asp
    130                 135                 140

Cys Arg Thr Ser Tyr Thr Cys Lys Ser Asn Trp His Lys Gly Trp Asn
145                 150                 155                 160

Trp Thr Ser Gly Phe Asn Lys Cys Ala Val Gly Ala Ala Cys Gln Pro
                165                 170                 175

Phe His Phe Tyr Phe Pro Thr Pro Thr Val Leu Cys Asn Glu Ile Trp
            180                 185                 190

Thr His Ser Tyr Lys Val Ser Asn Tyr Ser Arg Gly Ser Gly Arg Cys
        195                 200                 205

Ile Gln Met Trp Phe Asp Pro Ala Gln Gly Asn Pro Asn Glu Glu Val
    210                 215                 220

Ala Arg Phe Tyr Ala Ala Ala Gly Gly Ser Gly Gly Ser Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
```

```
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly
465


<210> SEQ ID NO 9
<211> LENGTH: 710
<212> TYPE: PRT
<213> ORGANISM: Mus musculus

<400> SEQUENCE: 9

Gln Val Gln Leu Gln Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Leu Ser Trp Val Arg Gln Thr Pro Asp Lys Arg Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Ser Leu Phe
65                  70                  75                  80

Leu Gln Met Ser Ser Leu Lys Ser Asp Asp Thr Ala Ile Tyr Ile Cys
                85                  90                  95

Ala Arg His Gly Asp Asp Pro Ala Trp Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

-continued

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Glu His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Gly Gly Ser Gly Gly Ser Gly Gly Ser Gly Gly Ser Asp Ile Gln
    450                 455                 460

Val Thr Gln Ser Pro Ser Leu Leu Ser Ala Ser Phe Gly Asp Lys Val
465                 470                 475                 480

Thr Ile Asn Cys Leu Val Thr Gln Asp Ile Thr Tyr Tyr Leu Ser Trp
                485                 490                 495

Tyr Gln Gln Lys Ser Gly Gln Pro Pro Thr Leu Leu Ile Tyr Asn Gly
            500                 505                 510

Asn Ser Leu Gln Ser Gly Val Pro Ser Arg Phe Ser Gly Gln Tyr Ser
        515                 520                 525

Gly Arg Thr Phe Thr Leu Ser Leu Ser Ser Leu Glu Pro Glu Asp Ala
    530                 535                 540

Gly Thr Tyr Tyr Cys Leu Gln His Tyr Ser Val Pro Phe Thr Phe Gly
545                 550                 555                 560

Gly Gly Thr Arg Leu Glu Ile Lys Gly Gly Gly Gly Ser Gly Gly Gly
                565                 570                 575

Asp Ser Gly Gly Gly Gly Ser Gly Gly Gly Gly Ser Gln Ile Gln Leu
            580                 585                 590

Gln Glu Ser Gly Pro Gly Leu Val Lys Pro Ala Gln Ser Leu Ser Leu
```

```
        595                 600                 605

Thr Cys Ser Ile Thr Gly Phe Pro Ile Thr Ala Gly Gly Tyr Trp Trp
    610                 615                 620

Thr Trp Ile Arg Gln Phe Pro Gly Gln Lys Leu Glu Trp Met Gly Tyr
625                 630                 635                 640

Ile Tyr Ser Ser Gly Ser Thr Asn Tyr Asn Pro Ser Ile Lys Ser Arg
                645                 650                 655

Ile Ser Ile Thr Arg Asp Thr Ala Lys Asn Gln Phe Phe Leu Gln Leu
            660                 665                 670

Asn Ser Val Thr Thr Glu Glu Asp Thr Ala Ile Tyr Tyr Cys Ala Arg
        675                 680                 685

Ala Gly Thr Ser Tyr Ser Gly Phe Phe Asp Ser Trp Gly Gln Gly Thr
    690                 695                 700

Leu Val Thr Val Ser Ser
705                 710


<210> SEQ ID NO 10
<211> LENGTH: 217
<212> TYPE: PRT
<213> ORGANISM: Mus musculus

<400> SEQUENCE: 10

Asp Ile Glu Leu Thr Gln Ser Pro Ala Leu Asn Ala Ala Ser Pro Gly
1               5                   10                  15

Glu Lys Val Thr Ile Thr Cys Ser Val Ser Ser Ser Ile Ser Ser Asn
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Leu Arg Phe Arg
    50                  55                  60

Gly Phe Gly Ser Gly Thr Ser Tyr Ser Leu Thr Ile Ser Ser Asn Glu
65                  70                  75                  80

Ala Glu Asp Ala Ala Thr Tyr Tyr Cys Gln Gln Trp Ser Ser Tyr Pro
                85                  90                  95

Tyr Met Tyr Thr Phe Gly Gly Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 11
<211> LENGTH: 710
<212> TYPE: PRT
<213> ORGANISM: Artificial Sequence
<220> FEATURE:
```

```
<223> OTHER INFORMATION: Artificially synthesized sequence

<400> SEQUENCE: 11

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Glu His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Gly Gly Ser Gly Gly Ser Gly Gly Ser Gly Gly Ser Asp Ile Gln
    450                 455                 460

Val Thr Gln Ser Pro Ser Leu Leu Ser Ala Ser Phe Gly Asp Lys Val
465                 470                 475                 480

Thr Ile Asn Cys Leu Val Thr Gln Asp Ile Thr Tyr Tyr Leu Ser Trp
                485                 490                 495

Tyr Gln Gln Lys Ser Gly Gln Pro Pro Thr Leu Leu Ile Tyr Asn Gly
            500                 505                 510

Asn Ser Leu Gln Ser Gly Val Pro Ser Arg Phe Ser Gly Gln Tyr Ser
        515                 520                 525

Gly Arg Thr Phe Thr Leu Ser Leu Ser Ser Leu Glu Pro Glu Asp Ala
    530                 535                 540

Gly Thr Tyr Tyr Cys Leu Gln His Tyr Ser Val Pro Phe Thr Phe Gly
545                 550                 555                 560

Gly Gly Thr Arg Leu Glu Ile Lys Gly Gly Gly Gly Ser Gly Gly Gly
                565                 570                 575

Asp Ser Gly Gly Gly Gly Ser Gly Gly Gly Gly Ser Gln Ile Gln Leu
            580                 585                 590

Gln Glu Ser Gly Pro Gly Leu Val Lys Pro Ala Gln Ser Leu Ser Leu
        595                 600                 605

Thr Cys Ser Ile Thr Gly Phe Pro Ile Thr Ala Gly Gly Tyr Trp Trp
    610                 615                 620

Thr Trp Ile Arg Gln Phe Pro Gly Gln Lys Leu Glu Trp Met Gly Tyr
625                 630                 635                 640

Ile Tyr Ser Ser Gly Ser Thr Asn Tyr Asn Pro Ser Ile Lys Ser Arg
                645                 650                 655

Ile Ser Ile Thr Arg Asp Thr Ala Lys Asn Gln Phe Phe Leu Gln Leu
            660                 665                 670

Asn Ser Val Thr Thr Glu Glu Asp Thr Ala Ile Tyr Tyr Cys Ala Arg
        675                 680                 685

Ala Gly Thr Ser Tyr Ser Gly Phe Phe Asp Ser Trp Gly Gln Gly Thr
    690                 695                 700

Leu Val Thr Val Ser Ser
705                 710


<210> SEQ ID NO 12
<211> LENGTH: 705
<212> TYPE: PRT
<213> ORGANISM: Artificial Sequence
<220> FEATURE:
<223> OTHER INFORMATION: Artificially synthesized sequence

<400> SEQUENCE: 12

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45
```

```
Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Glu His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Gly Gly Ser Gly Gly Ser Glu Ile Val Leu Thr Gln Ser Pro Gly
    450                 455                 460

Thr Leu Ser Leu Ser Pro Gly Glu Arg Ala Thr Leu Ser Cys Arg Ala
```

-continued

```
465                 470                 475                 480

Ser Gln Gly Ile Ser Arg Ser Tyr Leu Ala Trp Tyr Gln Gln Lys Pro
                485                 490                 495

Gly Gln Ala Pro Ser Leu Leu Ile Tyr Gly Ala Ser Ser Arg Ala Thr
            500                 505                 510

Gly Ile Pro Asp Arg Phe Ser Gly Ser Gly Ser Gly Thr Asp Phe Thr
        515                 520                 525

Leu Thr Ile Ser Arg Leu Glu Pro Glu Asp Phe Ala Val Tyr Tyr Cys
    530                 535                 540

Gln Gln Phe Gly Ser Ser Pro Trp Thr Phe Gly Gln Gly Thr Lys Val
545                 550                 555                 560

Glu Ile Lys Gly Gly Gly Gly Ser Gly Gly Gly Asp Ser Gly Gly Gly
                565                 570                 575

Gly Ser Gly Gly Gly Gly Ser Gln Val Gln Leu Gln Glu Ser Gly Pro
            580                 585                 590

Gly Leu Val Lys Pro Ser Gln Thr Leu Ser Leu Thr Cys Thr Val Ser
        595                 600                 605

Gly Gly Ser Ile Ser Ser Gly Asp Tyr Phe Trp Ser Trp Ile Arg Gln
    610                 615                 620

Leu Pro Gly Lys Gly Leu Glu Trp Ile Gly His Ile His Asn Ser Gly
625                 630                 635                 640

Thr Thr Tyr Tyr Asn Pro Ser Leu Lys Ser Arg Val Thr Ile Ser Val
                645                 650                 655

Asp Thr Ser Lys Lys Gln Phe Ser Leu Arg Leu Ser Ser Val Thr Ala
            660                 665                 670

Ala Asp Thr Ala Val Tyr Tyr Cys Ala Arg Asp Arg Gly Gly Asp Tyr
        675                 680                 685

Tyr Tyr Gly Met Asp Val Trp Gly Gln Gly Thr Thr Val Thr Val Ser
    690                 695                 700

Ser
705
```

COMPOSITIONS AND METHODS FOR MAKING AND USING BISPECIFIC ANTIBODIES

CROSS REFERENCE TO RELATED APPLICATIONS

This application is a national stage filing of PCT International Application No. PCT/US2018/060735, filed Nov. 13, 2018, incorporated herein by reference in its entirety, which claims priority under 35 U.S.C. § 119 (e) to U.S. Provisional Application Ser. No. 62/585,647 filed Nov. 14, 2017, the disclosure of which is incorporated by reference in its entirety herein.

STATEMENT REGARDING FEDERALLY SPONSORED RESEARCH OR DEVELOPMENT

This invention was made with government support under Grant Nos. W81XWH1810048 and W81XWH1810049 awarded by The Department of Defense. The government has certain rights in the invention.

BACKGROUND

Monoclonal antibodies (mAbs) that selectively target and eliminate cancer cells exploit multiple independent mechanisms (Tushir-Singh, 2017). Despite numerous FDA approvals for solid and blood cancers, antibodies against ovarian cancer (OvCa) enriched receptors such as folate receptor alpha-1 (FOLR1) and cancer antigen 125 (Ca125) have largely been disappointing in clinical trials (Armstrong et al., 2013; Berek et al., 2009). These antibodies have relied on IgG1 Fc dependent crosslinking of FcγRIIIA (CD16a), a widely expressed immunoglobulin superfamily receptor on natural killer (NK) cells to induce antibody directed cell cytotoxicity (ADCC) of tumor cells (Albanesi and Daeron, 2012). Their dismal clinical response is potentially due to insufficient infiltration of the NK and other immune effector cells to the hypoxic solid tumor bed (Kline et al., 2017; Sasaki et al., 2015). Interestingly, in case of farletuzumab, a humanized mAb that targets high-grade serous OvCa (HGSOC)-enriched FOLR1, improvement in survival has been reported for a small subset of patients expressing low levels of Ca125 (Vergote et al., 2016). Thus, it is reasonable to conclude that for the majority of patients whose OvCa highly overexpress Ca125, ADCC based strategies are not clinically feasible options.

There is a long felt need in the art for compositions and methods useful for treating cancer. The present invention satisfies this need.

SUMMARY OF THE INVENTION

Therapeutic antibodies targeting ovarian cancer (OvCa)-enriched receptors have largely been disappointing due to limited tumor specific antibody-dependent cellular cytotoxicity (ADCC). Disclosed herein is a symbiotic approach that is highly selective and superior compared to investigational clinical antibodies. This Bispecific-Anchored Cytotoxicity-Activator (BaCa) antibody is rationally designed to instigate "cis" and "trans" cytotoxicity by combining specificities against folate receptor alpha-1 (FOLR1) and death receptor 5 (DR5). Whereas the in vivo agonist DR5 signaling requires FcγRIIB interaction, the FOLR1 anchor functions as a primary clustering point to retain and maintain a high-level of tumor-specific apoptosis. Disclosed herein are studies that strategically make use of a tumor-cell enriched anchor receptor for agonist death-receptor targeting to generate a clinically viable strategy for OvCa.

Ovarian Cancer is the most lethal gynecological disease with no effective treatments. Disclosed herein is the discovery that FOLR1 and DR5 co-targeting by a single-agent antibody symbiotically compensates each other limitations to promote OvCa specific anti-tumor activity and further studies characterizing various antibodies and their effects. The described BaCa strategy is also highly superior to combinatorial Apo2L/TRAIL ligand and DR5 agonist antibodies. Three clinical bispecific configurations highlight the critical need of domain flexibility in choosing the optimal geometry for enhanced death receptor clustering and support biological insights for safe and selective tumor localization. In summary, BaCa antibody not only provides rational argument into limited preclinical efficacy of DR5 agonist antibodies but also offers a paradigm to clinically revive the ADCC activating antibodies using death receptor targeting approach.

To achieve a clinically applicable response in a larger OvCa population, we hypothesized elevating the anti-tumor activity of FOLR1 targeting antibodies (such as farletuzumab) beyond the activating limit of ADCC and even independently of it.

One such approach is pro-apoptotic receptor agonists (PARA) therapy using Trail ligand (Apo2L) or epithelial cancer enriched death receptor 5 (DR5/TRAIL-R2) activating antibodies (Ashkenazi, 2008). PARA activate extrinsic apoptotic pathway by oligomerizing DR5, a hallmark of tumor necrosis factor (TNF) receptor family members (Ashkenazi and Herbst, 2008). Although several DR5 agonist antibodies as a single agent or in combination with Apo2L instigate DR5 receptor aggregation and anti-tumor response, findings from clinical studies have failed to demonstrate significant benefits in phase-2 trials (Paz-Ares et al., 2013; Soria et al., 2010). The clinical data at biochemical levels have accounted for insufficient tumor specific cell death signaling due to sub-optimal clustering of DR5 receptor (Merchant et al., 2012; Niyazi et al., 2009). As one alternative, trans-engaging (stromal cell and tumor cell) antibodies have been described to enhance DR5 clustering (Brunker et al., 2016). However, in addition to fundamental dependency on another cell type, the described fibroblast activation protein (FAP) engaging antibodies represent critical safety concerns such as severe cachexia and bone toxicity due to non-specific targeting (Tran et al., 2013). In the present study we sought to investigate whether tumor cell specific FOLR1 and DR5 targeting by a single agent Bispecific-Anchored Cytotoxicity-Activator (BaCa) antibody will result in the symbiotic gain of OvCa selectivity, safety, and superior anti-tumor activity—the results herein demonstrate the surprising efficacy of such a model.

The present application provides compositions and methods for making and using bispecific antibodies directed against two different antigens. That is, disclosed herein is a single-agent with dual-specificity for targeting of FOLR1 and DR5 that is surprisingly effective against cancer cells. Therefore, the present application discloses compositions and methods for use of the single-agent with dual-specificity as an effective strategy for treating cancers such as ovarian cancer.

In one embodiment, bispecific antibodies of the invention are useful for treating cancer. In one aspect, a bispecific antibody of the invention has much greater efficacy in treating cancer than using two different antibodies where each antibody is directed against just one antigen.

In one embodiment, a bispecific antibody of the invention combines specificities against FOLR1 and TRAIL-R2/DR5.

The present application discloses methods for making bispecific antibodies that can be made to be directed at various antigens. In one aspect, the antibodies of the invention are useful for treating cancer or other proliferative diseases and disorders. In one aspect, the cancer is ovarian cancer. In one aspect, the cancer is breast cancer. In one aspect, the breast cancer is triple-negative breast cancer.

In one aspect, one antigen binding site of an antibody of the invention is an agonist. In another aspect, the other antigen binding site of an antibody of the invention is an antagonists against the antigen(s) against which it is directed.

It is disclosed herein that a BaCa antibody of the invention can restrict DR5-mediated apoptotic activation toward $FOLR1^+$ cancer cells. In one aspect, the cells are ovarian cancer cells. In one aspect, the ovarian cancer cells include, but are not limited to, metastatic high-grade serous carcinoma, high-grade endometrioid adenocarcinoma, and serous ovarian cancer. In one aspect, FOLR1 and DR5 are expressed by the cancer cell being targeted. In one aspect, cells adjacent to the cancer cell, such as other cancer cells or stromal cells, express DR5.

It is disclosed herein that co-targeting of FOLR1 and DR5 eliminates ADCC dependency to induce tumor cell death. In one aspect, FOLR1 and DR5 are expressed by the cancer cell being targeted. In one aspect, cells adjacent to the cancer cell, such as other cancer cells or stromal cells, express DR5.

It is disclosed herein that a BaCa antibody of the invention is much more effective than reported investigational DR5 activation/agonist strategies in the art.

In one embodiment, the anchored-mediated BaCa antibody strategy of the present application is useful for treating cancers other than ovarian cancer.

In one embodiment, a BaCa antibody of the invention is a bispecific antibody that binds to death receptor 5 (DR5) and folate receptor alpha-1 (FOLR1), wherein the antibody comprises an antigen binding site specific for DR5 and an antigen binding site specific for FOLR1.

The configuration of the antigen binding sites for the two different antigens can vary, including varied configurations as evidenced by the structures of BaCa-1, BaCa-2, and BaCa-3 (see FIG. 1A and see the sequences at the end of this Summary). Because a BaCa antibody is bispecific, the antigen binding sites for the two different antigens can, for example, both be in the variable region, either end to end (as in BaCa-3) or where one antigen binding site is on one Fab fragment and the other antigen binding site is on the other Fab fragment as in BaCa-2, or on opposite ends of the antibody as in BaCa-1.

In one embodiment, a BaCa antibody of the invention comprises an antigen binding site for an antigen at one end of the antibody and the other antigen binding site is at the other end of the antibody. In one aspect, it is BaCa-1. BaCa-1 consists of SEQ ID NO:1 and SEQ ID NO:2.

In one embodiment, a BaCa antibody of the invention comprises an antigen binding site for an antigen on one of the Fab fragments of the variable domain and an antigen binding site for a different antigen on the other Fab fragment of the variable domain region. In one aspect, the BaCa antibody is BaCa-2.

In one embodiment a BaCa antibody of the invention comprises two different antigen binding sites on the same end of the antibody and the sequences of the two sites are separated by a linker sequence. In one aspect, it is BaCa-3.

In one embodiment, a BaCa antibody of the invention is BaCa-1, which comprises SEQ ID NO:1 and SEQ ID NO:2, or biologically active fragments and homologs of SEQ ID NOs: 1 and 2, wherein SEQ ID NO: 1 is a heavy chain comprising a Farletuzumab (anti-FOLR1)-derived sequence and a Lexatumumab (anti-TRAIL-R2/DR5)-derived sequence and SEQ ID NO:2 is a Farletuzumab light chain derived from Farletuzumab.

In one embodiment, a BaCa antibody of the invention is BaCa-2, which comprises SEQ ID NO:3 and SEQ ID NO:4, or biologically active fragments and homologs of SEQ ID NOs: 3 and 4, wherein SEQ ID NO:3 is a Farletuzumab (anti-FOLR1) Knob single chain variable fragment and SEQ ID NO:4 is a Lexatumumab (anti-TRAIL1-R2/DR5) Hole single chain variable Fragment.

In one embodiment, a BaCa antibody of the invention is BaCa-3, which comprises SEQ ID NO:5 and SEQ ID NO:6, or biologically active fragments and homologs of SEQ ID NOs: 5 and 6, wherein SEQ ID NO:5 is a heavy chain comprising Farletuzumab (anti-FOLR1) and Lexatumumab (anti-TRAIL1-R2/DR5) and SEQ ID NO:6 is a light chain comprising Farletuzumab (anti-FOLR1) and Lexatumumab (anti-TRAIL1-R2/DR5) sequences.

Other useful BaCa antibodies of the invention include muBaCa (SEQ ID NO:9, heavy chain; SEQ ID NO:10, light chain), chimeric BaCa (ChiBaCa) (SEQ NO:11, heavy chain; SEQ ID NO:2, light chain), and AMG-655 BaCa (SEQ ID NO: 12, heavy chain; SEQ ID NO:2, light chain), and biologically active fragments and homologs thereof.

The present application also encompasses modifying a bispecific BaCa antibody of the invention to target additional cancer-enriched receptors. In one aspect, the cancer receptor is CDH17. In one aspect, a bispecific antibody of the invention comprising a sequence that binds to CDH17 is useful for targeting and treating gastrointestinal cancers expressing CDH17.

In one embodiment, the present invention provides composition and methods for treating cancer. In one embodiment, a bispecific antibody of the invention is administered in a therapeutically effective amount to a subject in need thereof. In one aspect, an additional therapeutic agent is administered. In one aspect, the method comprises administering to a subject with cancer a pharmaceutical composition comprising a pharmaceutically-acceptable carrier and an effective amount of a bispecific antibody that binds to death receptor 5 (DR5) and folate receptor alpha-1 (FOLR1), wherein the antibody comprises an antigen binding site specific for said DR5 and an antigen binding site specific for said FOLR1.

Because the antibodies of the invention can be prepared and used to work as cis or trans, the cancer being treated may comprise cancer cells expressing FOLR1 and DR5, or it may comprise cancer cells expressing FOLR1 and adjacent or nearby stromal cells or other cells expressing DR5.

In one aspect, the cancer cells being targeted express high levels of FOLR1.

In one embodiment, an antibody of the invention binds to both target antigens.

In one embodiment, the cancer being targeted for treatment is ovarian cancer. In one aspect, it is serous ovarian cancer and in one aspect, it is high-grade serous carcinoma.

In one embodiment, the cancer is endometrioid adenocarcinoma. In one aspect, the endometrioid adenocarcinoma is high-grade endometrioid adenocarcinoma.

In one embodiment, upon binding to DR5, DR5 oligomerization is induced.

In one embodiment, the method restricts DR5-mediated apoptotic activation toward FOLR1 positive cancer cells.

In one embodiment, the method eliminates antibody-dependent cellular cytotoxicity (ADCC).

In one embodiment, an antibody of the invention restricts DR5-mediated apoptotic activation toward FOLR1 positive cancer cells.

In one embodiment, treatment of a subject with cancer using the compositions and methods of the invention inhibits tumor growth.

In one embodiment, treatment of a subject with cancer using the compositions and methods of the invention causes tumor regression.

In one embodiment, treatment with a BaCa antibody of the invention stimulates cis cytotoxicity of cancer cells.

In one embodiment, treatment with a BaCa antibody of the invention stimulates trans cytotoxicity of cancer cells.

An antibody of the invention can be administered in any suitable fashion, including, but not limited to, intravenously, intraperitoneally, locally, and parenterally.

The dose of antibody to be administered, the number of doses to be delivered, and the time course of administration can be determined based on things such as the health and age of the subject and the severity of the cancer and the specific cancer being treated. In one aspect, a dose of an antibody of the invention can be from about 0.1 mg/kg body weight to about 20.0 mg/kg body weight. In one aspect, a dose is selected from the group consisting of 0.1, 0.5, 0.75, 0.83, 1.0, 1.25, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, and 20.0 mg/kg body weight.

The number of doses to be administered can be, for example, one or more per day, per week, per month or per year. This may vary, for example, depending on, for example, the response of the cancer to the treatment. The number of doses to be administered can be varied as well for the same reasons. When more than one dose is administered, the doses can be administered, for example every day, every other day, every third day, every fourth day, weekly, twice weekly, three times weekly, monthly, or any regimen determined by the clinician treating the subject.

The present invention further provides a pharmaceutical composition comprising an effective amount of at least one antibody of the invention, a pharmaceutically-acceptable carrier, and optionally at least one additional therapeutic agent.

The present invention further provides a kit. The kit may comprise at least one antibody of the invention, a pharmaceutical composition, a pharmaceutically-acceptable carrier, an applicator, and an instructional material for the use thereof.

The antibodies of the invention are also useful for detecting cancer cells when the antibodies are labeled with a detectable label.

Some Useful Sequences of the Invention

Summary by No. and Description

SEQ ID NO:1-Heavy Chain (Farletuzumab (anti-FOLR1) and Lexatumumab (anti-TRAIL-R2/DR5))

SEQ ID NO:2-Light chain (Farletuzumab (anti-FOLR1))

SEQ ID NO:3-Farletuzumab (anti-FOLR1) Knob single chain variable Fragment

SEQ ID NO:4-Lexatumumab (anti-TRAIL-R2/DR5) Hole single chain variable Fragment

SEQ ID NO:5-Heavy Chain (Farletuzumab (anti-FOLR1) and Lexatumumab (anti-TRAIL-R2/DR5))

SEQ ID NO:6-Light Chain (Farletuzumab (anti-FOLR1) and Lexatumumab (anti-TRAIL-R2/DR5))

SEQ ID NO:7—Recombinant DR5 (rDR5) amino acid sequence

SEQ ID NO:8—Recombinant FOLR1 (rFOLR1) amino acid sequence

SEQ ID NO:9—Heavy chain (LK26-MD5-1)

SEQ ID NO:10—Light chain (LK26)

SEQ ID NO:11—Heavy chain (Farletuzumab-MD5-1)

SEQ ID NO:12—Light chain (Farletuzumab)

Recombinant Antibody Sequences:

BaCa-1 (Also Referred to as HuBaCa, BaCa, and Lexatumumab BaCa) Amino Acid Sequences

```
Heavy Chain (Farletuzumab (anti-FOLR1) and
Lexatumumab (anti-TRAIL-R2/DR5)):
                                         SEQ ID NO: 1
EVQLVESGGGVVQPGRSLRLSCSASGFTFSGYGLSWVRQAPGKGLEWVAMI

SSGGSYTYYADSVKGRFAISRDNAKNTLFLQMDSLRPEDTGVYFCARHGDD

PAWFAYWGQGTPVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMI

SRTPEVTCVVVDVEHEDPEVKFNWYVDGVEVHNAKTKPREEQYNSTYRVVS

VLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFL

YSKLTVDKSRWQQGNVFSCSVMHEALHNHYTQKSLSLSLGKGGGSGGGSGG

GSSSELTQDPAVSVALGQTVRITCQGDSLRSYYASWYQQKPGQAPVLVIYG

KNNRPSGIPDRFSGSSSGNTASLTITGAQAEDEADYYCNSRDSSGNHVVFG

GGTKLTVLGGGGSGGGDSGGGGSGGGGSEVQLVQSGGGVERPGGSLRLSCA

ASGFTFDDYGMSWVRQAPGKGLEWVSGINWNGGSTGYADSVKGRVTISRDN

AKNSLYLQMNSLRAEDTAVYYCAKILGAGRGWYFDLWGKGTTVTVSS

Light chain (Farletuzumab (anti-FOLR1)):
                                         SEQ ID NO: 2
DIQLTQSPSSLSASVGDRVTITCSVSSSISSNNLHWYQQKPGKAPKPWIYG

TSNLASGVPSRFSGSGSGTDYTFTISSLQPEDIATYYCQQWSSYPYMYTFG

QGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGL

SSPVTKSFNRGEC
```

BaCa-2 Amino Acid Sequences

```
Farletuzumab (anti-FOLR1) Knob single chain
variable Fragment:
                                         SEQ ID NO: 3
DIQLTQSPSSLSASVGDRVTITCSVSSSISSNNLHWYQQKPGKAPKPWIY

GTSNLASGVPSRFSGSGSGTDYTFTISSLQPEDIATYYCQQWSSYPYMYT

FGQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGECGGGGSGGGGSGGGGSGGGGSGGGGSGGGGSGGG

GSGGGGSGGGGSGGGGSEVQLVESGGGVVQPGRSLRLSCSASGFTFSGYG

LSWVRQAPGKGLEWVAMISSGGSYTYYADSVKGRFAISRDNAKNTLFLQM
```

-continued

DSLRPEDTGVYFCARHGDDPAWFAYWGQGTPVTVSSASTKGPSVFPLAPS
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSREEMTKNQVSLYCLVKGFYPSDIAVEW
ESNGQPENNYKTTPPVLDSDGSFFLYSKLTVDKSRWQQGNVFSCSVMHEA
LHNHYTQKSLSLSPG

Lexatumumab (anti-TRAIL-R2/DR5) Hole single chain variable Fragment:

SEQ ID NO: 4

SSELTQDPAVSVALGQTVRITCQGDSLRSYYASWYQQKPGQAPVLVIYGK
NNRPSGIPDRFSGSSSGNTASLTITGAQAEDEADYYCNSRDSSGNHVVFG
GGTKLTVLRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGECGGGGSGGGGSGGGGSGGGGSGGGGSGGGGSGGGGS
GGGGSGGGGSGGGGSEVQLVQSGGGVERPGGSLRLSCAASGFTFDDYGMS
WVRQAPGKGLEWVSGINWNGGSTGYADSVKGRVTISRDNAKNSLYLQMNS
LRAEDTAVYYCAKILGAGRGWYFDLWGKGTTVTVSSASTKGPSVFPLAPS
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEW
ESNGQPENNYKTTPPVLDSDGSFFLTSKLTVDKSRWQQGNVFSCSVMHEA
LHNRFTQKSLSLSPG

BaCa-3 Amino Acid Sequences

Heavy Chain (Farletuzumab (anti-FOLR1) and Lexatumumab (anti-TRAIL-R2/DR5)):

SEQ ID NO: 5

EVQLVQSGGGVERPGGSLRLSCAASGFTFDDYGMSWVRQAPGKGLEWVSG
INWNGGSTGYADSVKGRVTISRDNAKNSLYLQMNSLRAEDTAVYYCAKIL
GAGRGWYFDLWGKGTTVTVSSGGSGGSGGSGGSEVQLVESGGGVVQPGRS
LRLSCSASGFTFSGYGLSWVRQAPGKGLEWVAMISSGGSYTYYADSVKGR
FAISRDNAKNTLFLQMDSLRPEDTGVYFCARHGDDPAWFAYWGQGTPVTV
SSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVD
VEHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKS
RWQQGNVFSCSVMHEALHNHYTQKSLSLSLG

Light Chain (Farletuzumab (anti-FOLR1) and

-continued

Lexatumumab (anti-TRAIL-R2/DR5)):

SEQ ID NO: 6

SSELTQDPAVSVALGQTVRITCQGDSLRSYYASWYQQKPGQAPVLVIYGK
NNRPSGIPDRFSGSSSGNTASLTITGAQAEDEADYYCNSRDSSGNHVVFG
GGTKLTVLGGSGGSGGSGGSDIQLTQSPSSLSASVGDRVTITCSVSSSIS
SNNLHWYQQKPGKAPKPWIYGTSNLASGVPSRFSGSGSGTDYTFTISSLQ
PEDIATYYCQQWSSYPYMYTFGQGTKVEIKRTVAAPSVFIFPPSDEQLKS
GTASVVCLLNNFYPREAKVQWKVDNALQSGNSQESVTEQDSKDSTYSLSS
TLTLSKADYEKHKVYACEVTHQGLSSPVTKSFNRGEC

Recombinant DR5 (rDR5) Amino Acid Sequence:

SEQ ID NO: 7

ITQQDLAPQQRAAPQQKRSSPSEGLCPPGHHISEDGRDCISCKYGQDYST
HWNDLLFCLRCTRCDSGEVELSPCTTTRNTVCQCEEGTFREEDSPEMCRK
CRTGCPRGMVKVGDCTPWSDIECVHKESGGGSGGSESKYGPPCPPCPAPE
FLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWES
NGQPENNYKTTPPVLDSDGSFFLYSKLTVDKSRWQEGNVFSCSVMHEALH
NHYTQKSLSLSLG

Recombinant FOLR1 (rFOLR1) Amino Acid Sequence:

SEQ ID NO: 8

AQRMTTQLLLLLVWVAVVGEAQTRIAWARTELLNVCMNAKHHKEKPGPE
DKLHEQCRPWRKNACCSTNTSQEAHKDVSYLYRFNWNHCGEMAPACKRH
FIQDTCLYECSPNLGPWIQQVDQSWRKERVLNVPLCKEDCEQWWEDCRT
SYTCKSNWHKGWNWTSGFNKCAVGAACQPFHFYFPTPTVLCNEIWTHSY
KVSNYSRGSGRCIQMWFDPAQGNPNEEVARFYAAAGGSGGSESKYGPPC
PPCPAPEFLGGPSVFLFPPKPKDTLMISRTPEVTCVVVDVSQEDPEVQF
NWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFY
PSDIAVEWESNGQPENNYKTTPPVLDSDGSFFLYSKLTVDKSRWQEGNV
FSCSVMHEALHNHYTQKSLSLSLG

Murine BaCa (muBaCa) Amino Acid Sequences

Heavy chain (LK26-MD5-1):

SEQ ID NO: 9

QVQLQESGGDLVKPGGSLKLSCAASGFTFSGYGLSWVRQTPDKRLEWVAM
ISSGGSYTYYADSVKGRFAISRDNAKNSLFLQMSSLKSDDTAIYICARHG
DDPAWFAYWGQGTLVTVSAASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPEAAGGPSVFLFPPKPK
DTLMISRTPEVTCVVVDVEHEDPEVKFNWYVDGVEVHNAKTKPREEQYNS
TYRVVSVLTVLHQDWLNGKEYKCKVSNKALPAPIEKTISKAKGQPREPQV

-continued

```
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSLGKG
GSGGSGGSGGSDIQVTQSPSLLSASFGDKVTINCLVTQDITYYLSWYQQK
SGQPPTLLIYNGNSLQSGVPSRFSGQYSGRTFTLSLSSLEPEDAGTYYCL
QHYSVPFTFGGGTRLEIKGGGGSGGGDSGGGGSGGGGSQIQLQESGPGLV
KPAQSLSLTCSITGFPITAGGYWWTWIRQFPGQKLEWMGYIYSSGSTNYN
PSIKSRISITRDTAKNQFFLQLNSVTTEEDTAIYYCARAGTSYSGFFDSW
GQGTLVTVSS
```

Light chain (LK26):
SEQ ID NO: 10

```
DIELTQSPALNAASPGEKVTITCSVSSSISSNNLHWYQQKSETSPKPWIY
GTSNLASGVPLRFRGFGSGTSYSLTISSNEAEDAATYYCQQWSSYPYMYT
FGGGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEVT
HQGLSSPVTKSFNRGEC
```

Chimeric BaCa (ChiBaCa) Amino Acid Sequences

Heavy chain (Farletuzumab-MD5-1):
SEQ ID NO: 11

```
EVQLVESGGGVVQPGRSLRLSCSASGFTFSGYGLSWVRQAPGKGLEWVAM
ISSGGSYTYYADSVKGRFAISRDNAKNTLFLQMDSLRPEDTGVYFCARHG
DDPAWFAYWGQGTPVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPEAAGGPSVFLFPPKPK
DTLMISRTPEVTCVVVDVEHEDPEVKFNWYVDGVEVHNAKTKPREEQYNS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSLGKG
GSGGSGGSGGSDIQVTQSPSLLSASFGDKVTINCLVTQDITYYLSWYQQK
SGQPPTLLIYNGNSLQSGVPSRFSGQYSGRTFTLSLSSLEPEDAGTYYCL
QHYSVPFTFGGGTRLEIKGGGGSGGGDSGGGGSGGGGSQIQLQESGPGLV
KPAQSLSLTCSITGFPITAGGYWWTWIRQFPGQKLEWMGYIYSSGSTNYN
PSIKSRISITRDTAKNQFFLQLNSVTTEEDTAIYYCARAGTSYSGFFDSW
GQGTLVTVSS
```

Light chain (Farletuzumab):
SEQ ID NO: 2

```
DIQLTQSPSSLSASVGDRVTITCSVSSSISSNNLHWYQQKPGKAPKPWIY
GTSNLASGVPSRFSGSGSGTDYTFTISSLQPEDIATYYCQQWSSYPYMYT
FGQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEVT
HQGLSSPVTKSFNRGEC
```

AMG-655 BaCa Amino Acid Sequences

Heavy Chain (Farletuzumab and AMG-655):
SEQ ID NO: 12

-continued

```
EVQLVESGGGVVQPGRSLRLSCSASGFTFSGYGLSWVRQAPGKGLEWVAM
ISSGGSYTYYADSVKGRFAISRDNAKNTLFLQMDSLRPEDTGVYFCARHG
DDPAWFAYWGQGTPVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVEHEDPEVKFNWYVDGVEVHNAKTKPREEQYNS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSLGKG
GSGGSEIVLTQSPGTLSLSPGERATLSCRASQGISRSYLAWYQQKPGQAP
SLLIYGASSRATGIPDRFSGSGSGTDFTLTISRLEPEDFAVYYCQQFGSS
PWTFGQGTKVEIKGGGGSGGGDSGGGGSGGGGSQVQLQESGPGLVKPSQT
LSLTCTVSGGSISSGDYFWSWIRQLPGKGLEWIGHIHNSGTTYYNPSLKS
RVTISVDTSKKQFSLRLSSVTAADTAVYYCARDRGGDYYYGMDVWGQGTT
VTVSS
```

Light chain (Farletuzumab):
SEQ ID NO: 2

```
DIQLTQSPSSLSASVGDRVTITCSVSSSISSNNLHWYQQKPGKAPKPWIY
GTSNLASGVPSRFSGSGSGTDYTFTISSLQPEDIATYYCQQWSSYPYMYT
FGQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEVT
HQGLSSPVTKSFNRGEC
```

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(B) Summary of BaCa-1, BaCa-2, BaCa-3 and parental IgG1 properties (C) NIH-OVCAR-3 cells were treated with increasing concentrations of the indicated antibodies or cisplatin. The cell death was quantified using cell viability assays (n=3).

(D) rFOLR1 and rDR5 were coated on 96 well plates in 5:1 ratio. Relative avidity index of indicated antibodies was determined in presence of 6 M urea.

(E) The binding kinetics of immobilized biotinylated rDR5 against lexatumumab and BaCa or biotinylated rFOLR1 against farletuzumab and BaCa were measured using bio-layer interferometry (BLI) optical analytical technique.

(F) Domain organization of the non-anchoring BaCa (NBaCa) antibody.

(G) Cell viabilities of NIH-OVCAR-4 cells were analyzed in the presence of BaCa, lexatumumab, or NBaCa antibodies. $IC_{50}$ values are shown at the bottom (n=3).

Figure 1A:
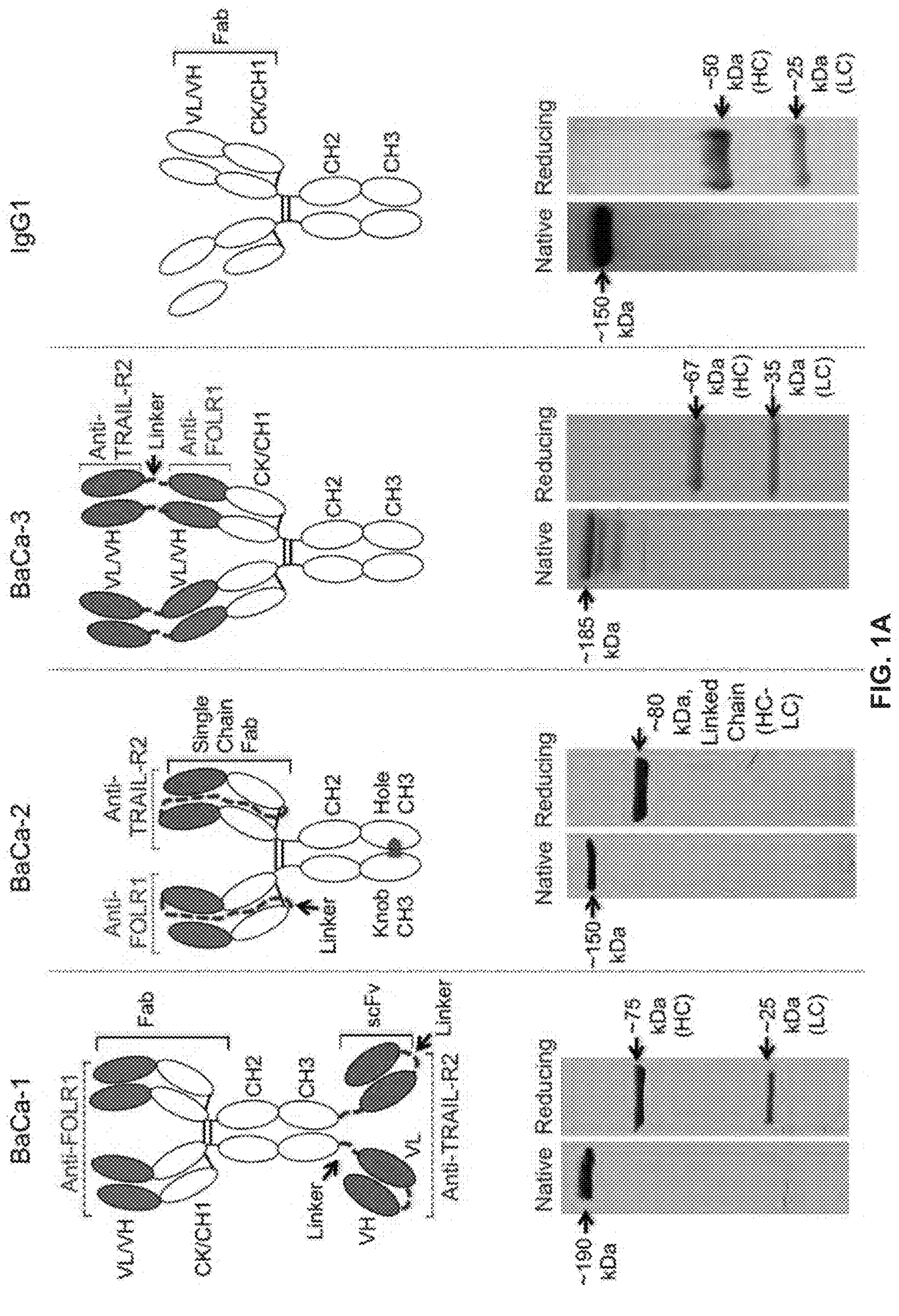
FIG. 1, comprising FIGS. 1A to 1G. Engineering and characterizing BaCa antibodies with superior cytotoxicity against ovarian cancer cells (A) Domain organization, and SDS-PAGE analyses of BaCa-1, BaCa-2, BaCa-3, and IgG1 antibodies in native and reducing conditions. Individual gel lanes for each antibody types are cropped from the same blot.
Figure 1C:
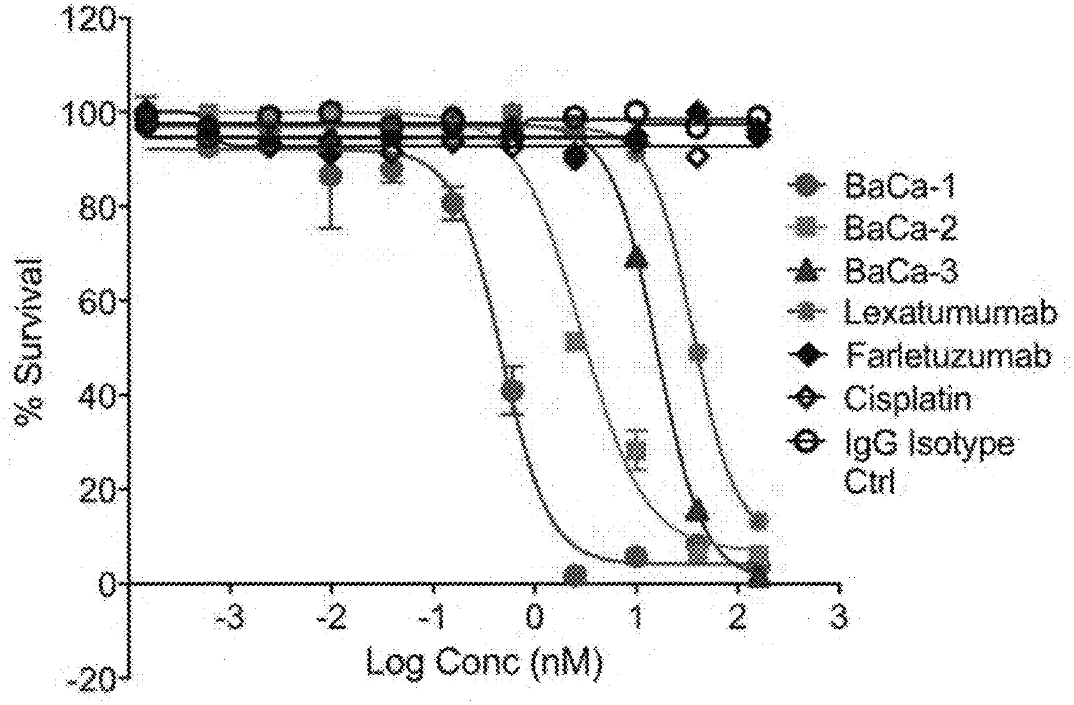
Figure 1D:
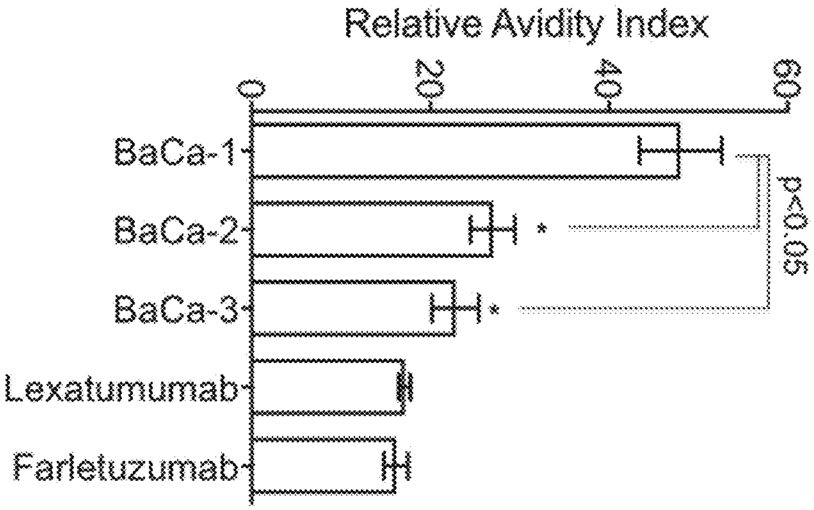

Abbreviation used in FIGS. 1A and B: *=1-step protein-A purification, =Total % recovery after size exclusion purification (SEC), *=Farletuzumab data is shown (Lexatumumab was comparable), Native=Antibody run on gel with non-reducing dye, Reducing=Antibody run on gel with reducing dye, HC=Heavy chain, LC=Light chain, Fab=Fragment antigen binding, Fv=Fragment variable, scFv=Single chain fragment variable, VL=Variable domain of light chain, VH=Variable domain of heavy chain, CK=Kappa chain Error bars in C, D and G represent SEM. Unpaired Welch's t-test was used to determine p values. See also FIGS. 8 and 9.

FIG. 2, comprising FIGS. 2A to 2H. BaCa antibody mediated higher order TRAIL-R2 receptor clustering requires anchor and death receptor co-engagement (A) Survival of OVCAR-3 cells treated with the indicated antibodies without or with pre-blocking with rDR5, rFOLR1, or rDR5+rFOLR1 (n=3).

(B) OVCAR-4 cells were treated with indicated antibodies for 24 hr, followed by lysis using RIPA buffer. DR5, total caspase-3 and cleaved caspased-3 were analyzed by immunoblotting.

(C) DR5 clustering and caspase-3 activity in OVCAR-3 cells treated with the indicated antibodies without or with pre-blocking with rDR5. Protein lysates were analyzed by immunoblotting.

(D) Survival of OVCAR-3 cells treated with 10 nM or 100 nM of lexatumumab, BaCa and IgG for 48 hr (n=3).

(E) Time dependent cleaved caspase-3 and DR5 trimerization (120 kDa) profile in OVCAR-3 cells treated with 100 nM lexatumumab and BaCa antibodies (n=3).

(F) Time-dependent cell killing activity of 100 nM of lexatumumab and BaCa antibodies (n=3).

(G) OVCAR-3 cells treated with indicated antibodies (100 nM), were analyzed by $7AAD^+$ labeling using FACS analysis (n=3).

(H) Quantitation of $7AAD^+$ labeling as described in G.

Error bars in (A, D F and H) represent SEM. Unpaired two-tailed Welch's t-test was used to determine p values. See also FIGS. 9A-9L.

FIG. 3, comprising FIGS. 3A to 3G. BaCa antibody is broadly effective and is highly superior over described cooperativity (A) E-cadherin, DR5 and FOLR1 expression profile across various OvCa cell lines. Tubulin is loading control.

(B) Survival analysis of OvCa cell lines treated with indicated antibodies for 72 hr (n=3).

(C) FACS analysis of DR4 and DR5 on the cell surface of OVCAR-3 cells.

(D) OVCAR-3 cells were treated with lexatumumab or BaCa antibody (generated with lexatumumab) with and without Apo2L as indicated (n=3). $IC_{50}$ values are shown at the bottom.

(E) OVCAR-3 cells were treated with AMG-655 (a fully humanized agonist antibody against DR5) or BaCa antibody (generated with AMG-655) with and without Apo2L as indicated (n=3). $IC_{50}$ values are shown at the bottom.

(F) Cleaved caspase-3 levels in OVCAR-3 cells treated with indicated antibodies (with and without Apo2L) for the indicated period of time. Lysates were analyzed by immunoblotting.

(G) BaCa antibody was engineered with CDH17 specific A4 antibody (see U.S. patent application Ser. Nos. 13/880,320 and 14/549,176) instead of farletuzumab (anti-FOLR1) and tested against Colo-205 cells (n=3).

Error bars in B, D, E, G represent SEM. Bar graphs in B were compared using Student's t-test. * p<0.05,  p<0.005, * p<0.001. See also FIG. 10.

FIG. 4, comprising FIGS. 4A to 4L. BaCa activity is highly selective towards FOLR1 overexpressing OvCa cancer cells.

(A) Cell viability analysis of lexatumumab and lexatumumab containing BaCa antibody±anti-Fc crosslinking (n=3).

(B) Cell viability analysis of AMG-655 and AMG-655 containing BaCa antibody±anti-Fc crosslinking (n=3).

(C) qRT-PCR analysis of FOLR1 and TRAIL-R2 transcripts in OVCAR-4 and Colo-205 cells (n=5).

(D) Cell viability assays using BaCa antibody in OVCAR-4 and Colo-205 cells. $IC_{50}$ values are shown in right (n=3).

(E) Schematic of results described in F. 50% $GFP^-$ OVCAR-4 and 50% $GFP^+$ Colo-205 cells were co-cultured. After 24 hr, cells were treated with indicated antibodies at constant 0.1 nM. After 36-48 hr, cells were analyzed using fluorescent microscope.

(F) Represented images as described in E with indicated antibody treatment (scale bar represent 400 μm).

(G) Immunoblot analysis for GFP and tubulin of $GFP^+$ Colo-205 cells co-cultured with equal number of $GFP^-$ OVCAR-4 or $GFP^-$ Colo-205 cells and treated with the indicated concentrations of BaCa antibody (H) The normalized relative intensities of GFP signal were plotted for the increasing BaCa dose in co-cultured conditions (filled black circles: 50% GFP-OVCAR-4 and 50% $GFP^+$ Colo-205) against constant 10 nM dose (filled red circle: 50% $GFP^-$ Colo-205 and 50% $GFP^+$ Colo-205).

(I) Co-cultured MC38 ($GFP^-$) and Colo-205 ($GFP^+$) cells were treated with 50 nM of indicated antibodies. After 48 hr, lysates were run on gel and blotted for tubulin and GFP.

(J) Cell viability of MC38 cells treated with LK26, LK26+anti-Fc, LK26-AMG-655 bispecific and BaCa antibody (n=3).

(K) Cell viability of OVCAR-3 cells treated with AMG-655, AMG-655+anti-Fc, LK26-AMG-655 bispecific and BaCa antibody (n=3).

(L) Co-cultured MC38 and OVCAR-3 cells were treated with the increasing concentration of indicated antibodies. After 48 hr, cell viability was analyzed using MTT assays.

Error bars in A, B, C, D, J, K and L represent SEM. See also FIG. 11.

Figure 5A:
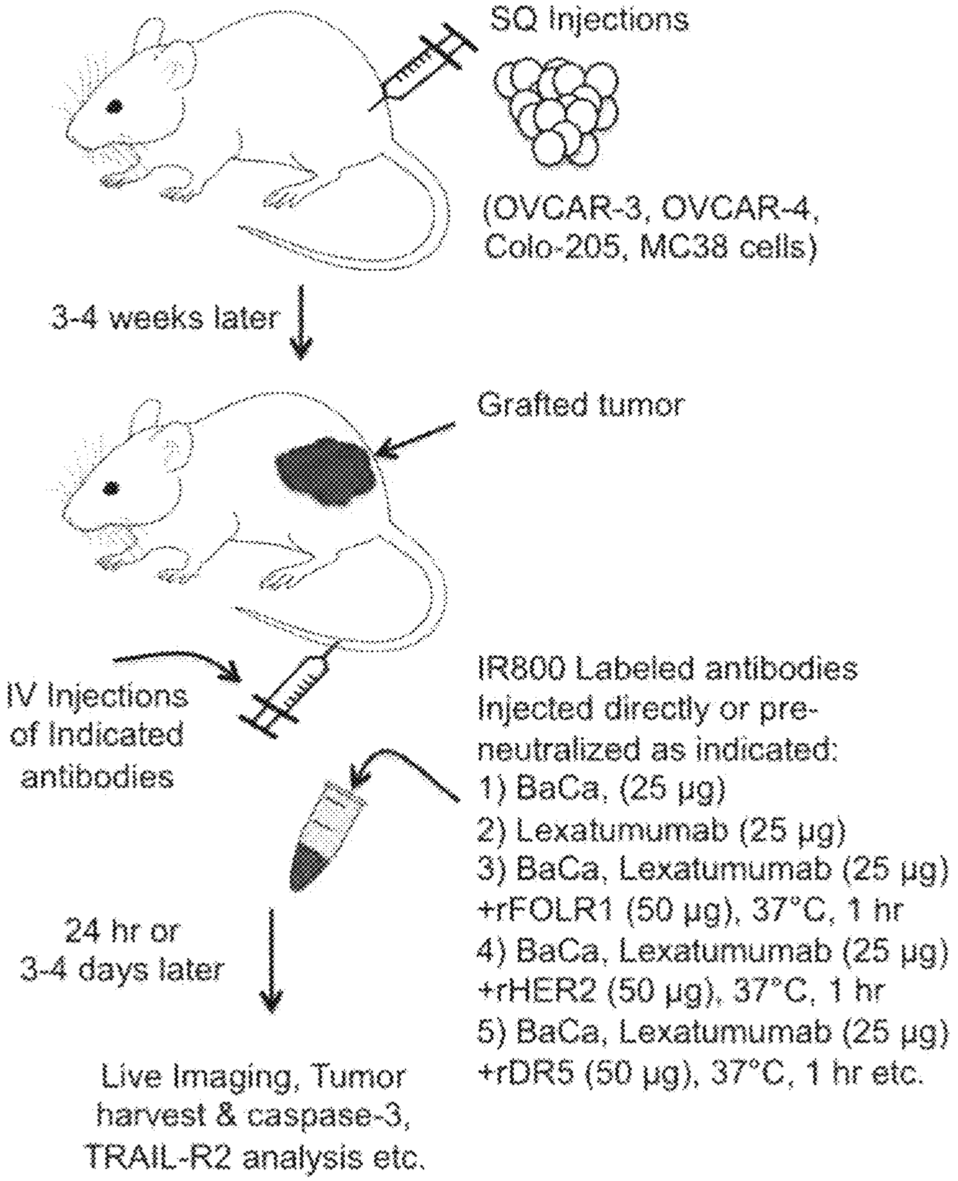
Figure 5B:
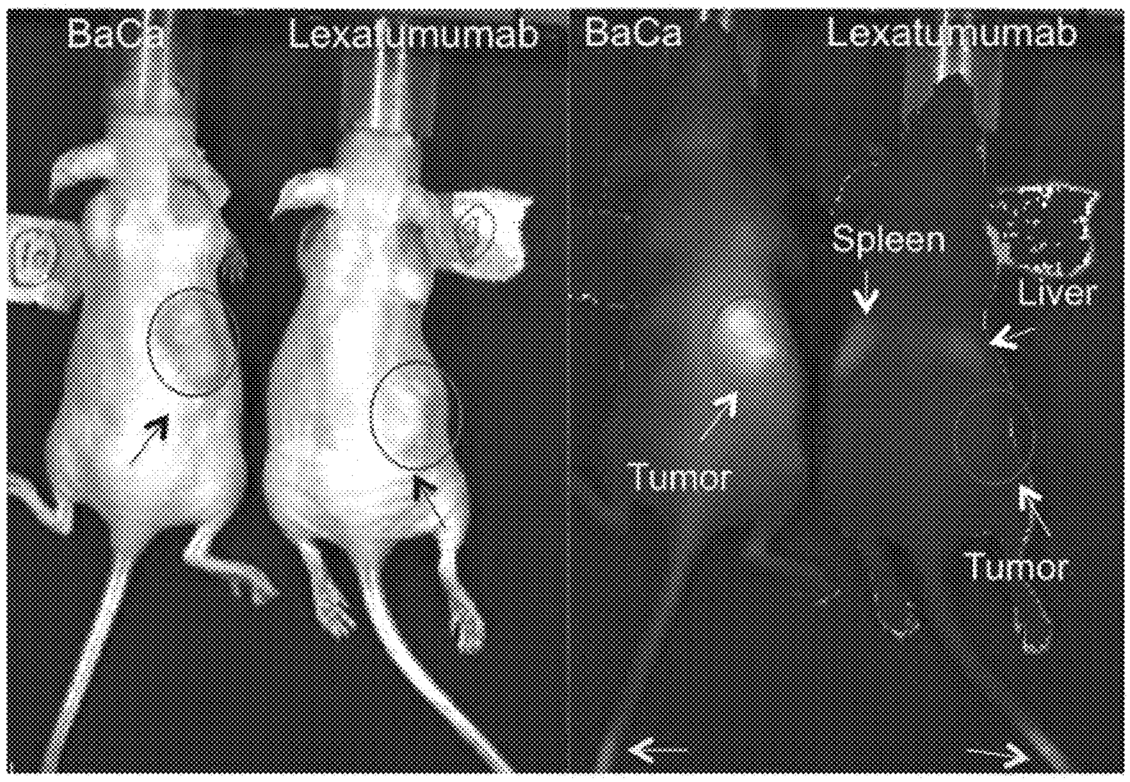
Figure 5C:
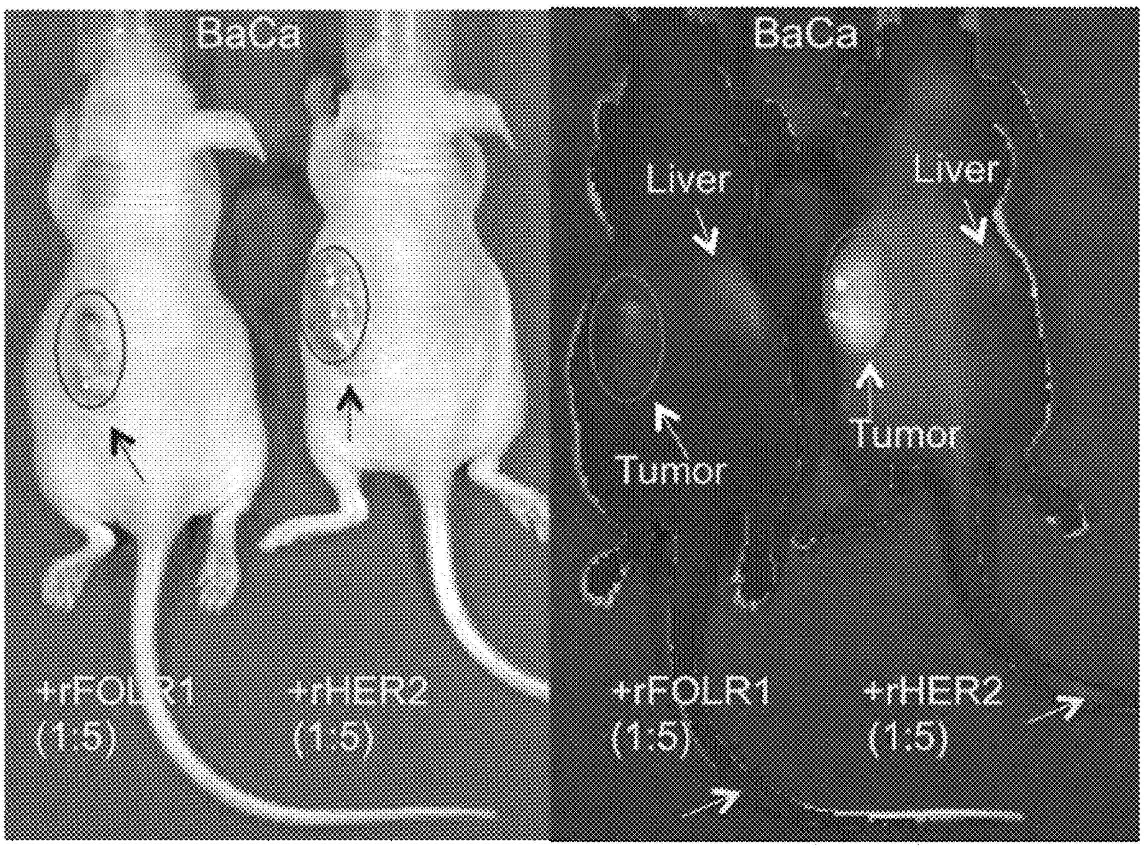
Figure 5D:
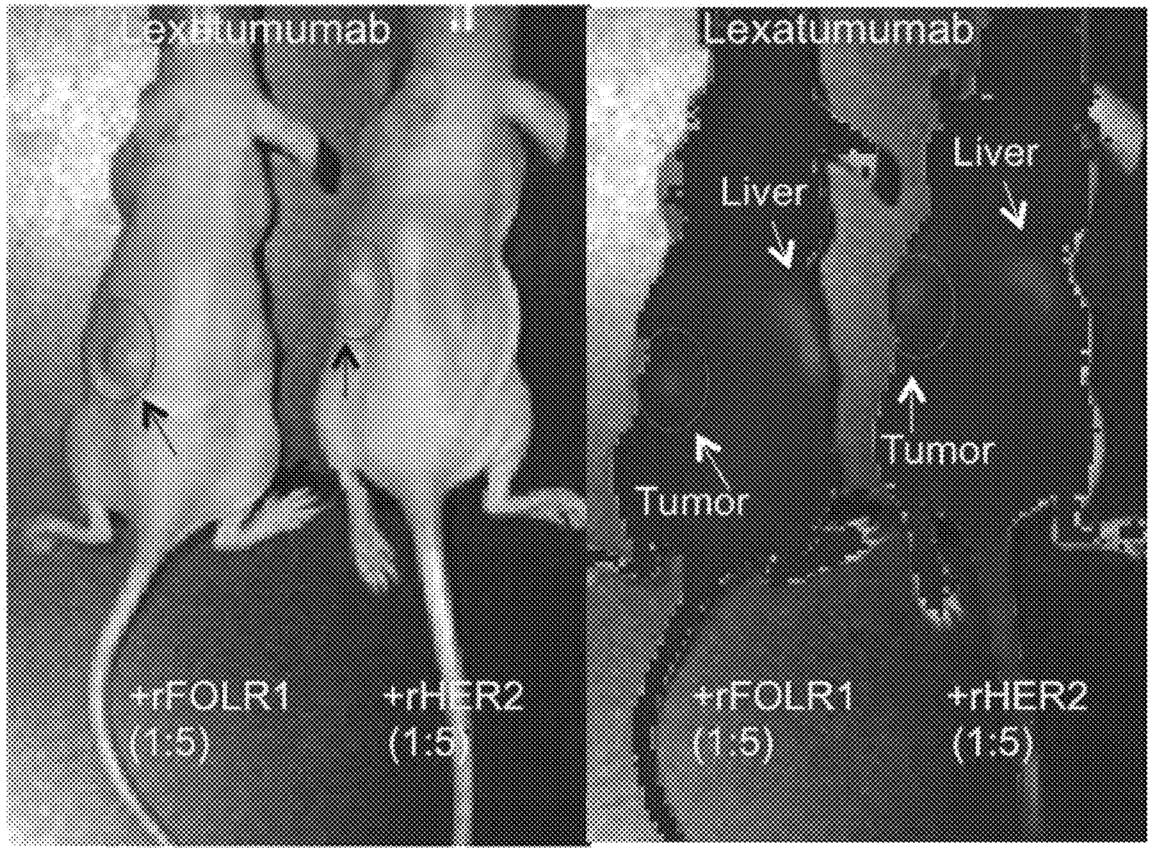
Figure 5E:
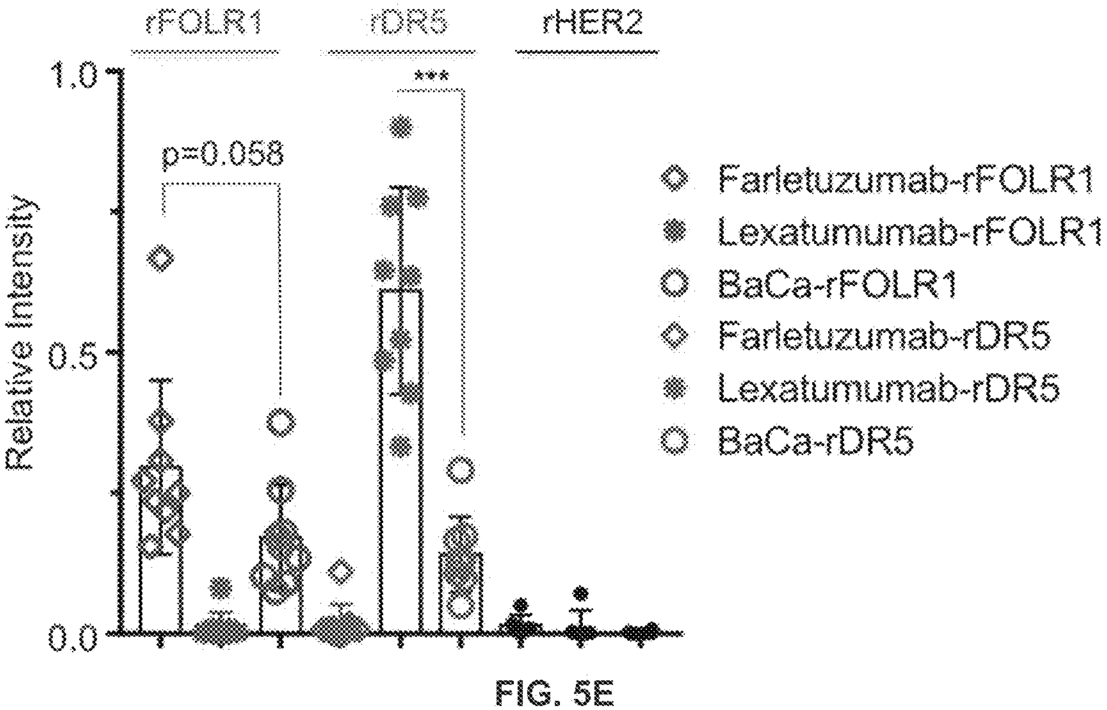
Figure 5F:
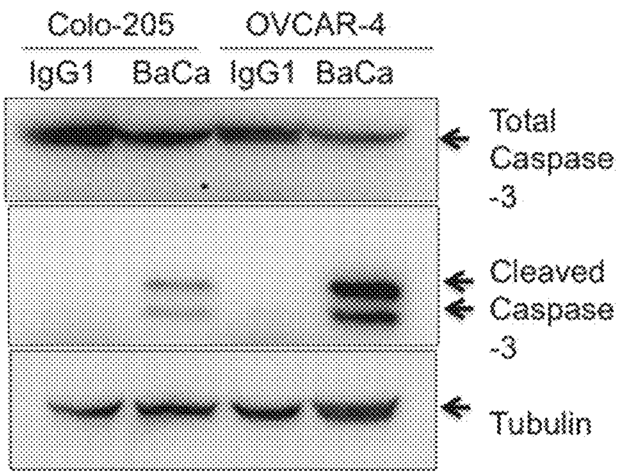
Figure 5G:
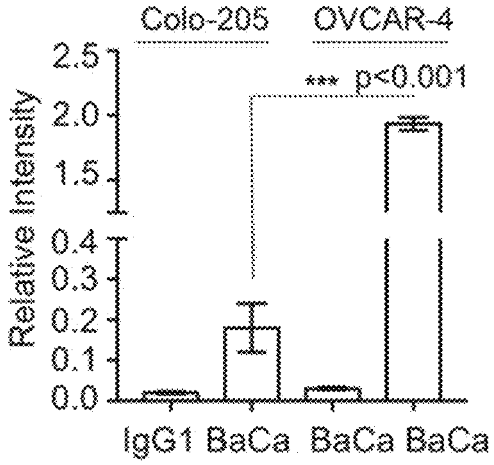
Figure 5H:
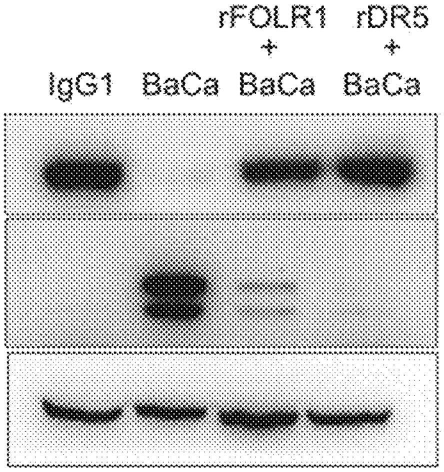
Figure 5I:
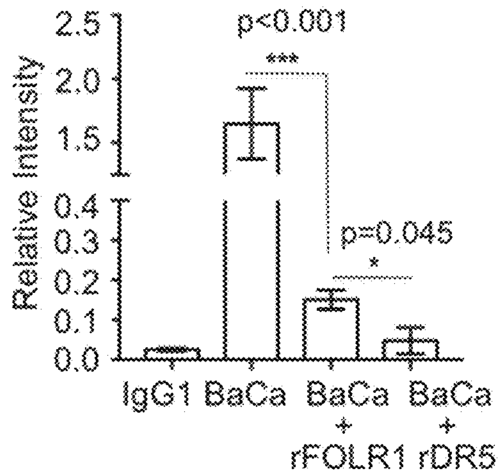
Figure 5J:
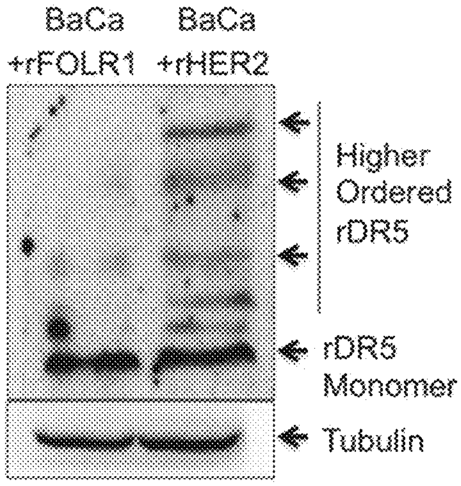
Figure 5K:
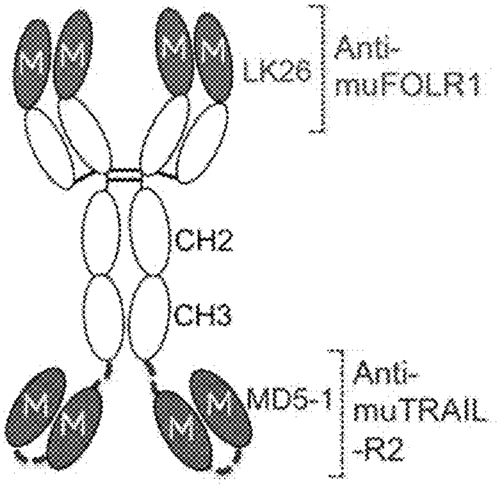
Figure 5L:
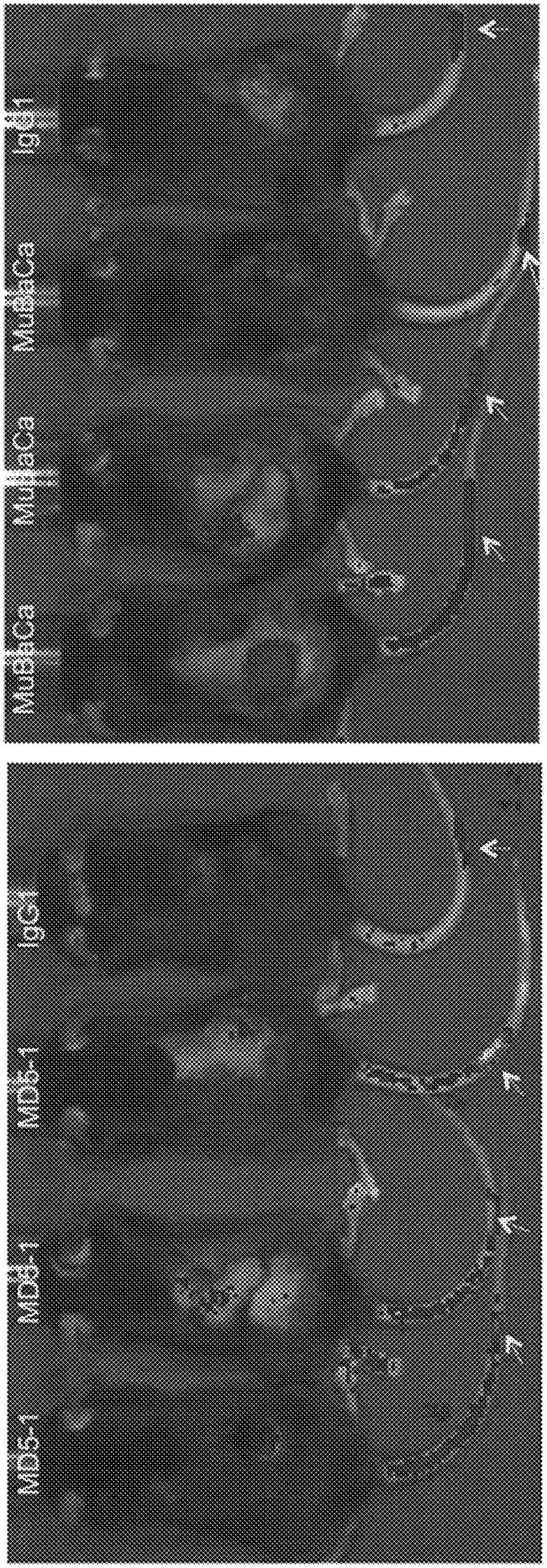
Figure 5M:
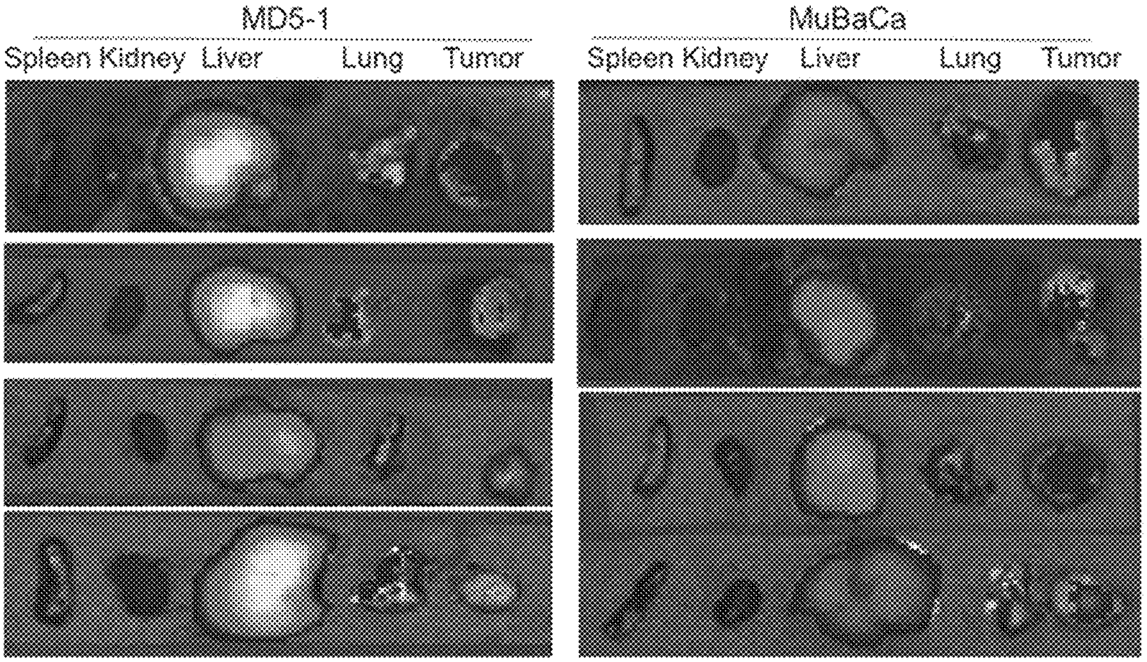
Figure 5N:
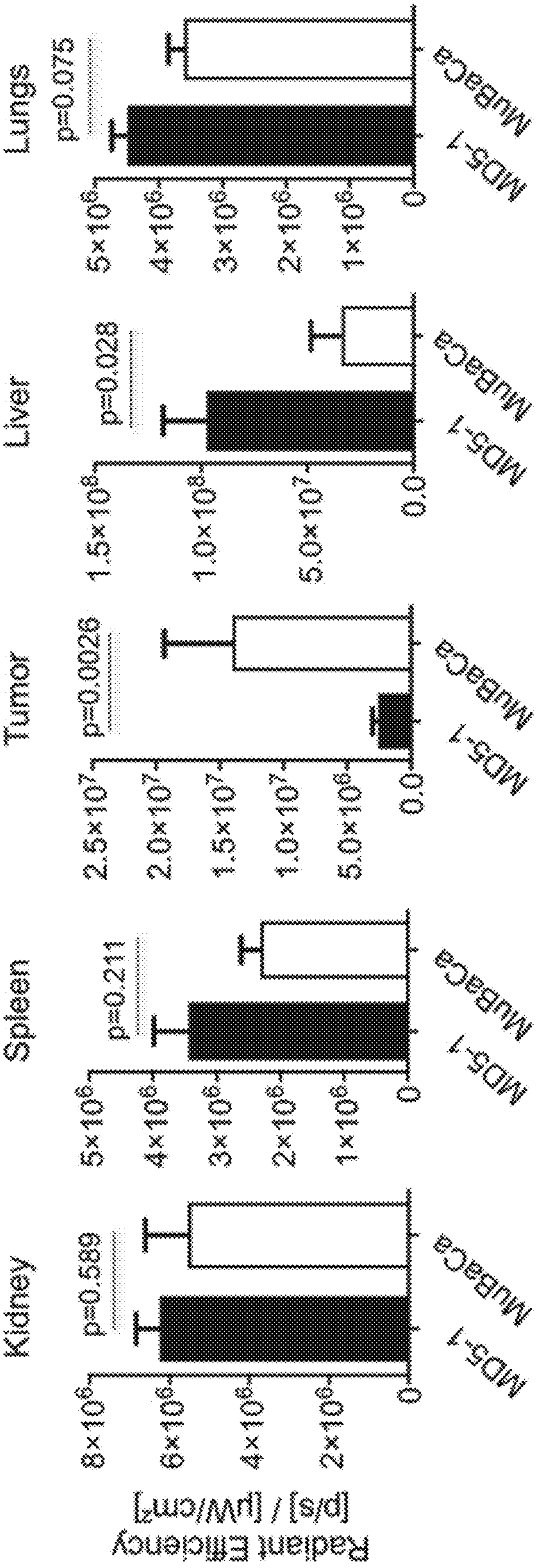
Figure 5O:
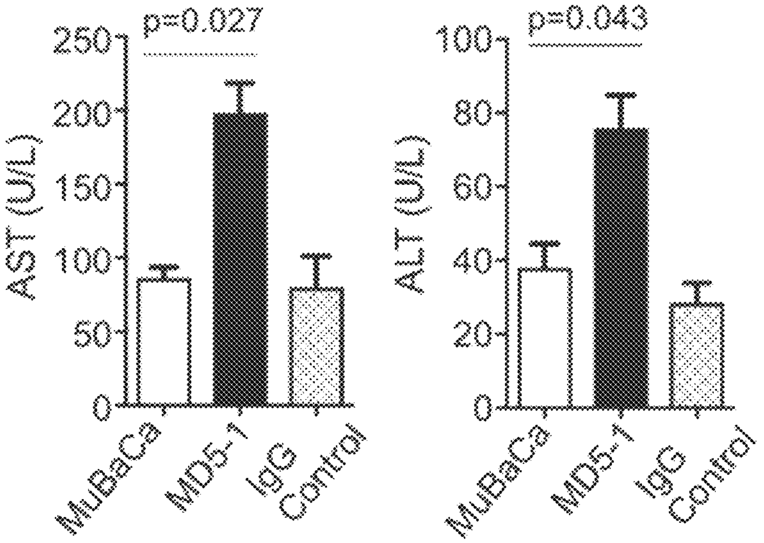

FIG. 5, comprising FIGS. 5A to 5O. BaCa activity is highly selective towards FOLR1 overexpressing OvCa tumors in vivo.

(A) Experimental schematic of tumor formation and antibody treatments. 6-8 weeks old athymic nude or C57BL/6 mice were grafted with indicated cells via subcutaneous (SQ) injections. 3-4 weeks later (tumor ~200 $mm^3$), mice were IV injected with indicated antibodies followed by imaging, or were harvested for biochemical analysis and ELISA as indicated.

(B) Tumor bearing mice were IV injected with IR800 labeled lexatumumab or BaCa antibody followed by live imaging.

(C, D) Tumor bearing mice were IV injected with BaCa antibody (C) or lexatumumab (D) pre-neutralized with rFOLR1 or rHER2 followed by live imaging.

(E) Relative amount of liver accumulated antibodies were detected using ELISA against coated rFOLR1, rDR5 and rHER2 from liver lysates as indicated (n=3).

(F) Harvested OVCAR-3 and Colo-205 tumors after BaCa and IgG1 treatments were analyzed by immunoblotting as indicated.

(G) Quantitation of caspase-3 activity as described in F.

(H) OVCAR-3 tumors harvested from mice injected with BaCa antibody pre-neutralized as indicated were analyzed by immunoblotting as indicated.

(I) Quantitation of caspase-3 activity as described in H.

(J) OVCAR-3 tumors harvested from mice injected with BaCa antibody pre-neutralized as indicated were analyzed for DR5 using immunoblotting.

(K) Schematic representation of muBaCa antibody consisting of LK26 and MD5-1 antibodies against muFOLR1 and muDR5, respectively.

(L) C57BL/6 mice bearing SQ tumors were IV injected with IR800 labeled MD5-1 and muBaCa antibodies followed by live imaging. Yellow arrows indicate residual signal at the site of injection.

(M) Necropsies from animals in L were analyzed by fluorescent imaging for detailed organ specific distribution of IR800 labeled antibodies (n=4).

(N) Quantitation of accumulated IR800 signal (radiant efficiency) from the indicated tissues after MD5-1 and muBaCa injections. IgG1 was used to subtract the background signal (n=4).

(O) AST, ALT assays were carried out using MC38 tumor bearing C57BL/6 mice after IV injection of MD5-1 and muBaCa antibodies (n=3). IgG was used for control.

Yellow arrows (in B, C, and D) indicate residual signal from the site of injection, white arrows mark nonspecific localization of antibody in other tissues along with tumors. Black arrows show the location of tumors.

Error bars in (E, G, I, N, and O) indicate SEM and p values were determined using unpaired t-test with Welch's correction. See also FIGS. 12 and 13.

FIG. 6, comprising FIGS. 6A to 6I. Anti-tumor activity of BaCa antibody (A, B) Six-eight weeks old mice bearing SQ OVCAR-3 (A) or OVCAR-4 (B) tumor were IP (A) or IV (B) injected with 25 μg of indicated antibody every third day (n=4-6). Tumor volumes were quantified at indicated days by caliper measurements.

(C) OVCAR-3 tumor volume in tumor bearing mice IP injected with BaCa antibodies (25 μg) having WT-Fc or LALA Fc.

(D) Indicated antibodies generated with E267S mutation in CH2 domain were compared for their ability to regress OVCAR-3 tumors (E) Tumor size of OVCAR-4 and Colo-205 tumors in mice IV injected with BaCa antibodies at 25 μg dose for indicated days.

(F) C57BL/6 mice bearing SQ MC38 tumor were IP injected (25 μg) with the indicated antibodies having LALA Fc mutations. Tumor volumes were quantified at indicated days by caliper measurements.

(G) Same as (F), except chimeric BaCa (ChiBaCa) with affinity against huFOLR1 and muDR5 was compared with MD5-1 (n=5).

(H) Total and cleaved caspase-3 levels in tumors from mice after 3 doses of MD5-1, muBaCa or chiBaCa.

(I) Tumor sizes of cisplatin resistant PDX tumors in 6-8 weeks old mice IP injected with 5 mg/kg dose of indicated antibodies (Lexatumumab n=3, BaCa antibody n=4).

Error bars indicate in A, B, C, D, E, F, G, and I represent SEM and p values were determined by two-tailed paired Wilcoxon Mann-Whitney test. See also FIG. 14.

Figure 7A:
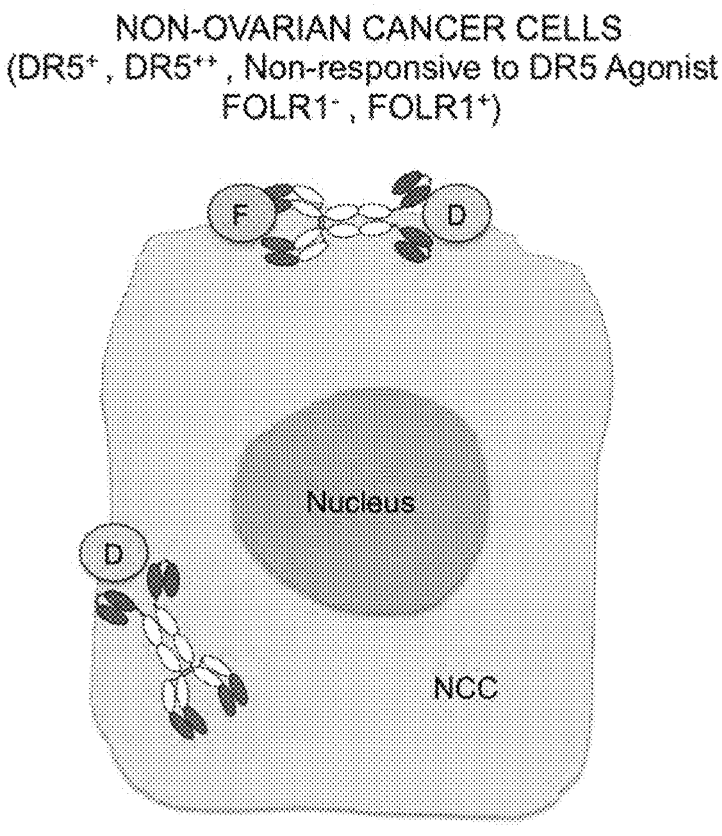
Figure 7B:
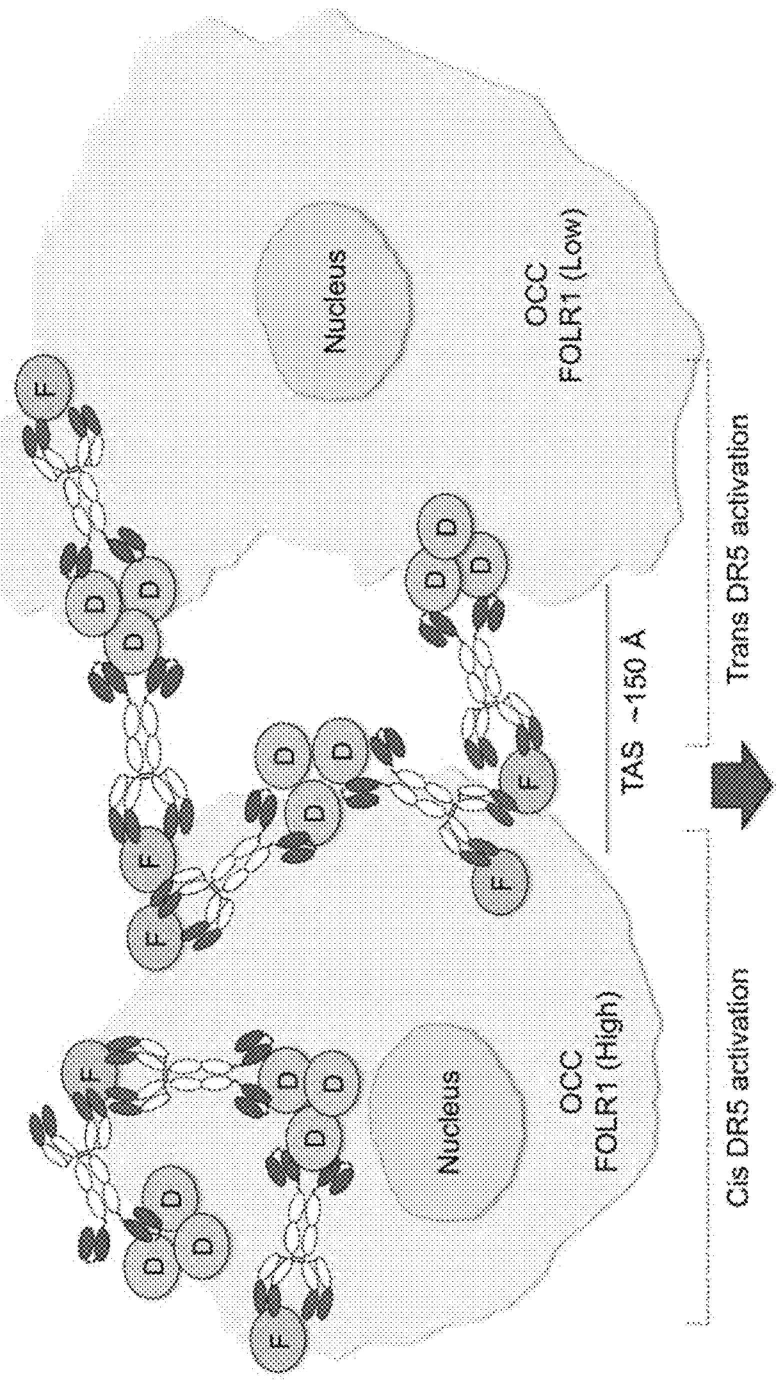
Figure 7C:
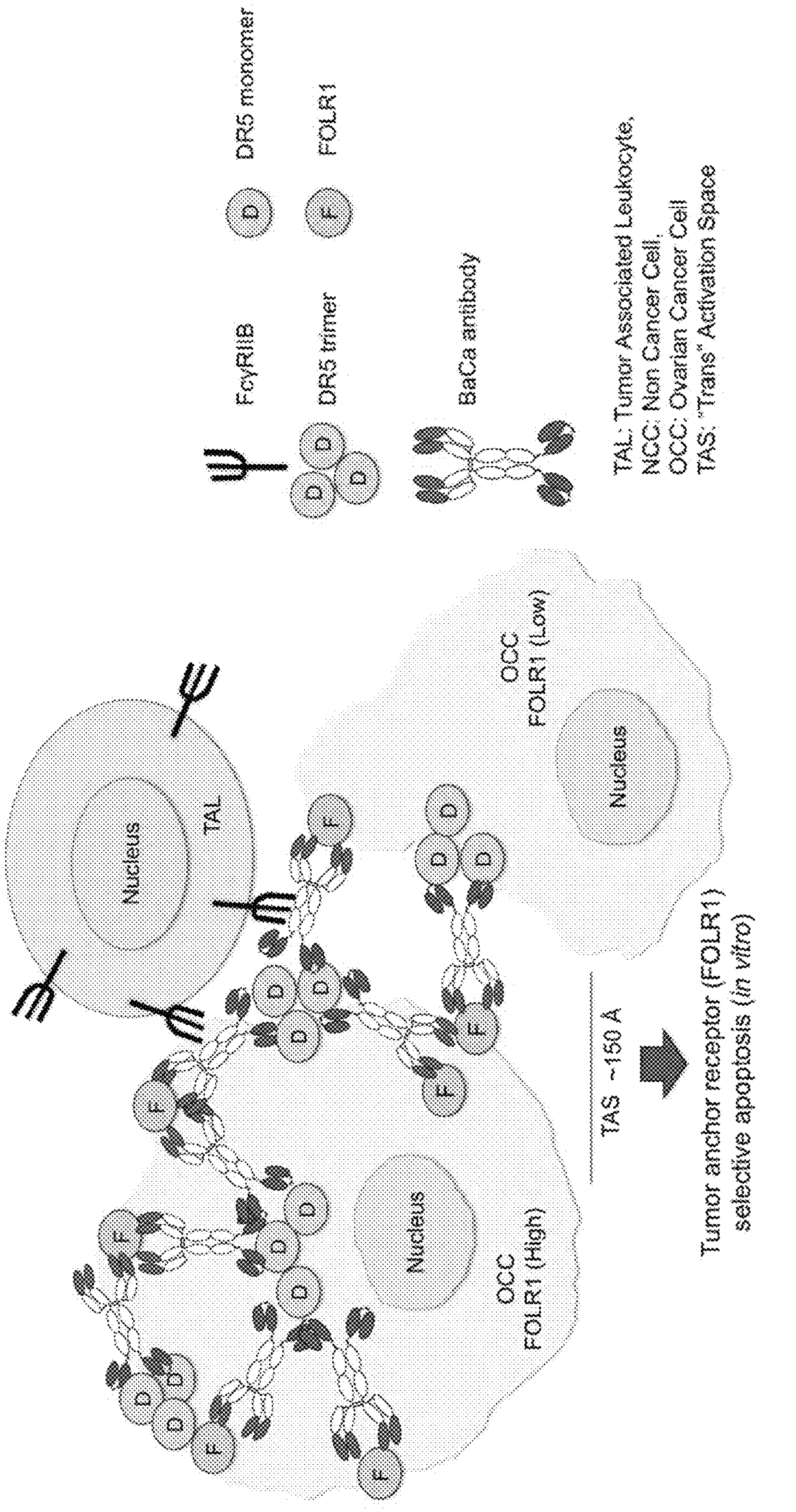

FIG. 7, comprising FIGS. 7A to 7C. Working model of BaCa antibody.

(A) Healthy tissues are generally non-responsive to agonist DR5 therapy because they express no or very low level of FOLR1, thus DR5 oligomerization and activation is very minimal.

(B) In heterogeneous FOLR1 expressing OvCa cells in vitro, FOLR1 acts as an anchoring ligand to recruit BaCa antibody close to DR5 antigen at cell surface in an avidity-optimized manner. This induces a high level of DR5 clustering and activation of apoptotic pathway in both "cis" and "trans" manner selectively in FOLR1$^+$ OvCa cells.

(C) In-vivo, tumor associated leukocytes (TAL) express inhibitory FcγRIIB receptor, which is required for the activity of DR5 agonist antibodies. Once engaged via FcγRIIB, the BaCa antibody additionally crosslinks the initial ternary complex (FcγRIIB-BaCa-DR5) via FOLR1 anchor into a high affinity stable quaternary complex (FOLR1-FcγRIIB-BaCa-DR5), which not only retains the antibody in the tumor tissue but also induces a highly superior TRAIL-R2 activation.

FIG. 8, comprising FIGS. 8A-8G, related to FIG. 1.

(A) BaCa antibodies engineered with indicated glycine-serine (GS) linker lengths were subjected to single step protein-A purification after 10 days of expression in suspension cultures. The percent monomer recoveries of BaCa antibodies were measured with size exclusion chromatography against indicated linker lengths. The GS linkers indicate the separating distance between: Fc- and scFv for BaCa-1 antibody, Kappa Chain of VL and N-terminal of VH for BaCa-2 antibody, two variable domains of light (VL) and heavy chain (VH) for BaCa-3 antibody as shown in FIG. 1A.

(B) Schematic of recombinant FOLR1 (rFOLR1) and recombinant DR5 (rDR5) antigens generated as IgG4-Fc fusion proteins. The DR5 and FOLR1 sequences represent the extracellular domain of the receptors. Recombinant proteins were expressed using the CHO expression system and were purified using protein-A columns.

Figure 8A:
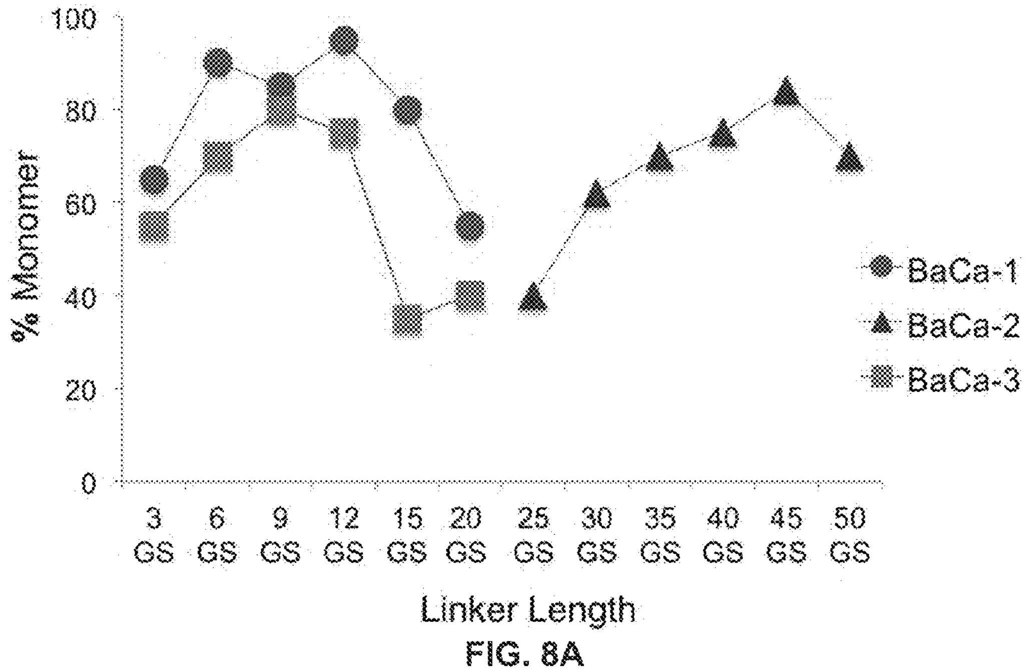
Figure 8B:
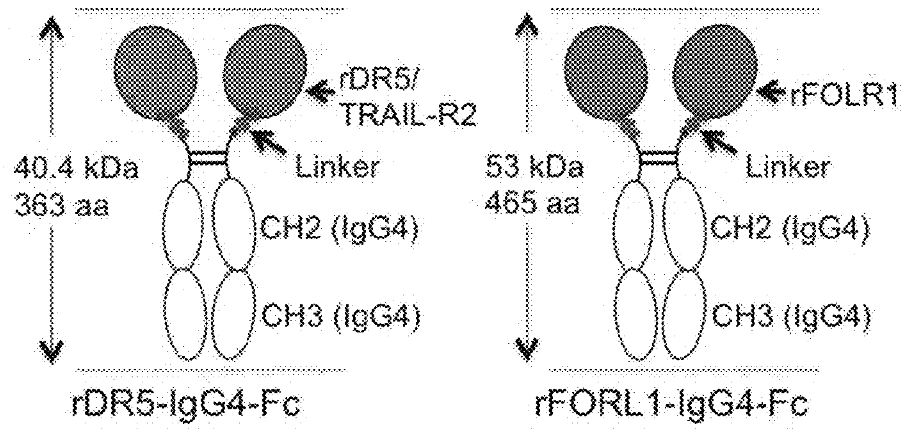

(C) Protein-A purified Fc-conjugated rFORL1 and rDR5 were run on SDS-PAGE in reducing conditions. 40.4 kDa and 53 kDa respectively indicate the size of rDR5-IgG4 and rFOLR1-IgG4, as indicated in FIG. 8B.

(D) IgG4-Fc tagged rDR5 antigen was coated on 96 well plates overnight. Coated plates were treated with the increasing concentrations of either isotype control IgG, lexatumumab, BaCa-1, BaCa-2, and BaCa-3 antibodies as indicated. Following numerous washes, the HRP conjugated secondary antibody that is specific to IgG1-Fc (but not IgG4-Fc) was used to measure the binding strength using TMB substrate and ELISA plate reader capable of reading at 450 nm (n=3).

(E) Same as D except IgG4-Fc tagged rFOLR1 antigen was coated on 96 well plates overnight and coated plates were treated with the increasing concentrations of either isotype control IgG1, farletuzumab, BaCa-1, BaCa-2, and BaCa-3 antibodies as indicated (n=3).

(F-G) Biotinylated rFOLR1-DR5 and rFOLR1-IgG4 were immobilized on streptavidin (SA) biosensors, followed by binding assays using Bio-Layer Interferometry (BLI) on ForteBio OCTET® 96 platform. Association and dissociation measurements were carried out using serial dilutions of antibodies (4-160 nM). Kinetic parameters ($K_{on}$ and $K_{off}$) and affinities (Kd) were analyzed using OCTET® data analysis software, version 9.0.

Error bars in D and E represent SEM.

FIG. 9, comprising FIGS. 9A to 9L, related to FIGS. 1 and 2.

(A) Schematic of genetic construction of BaCa (left) and NBaCa (right) antibodies. In NBaCa antibody, farletuzumab VH/VL domain (Blue) with affinity against FOLR1 has been replaced with anti-PRADAXA® VH/VL domain (Green).

(B) Reducing gel image of BaCa and NBaCa antibodies. IgG1 is control for size. A 75 kDa band of heavy chain (HC) and 25 kDa band of light chain (LC) is evident upon reduction.

(C) Cell killing activity of OVCAR-4 cells treated with BaCa and NBaCa antibodies. IgG isotype was used as a control treatment.

(D) Schematic of genetic construction of BaCa-2 (left) and NBaCa-2 (right) antibodies. In NBaCa-2 antibody, farletuzumab VH/VL domain (Blue) with affinity against FOLR1 has been replaced with anti-PRADAXA® VH/VL domain (Green) and is monovalent.

(E) Reducing gel image of BaCa-2 and NBaCa-2 antibodies. An 80 kDa band of heavy chain (HC) linked by 45 GS linker to the light chain (LC) is evident upon reduction.

(F) Cell killing activity of OVCAR-4 cells treated with BaCa-2 and NBaCa-2 antibodies. IgG isotype was used as a control treatment.

(G) Schematic of BaCa (left) and bispecific anchored Non-cytotoxicity activator (BaNCa, right) antibodies genetic construction. In BaNCa antibody, lexatumumab scFv domain (Red) was replaced with anti-PRADAXA® scFv domain (Green), while farletuzumab Fab domain (Blue) remained unchanged.

(H) Reducing gel image of BaCa and BaNCa antibodies. A 75 kDa band of heavy chain (HC) and 25 kDa band of light chain (LC) was evident upon reduction in both BaCa and BaNCa lanes.

(I) Cell killing activity of indicated antibodies (G, H) against OVCAR-4 cells. IgG1 isotype was used as a control treatment.

(J) Schematic of BaCa (left) and reverse BaCa (R-BaCa, right) antibodies. In R-BaCa antibody, farletuzumab VH/VL domain (Blue) was scFv instead of Fab, while lexatumumab VH/VL domain (Red) was Fab instead of scFv.

(K) Reducing gel image of BaCa and R-BaCa antibodies. A 75 kDa band of heavy chain (HC) and 25 kDa band of light chain (LC) was evident upon reduction in both BaCa and R-BaCa lanes.

(L) Cell killing activity of indicated antibodies (J, K) against OVCAR-4 cells. IgG1 isotype was used as a control treatment.

Error bars in C, F, I, L represent SEM.

FIG. 10, comprising FIGS. 10A to 10G (related to FIGS. 3 and 4).

(A) Detailed cell viability assays of various OvCa cell lines (as indicated) and HEK293 cells using BaCa, NBaCa, lexatumumab, farletuzumab, and IgG1 control antibodies (n=3).

(B) Four different high-grade patient derived cell lines (V584, V565, 135R and 111) were tested in cell viability assays with BaCa, lexatumumab, farletuzumab, and IgG1 isotype antibodies. Following are the source of patient derived cells: V565—metastatic high-grade serous carcinoma, V584—high-grade endometrioid adenocarcinoma, 135R—stage 3 serous ovarian cancer, 111—stage 3C serous ovarian cancer.

(C) Relative mRNA levels of TRAIL-R2 in Colo-205, OVCAR-3, and SKOV3 cells analyzed with standard RT-PCR. $RT^-$ and $RT^+$ indicates cDNA synthesis in presence and absence of reverse transcriptase.

(D) Relative mRNA levels of GALNT3 in Colo-205, OVCAR-3, and SKOV3 cells analyzed with standard RT-PCR. GAPDH is loading control. $RT^-$ and $RT^+$ indicates cDNA synthesis in presence and absence of reverse transcriptase. GAPDH was used for loading control.

(E) qRT-PCR profile of normalized GALNT3 transcript in Colo-205, OVCAR-3, and SKOV3 cells. GAPDH was used for normalization.

(F) Western blot profile of DR4 and DR5 in indicated cells. Tubulin is loading control.

(G) OVCAR-3 cells growing in 96 wells were treated with lexatumumab and Apo2L with and without rDR5 in the culture media. After 48 hrs, MTT assay was carried out to determine the cell survival. IgG was used for a control treatment.

(H) OVCAR-3 cells growing in 96 wells were treated with commercial Apo2L (R&D systems, 375-TL) and His-Apo2L generated in our lab. After 48 hrs, MTT assay was carried out to compare the cytotoxic activity of Apo2L. IgG was used for a control treatment.

The bar graphs in A, B, E, G and H represent SEM.

FIG. 11, comprising FIGS. 11A to 11I, related to FIG. 4.

Figure 4A:
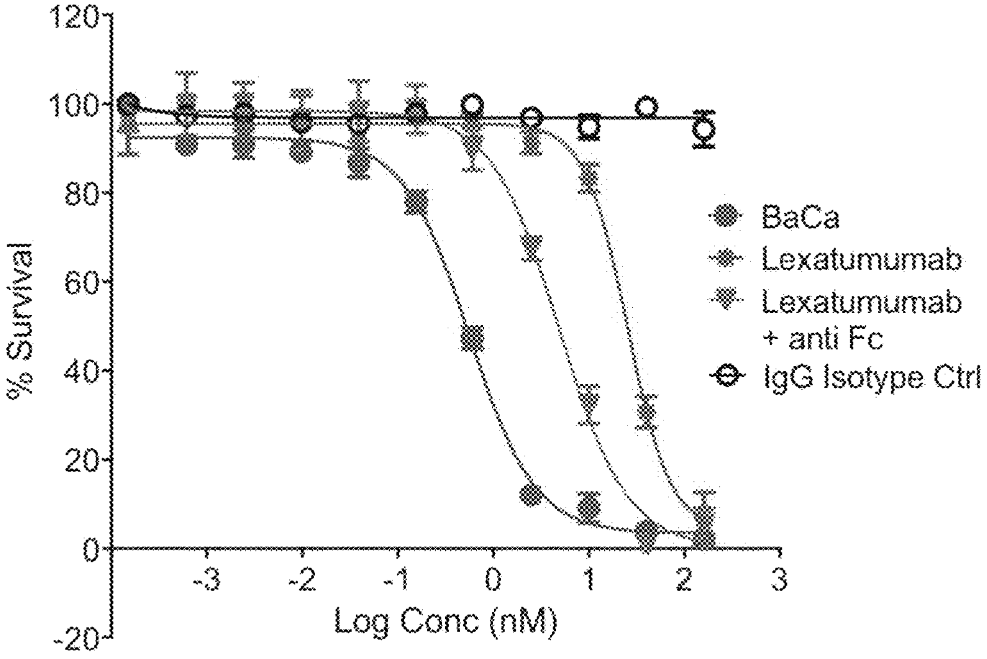
Figure 4B:
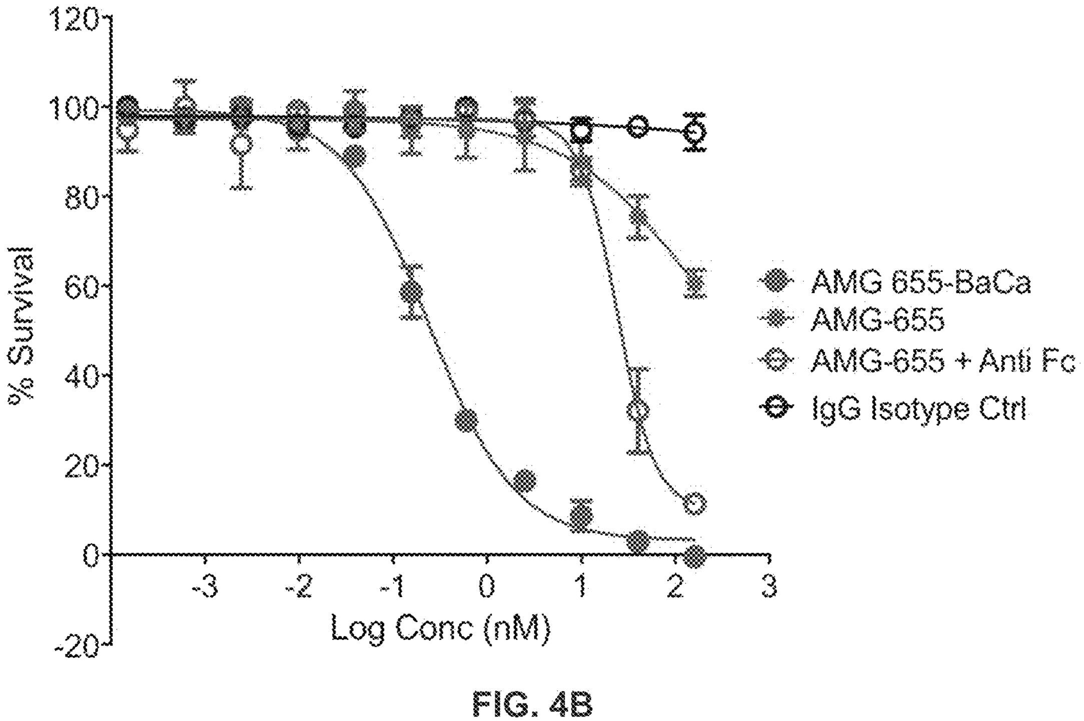
Figure 4C:
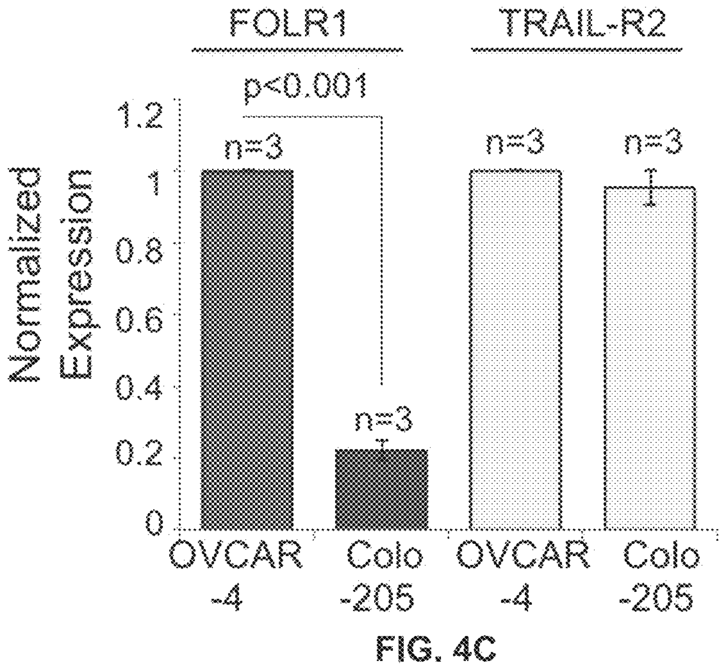
Figure 4D:
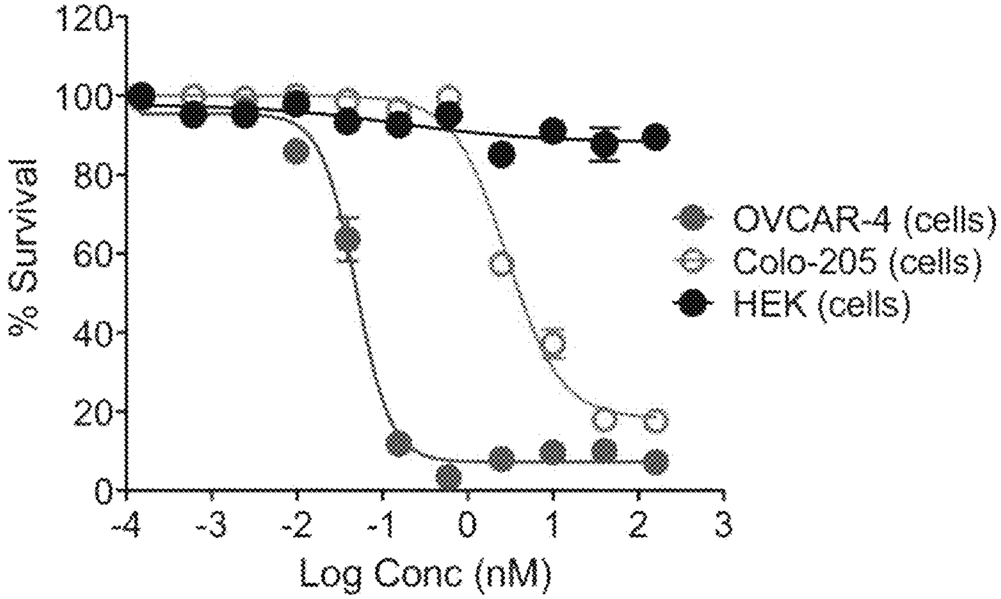
Figure 4E:
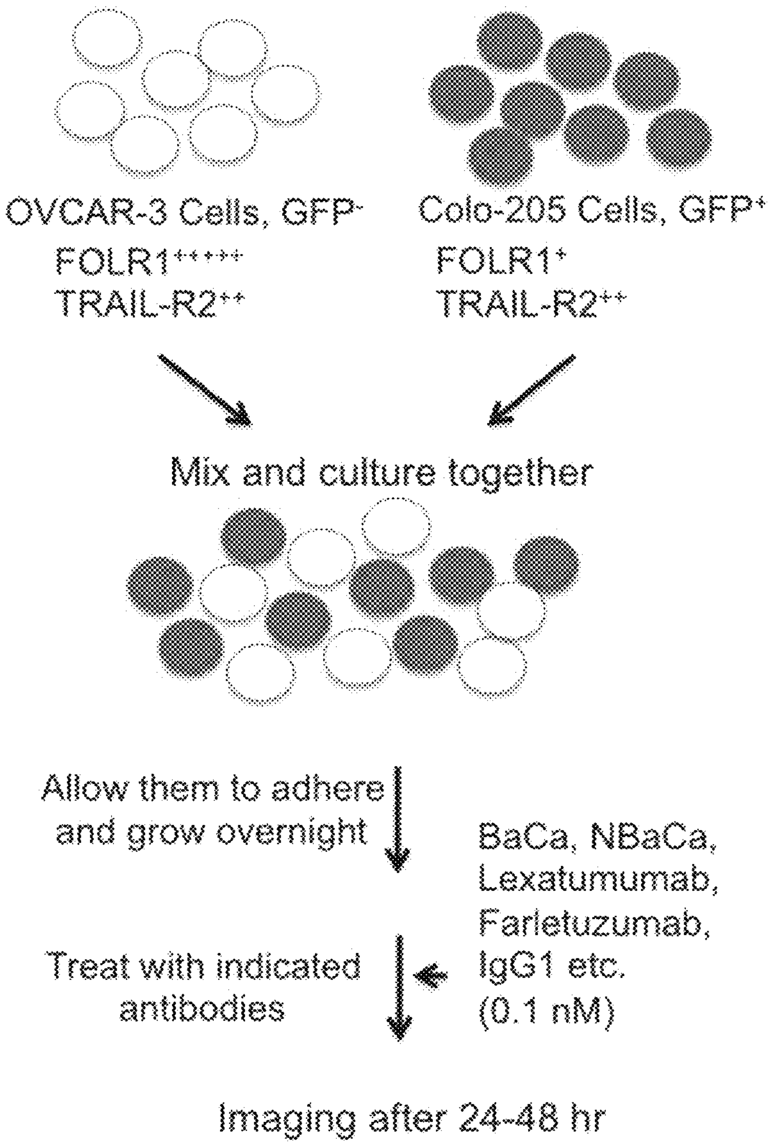
Figure 4F:
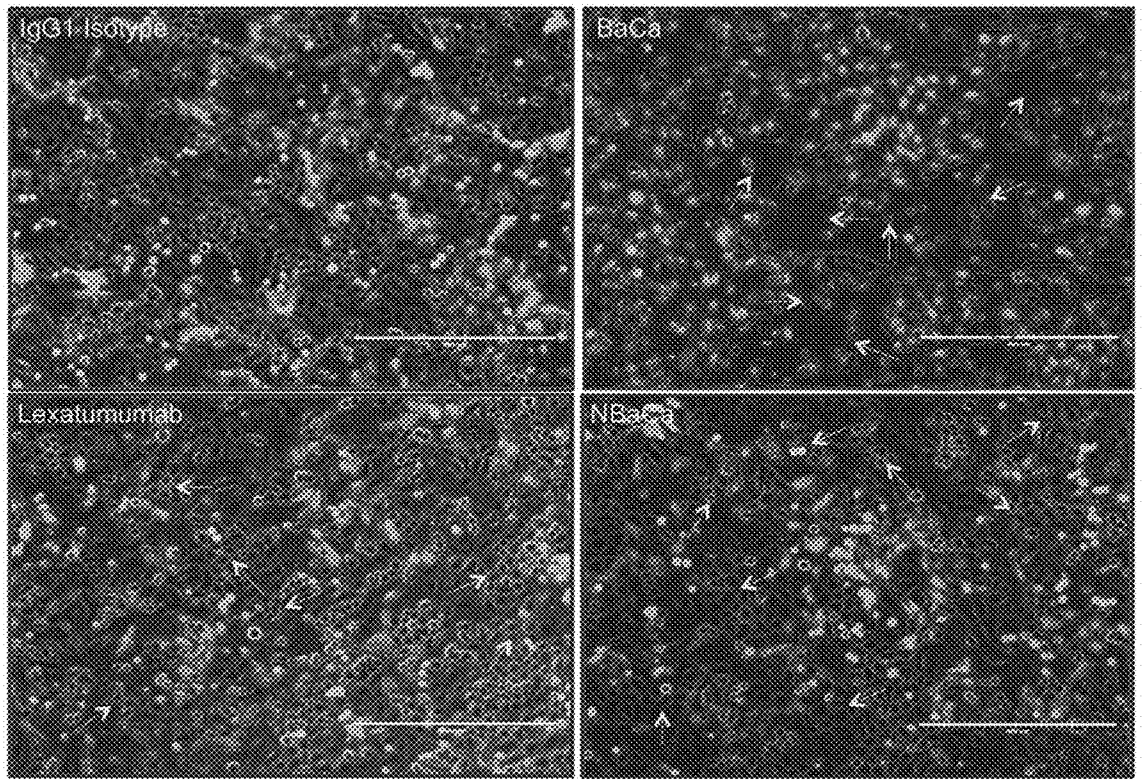

(A) Quantitation of surviving $GFP^+$ (Colo-205) and $GFP^-$ (OVCAR-4) cells in co-culture assays after 0.1 nM BaCa treatment as shown in FIG. 4F.

(B) BaCa antibody was engineered with AMG-655 scFv instead of lexatumumab. OVCAR-4 ($GFP^-$) and Colo-205 ($GFP^+$) cells were mixed together (50:50) and plated in 6 well plates. After 24 hr, cells were treated with indicated antibodies at a 0.1 nM dose. Following 36-48 hr of antibodies treatment, cells were analyzed using EVOS digital inverted fluorescent microscope. Yellow arrows indicate the dying non-GFP expressing OVCAR-3 cells. Scale bar represent 400 μm.

(C) Co-cultured OVCAR-4 ($GFP^-$) and Colo-205 ($GFP^+$) cells were treated with 2 nM lexatumumab and BaCa antibodies for 24 hr, followed by live imaging. Yellow arrows indicate the dying GFP expressing Colo-205 cells. Scale bar represents 400 μm.

(D) Co-cultured OVCAR-4 ($GFP^-$) and Colo-205 ($GFP^+$) cells in 70:30 ratio (as indicated on the top of blot) were treated with the increasing concentration of BaCa antibody. As a control, 70% $GFP^-$ Colo-205 and 30% $GFP^+$ Colo-205 cells were co-cultured and treated with 10 nM BaCa antibody (last lane). After 24 hr, lysates were run on gel and blotted with tubulin and GFP together.

(E) The normalized relative intensities of GFP signal were plotted for the increasing BaCa dose in co-cultured conditions (filled Black circles: 70% GFP-OVCAR-4 and 30% $GFP^+$ Colo-205) against constant 10 nM dose (filled Red circles: 70% $GFP^-$ Colo-205 and 30% $GFP^+$ Colo-205 culture).

(F) Mouse monoclonal LK26 antibody (WO2012061759A2) was engineered and tested in FACS binding assays against indicated OCVAR-3 and MC38 cells. IgG1 was used as a control for binding studies.

(G) Genetic construction schematic (left) and working mechanism (right) of "trans" engaging DR5 bispecific antibody having specificities against murine FOLR1 (LK26 antibody) and human DR5 (AMG-655 antibody).

(H) Cell viability analysis and comparison of AMG-655 alone, AMG-655+anti-Fc, LK26-AMG-655 bispecific antibody, and BaCa antibody (Farletuzumab-AMG-655) in 96-well plate format against OVCAR-4 cells. IgG is an isotope control (n=3).

(I) MC38 and OVCAR-4 cells were mixed together and plated in 96 well plates. Next day, cells were treated with the increasing concentration of indicated antibodies. After 48 hr, cell viability was analyzed using MTT assays as described in FIG. 4L.

Error bars in A, H and I represent SEM.

FIG. 12, comprising FIGS. 12A to 12J, related to FIG. 5.

(A) BaCa antibody was incubated at different temperatures for different days as indicated and was tested for cell killing activity against OVCAR-3 cells (n=3).

(B, C) Serum half-life analysis of BaCa-1, BaCa-2, lexatumumab, and farletuzumab antibodies. CD1 mice were injected intravenously with a single dose of indicated antibodies (100 μg). On indicated days, blood samples isolated from animals were analyzed for antibody presence in serum using ELISA. (B) rFOLR1 antigen was used to detect BaCa-1, BaCa-2, and farletuzumab antibodies. (C) rDR5 protein antigen was used to detect BaCa-1, BaCa-2, and lexatumumab antibodies (n=4).

(D) IgG4-Fc tagged rDR5 receptor was coated in 96 well plates overnight. Next day, the coated plates were treated with the increasing concentrations of IgG1 isotype control, lexatumumab, lexatumumab-IR800, BaCa and BaCa-IR800 antibodies as indicated. Following numerous washes, the HRP-conjugated secondary antibody that is specific to IgG1-Fc (but not IgG4-Fc) was used to measure the binding strength using TMB substrate and ELISA plate reader capable of reading at 450 nm (n=3).

(E) Similar to the data in FIG. 5B, subcutaneous (SQ) OVCAR-3 tumor bearing mice were IV injected either with IR800 labeled lexatumumab and BaCa antibodies. Next day following live imaging, mice were euthanized and necropsied.

(F) The selected organs from the necropsied animal (as in E) were examined side-by-side along with IR800 labeled IgG1 control antibody.

(G) Schematic of genetic construction of muBaCa, huBaCa and chimeric BaCa (chiBaCa) antibodies.

(H) Murine MC38 cells growing in 96 wells were treated with commercial MD5-1 antibody (Abcam: ab171248) and MD5-1 IgG1 generated in our laboratory. After 48 hrs, MTT assay was carried out to compare the cytotoxic activity of MD5-1 antibodies. IgG1 was used for a control treatment.

(I) MC38 cells were treated with the increasing concentration of indicated antibodies were analyzed using cell viability assays In the case of MD5-1 antibody, anti-Fc crosslinking was also compared as indicated.

(J) Similar to FIGS. 5L and M, subcutaneous (SQ) MC38 tumor bearing C57BL/6 mice were injected via IV either with IR800 labeled MD5-1 or muBaCa or IgG1 control antibodies. Necropsied animals were analyzed for organ specific imaging.

Error bars in A, B, C, D, H and I represent SEM.

Figure 13A:
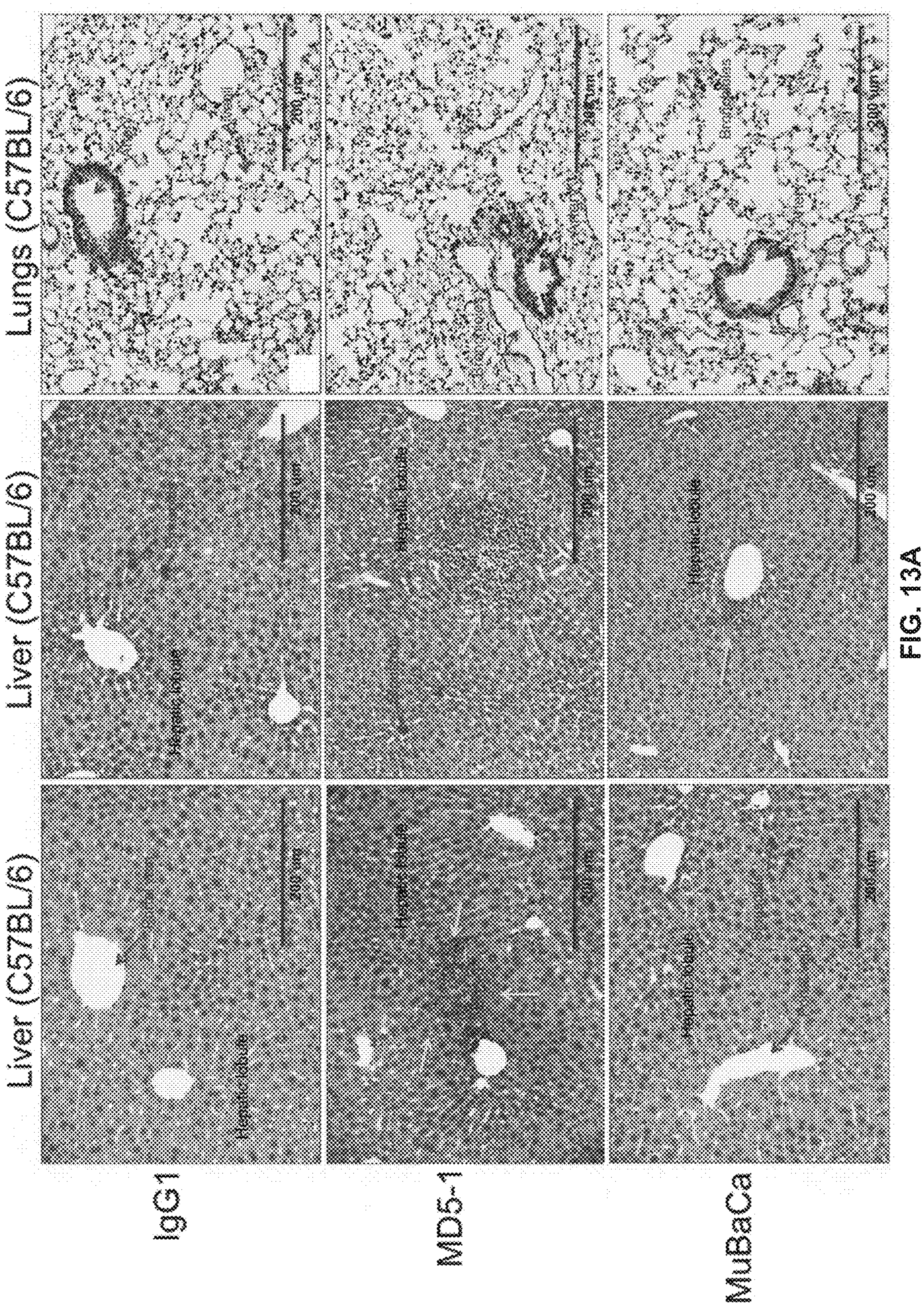
Figure 13B:
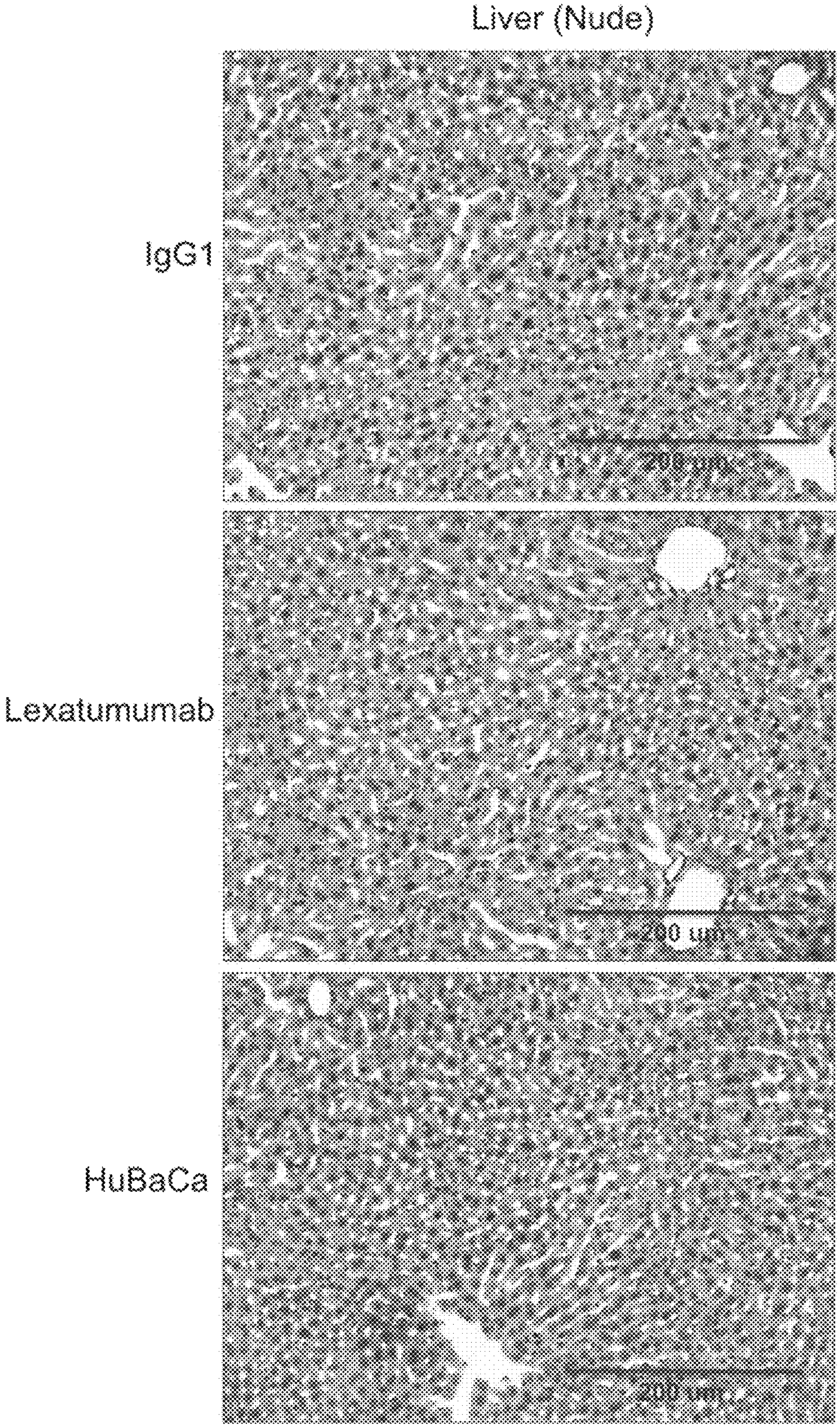

FIG. 13, comprising FIGS. 13A to 13B, related to FIG. 5.

(A) H&E staining of the liver and lung sections from C57BL/6 animals intravenously injected with IgG1 control, MD5-1, and muBaCa antibodies. The infiltrating neutrophils (marked by Yellow arrows) around the branch of portal vein and sinusoids in the liver sections of the animals treated with MD5-1 and muBaCa are shown. Scale bars represent 200 μm.

(B) H&E staining of the liver sections from athymic nude animals expressing non-binding DR5 receptor antigen against lexatumumab or huBaCa. Scale bars represent 200 μm.

FIG. 14, comprising FIGS. 14A to 14F, related to FIG. 6.

(A) To specifically examine the antibody Fc domain interactions with Fc receptors we utilized lexatumumab antibody in flow cytometry investigations. The lexatumumab Fab domains were blocked by pre-incubation with recombinant DR5 (rDR5) antigen. The rDR5 blocking was validated by performing control binding experiment with OVCAR-3 cells.

(B) Experiment in B is similar to A in terms of DR5 blocking. However in this case, surface FcγRIIIA and FcγRIIB expressing myelogenous leukemia line K562 were tested for binding with lexatumumab harboring KO-Fc (LALA) mutations and E267S mutations (Red line), harboring KO-Fc (LALA) mutations and S267E (Blue line), harboring WT-Fc (LL) mutations and E267S (Green line), harboring WT-Fc (LL) mutations and S267E mutations (Violet line) using flow cytometry investigations. IgG isotype control LALA-Fc-S267E is the negative control for Fc receptor binding (Black line). (LL=WT-Fc capable of binding to FcγRIIIA, S267E=Fc capable of binding to FcγRIIB, LALA=KO-Fc not capable of binding to FcγRIIIA, E267S=mutation in Fc that impairs FcγRIIB binding).

(C-D) As described above and in the text, various BaCa antibodies were generated with mutations in Fc (CH2 domain) such as LALA (KO-Fc), LL (WT-Fc), and S267E. BaCa antibodies generated with described Fc mutations were tested for binding to rFOLR1 (C) and rDR5 (D) as indicated. Binding affinities (nM) are shown at the bottom (n=3).

(E-F) BaCa antibodies were generated with indicated mutations in Fc (CH2 domain) were tested in cell viability assays (n=3). The $IC_{50}$ values are shown at the bottom.

Error bars in C, D, E, and F represent SEM.

DETAILED DESCRIPTION

Abbreviations and Acronyms

7-ADD—7-aminoactinomycin D

ADCC—antibody directed cell cytotoxicity (also referred to as antibody-dependent cellular cytotoxicity)

AISB—Appended Ig symmetrical bispecific

ALT—alanine aminotransferase

Apo2L—Trail ligand

AST—aminotransferase

BaCa—Bispecific-Anchored Cytotoxicity-Activator—as used herein is a bivalent antibody with properties disclosed herein BaCa-1—bivalent anti-FOLR1 and anti-DR5 antibody with affinities at opposite ends; also referred to herein as the lead antibody or as BaCa or HuBaCa whenever stated BaCa-2—bivalent antibody against FOLR1 and DR5 resembling IgG1 with similarity to the configuration of CrossMab antibodies BaCa-3—bivalent antibody, but unlike BaCa-1, two variable domains of light and heavy chains against FOLR1 and DR5 are fused next to one another via GS linkers BLI—bio-layer interferometry Ca125—cancer antigen 125 chiBaCa—chimeric BaCa

CK—kappa chain

DR5—death receptor 5 (also known as TRAIL receptor 2 (TRAILR2) and sometimes referred to as TRAIL-R2/DR5)

DVD-Ig—Dual variable domain Ig

Fab—antigen binding fragment (also referred to as Fragment antigen-binding)

FAP—fibroblast activation protein

Farletuzumab—a humanized anti-FOLR1 monoclonal antibody

FOLR1—folate receptor alpha-1

Fv—Variable fragment
G4S—Glycine-Serine linkers
GALNT3—N acetylgalactosaminyltransferase 3
GS—glycine-serine
H—Knob-hole chains.
HC—Heavy Chain
HGSOC—high-grade serous ovarian carcinoma
hu—human
IA—Intact Antibody
IV—intravenously
L—variable domain light chain
LC—Light Chain
Lexatumumab—anti-TRAIL-R2/DR5 antibody
LK26—murine monoclonal antibody against FOLR1
mAb—monoclonal antibody
mu—murine
NBaCa—non-anchoring BaCa
NK—natural killer cell
NR—non-reducing
OvCa—ovarian cancer
PARA—pro-apoptotic receptor agonists
PDX—patient-derived xenograft
r—recombinant
R—reducing
SA—streptavidin
sc—single chain
scFv—Single-chain-Fv
scLB—single chain linkered bispecific antibody
SEC—size exclusion chromatography
SQ—subcutaneous
TAL—Tumor infiltrated/associated leukocytes
TRAIL—TNF related apoptosis inducing ligand
TRAIL-R2—TRAIL receptor 2 (also known as death receptor 5 (DR5) and sometimes referred to as and sometimes referred to as TRAIL-R2/DR5)
TNF—tumor necrosis factor
VH—variable domain heavy chain

Definitions

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

The term "alterations in peptide structure" as used herein refers to changes including, but not limited to, changes in sequence, and post-translational modification.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

Amino acids have the following general structure:

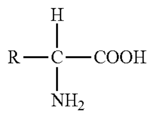

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog", or "analogue" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the subject.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

As used herein, the term "attach", or "attachment", or "attached", or "attaching", used herein interchangeably with "bind", or "binding" or "binds" or "bound" refers to any physical relationship between molecules that results in forming a stable complex, such as a physical relationship between a ligand, such as a peptide or small molecule, with a "binding partner" or "receptor molecule." The relationship may be mediated by physicochemical interactions including, but not limited to, a selective noncovalent association, ionic attraction, hydrogen bonding, covalent bonding, Van der Waals forces or hydrophobic attraction.

As used herein, the term "avidity" refers to a total binding strength of a ligand with a receptor molecule, such that the strength of an interaction comprises multiple independent binding interactions between partners, which can be derived from multiple low affinity interactions or a small number of high affinity interactions.

The term "BaCa", as used herein refers to Bispecific-Anchored Cytotoxicity-Activator, as related to a bivalent antibody with properties disclosed herein. This Bispecific-Anchored Cytotoxicity-Activator antibody is rationally designed to instigate "cis" and "trans" cytotoxicity by combining specificities against folate receptor alpha-1 (FOLR1) and death receptor 5 (DR5). The antibody is capable of binding to FOLR1 and/or DR5 with sufficient affinity such that the antibody is useful as a diagnostic and/or therapeutic agent in targeting cells expressing DR5 and/or FOLR1.

The term "BaCa-1" as used herein refers to a bivalent BaCa that is an anti-FOLR1 and anti-DR5 antibody with affinities at opposite ends.

The term "BaCa-2" as used herein refers to a bivalent BaCa antibody against FOLR1 and DR5 resembling IgG1 with similarity to the configuration of CrossMab antibodies.

The term "BaCa-3" as used herein refers to a bivalent BaCa antibody, but unlike BaCa-1, two variable domains of light and heavy chains against FOLR1 and DR5 are fused next to one another via GS linkers. In FIG. 1A, the N terminal comprises the anti-TRAILR2-DR5 sequence, linked on its C terminal end to the anti-FOLR1 sequence.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein or sequence that are capable of specific binding to their natural ligand or of performing the function of the protein.

The term "biological sample," as used herein, refers to samples obtained from a subject, including, but not limited to, sputum, CSF, blood, serum, plasma, gastric aspirates, throat swabs, skin, hair, tissue, blood, plasma, serum, cells, sweat and urine.

As used herein, the term "biopsy tissue" refers to a sample of tissue that is removed from a subject for the purpose of determining if the sample contains cancerous tissue. In some embodiment, biopsy tissue is obtained because a subject is suspected of having cancer. The biopsy tissue is then examined for the presence or absence of cancer.

"Blood components" refers to main/important components such as red cells, white cells, platelets, and plasma and to other components that can be derived such as serum.

As used herein, the term "carrier molecule" refers to any molecule that is chemically conjugated to the antigen of interest that enables an immune response resulting in antibodies specific to the native antigen.

The terms "cell," "cell line," and "cell culture" as used herein may be used interchangeably. All of these terms also include their progeny, which are any and all subsequent generations. It is understood that all progeny may not be identical due to deliberate or inadvertent mutations.

The term "cell surface protein" means a protein found where at least part of the protein is exposed at the outer aspect of the cell membrane. Examples include growth factor receptors.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above, as well as to biologics. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;

II. Polar, negatively charged residues and their amides:
Asp, Asn, Glu, Gln;

III. Polar, positively charged residues:
His, Arg, Lys;

IV. Large, aliphatic, nonpolar residues:
Met Leu, Ile, Val, Cys

V. Large, aromatic residues:
Phe, Tyr, Trp

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein, "Fab fragment" refers to an antibody fragment comprising a light chain fragment comprising a VL domain and a constant domain of a light chain (CL), and a VH domain and a first constant domain (CH1) of a heavy chain. In one embodiment the bispecific antibodies of the invention comprise at least one Fab fragment, wherein either the variable regions or the constant regions of the heavy and light chain are exchanged. Due to the exchange of either the variable regions or the constant regions, said Fab fragment is also referred to as "cross-Fab fragment" or "xFab fragment" or "crossover Fab fragment". Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab(VLVH). On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab(CLCH1).

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" molecule is a molecule in a form in which it exhibits a property or activity by which it is characterized. A functional enzyme, for example, is one that exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "induction of apoptosis" means a process by which a cell is affected in such a way that it begins the process of programmed cell death, which is characterized by the fragmentation of the cell into membrane-bound particles that are subsequently eliminated by the process of phagocytosis.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit", as used herein, refers to the ability of a compound, agent, or method to reduce or impede a described function, level, activity, rate, etc., based on the context in which the term "inhibit" is used. The term also refers to inhibiting any metabolic or regulatory pathway which can regulate the synthesis, levels, activity, or function of a protein, mRNA, or other molecule of interest. Preferably, inhibition is by at least 10%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

The term "linker", when used in the context of a peptide linker, refers to preferably a peptide with an amino acid sequence with a length of at least 5 amino acids, preferably with a length of 5 to 100, more preferably of 10 to 50 amino acids. In one embodiment said peptide linker is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In one embodiment said peptide linker is (G4S)2.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "modulate", as used herein, refers to changing the level of an activity, function, or process. The term "modulate" encompasses both inhibiting and stimulating an activity, function, or process.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject. These can be used as controls, as can standard samples comprising known amounts of the target to be detected or measured.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

As used herein, the term "peptide ligand" (or the word "ligand" in reference to a peptide) refers to a peptide or fragment of a protein that specifically binds to a molecule, such as a protein, carbohydrate, and the like. A receptor or binding partner of the peptide ligand can be essentially any type of molecule such as polypeptide, nucleic acid, carbohydrate, lipid, or any organic derived compound. Specific examples of ligands are peptide ligands of the present inventions.

The term "per application" as used herein refers to administration of a compositions, drug, or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "receptor" is a compound that specifically binds to a ligand.

A "ligand" is a compound that specifically binds to a target receptor.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, term "regulatory elements" is used interchangeably with "regulatory sequences" and refers to promoters, enhancers, and other expression control elements, or any combination of such elements.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, DC, p. 574).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide that has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

As used herein, the term "treating" can include prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat," as used herein, means reducing the frequency with which symptoms are experienced by a patient or subject or administering an agent or compound to reduce the frequency with which symptoms are experienced. By the term "vaccine," as used herein, is meant a composition which when inoculated into a subject has the effect of stimulating an immune response in the subject, which serves to fully or partially protect the subject against a condition, disease or its symptoms. In one aspect, the condition is conception. The term vaccine encompasses prophylactic as well as therapeutic vaccines. A combination vaccine is one which combines two or more vaccines, or two or more compounds or agents.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

A dosage regimen for treatment with the active agents is based on a variety of factors, including the type of injury, the age, weight, sex, medical condition of the individual, the severity of the condition, the route of administration, and the particular compound employed. Thus, the dosage regimen may vary, but can be determined routinely by a physician using standard methods.

In one aspect, an antibody of the invention can be administered at a dose of about 0.01 mg/kg to about 100 mg/kg body weight. In another aspect, an antibody of the invention can be administered at a dose of about 0.1 mg/kg to about 50 mg/kg. In yet another aspect, an antibody of the invention can be administered at a dose of about 1.0 mg/kg to about 25 mg/kg body weight. In another aspect, an antibody of the invention can be administered at a dose of about 0.1, 0.5, 0.75, 0.833, 1.0, 1.25, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, and 20.0 mg/kg body weight. The invention further encompasses similar increments within each range of doses described herein.

In one embodiment, the agonist or additional therapeutic agent is administered at a dose of about 1 ag/kg body weight to about 1 g/kg body weight.

The treatment regimen will vary depending on the disease being treated, based on a variety of factors, including the type of injury, the age, weight, sex, medical condition of the individual, the severity of the condition, the route of administration, and the particular compound employed. The treatment can include administration of a pharmaceutical composition of the invention once or more than once. Other therapeutic drugs and agents can be administered as well.

In one embodiment, a dose can be administered once a week. In another embodiment, a dose can be administered at least once a week. In one embodiment, a dose is administered two or more times a week. In another embodiment, a dose is administered three or more times a week. In another embodiment, a dose is administered ever third day. In one embodiment, the duration of treatment can be for up to one year, or up to six months, or up to three months.

In one embodiment, an antibody of the invention is purified.

In one embodiment, an antibody of the invention is substantially pure.

The invention further provides for the use of the proteins or peptides where one or more conservative amino acid substitutions are made in the sequence and that the substitution has no effect on the desired biological activity, where such activity is desired. In one aspect, one conservative amino acid substitution is made. In one aspect, at least two conservative amino acid substitutions are made. When two or more substitutions are made, they do not have to be at adjacent amino acid residue positions.

Methods of generating antibodies (i.e., monoclonal and polyclonal) are well known in the art. Antibodies may be generated via any one of several methods known in the art, which methods can employ induction of in-vivo production of antibody molecules, screening of immunoglobulin libraries (Orlandi D. R. et al., 1989. Proc. Natl. Acad. Sci. U.S.A. 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256: 495-497; Kozbor D. et al., 1985. J. Immunol. Methods 81:31-42; Cote R J. et al., 1983. Proc. Natl. Acad. Sci. U.S.A. 80:2026-2030; Cole S P. et al., 1984. Mol. Cell. Biol. 62:109-120).

It will be appreciated that for human therapy or diagnostics, humanized antibodies can be used. Humanized forms of nonhuman (e.g., murine) antibodies are genetically engineered chimeric antibodies or antibody fragments having—preferably minimal—portions derived from nonhuman antibodies. Humanized antibodies include antibodies in which complementary determining regions of a human antibody (recipient antibody) are replaced by residues from a complementarity determining region of a nonhuman species (donor antibody) such as mouse, rat, or rabbit having the desired functionality. In some instances, Fv framework residues of the human antibody are replaced by corresponding nonhuman residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a nonhuman antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596).

Methods for preparing bispecific antibodies of the present invention are disclosed herein.

Methods for humanizing nonhuman antibodies are well known in the art. Generally, a humanized antibody has one or more amino acid residues introduced into it from a source which is nonhuman. These nonhuman amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a nonhuman species. In practice, humanized antibodies may be typically human antibodies in which some complementarity determining region residues and possibly some framework residues are substituted by residues from analogous sites in rodent antibodies.

Human antibodies can also be produced using various techniques known in the art, including phage or yeast display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147:86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368:812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

Once antibodies are obtained, they may be tested for activity, for example via ELISA.

According to some aspects of the present invention, the method includes providing to the subject a therapeutic compound in combination with a pharmaceutically acceptable carrier.

According to some aspects of the present invention, the antibody or combination can be provided using any one of a variety of delivery methods. Delivery methods and suitable formulations are described herein below with respect to pharmaceutical compositions.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($—NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Antibodies and their Preparation

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

The antigenic fragments of the proteins of the invention may include, for example, peptide antigens that are at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 or up to about 200 amino acids in length. Of course, these are prepared based on the length of the starting protein or peptide. Also included are full-length unprocessed protein as well as mature processed protein. These various length antigenic fragments may be designed in tandem order of linear amino acid sequence of the immunogen of choice, such as SAS1R, or staggered in linear sequence of the protein. In addition, antibodies to three-dimensional epitopes, i.e., non-linear epitopes, can also be prepared, based on, e.g., crystallographic data of proteins. Hosts may also be injected with peptides of different lengths encompassing a desired target sequence.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals.

In one embodiment, any new monoclonal antibody described herein, or made using the methods described herein, and the hybridomas making the antibodies, as well as those not described herein, will be deposited with the American Type Culture Collection (10801 University Boulevard, Manassas, Va. 20110-2209) and assigned Accession Numbers. The deposits will be maintained under the terms of the Budapest Treaty on the International Recognition of the Deposit of Microorganisms for the Purposes of Patent Procedure and made available for use under those terms. This assures maintenance of a viable culture of the deposit for 30 years from the date of deposit. The deposits will be made available by ATCC® under the terms of the Budapest Treaty, and subject to an agreement between the University of Virginia and ATCC®, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC section 122 and the Commissioner's rules pursuant thereto (including 37 CFR section 1.14 with particular reference to 886 OG 638). The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws. Nucleic acid and amino acid sequences will be deposited with GenBank and made accessible to the public.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369). Detailed methods for preparation of chimeric (humanized) antibodies can be found in U.S. Pat. No. 5,482,856.

In another embodiment, this invention provides for fully human antibodies. Human antibodies consist entirely of characteristically human polypeptide sequences. The human antibodies of this invention can be produced in using a wide variety of methods (see, e.g., U.S. Pat. No. 5,001,065, for review).

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, Science 246:1275-1281) are utilized to allow rapid and easy identification of monoclonal Fab fragments possessing the desired specificity for specific antigens, proteins, derivatives, or analogs of the invention.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies, cross-Fab fragments; linear antibodies; single-chain antibody molecules (e.g. scFv); and multispecific antibodies formed from antibody fragments. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

A single-chain variable fragment (scFv) is not actually a fragment of an antibody, but instead is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. The image to the right shows how this modification usually leaves the specificity unaltered.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, NY) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, NY).

Bacteriophage which encode the desired antibody may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Illinois; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method that utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic, or other assay is used to monitor purification at each stage in the procedure. Protein purification methods are well known in the art, and are described, for example in Deutscher et al. (ed., 1990*, Guide to Protein Purification*, Harcourt Brace Jovanovich, San Diego).

The invention further encompasses the use of aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)]. Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

The present invention also encompasses pharmaceutical and therapeutic compositions comprising the compounds of the present invention.

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

In one embodiment, when used in vivo for therapy, the antibodies of the invention are administered to the subject in therapeutically effective amounts (i.e., amounts that have a desired therapeutic effect). In one aspect, it is administered intravenously, intraperitoneally, rectally, vaginally, pulmonary, nasally, parenterally, orally (gingival, sublingual, buccal, etc.), subcutaneously, or intramuscularly.

The dose and dosage regimen will depend, for example, upon the extent or stage of the cancer, the characteristics of the particular antibody or other compound used, e.g., its therapeutic index, the subject, and the subject's history. In one embodiment, at least one antibody or other agonist compound is administered once, or more than once, or even continuously over a period of 1-2 weeks.

The antibody compositions used can be formulated and dosages established in a fashion consistent with good medical practice taking into account the condition or disorder to be treated, the condition of the individual patient, the site of delivery of the composition, the method of administration, and other factors known to practitioners. The antibody compositions are prepared for administration according to the description of preparation of polypeptides for administration, infra. In accordance with one embodiment, a method of treating a subject in need of treatment is provided. The method comprises administering a pharmaceutical composition comprising at least one compound of the present invention to a subject in need thereof. Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

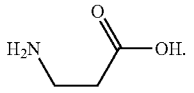

beta alanine

Sequences are provided herein which use the symbol "βA", but in the Sequence Listing submitted herewith "PA" is provided as "Xaa" and reference in the text of the Sequence Listing indicates that Xaa is beta alanine.

Peptides useful in the present invention, such as standards, or modifications for analysis, may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Illinois; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high performance liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990*, Guide to Protein Purification*, Harcourt Brace Jovanovich, San Diego).

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues. In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2'-, 3'-, or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids can include various hydropathic indices. In one aspect, the hydropathic indices are within +/−2, in another they are within +/−1, and in one aspect, they are within +/−0.5.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) In one aspect, the replacement of amino acids with others of similar hydrophilicity is provided by the invention.

Other considerations include the size of the amino acid side chain. For example, it would generally not be preferable to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, g1n; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix, and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

The draft manuscript used to prepare the provisional patent application (U.S. Provisional Application Ser. No. 62/585,647, filed Nov. 14, 2017) for the application described herein has since published as Shivange et al., 2018, Cancer Cell, 34, 331-345.

EXAMPLES

Experimental Models and Subject Details—
Patient Derived Cell Lines and Human Subjects Patient derived V565, patient derived V584, patient derived 135R, and patient derived 111 cells were isolated from ovarian cancer patients with respective ages of 65.9, 69.4, 64.5, and 54.4 years at diagnosis. Following are the tissue sources of patient derived cells: V565—metastatic high-grade serous carcinoma, V584—high-grade endometrioid adenocarcinoma, 135R—stage 3 serous ovarian cancer, 111—stage 3C serous ovarian cancer. Remnant surgical resections of omental metastatic ovarian cancer tissues (as indicated above) used for cell culture and patient-derived xenograft experiments were collected into a tissue bank by waiver of consent and approved by the University of Virginia Institutional Review Board for Health Sciences Research. The UVa Biorepository and Tissue Research Facility procured remnant samples under this protocol from UVa Pathology. De-identified tissues were pulled from this bank and used in experiments approved by UVa IRB-HSR.

Mouse Tumor Animal Models:

6-8 weeks old (Age), 20-25 gram (Weight) female (Sex) mice were used for in vivo efficacy, imaging and safety studies. 4-6 weeks old (Age), 20-24 gram (Weight), randomized male/female (Sex) mice were used for serum half-life assays. Tumor xenografts live animal imaging, and liver ELISA studies with human cancer cells were carried out using immunodeficient BALB/c derived athymic Nude Foxn1$^{nu}$/Foxn1$^{+}$ (Envigo) mice model carrying functional B cell and NK (innate immunity) cells. Randomly selected and weight matched male and female Crl: CD1(ICR) mice (Charles River), a well establish strain for pharmacokinetics studies, were used for serum half-life studies. For surrogate animal studies female (Sex) 6-8 weeks-old (Age) C57BL/6J mice, 22-26 gram (Weight) were used for investigating liver toxicity, detailed tissue distribution, H&E staining, AST/ALT assays, and surrogate in vivo efficacy using MD5-1, muBaCa and chiBaCa antibodies as indicated in Figure legends. For assessing plat resistant patient derived xenografts, female (Sex) SCID C.B-17/IcrHsd-Prkdc (Envigo, Dublin, VA) mice that were 6-8 weeks old (Age) with 20-25 grams were used. Procedures involving animals handling, tumor xenografts and serum half-life studies were reviewed and approved by the Institutional Animal Care and Use Committee here at the University of Virginia and conform to the relevant regulatory standards.

Cell Lines

The following cell lines were used in the study: OVCAR-3, OVCAR-4, OVCAR-5, OV90, OVSAHO, COV362, CAV0362, SKOV3, Colo-205, MC38, ID8 and patient derived cell lines (next section). All the cell lines were maintained in RPMI-1640 medium supplemented with 10% heat-inactivated fetal bovine serum (FBS), 2 mM glutamine, 100 U/ml penicillin, and 100 ag/ml streptomycin (complete medium) unless otherwise specified. MC38 cells (provided by S. Ostrand-Rosenberg, University of Maryland) were cultured in DMEM supplemented with 10% (vol/vol) FCS and 1 mM penicillin/streptomycin. Patient derived cells lines were maintained in 20% FBS and 100 mM sodium pyruvate in RPMI 1640 media supplemented with glutamax (Gibco) and 1% penicillin/streptomycin (Gibco). Various cell lines were trypsinized and expanded as follow: After digestion, the cell suspension was neutralized with complete media and centrifuged 5 min at 1500 rpm. The cell pellets were suspended in relevant DMEM/RPMI media and either expanded or seeded after counting using countess II (Life technologies). Passaged cell lines were routinely tested for *Mycoplasma* using MycoAlert Detection Kit (Lonza).

Method Details

Recombinant Antibody Cloning

Various BaCa antibodies were engineered by genetically linking variable regions of farletuzumab (Anti-FOLR1 antibody) and lexatumumab (Anti-TRAIL-R2/DR5 antibody) into human IgG1 framework as shown in FIG. 1. The DNA sequences were retrieved from the open sources (IMT-G.ORG or publicly available patents) and synthesized as gene string using Invitrogen GeneArt. After PCR amplification, DNA was gel purified and inserted into pcDNA $3.1^+$ vector (CMV promoter) by making use of IN-FUSION® HD Cloning Kits (Takara Bio). EcoRI and HindIII digested vector was incubated with overlapping PCR fragments (of various different recombinant DNAs, see list of clones in Key Resource Table) with infusion enzyme (1:2, vector: insert ratio) at 55° C. for 30 min, followed by additional 30 min incubation on ice after adding *E. coli* STELLAR™ cells (Clontech). Transformation and bacterial screening was carried out using standard cloning methods. Positive clones were sequence confirmed in a 3-tier method. Confirmed bacterial colonies were Sanger sequenced upon PCR followed by re-sequencing of mini-prep DNA extracted from the positive colonies. Finally, maxiprep were re-sequenced prior to each transfection. Recombinant antibodies were also re-confirmed by ELISA and flow cytometry surface binding studies. MuBaCa, chiBaCa, LK26, MD5-1, AMG-655, NBaCa, and other indicated bispecific antibodies were similarly engineered.

Recombinant Antibody Expression

Free style CHO-S cells (Invitrogen, Key Resource Table) were cultured and maintained according to supplier's recommendations (Life technologies) biologics using free style CHO expression system (life technologies) and as previously described (Durocher and Butler, 2009). A ratio of 2:1 (light chain, VL: heavy chain, VH) DNA was transfected using 1 μg/ml polyethylenimine (PEI). After transfection, cells were kept at 37° C. for 24 hr. After 24 hr, transfected cells were shifted to 32° C. to slow down the growth for 9 additional days. Cells were routinely fed (every $2^{nd}$ day) with 1:1 ratio of Tryptone feed and CHO Feed B. After 10 days, supernatant from cultures was harvested and antibodies were purified using protein-A affinity columns. The detailed amino acid sequences of recombinant BaCa antibodies are provided below. Various recombinant antibodies used in this study (Parental antibodies: farletuzumab, lexatumumab, AMG-655, LK26, MD5-1 and BaCa, NBaCa, R-BaCa, BaNCa, muBaCa, chiBaCa etc.) and recombinant target antigens were engineered, expressed and purified in Singh Laboratory of Novel Biologics as described above.

Figure 10A:
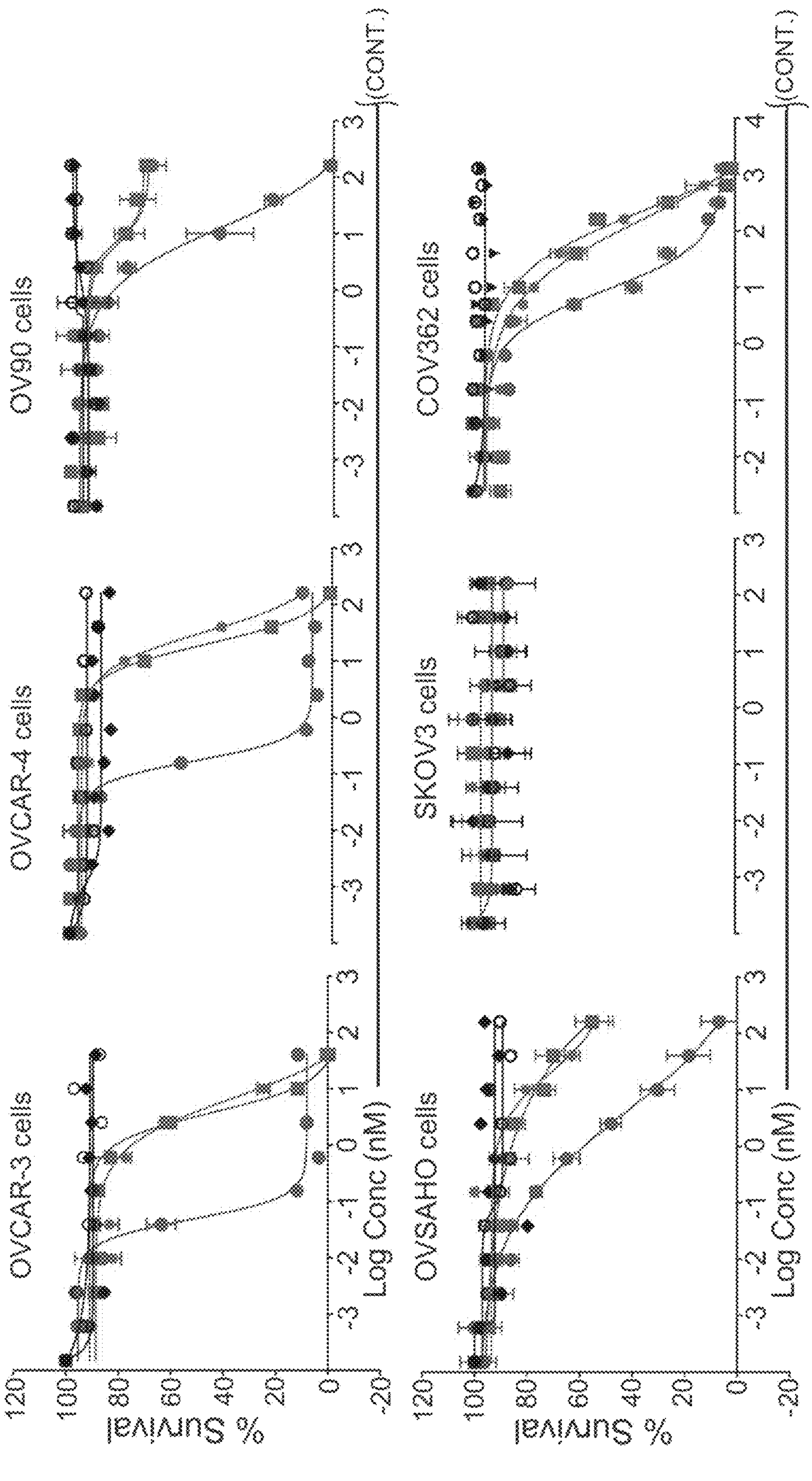
Figure 10A:
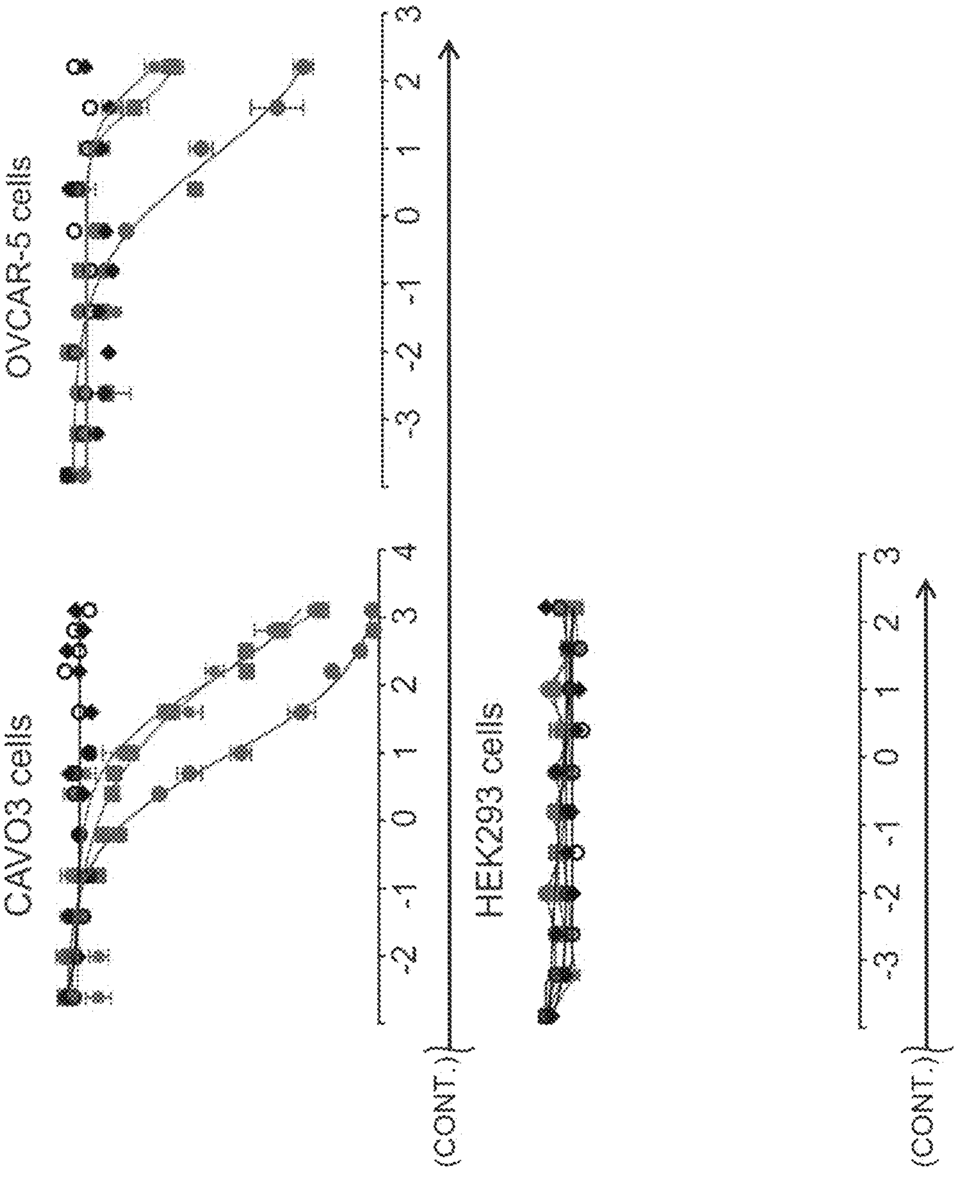
Figure 10B:
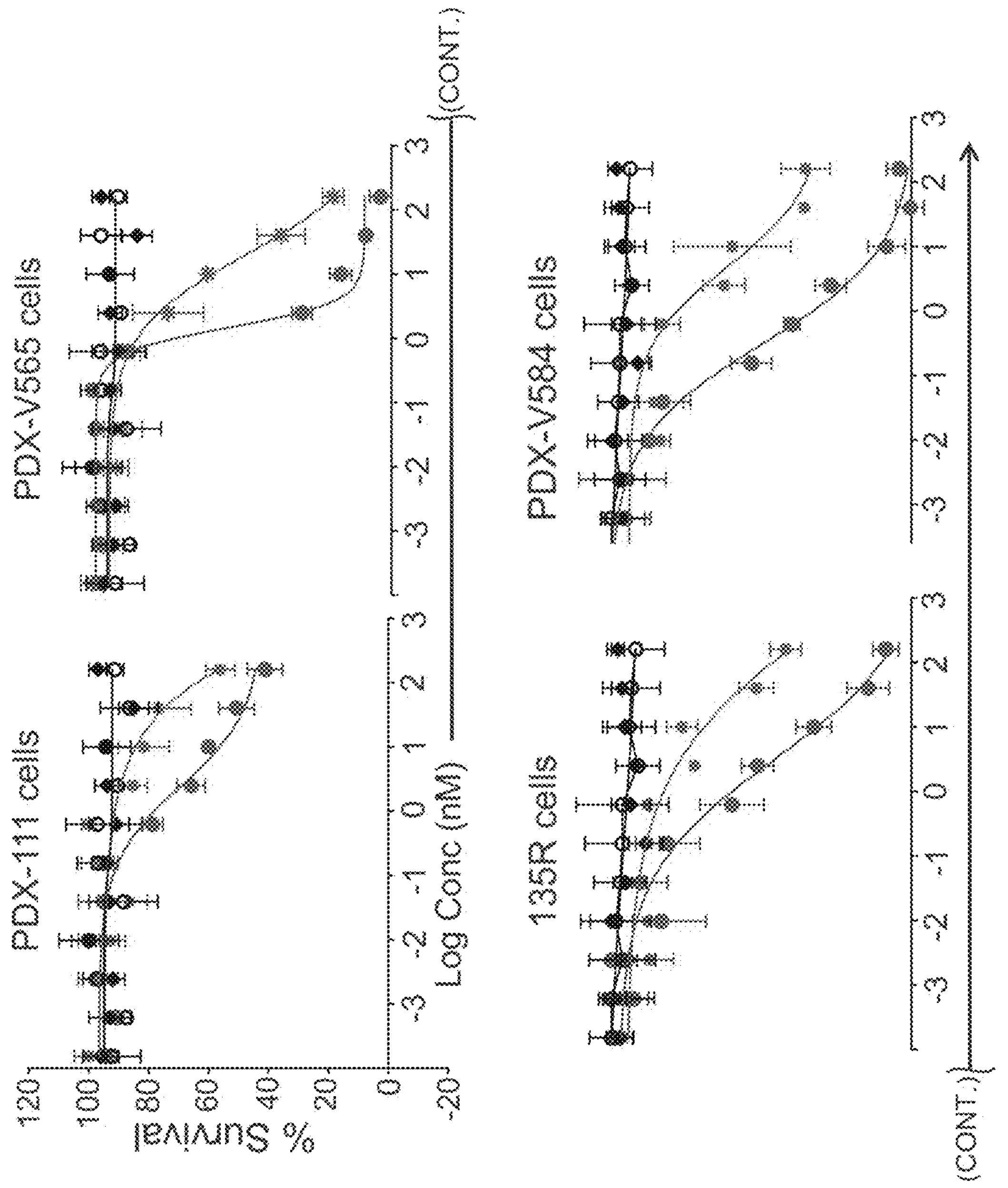
Figure 10C:
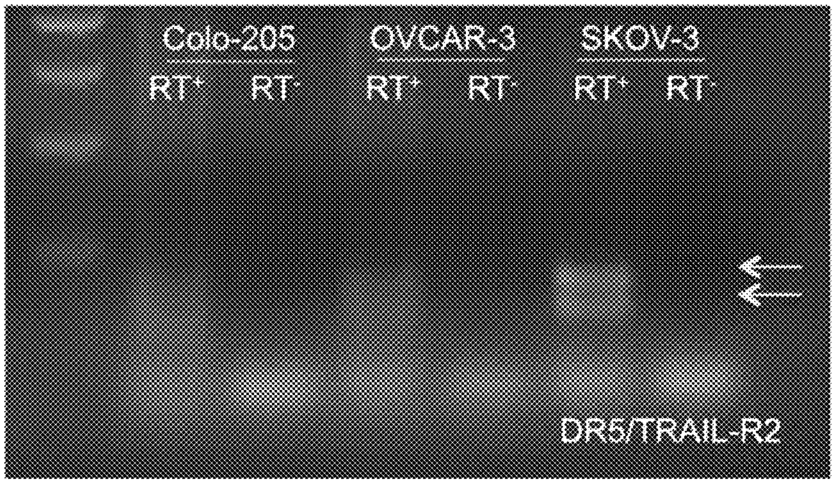
Figure 10D:
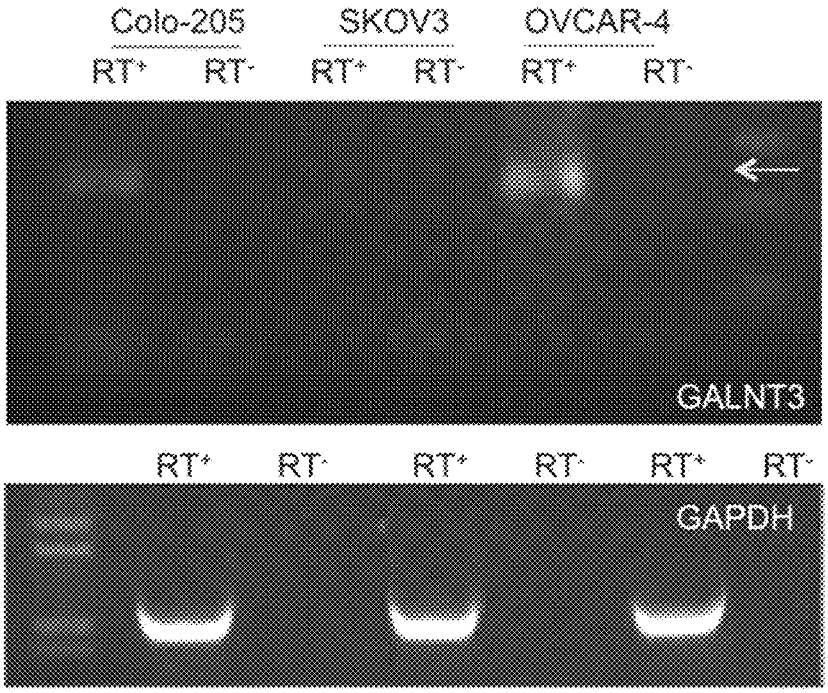
Figure 10E:
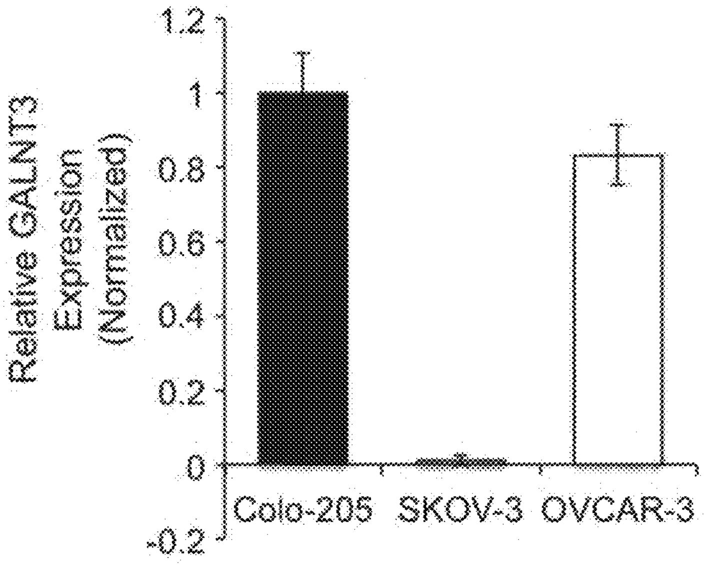
Figure 10F:
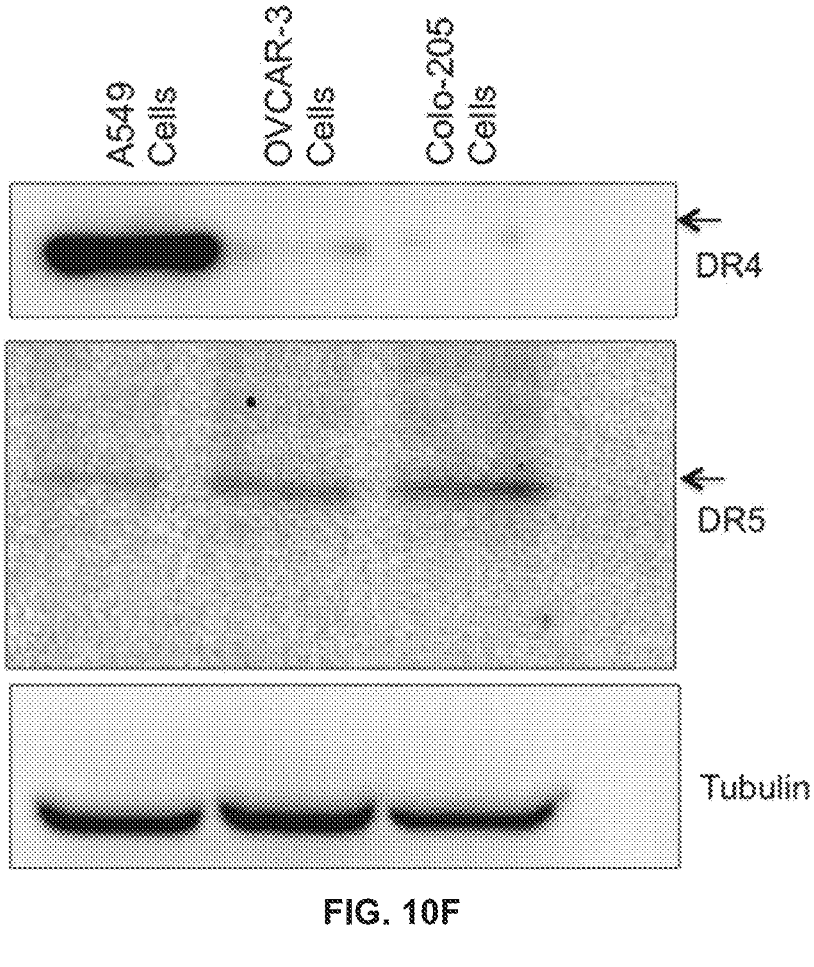
Figure 10G:
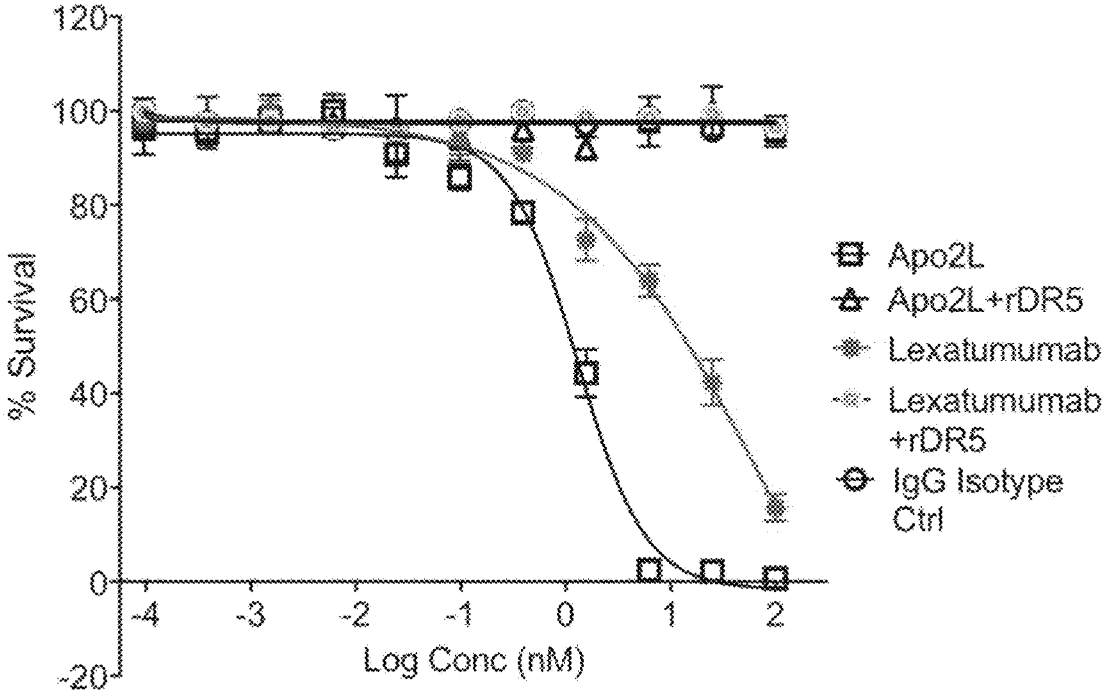
Figure 10H:
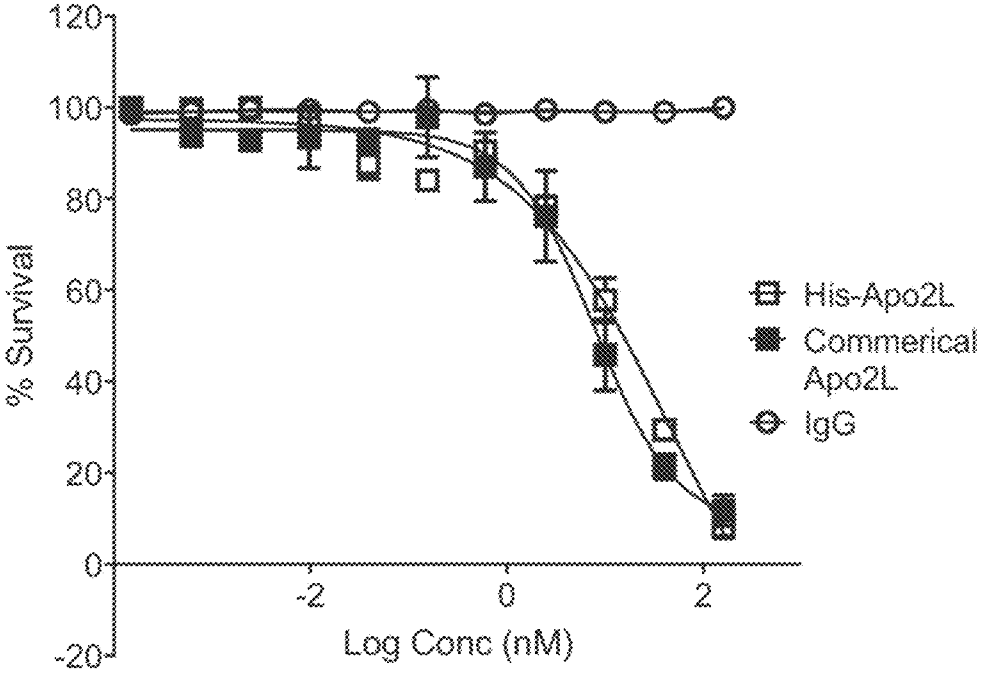
Figure 11A:
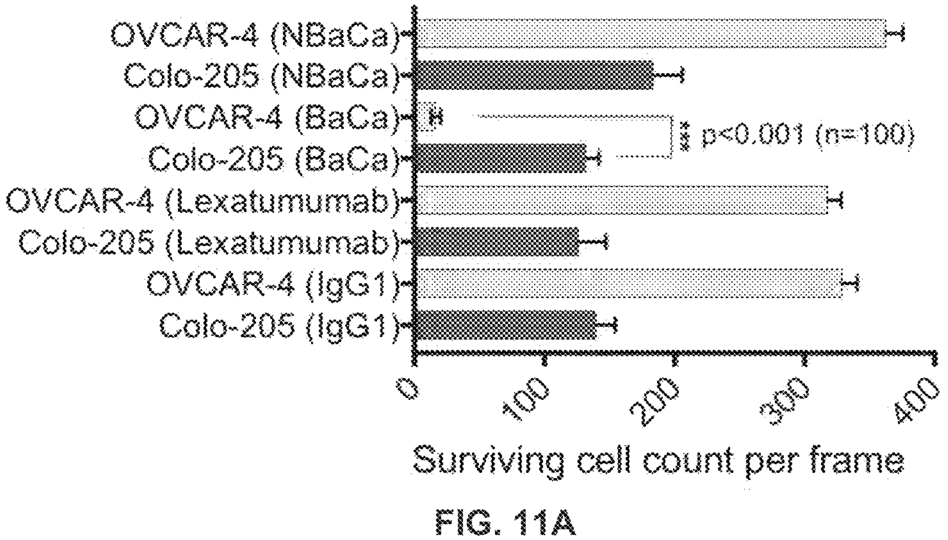
Figure 11B:
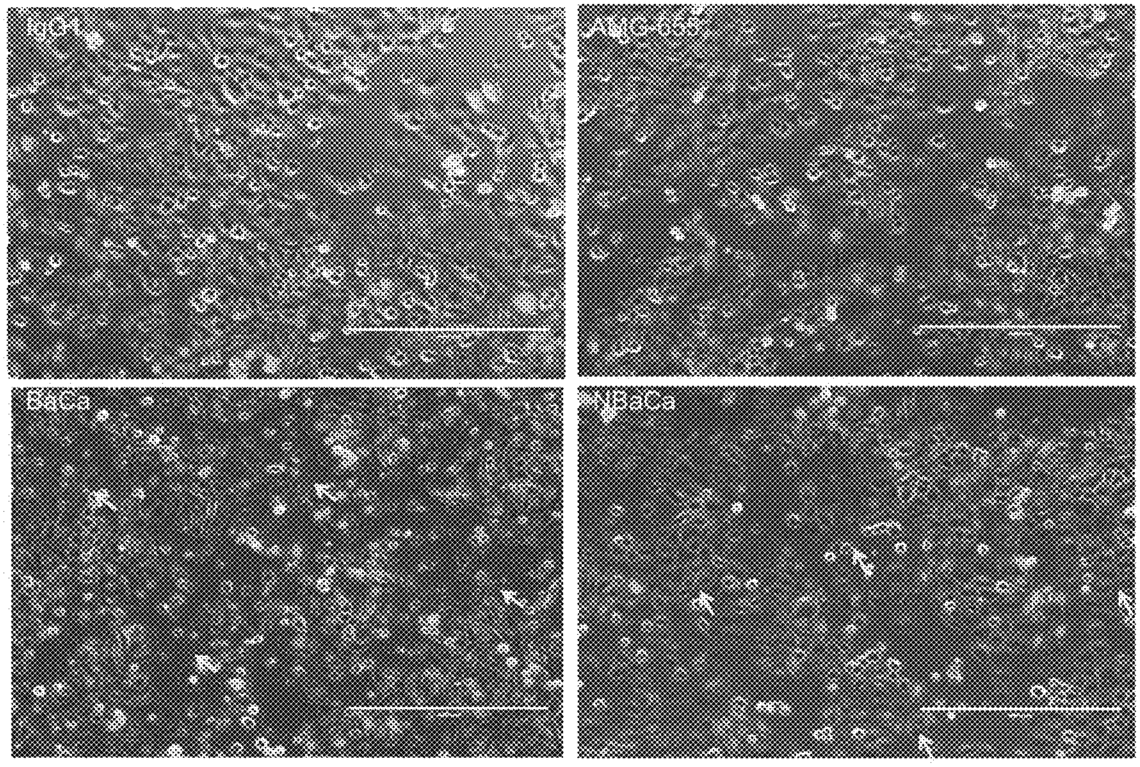

Recombinant human Apo2L/TRAIL was obtained from R&D systems. His-tag Apo2L was also expressed and purified using nickel NTA columns using standard BL21 bacterial expression system. His-Apo2L generated in our laboratory was confirmed (alongside commercial Apo2L) using multiple cancer lines (FIGS. 10A-10H). Similarly the activity of commercial MD5-1 antibody was compared next to recombinant MD5-1 generated in our laboratory using two different cell lines (FIG. 11I and data not shown).

Antibody Purification

Various transfected monospecific and bispecific antibodies (as indicated in text and Figure legends) were affinity purified using HITRAP™ MABSELECT SURE™ (GE, 11003493) protein-A columns. Transfected cultures were harvested after 10 days and filtered through 0.2 micron PES membrane filters (Millipore Express Plus). Cleaning-in-place (CIP) was performed for each column using 0.2 M NaOH wash (20 min). Following cleaning, columns were washed 3 times with Binding buffer (20 mM sodium phosphate, 0.15 M NaCl, pH 7.2). Filtered supernatant containing recombinant antibodies or antigens were passed through the columns at 4° C. Prior to elution in 0.1 M sodium citrate, pH 3.0-3.6, the columns were washed 3 times with binding buffer (pH 7.0). The pH of eluted antibodies was immediately neutralized using sodium acetate (3 M, pH 9.0). After protein measurements at 280 nm, antibodies were dialyzed in PBS using SLIDE-A-LYZER™ 3.5K brand mini dialysis device (Thermo Scientific, 66330). Antibodies were run on gel filtration columns (next section) to analyze the percent monomers. Whenever necessary a second step size exclusion chromatography (SEC) was performed. Recombinants IgG4-Fc tagged extracellular domain antigens such as FOLR1, DR5, and HER2 were also similarly harvested and purified using protein-A columns.

Size Exclusion Chromatography

The percent monomer of purified antibodies was determined by size exclusion chromatography. 0.1 mg of purified antibody was injected into the AKTA™ protein purification system (GE Healthcare Life Sciences) and protein fractions were separated using a SUPERDEX®-200 10/300 column (GE Healthcare Life Sciences) with 50 mM TRIS® (pH 7.5) and 150 mM NaCl. The elution profile was exported as Excel file and chromatogram was developed. The protein sizes were determined by comparing the elution profile with the gel filtration standard (Bio-Rad Gel Filtration Standard 1511901).

Any protein peak observed in void fraction was considered as antibody aggregate. The area under the curve was calculated for each peak and a relative percent monomer fraction was determined. The percent monomers of various BaCa-1, BaCa-2, and BaCa-3 antibodies generated with various linker lengths were determined as above (See FIG. 8A).

BaCa Antibodies Details and Structural Integrity Confirmation on SDS-PAGE

Schematic of genetic construction and domain organization of BaCa antibodies are shown in FIG. 1A. The BaCa-1 antibody configuration contains bivalent anti-FOLR1 and anti-TRAIL-R2 affinities. The average distance of a N-terminal of variable (Fv) domain to the C-terminal of CH3 domain in an IgG is 150 Å, the genetic ligation of anti-FOLR1-IgG1-CH3 domain to TRAIL-R2 single-chain-Fv (scFv) with 12 GS linkers add an extra linear and flexible distance of ~20 Å and ~35-50 Å respectively in BaCa-1 antibody (Zhang et al., 2015). Therefore, because of total separating distance of >170 Å (150 Å+~20 Å) BaCa-1 antibody affinities against FOLR1 and TRAIL-R2 receptors are at the opposite ends (Blue and Red). BaCa-1 antibody when run on SDS-PAGE has ~75 kDa heavy (FOLR1-VH chain joined with TRAIL-R2 scFv) and ~25 kDa light chain (FOLR1-VL) in reducing conditions. The BaCa-2 antibody configuration resembles an IgG1 and is similar to CrossMab antibodies of Genentech. In this configuration, the affinities against TRAIL-R2 and FOLR1 are monovalent (Blue and Red). BaCa-2 was engineered by making use of: a) knob/hole mutations to allow heterodimerization of two IgG chains that only differ in Fv domain (Ridgway et al., 1996), b) H435R and Y436F mutations in the CH3 domain of the hole chain in order to prevent protein-A binding to the hole-hole homodimers, and c) Glycine-serine linkers (45 GS) that are genetically linked between 3' end of c-kappa and 5' end of VH for proper light chain pairing. Therefore, when run in reducing conditions, BaCa-2 antibody showed a single band of ~75 kDa as light chain and heavy chain are genetically linked by GS linkers (FIG. 1A). In BaCa-3 antibody (similar to Dual-Variable-Domain Ig platform of Abbvie Inc.), two different FOLR1 and TRAIL-R2 light and heavy chains are genetically linked via 12 GS linkers next to each other. Thus, despite being bivalent, the specificities against TRAIL-R2 and FOLR1 receptors are only 10-30 Å apart (Blue and Red). Thus, ~67 kDa (TRAIL-R2-VH joined with FOLR1-IgG1) and ~36 kDa (TRAIL-R2-VL joined with FOLR1-VL-Ck) bands are evident upon reduction, which are of different size than heavy and light chains of BaCa-1 antibody. Multiple bands in intact BaCa-3 (native conditions lane) indicate aggregated forms. IgG1 isotype antibody produced a heavy chain (~50 kDa) and a light chain (~25 kDa) after reduction. Fab=Fragment antigen binding, scFv=Single-chain-Fv, Fv=Variable fragment, VL=variable domain light chain, VH=variable domain heavy chain, GS=Glycine-Serine linkers, IA=Intact Antibody, HC=Heavy Chain, LC=Light Chain, NR=Antibody run on gel with non-reducing dye, R=Antibody run on gel with reducing dye, K, H=Knob-hole chains.

Figure 12A:
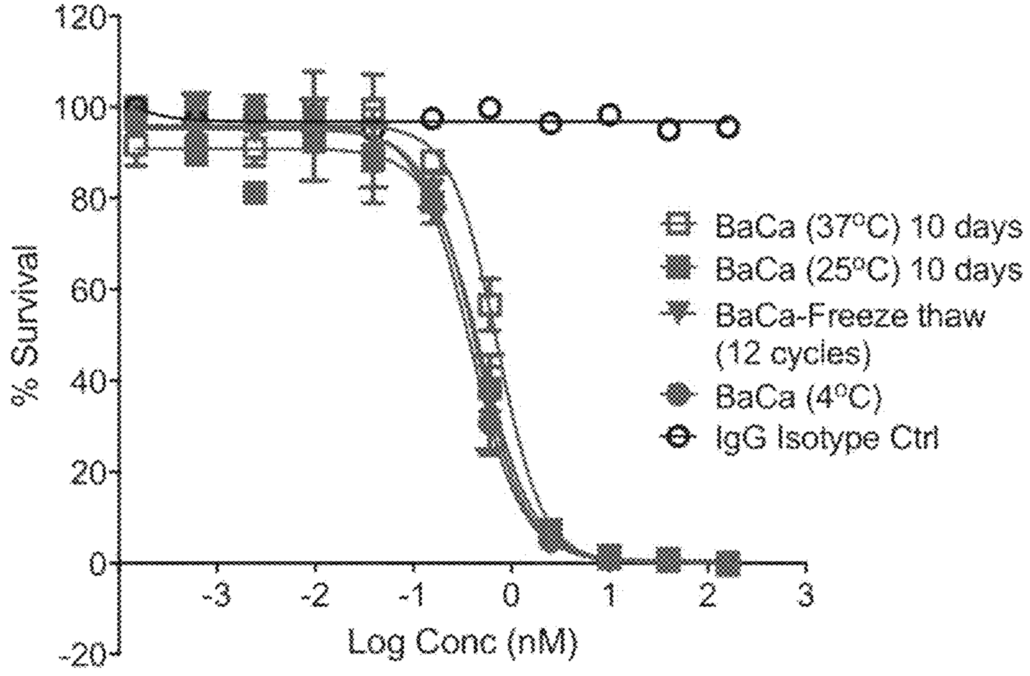

BaCa Antibody In Vitro Stability Assay:

Freshly purified antibodies were dialyzed in PBS using SLIDE-A-LYZER™ 3.5K mini dialysis device (Thermo Scientific, 66330). From the same lot, equal amount of antibodies (in PBS) were distributed in various 1.5 ml tubes. One tube was left at 4° C. and others were stored at 25° C., 37° C., or −80° C. (followed by multiple freeze thaw cycles) as indicated in FIG. 12A. At the end of various incubation periods, all antibodies were quantified and tested for antigen binding and cytotoxicity activity together. As a positive control, farletuzumab and FDA approved adalimumab antibody (standard in our lab) were incubated together and were analyzed for percent monomer.

Binding Studies by ELISA

Binding studies by ELISA Binding specificity and affinity of various described IgG1 subclasses were determined by ELISA using the recombinant extracellular domain of FOLR1 and/or DR5/TRAIL-R2. For coating 96-well ELISA plates (Olympus), the protein solutions (2 pg/ml) were prepared in coating buffer (100 mM Sodium Bicarbonate pH 9.2) and 100 pl was distributed in each well. The plates were then incubated overnight at 4° C. Next day, the unbound areas were blocked by cell culture media containing 10% FBS, 1% BSA and 0.5% sodium azide for 2 hr at room temperature. The serial dilutions of antibodies (2-fold dilution from 50 nM to 0.048 nM) were prepared in blocking solution and incubated in target protein coated plates for 1 hr at 37° C. After washing with PBS solution containing 0.1% TWEEN® 20 surfactant, the plates were incubated for 1 hr with horseradish peroxidase (HRP) conjugated anti-human IgG1 (Thermo Scientific, A10648). Detection was performed using a two-component peroxidase substrate kit (BD biosciences) and the reaction was stopped with the addition of 2 N Sulfuric acid. Absorbance at 450 nm was immediately recorded using a Synergy Spectrophotometer (BioTech), and background absorbance from negative control samples was subtracted. The antibody affinities (Kd) were calculated by non-linear regression analysis using GraphPad Prism software.

Binding Studies by BioLayer Interferometry (BLI)

Binding kinetics measurements were performed using Bio-Layer Interferometry on FortéBio Red OCTET® 96 bioanalytical instrument (Pall). Biotin-Streptavidin based sensors were employed for the studies. Recombinant Fc linked antigens; DR5-Fc and FOLR1-Fc were biotinylated using EZ-LINK™ Sulfo-NHS-SS-Biotin biotinylation reagent (Thermo Scientific 21331) following the manufacturer's instructions. Unbound Sulfo-NHS-SS-Biotin was removed via dialysis in PBS. For kinetic analysis biotinylated antigens (1 μg/mL) were immobilized on streptavidin (SA) biosensors (Pall) for 300 sec to ensure saturation. The 96-well microplates used in the OCTET® bioanalytical instrument were filled with 200 μL of test antibody dilutions or buffer per well. All interaction analyses were conducted at 35° C. in PBS buffer containing 2 mg/ml BSA. Following a washing step, association and dissociation measurements were carried out using serial dilutions of antibodies (4 to 160 nM). Kinetic parameters ($K_{on}$ and $K_{off}$) and affinities (KD) were analyzed using Octet data analysis software, version 9.0 (Pall).

In Vitro Cell Viability Assays

Figure 2A:
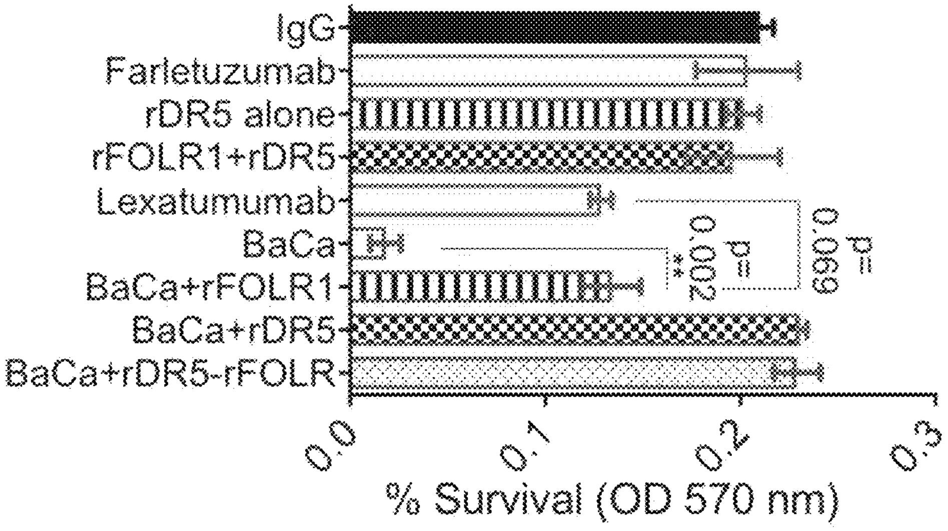
Figure 2B:
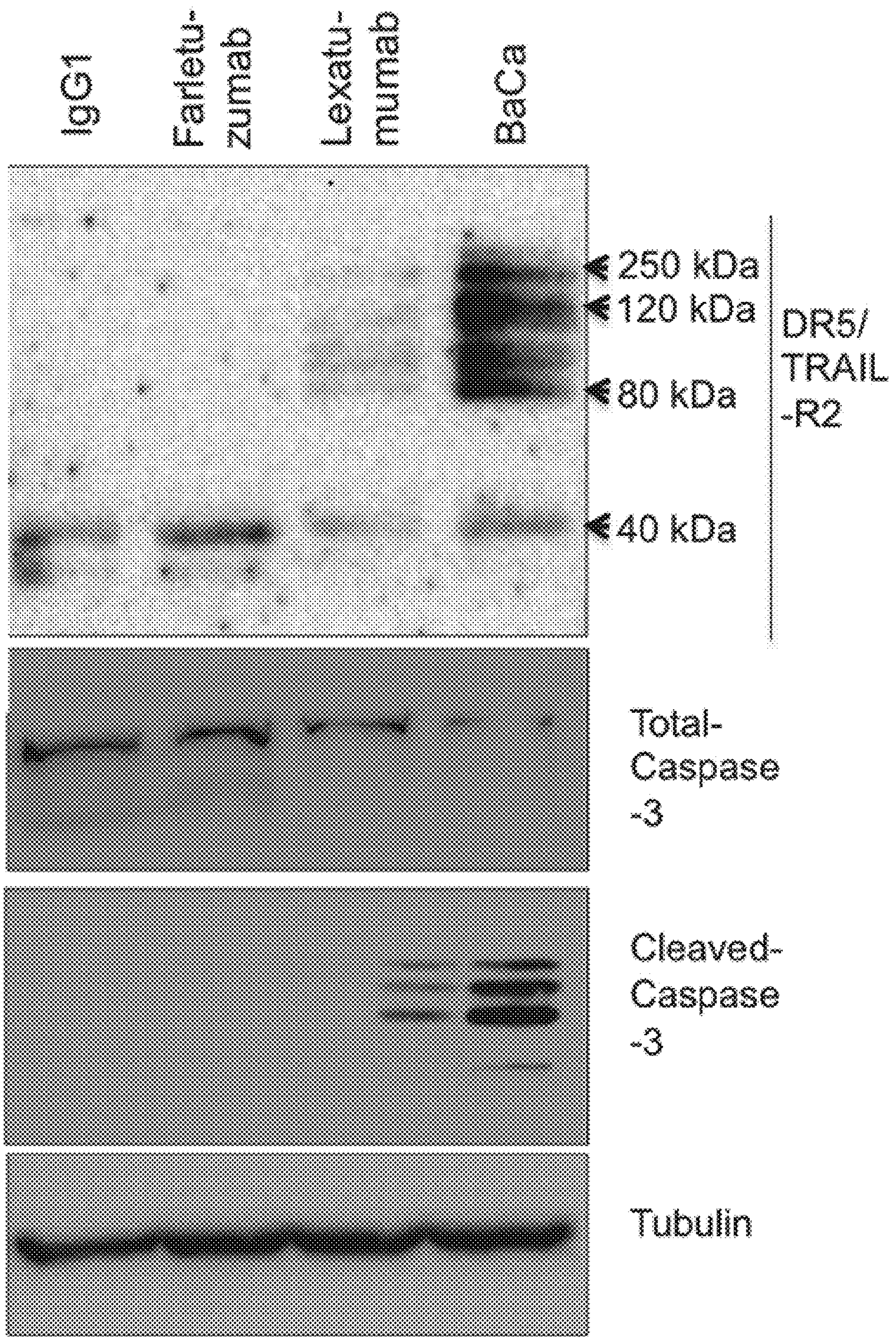
Figure 2C:
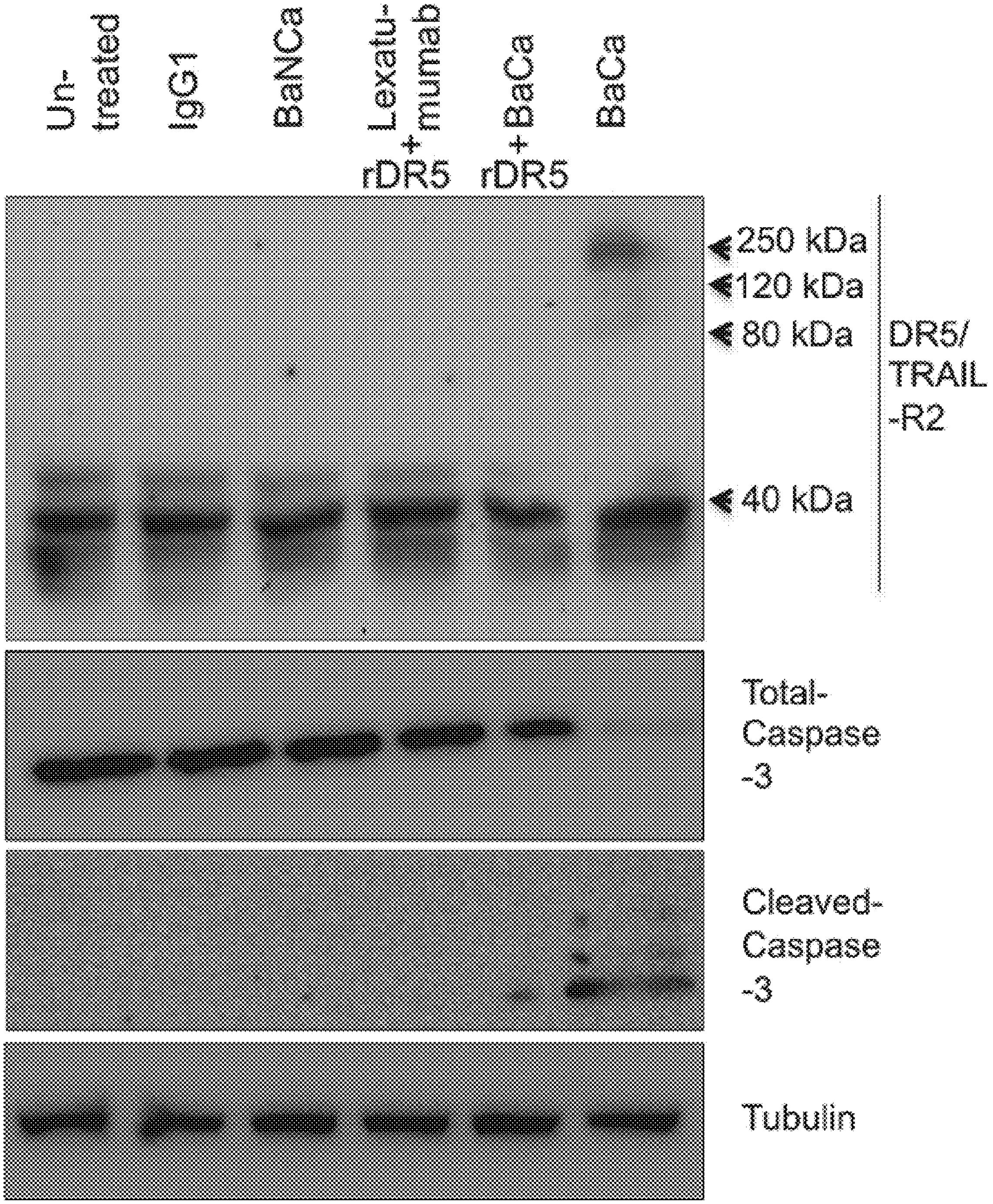
Figure 2D:
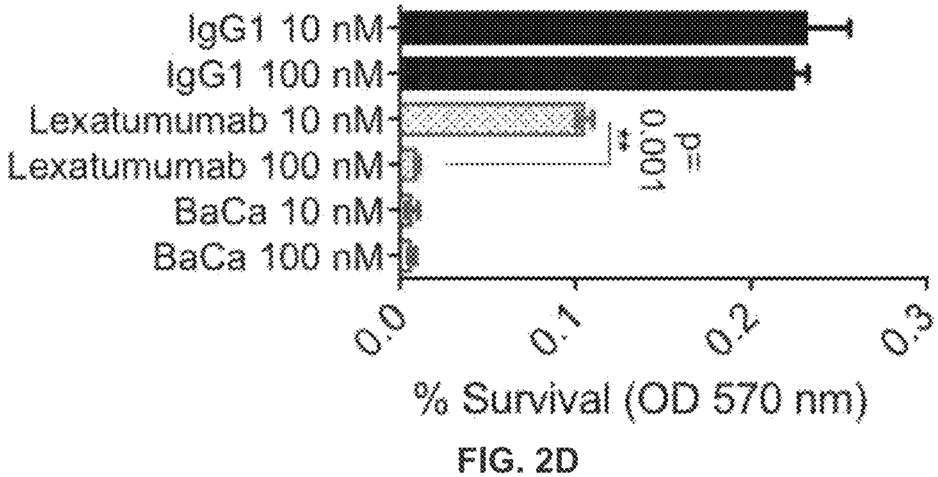
Figure 2E:
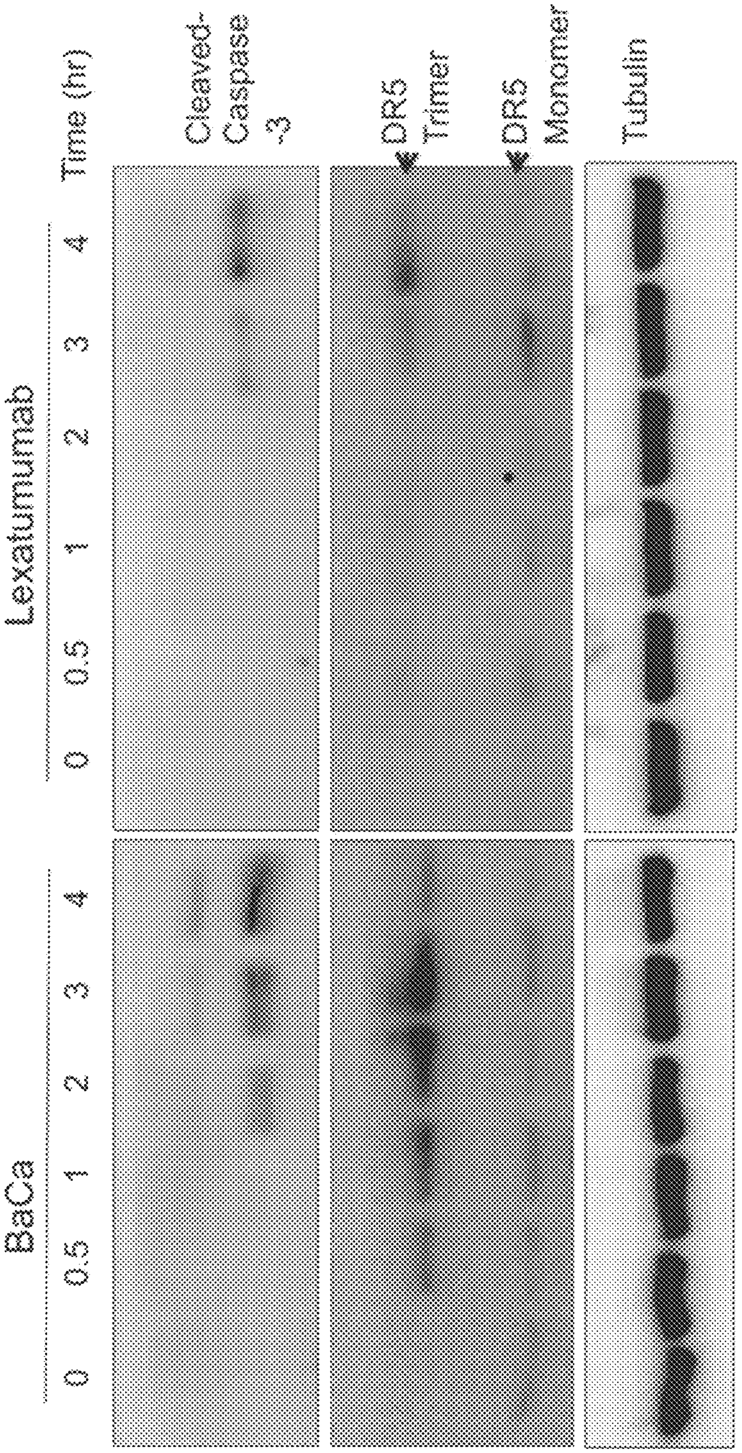
Figure 2F:
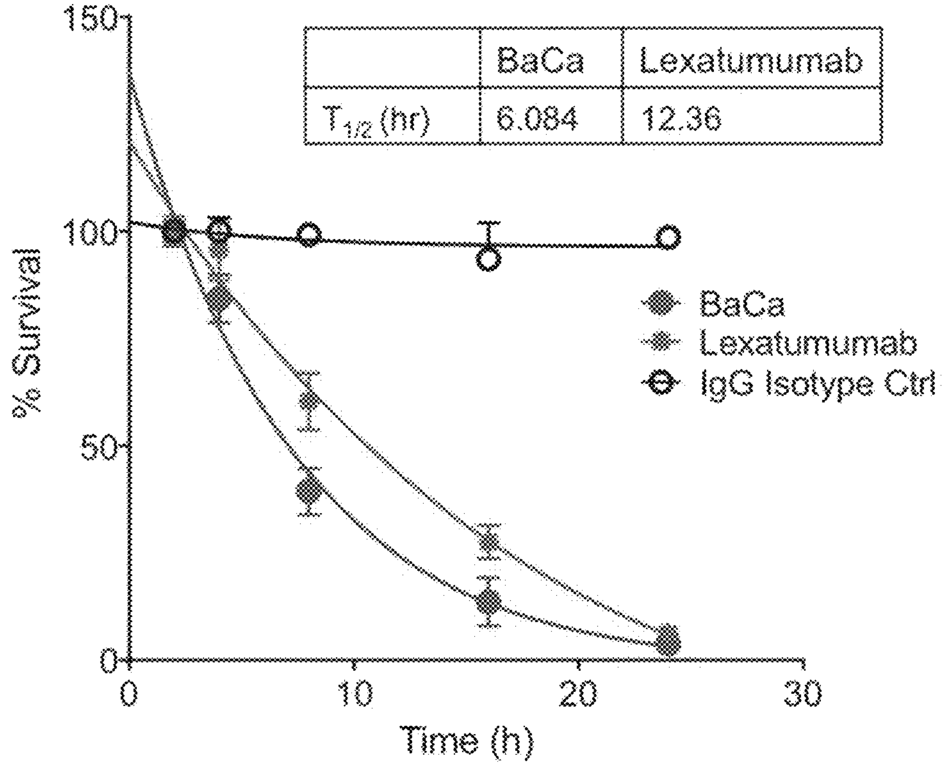
Figure 2G:
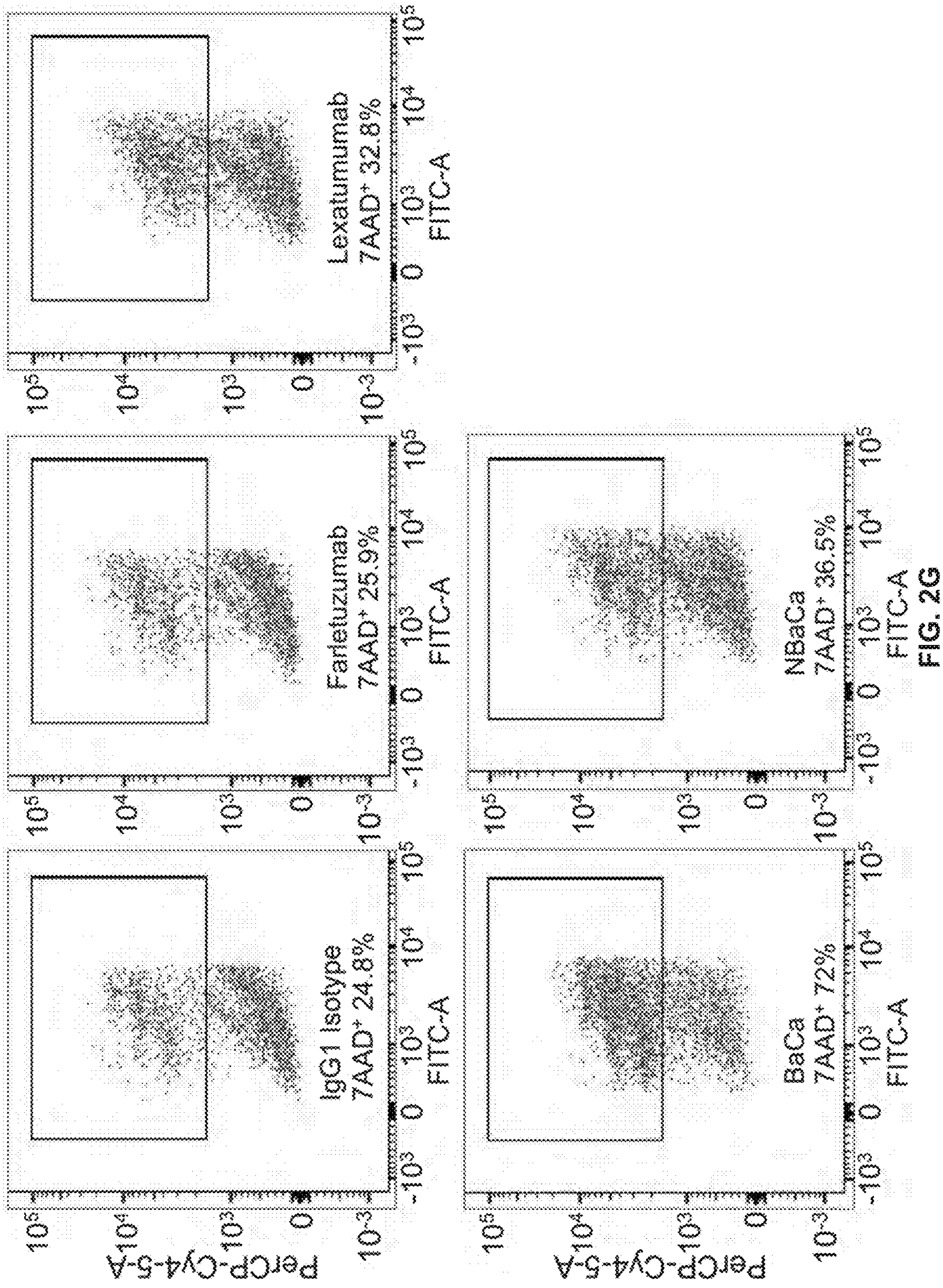
Figure 2H:
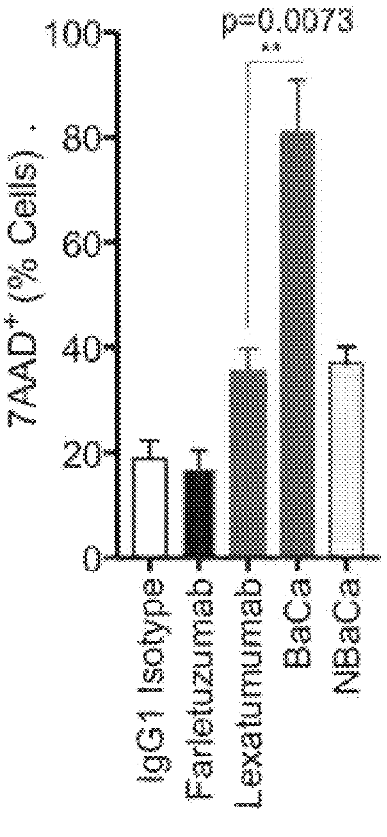

Cell viability following lexatumumab, AMG-655, MD5-1, BaCa, NBaCa, muBaCa etc. treatments (as indicated in various figures) either alone or in combination with human Apo2L/TRAIL ligand or in combination with an antihuman (Fab') 2 reagent were determined using the ALAMARBLUE™ cell viability assays and MTT cell proliferation assays as per manufactured protocols. Briefly, cells (indicated cells in main text or Figure legends) were treated with increasing concentration of various antibodies (as indicated) along with relevant positive and negative control antibodies for 6 hr, 24 hr or 48 hr (as indicated according to the experiment). For each cell killing assay, the Figures show the representative profiles from n=2-4 with different cultured confluency. Whenever used for immunoblotting, following antibodies treatment, caspase-3 processing in tumor cells was monitored using selective antibodies that recognize cleaved human caspase-3 or total caspase-3 (Cell signaling, 9661 and 9668). TRAIL-R2 receptor in oligomerization was determined using immunoblotting assays (cell signaling Rabbit mAb, 8074). Cell viability was additionally examined by flow cytometry based apoptotic detection methods using 7-aminoactinomycin D (7-ADD) exclusion from live cells. Statistical significance for 7AAD FACS studies was calculated using unpaired two-tailed parametric Welch's t-test. FIG. 2H: Lexatumumab vs BaCa p-0.0073 (**). Error bars show±SEM.

$IC_{50}$ Determination $IC_{50}$ values were calculated using MTT assays. Cells were seeded in 96 well plates. Next day, when cultures became adherent, cells were incubated for 48 hr at 37° C. (5% $CO_2$) with the increasing concentrations of the antibodies or drug (such as cisplatin) as indicated in experiments. Before treatments, various antibodies were dialyzed into PBS and typically had a pH of 7.5. Values obtained after reading the 96 well plates were normalized to IgG control antibody control and $IC_{50}$ values were calculated using nonlinear dose-response regression curve fits using GraphPad Prism software. The final results shown in the histograms were obtained from three independent experiments. Whenever provided in the curves, the error bars show ±SEM.

Western Blotting

Cells were cultured overnight in tissue culture-treated 6-well plates prior to treatment. After antibody treatment for 48 hr (or indicated time), cells were rinsed with PBS and then lysed with RIPA buffer supplemented with protease inhibitor cocktail (Thermo Scientific). After spinning at 14000 rpm for 30 min cleared protein lysates were quantified by Pierce BCA protein assay kit. Western blotting was performed using the Bio-Rad SDS-PAGE Gel system. Briefly, 30 pg of protein was resolved on 10% Bis-TRIS® gels and then transferred onto PVDF membrane. Membranes were blocked for one hour at room temperature in TBS+0.1% TWEEN® surfactant (TBST) with 5% non-fat dry milk. Membranes were probed overnight at 4° C. with primary antibodies. Membranes were washed three times in TBST and then incubated with anti-rabbit or anti-mouse secondary antibodies (1/10,000 dilution, coupled to peroxidase) for 1 hr at room temperature. Membranes were then washed three times with TBST and Immunocomplexes were detected with SUPERSIGNAL® West Pico Chemiluminescent Substrate (Thermo Fisher Scientific). Images were taken using a Bio-Rad Gel Doc Imager system. Primary antibodies are listed in the Key Resource Table.

Pre-Neutralization Assays

Whenever indicated throughout the manuscript or in Figure legends, variable domain pre-neutralization of BaCa antibody (or lexatumumab, or farletuzumab) was carried out to confirm the function of FOLR1 anchor in gain in cytotoxicity. For in vitro and in vivo studies, indicated antibodies and recombinant antigens (rFOLR1, rDR5 etc.) were incubated together (either 1:1 or 1:5 ratio, as indicated) at 37° C. for 1 hr shaking on a platform. As a control, indicated non-preneutralized antibodies were also incubated at 37° C. for 1 hr shaking on a platform either with PBS alone or with recombinant non-specific proteins such as rHER2 or rGFP. Following pre-neutralization, antibodies were either used in vitro for cell killing assays, for cellular/tumor lysates generation (immunoblotting), or for live in vivo live imaging etc. as indicated. Statistical significance was calculated using unpaired two-tailed parametric Welch's t-test. The following are the values for FIG. 2A: Lexatumumab vs BaCa+rFOLR1 p=0.6669 (ns), BaCa vs BaCa+rFOLR1 p=0.0022 () and FIG. 2D: Lexatumumab 10 nM vs Lexatumumab 100 nM p=0.0015 (). Error bars show ±SEM.

Liver Accumulation of Antibodies

To examine the liver accumulation of BaCa (HuBaCa) and lexatumumab, 6-8 weeks old weight matched female athymic Nude Foxn1$^{nu}$/Foxn1$^{+}$ mice (envigo) were allowed to develop tumor. When tumor reached ~200 mm$^3$, a single dose (50 μg) of lexatumumab, farletuzumab and BaCa antibodies were injected intravenously (n=6). All injected therapeutic antibodies had LALA mutations in Fc to avoid any interference with FcR binding (Li and Ravetch, 2012). Roughly after 4 days of treatments, mice were euthanized for liver study. Following animal necropsies, liver lysates were prepared in RIPA buffer supplemented with protease inhibitor cocktail (Thermo Scientific). rFOLR1, rDR5 and rHER2 antigens were coated on the 96-well ELISA plate and relative quantity of the antibody in liver lysate was determined by binding experiment as described above (n=6). Quantification of liver accumulation (by ELISA) for each antibody treatment (n=6) was performed by unpaired two-tailed Welch's t-test. The following were the p values: BaCa-rDR5 vs Lexatumumab-rDR5, p=<0.0001 (*), BaCa-rFOLR1 vs Farletuzumab-rFOLR1, p=0.0584 (ns), as shown in FIG. 5**E.

AST/ALT Assays and Hematoxylin/Eosin Staining

To study the hepatotoxic effect of BaCa antibody, female C57BL/6 mice (n=4-5) were treated intraperitoneally with 50 μg of MD5-1, murine BaCa, or IgG1 control (in PBS) at two-day interval for 10 days. At the end of the experiment, serum was isolated from blood samples and assessed for aspartate aminotransferase (AST) and alanine aminotransferase (ALT) levels using Liquid AST (SGOT) reagent set (Pointe Scientific A7561450) and ENZYCHROME™ Alanine Transaminase Assay Kit (Bioassay Systems EALT-100) respectively, as per manufacturer instructions and as described earlier (Takeda et al., 2008). Following blood collection, the mice were perfused with 10% neutral buffered formalin and isolated liver sections were fixed in 10% neutral buffered formalin overnight at 4° C. The paraffin embedding and H&E staining was performed by Research Histology Core here at University of Virginia School of Medicine (National Cancer Institute P30 UVA Center Grant). For AST/ALT assays, p values were determined by unpaired t-test with Welch's correction. ALT: p=0.043 (*), AST: p=0.0274 (*) as shown in FIG. 5.

Flow Cytometry

The cell surface expression of DR4/DR5 was analyzed by flow cytometry. Overnight grown OVCAR-3 cells were trypsinized and suspended in FACS buffer (PBS containing 2% FBS). The single cell suspension was then incubated with primary DR4/DR5 antibodies for 1 hr at 4° C. with gentle mixing. Following the wash with FACS buffer, the cells were then incubated with fluorescently labeled anti-Rabbit antibody for 1 hr. Cells were washed and flow cytometry was performed using FACSCalibur. The data was analyzed by FCS Express (De Novo Software) and FlowJo. Similar FACS studies were performed for farletuzumab, lexatumumab, AMG-655, LK26, MD5-1 and BaCa antibodies whenever necessary (as indicated in text and Figure legends).

Quantitative RT-PCR (qRT-PCR)

For qRT-PCR assays, RNA was extracted using the Trizol Reagent (Invitrogen). cDNA was prepared by amplifying 500 ng of RNA by the SUPERSCRIPT-II™ reverse transcriptase cDNA Synthesis Kit (Life Technologies). Quantitative PCR was performed using PowerUp SYBR® cyanine dye Green Master mix (Applied Biosystems) following manufacturer's instructions. Data was analyzed using StepOneV2.0 software (Applied Biosystems). The relative expression levels were normalized to GAPDH. Statistical significance was determined by an unpaired t-test with Welch's correction using Graph Pad Prism software (n=4). Error bar show±SEM. Appropriate forward and reverse primers were used for: huFOLR1, huTRAIL-R2, GALNT3, and FUT3.

Live Imaging and Tissue Distribution Studies

Figure 12B:
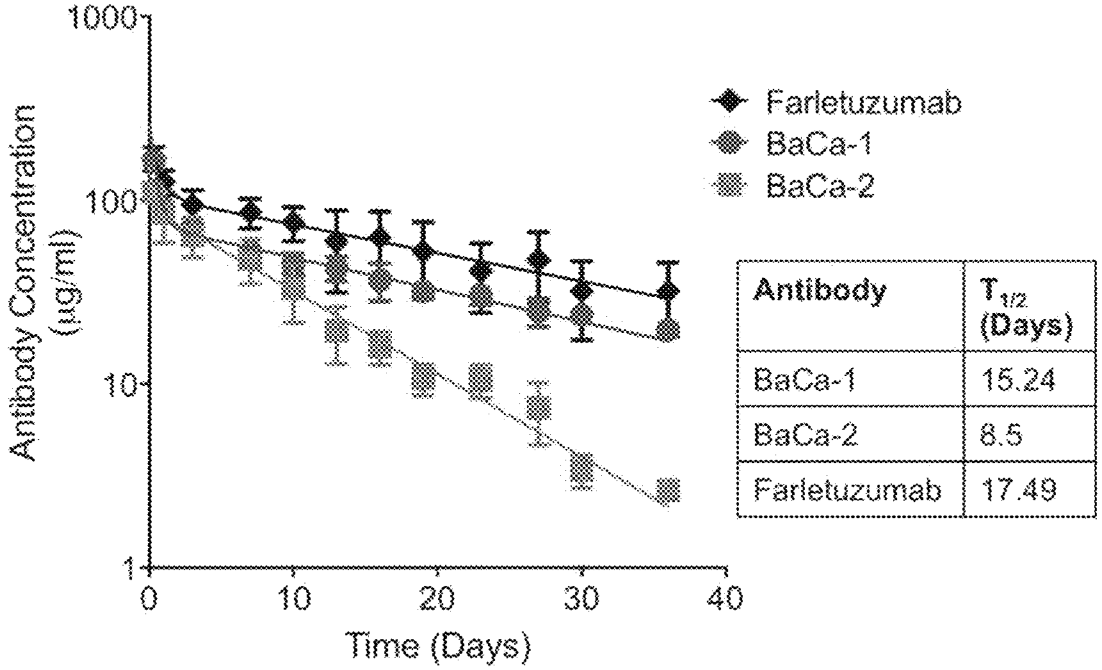
Figure 12C:
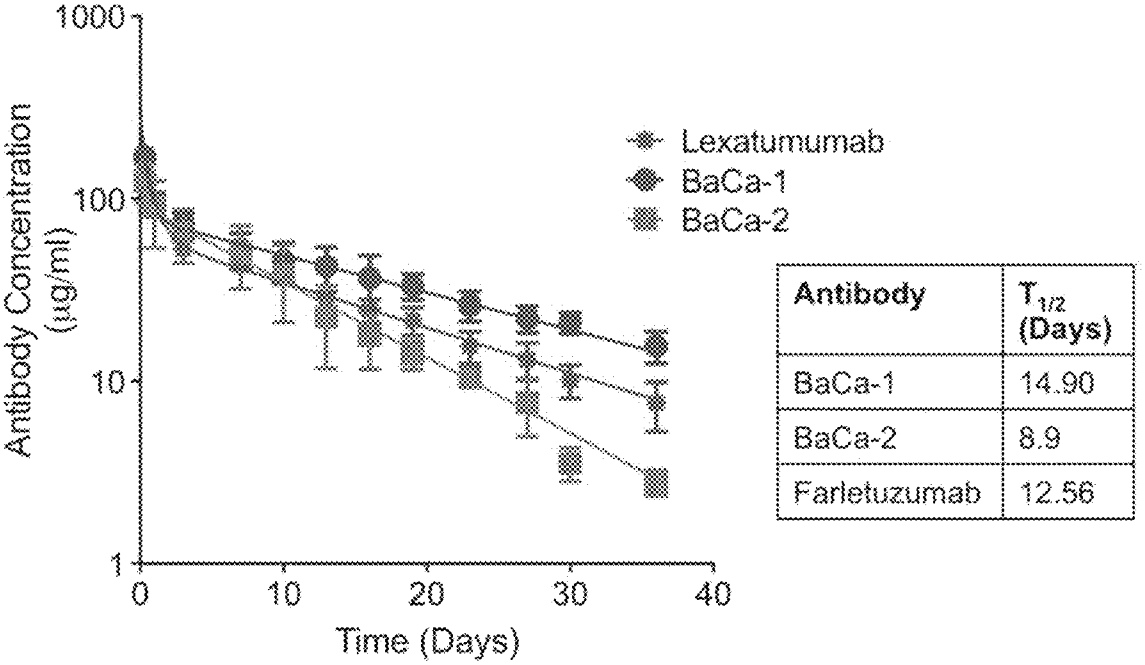
Figure 12D:
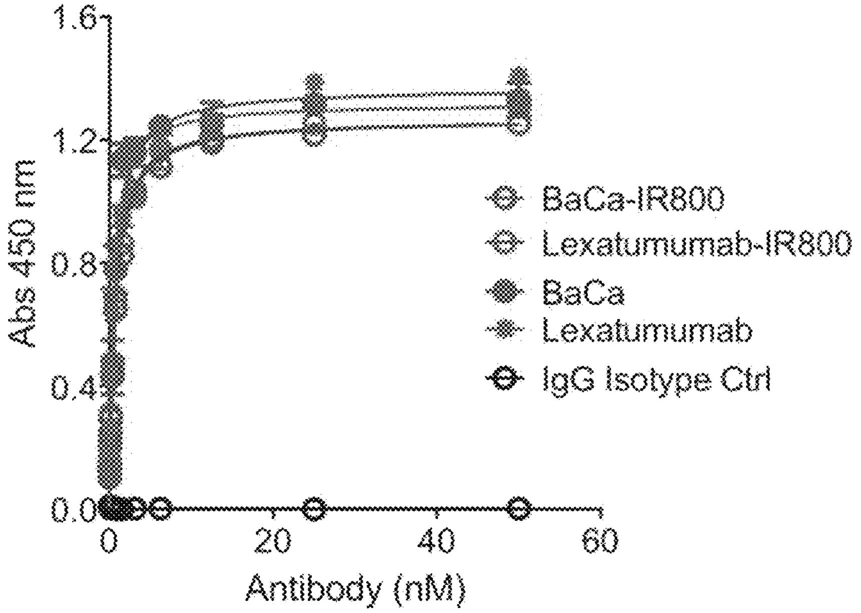

Indicated antibodies (Lexatumumab, HuBaCa, MD5-1, MuBaCa and IgG1 control) were tagged with IRDYER 800CW NHS Ester (Li-Cor) fluorochrome. Briefly, antibody solutions were prepared in 100 mM phosphate buffer pH 8.5 and mixed with IRdye 800-NHS (0.04 mg dye per 1 mg of antibodies). The conjugation was carried out at 20° C. for 2 hr and unconjugated dye was separated by dialysis in PBS. It was confirmed that IR800 dye labeling did not affect antibody binding to respective antigens for all the antibodies (FIG. 12D and data not shown). Subcutaneous tumors were generated by injecting either 1×10$^6$ OVCAR-3 cells, 2×10$^6$ OVCAR-4, $2\times10^6$ Colo-205, or $5\times10^5$ MC38 cells (in MATRIGEL® matrix) respectively as described in earlier section. OVCAR-3 or MC38 tumors were grown in athymic nude or WT C57BL/6 mice respectively. 25 pg of fluorescent antibody was injected intravenously (IV) as indicated and the mice were imaged after 24 hr using Xenogen IVIS® spectrum In Vivo Imaging System (PerkinElmer Inc.). For tissue distribution studies, various organs (Spleen, Kidney, Liver, lungs and stomach) were isolated along with tumor and exposed directly to the excitation wavelength (772 nm) to monitor the tissue specific fluorescent signal of each antibody. Radiant efficiency (fluorescent intensity) was calculated after subtracting the fluorescent signal from IgG1 (IRDYER 800 labeled) injected animals in the exactly similar conditions. Statistical significance of differential distribution was determined by an unpaired t-test with Welch's correction using Graph Pad Prism software (n=4). Error bar show±SEM. Following are the p values in FIG. 5, Kidney: p-0.5893 (ns), Liver: p=0.0283 (*), Lung: p=0.0750 (ns), Spleen: p=0.2H8 (ns), Tumor: p=0.0026 (**).

Serum Half-Life

Animal care and all experiments performed were in accordance with IACUC guidelines and have been approved by university ACUC authorities. Male and female CD1 mice (4-6 weeks, 20-25 grams) were randomized in groups (See FIGS. 12B, 12C) and injected intravenous with 25 μg of antibodies in a total volume of 100 μl. The blood samples (50-100 μl) were collected by pricking tail vein at indicated time interval and allowed to clot at room temperature for 30 min as described earlier (Hutt et al., 2012). Clotted blood was centrifuged at 13000×g for 20 min at 4° C. and serum sample was stored in −80° C. in small aliquots. As described above, serum concentration of antibodies were determined using ELISA. Sets of 4-5 mice were used for each antibody study. The serum half-lives of antibodies were determined using one phase exponential decay equation model fitted by non-linear regression of % concentration of leftover antibody in serum vs. time using Prism version 5.01 software (Graph Pad Software, Inc.). For comparison, the antibody concentration of first collected serum sample (30 min) was set as 100% and relative % concentrations of each antibody were determined for different time point earlier (Hutt et al., 2012). Next, we transformed the data in semi-log plot (shown in FIGS. 12B, 12C). For that, we recalculated the serum antibody concentrations in μg/ml for each time point and analyzed by two-phase exponential decay model fitted by log antibody concentrations vs. time using Prism 5.01 software. The serum half-life calculations of the elimination phase were determined using the formula $t_{1/2}=\ln 2/\beta$, where $\beta$ is the negative slope of the line. Very similar values were obtained with semi-log plot and two-phase exponential analyses.

Avidity Assays

To assess the collective binding affinity of the lexatumumab, farletuzumab and various BaCa antibodies, both of the target antigens rFOLR1 and rTRAILR2 were coated in 96 well plates in 5:1 ratio. 20 nM of parental and BaCa antibodies (BaCa-1, BaCa-2, BaCa-3) were allowed to bind the target protein for 60 min at 37° C. Wells were then washed with PBS and exposed to 6 M urea for 10 min as described earlier (Levett et al., 2005). After washing, the concentrations of remaining antibodies were determined as described above. A relative avidity index was calculated for each antibody by representing the percentage of reactivity remained in urea treated wells compared to PBS treated wells. Statistical significance was determined by an unpaired t-test with Welch's correction using Graph Pad Prism software (n=4), p=0.0286(*). Error bar show ±SEM.

Nude Tumor Xenograft Studies

Figure 6A:
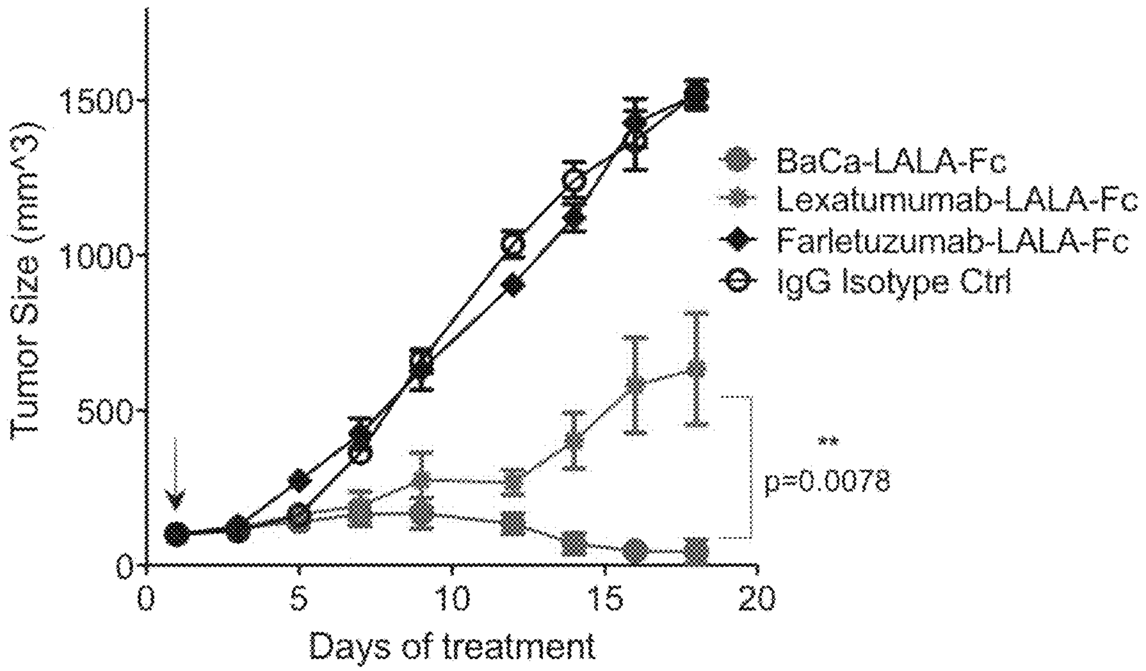

All animal procedures were conducted under the accordance of University of Virginia Institutional Animal Care and Use Committee (IACUC) with approved protocol (#4112). Following different cell lines were used for tumor nude xenograft studies: 1) OVCAR-3 cells, 2) OVCAR-4 cells, and 3) Colo-205 cells. Since OvCa is a female pathology, female animals were given a 2 weeks acclimation period after arrival to the vivarium and all animal procedures were conducted under institutional policies. Weight and age (6-8 weeks old) matched female athymic Nude Foxn1$^{nu}$/Foxn1+ (Envigo) mice were injected subcutaneously (SC) in their right flank with indicated cell lines in Matrigel MATRIGEL® matrix. $1\times10^6$ OVCAR-3 cells, $1\times10^6$ COLO-205 cells or $2\times10^6$ OVCAR-4 cells were injected in 100 μl volume. Colo-205 cells formed tumors between 2-3 weeks, while both OVCAR-3 and OVCAR-4 produced tumors after ~3-4 weeks. For antitumor efficacy studies, mice bearing ~100 $mm^3$ tumors weight matched animals were randomly assigned into groups and injected (either 25 μg or indicated different dose) either intraperitoneally or intravenously (as indicated in Figure legends) three times per week with lexatumumab IgG1 (WT-Fc or KO-Fc or E267 mutation as indicated), farletuzumab IgG1 (WT-Fc or KO-Fc or E267S mutation as indicated), BaCa antibody (WT-Fc or KO-Fc or E267 mutation as indicated) or IgG1 isotype control (WT-Fc or KO-Fc or E267 mutation as indicated). Tumors were measured in two dimensions using a caliper as described previously (Graves et al., 2014; Wilson et al., 2011). Tumor volume was calculated using the formula: $V=0.5axb^2$, where a and b are the long and the short diameters of the tumor respectively. (n=4-6 animals were used for each therapeutic antibody injection). The p values are determined by two-tailed paired Wilcoxon Mann-Whitney test. FIG. 6A: BaCa-LALA-Fc vs Lexatumumab-LALA-Fc, p=0.0078 (), FIG. 6**B: BaCa-LALA-Fc vs Lexatumumab-LALA-Fc, p=0.0156 (*), FIG. 6C: BaCa-S267E-WTFc vs BaCa-S267E-LALA-Fc, p=0.0781 (ns).

Surrogate Tumor Xenograft Studies

Figure 6B:
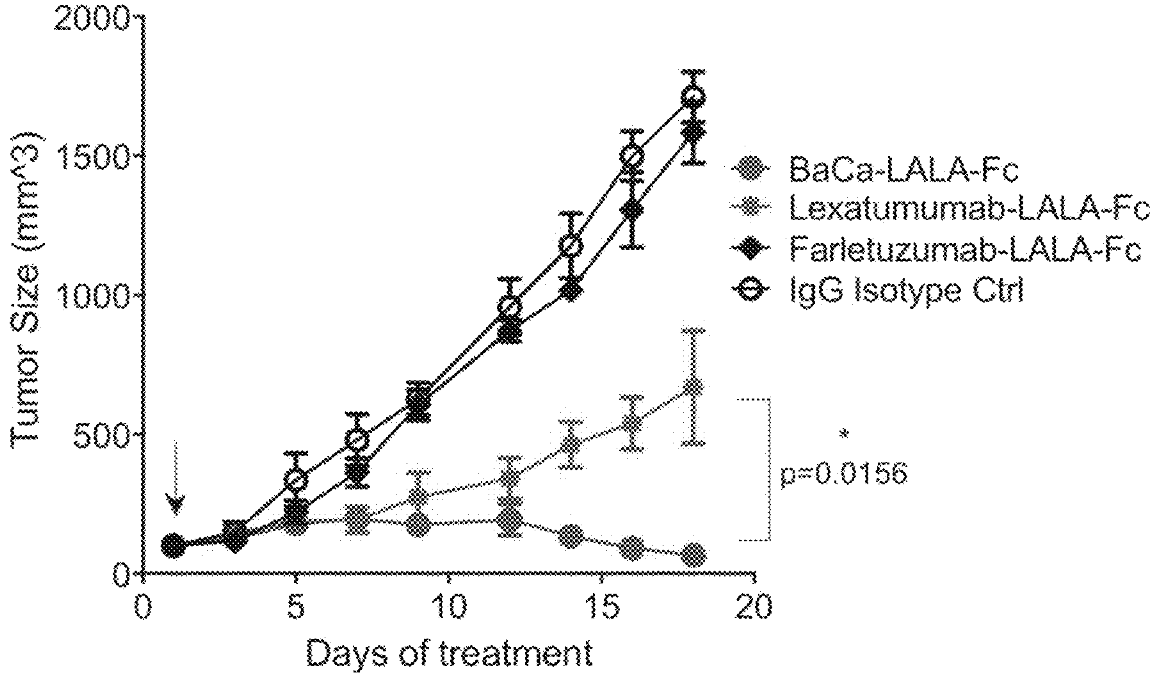
Figure 6C:
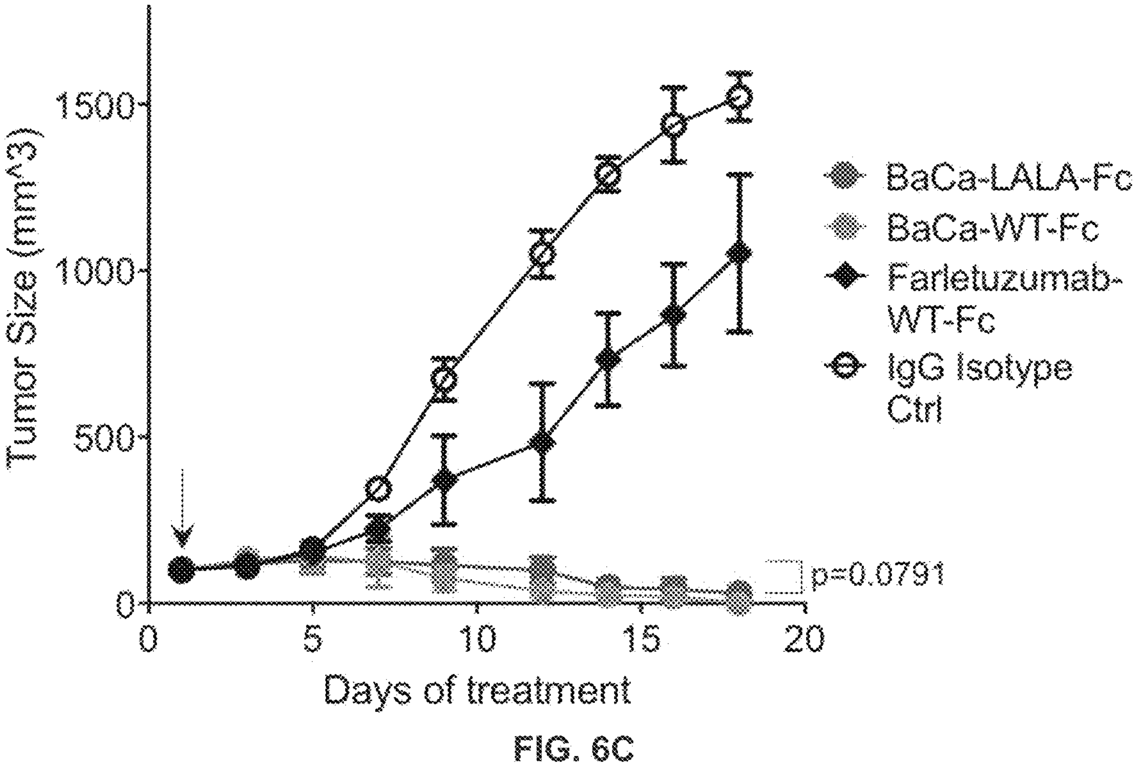

All animal procedures were conducted under the accordance of University of Virginia Institutional Animal Care and Use Committee (IACUC) with approved protocol (#4112). Since OvCa is a female pathology, female mice (C57BL/6J) were used for surrogate xenograft studies. MC38 cells were used for surrogate tumor grafts. 6-8 weeks old female littermate of matched size and weight C57BL/6J mice were injected subcutaneously (SC) in their right flank with $0.5\times10^6$ MC38 cells lines in MATRIGEL® matrix. MC38 cells consistently formed tumors within 2-3 weeks as described (Takeda et al., 2008). For tumor regression studies, mice bearing ~100 $mm^3$ tumors were (after matching tumor size, n=4-6) randomly assigned into groups and injected with therapeutic antibodies (25 μg dose) intraperitoneally three times per week. For surrogate efficacy studies, MD5-1, muBaCa or chiBaCa and IgG1 control were engineered with KO-Fc and S267E mutations. Tumors were measured three times a week and volumes were calculated as the product of three orthogonal diameters similar to nude animal studies as described in previous section. The p values are determined by two-tailed paired Wilcoxon Mann-Whitney test. FIG. 6F: MD5-1 vs MuBaCa, p=0.0312 (*), FIG. 6G: ChiBaCa vs MD5-1, p-0.745, ns). For Biochemical analysis of tumors, mice were euthanized when tumor diameter reached >100 mm. For in vivo caspase-3 activity and comparison, tissues were harvested and processed as described earlier (n=2) (Li and Ravetch, 2012; Wilson et al., 2011).

Cisplatin Resistant Patient Derived Xenografts (PDXs) Efficacy Studies

Mice and surgical procedures: All animal procedures were conducted under the approval of the Institutional Animal Care and Use Committee (IACUC) of the University of Virginia (#4111). Procedures with mice were conducted in collaboration with the University of Virginia Molecular Assessments and Preclinical Studies (MAPS) Core Facility. Adult (6-8 weeks of age) female SCID C.B-17/IcrHsd-Prkdc (Envigo, Dublin, VA) mice were given a 2 week acclimation period after arrival to the facility where they were maintained on a 10:14 light: dark schedule (lights on at 6am) in a dedicated immune compromised housing room for mice with filter top cages, distilled H20 and a diet optimized for immune compromised mice consisting of every other week feeding of Teklad LM-485 irradiated standard rodent diet (Envigo, 7912) and UNIPRIM® antibiotic (Envigo, TD.06596). For surgical implantation, mice were administered a cocktail of Ketamine (60-80 mg/kg) and Xylazine (5-10 mg/kg) intraperitoneally and prepped for sterile surgery using aseptic technique. A small dorsal incision was made and the skin undermined along the flanks of each mouse to prep the site for subcutaneous implantation of tumor. Previously frozen cisplatin resistant patient-derived xenograft (PDX) tumors were implanted bilaterally into the flanks and the incision site was closed with wound clips or skin adhesive. PDX tumor from this model was confirmed to be human by RNA-Seq alignment to both mouse and human genomes, and by comparing original human tumor sequencing to PDX (data not shown). Mice were monitored after surgery until recovery, and administered analgesic for several days at the end of which wound clips were removed. Mice were monitored closely for tumor growth and overall health throughout the study. Tumor take rate was >90%, with 13 out of 14 mice implanted successfully growing tumor and treated. Mice were treated with PBS, lexatumumab (LALA-Fc) and BaCa (LALA-Fc) antibodies at 5 mg/kg dose, as indicated, and tumor measurements were carried out as described in earlier sections. The p values are determined by two-tailed paired Wilcoxon Mann-Whitney test. FIG. 6I: BaCa vs Lexatumumab, p=0.0020 (**).

Recombinant Antibody Sequences

Sequences are provided above in the Summary of the Invention.

Quantitation and Statistical Analysis

Data, unless indicated otherwise, are presented as mean±SEM. In general, when technical replicates were shown for in vitro experiments (FIGS. 3B, 4C, 10A-10H), student t-test was used for statistical analysis and the same experiment was at least repeated once with similar trend observed. When data from multiple experiments was merged into one Figure, statistical significance was determined by an unpaired t-test with Welch's correction using Graph Pad Prism 5.0 software. Quantification of tumor burden in described experiments performed with mice samples were analyzed using Wilcoxon Mann-Whitney test. For comparative therapeutic antibody in vivo efficacy analysis (FIGS. 6A, 6B, 6C, 6E, 6F, 6G), on average, tumor bearing mice (n=4-6) were quantified and group comparison from animals injected with indicated antibody (such as BaCa vs Lexatumumab, muBaCa vs MD5-1) was performed and calculated with 95% confidence with the two-tailed paired nonparametric t-test. Tumor growth curves are displayed as mean±SEM. For all the statistical experiments p values, $p<0.05$ (*), $p<0.01$ () and $p<0.001$ (*) were considered statistically different whereas specific p values indicated otherwise or "ns" indicates non-significant.

Results—

Generation, Characterization, and Lead BaCa Antibody Selection

Various dual-specificity antibody configurations are in clinical trials for cancers (Brinkmann and Kontermann, 2017). To co-target FOLR1 and DR5, we engineered IgG1 Fc-based dual-specificity antibodies for the following 3 reasons: a) there is a defined requirement of FcγRIIB and IgG1 CH2 domain engagement for DR5 agonist antibodies in vivo (Li and Ravetch, 2012; Wilson et al., 2011), b) upon Apo2L ligand binding activated DR5 receptors form a tripartite structure, which is approximately ~40 Å on each side (Mongkolsapaya et al., 1999) and, c) a critical need for effective serum half-life. Hypothetically, IgG1 based antibody is best suited to provide flexible distance and longer serum half-life. Three different bispecific antibodies were generated (FIG. 1A, see STAR methods). The BaCa-1 antibody contains bivalent anti-FOLR1 (Blue) and anti-DR5 (Red) affinities at opposite ends. The BaCa-2 antibody resembles an IgG1 and is similar to CrossMab antibodies of Genentech (Ridgway et al., 1996; Schaefer et al., 2011). In BaCa-3 antibody, unlike BaCa-1, two variable domains of light and heavy chains against FOLR1 and DR5 are genetically fused next to each other via GS linkers (Gu and Ghayur, 2012). Therefore, despite being bivalent, the specificities against DR5 and FOLR1 receptors are only 10-30 Å apart. The amino acid sequences of described antibodies are provided in the STAR Methods. For BaCa-1, BaCa-2 and BaCa-3, a separating linker length of 12 GS, 45 GS, and 9 GS respectively resulted in the highest monomer recovery (Durocher and Butler, 2009) (FIG. 8A). The comparison of various properties of BaCa antibodies is shown in FIG. 1B. BaCa-1 antibody not only had significantly higher cytotoxicity against OvCa cells (FIG. 1C), but also exhibited higher yield and stability over BaCa-2 and BaCa-3. Thus, BaCa-1 was selected as the lead antibody (BaCa or HuBaCa whenever stated) for proof of concept studies. The observed high activity of BaCa-1 antibody could be explained by geometrical flexibility of its affinities against FOLR1 and DR5 (Zhang et al., 2015). The separating distance of >170 Å between two variable domains is largest in BaCa-1 antibody to simultaneously engage FOLR1 and DR5 receptors. It is highly likely that BaCa-3 antibody once bound to FOLR1 (via inner variable domain) was not able to simultaneously engage DR5, by outer domain and vice versa, due to steric hindrance (FIG. 1A). Although BaCa-2 antibody has optimal flexibility to engage FOLR1 and DR5 simultaneously, it is less effective due to being monovalent, potentially resulting in lower avidity optimized binding as described for single Fab fragments (Graves et al., 2014). As expected, when incubated in 96 wells immobilized with rFOLR1 and rDR5 receptors together, lead BaCa antibody showed the highest relative avidity index after treatment with 6 M Urea (FIG. 1D) (Levett et al., 2005).

Figure 1E:
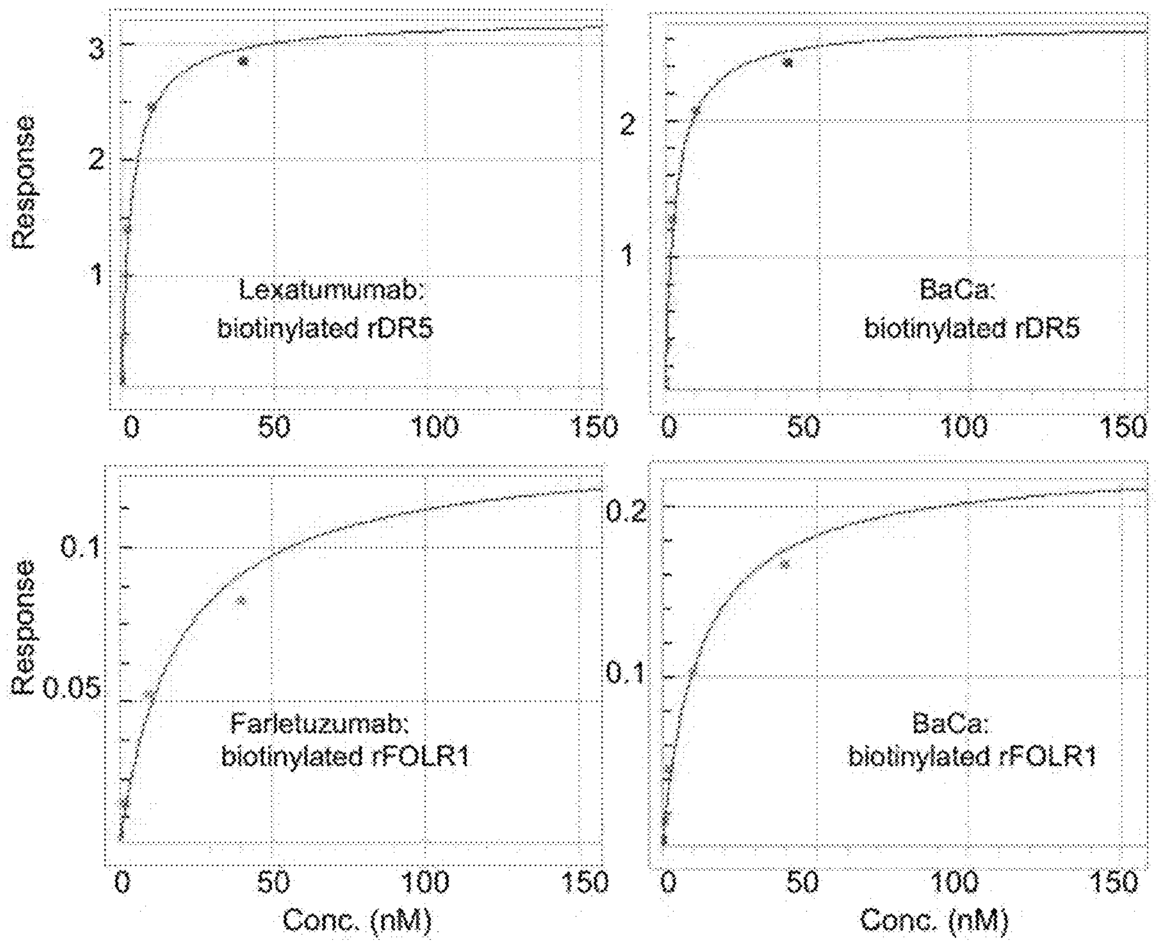
Figure 1F:
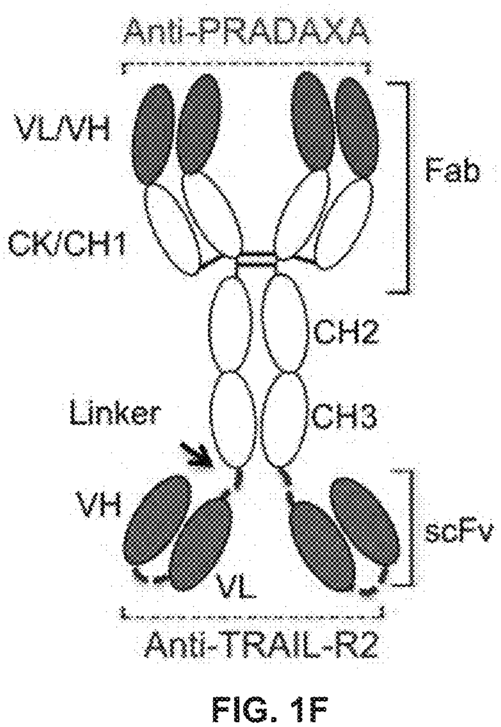
Figure 1G:
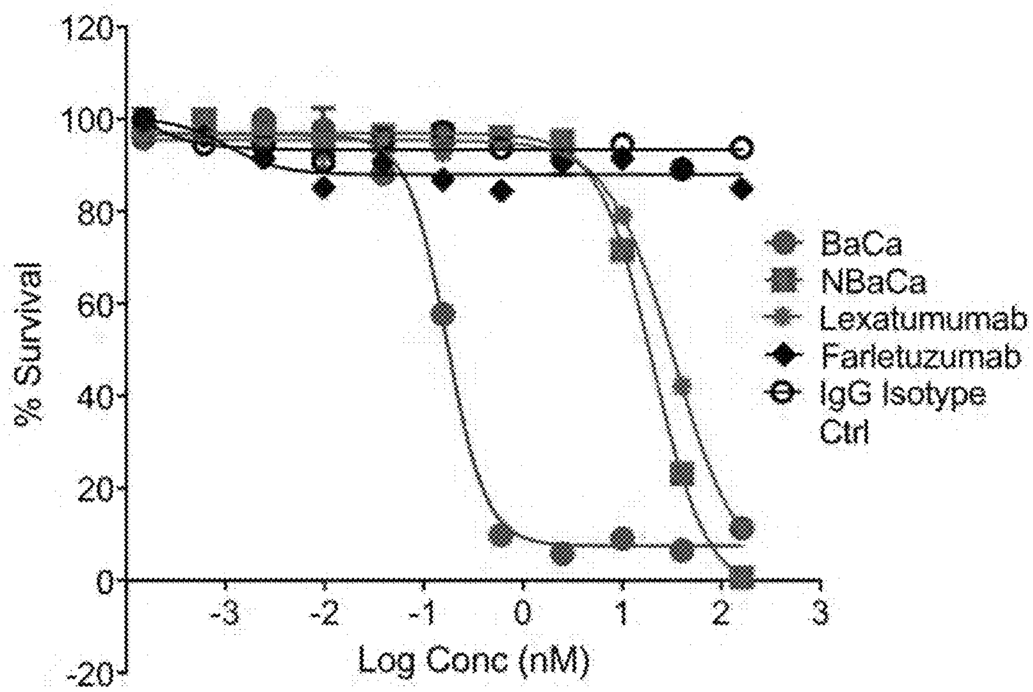
Figure 8C:
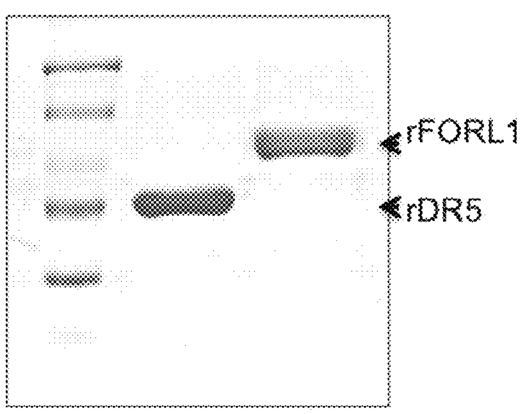
Figure 8D:
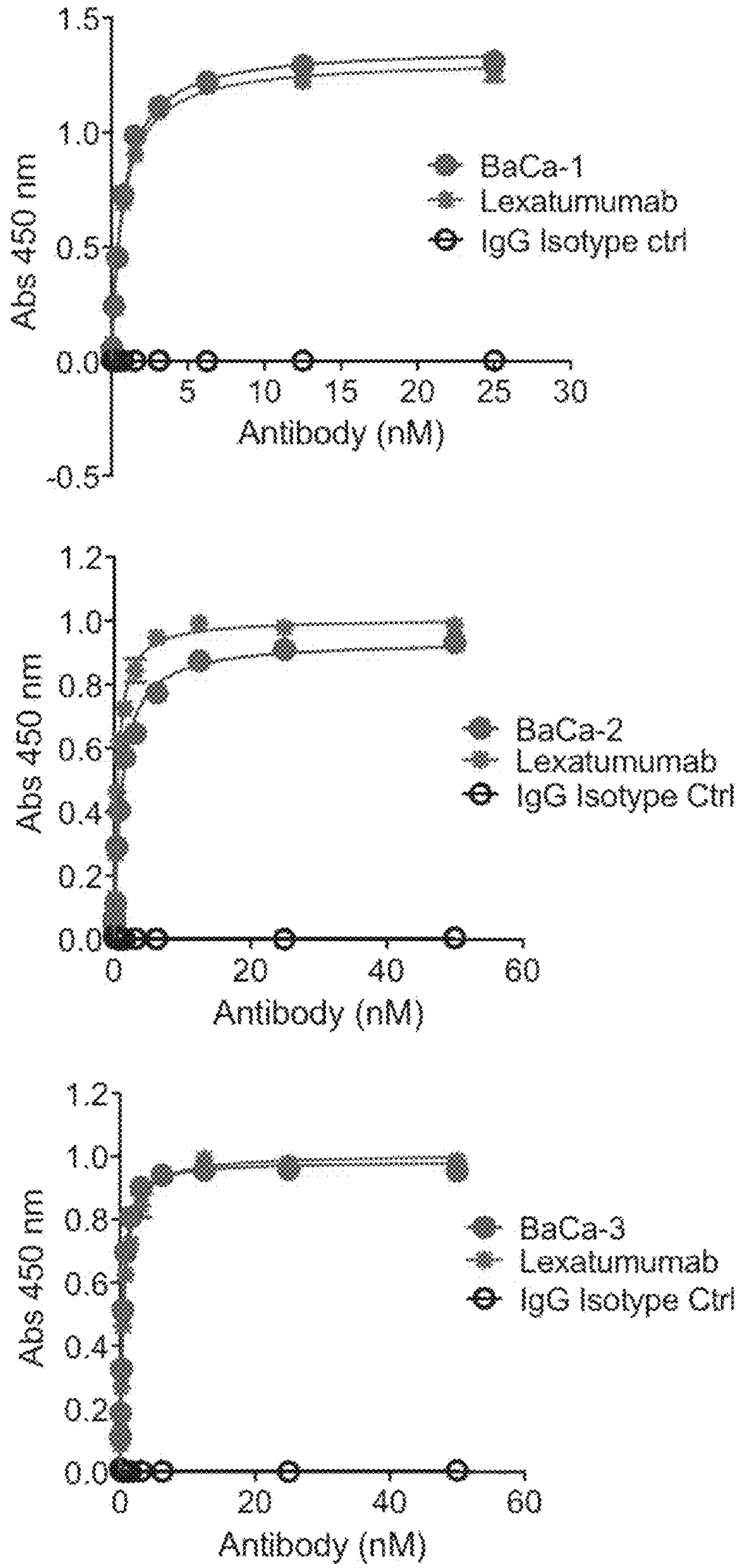
Figure 8E:
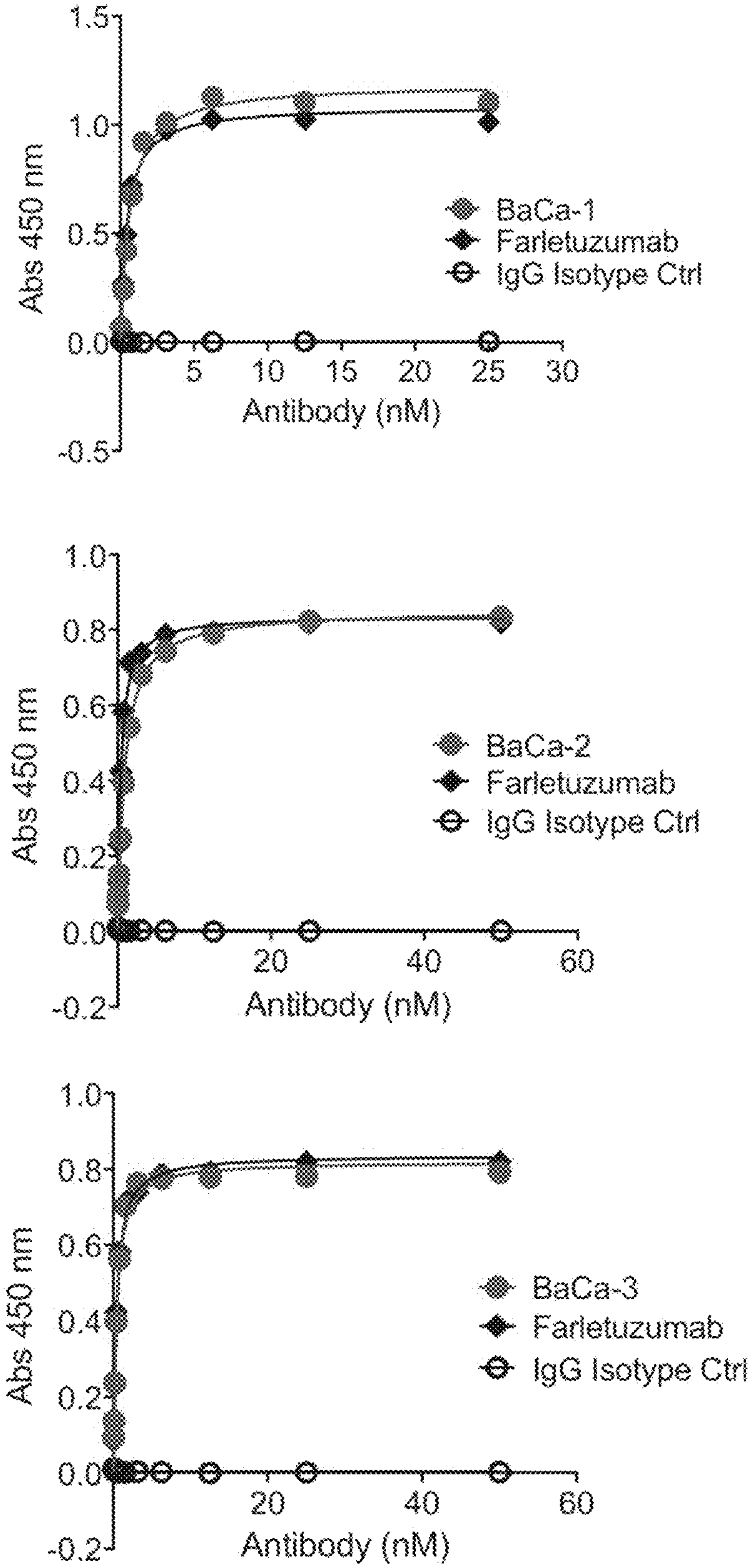
Figure 8F:
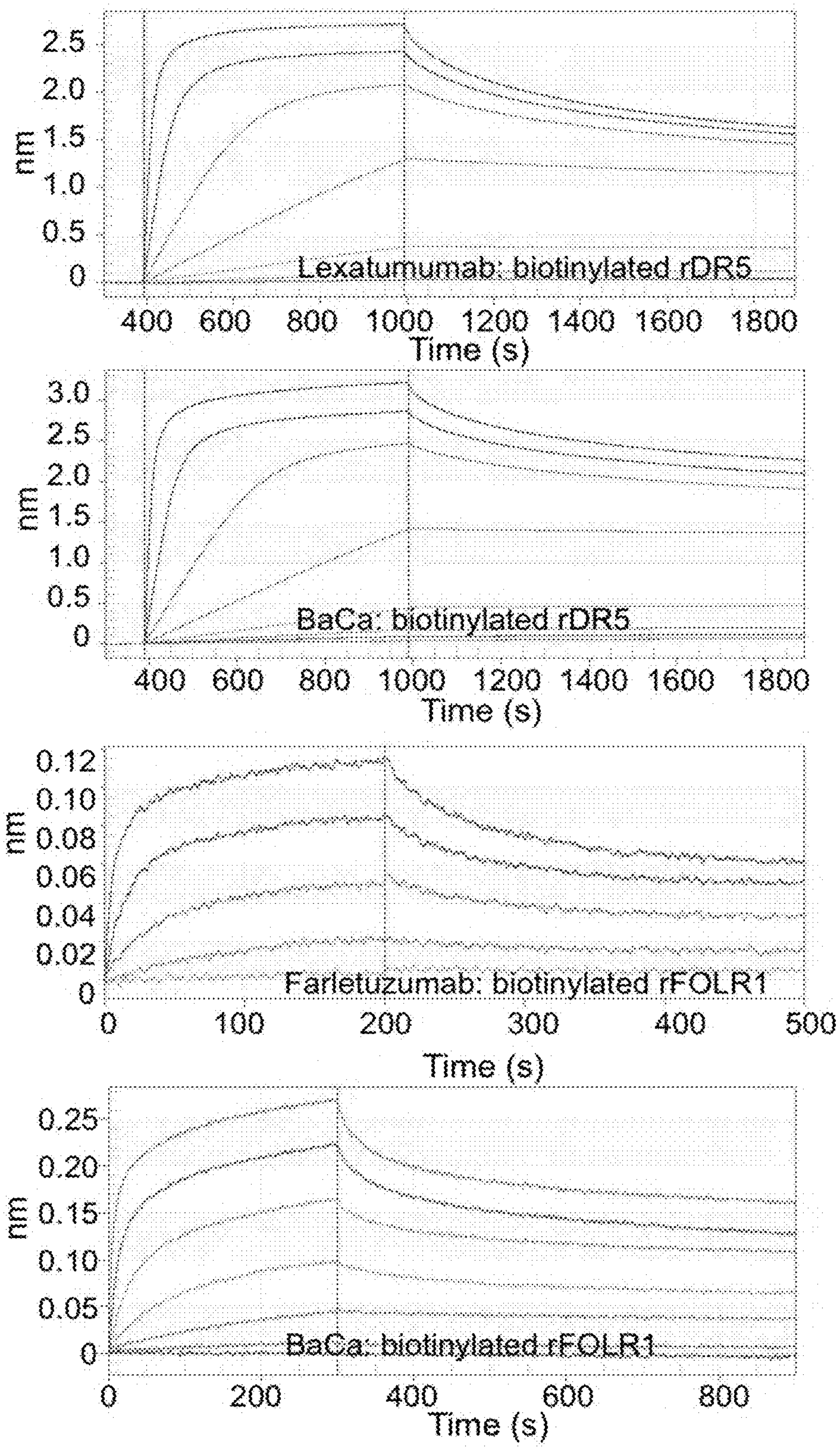
Figures 8G, 9A:
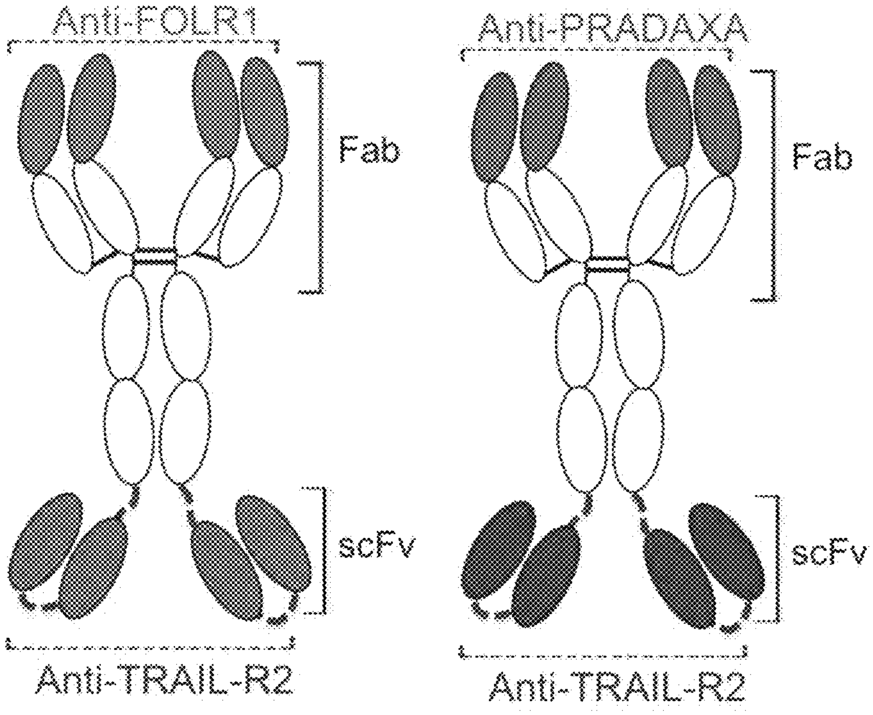
Figure 9B:
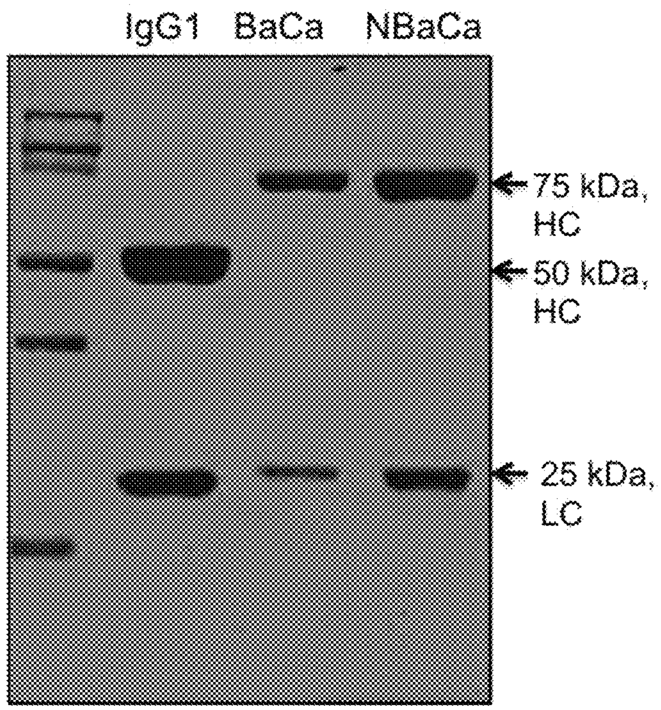
Figure 9C:
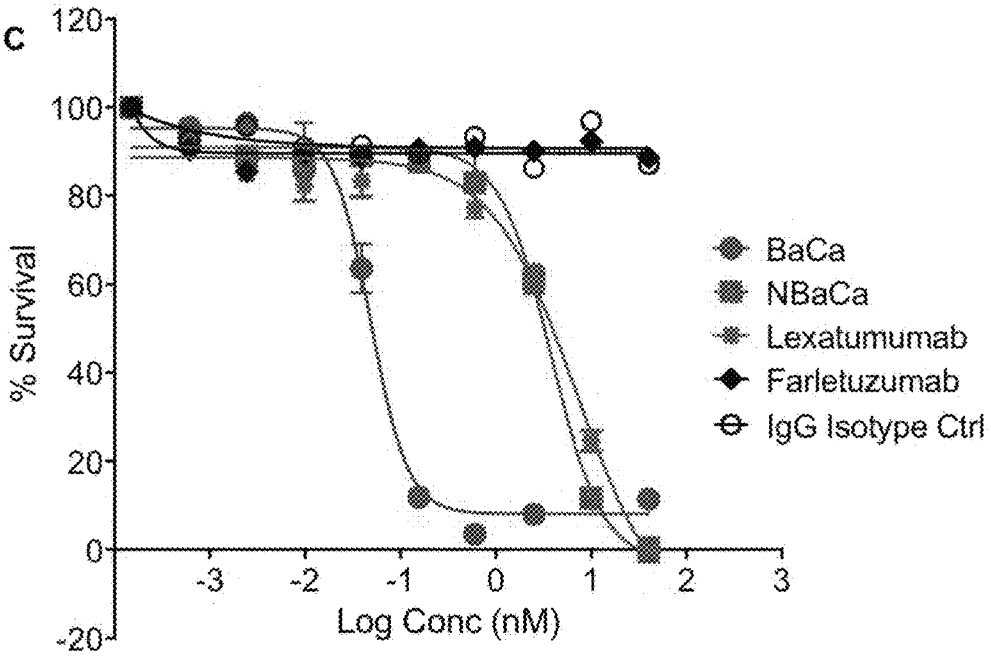
Figure 9D:
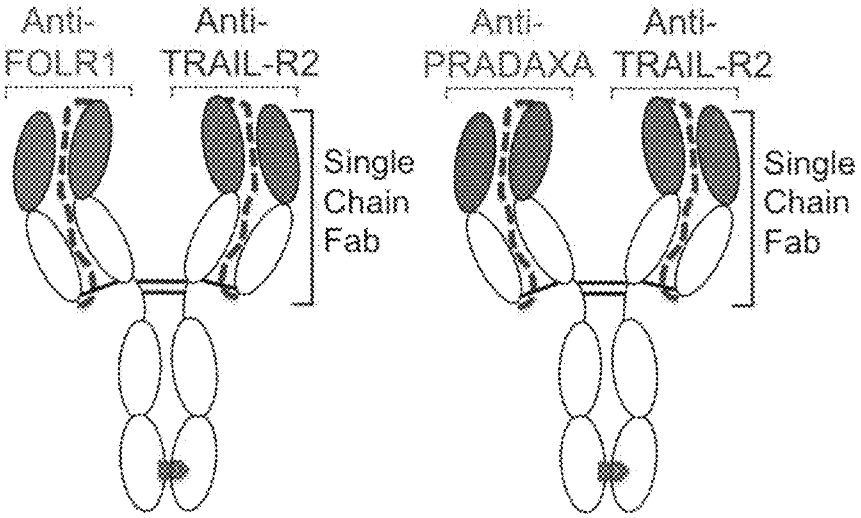
Figure 9E:
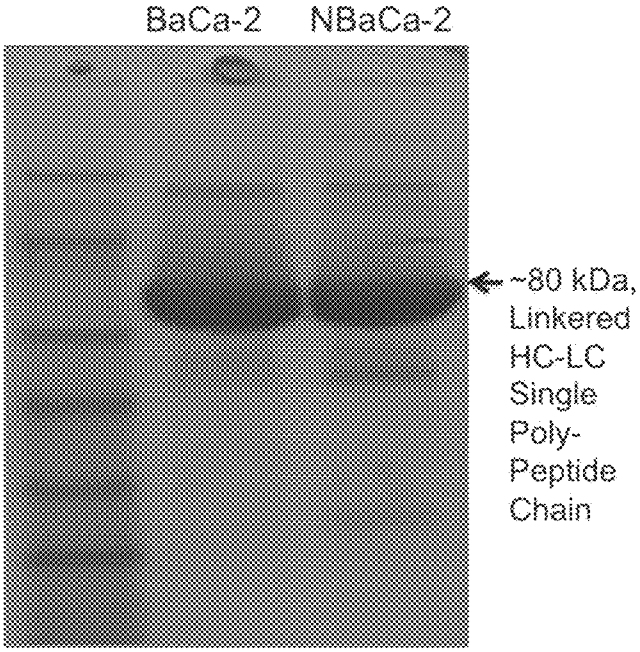
Figure 9F:
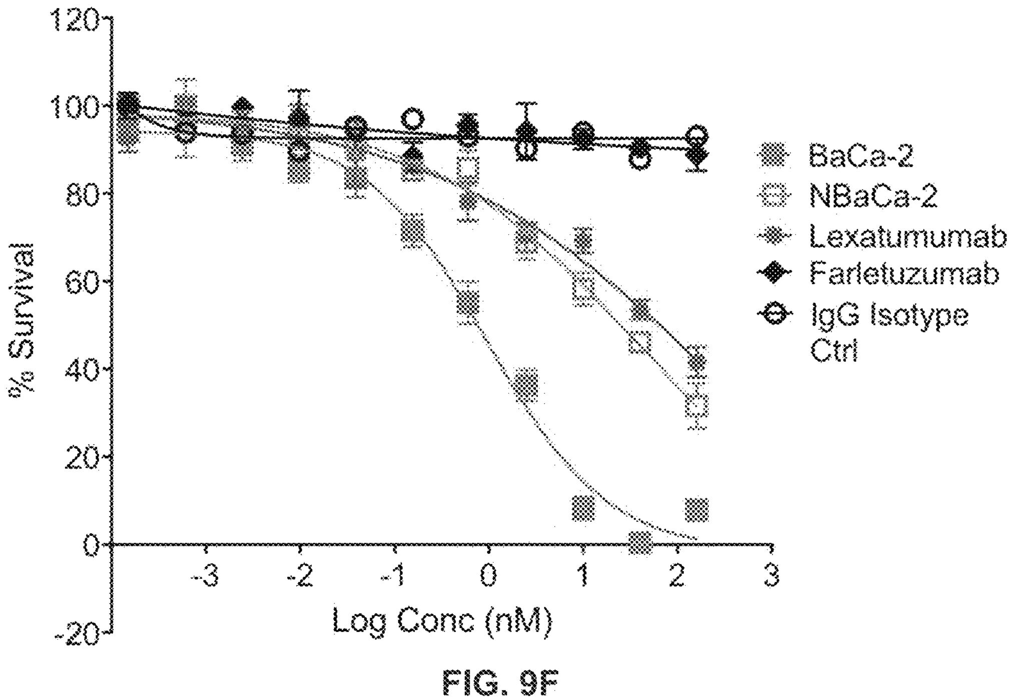
Figure 9G:
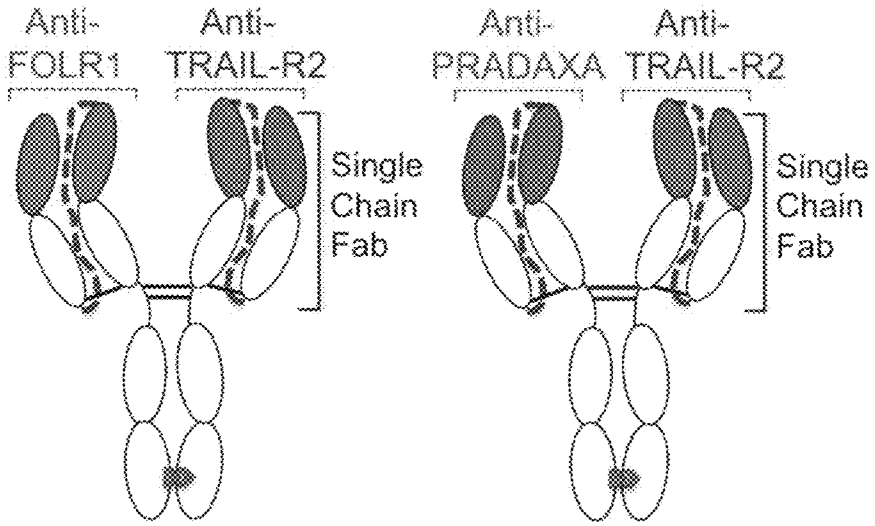
Figure 9H:
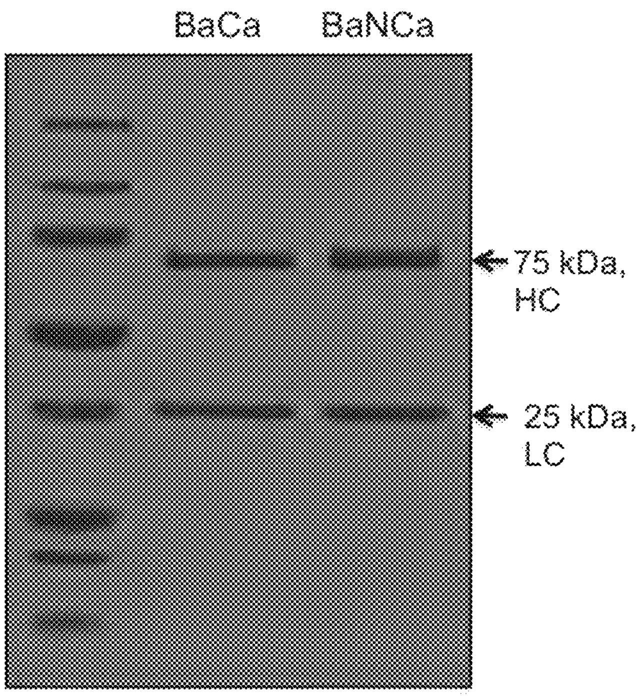
Figure 9I:
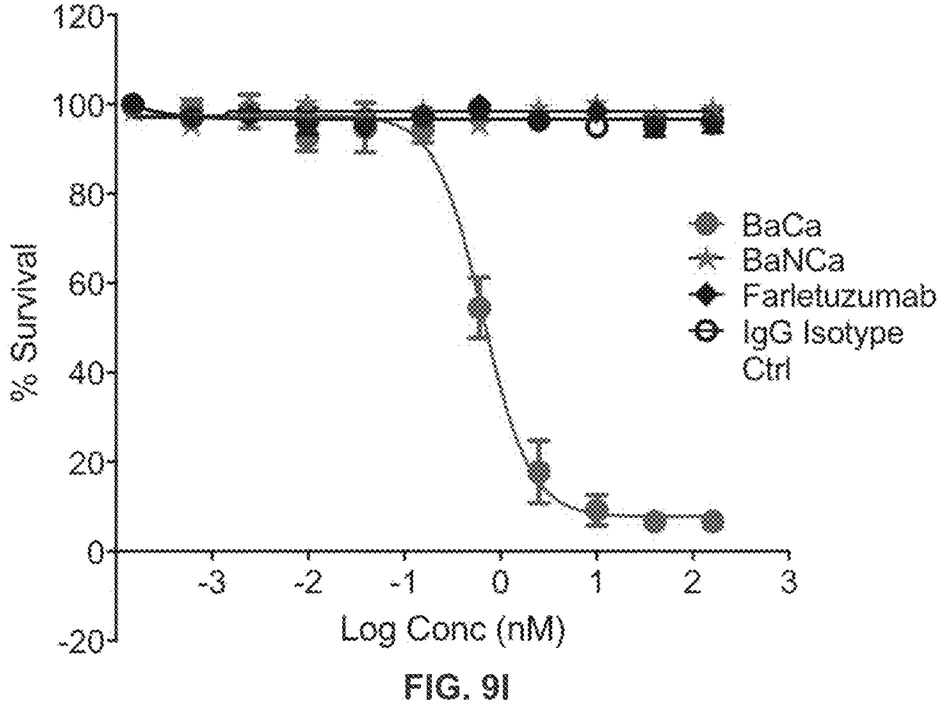

Higher Order DR5 Oligomerization and Activation is Due to Co-Engagement of Target Receptors by BaCa Antibody To test simultaneous receptor co-engagement, we expressed and purified IgG4-Fc conjugated extracellular fragment of recombinant DR5 (r-DR5) and rFOLR1 (FIGS. 8B, 8C). Next, we analyzed the binding affinities of three BaCa and parental antibodies using ELISA (FIGS. 8D, 8E) and subsequently confirmed the binding kinetics of lead BaCa using ForteBio OCTET® HTX bioanalytical instrument (FIGS. 1E, 8F, 8G). The individual receptor binding affinities of BaCa antibodies against FOLR1 and DR5 remained unchanged after conversion into bispecific configurations from their respective mAbs. This suggested that disparity in their cellular cytotoxic activities (IC50 values, FIG. 1B) is due to their varying ability to engage, cluster, and activate DR5. Thus, next we generated Non-anchoring-BaCa (NBaCa) antibodies, where anti-FOLR1 variable domain has been replaced with PRAXBIND® dabigatran-binding agent, an antidote for anticoagulant medication PRADAXA® (Teleb et al., 2016) (FIGS. 1F, 9A, 9B). NBaCa antibody has bivalent binding against DR5 receptor and the same structural framework of a BaCa antibody. When tested, NBaCa antibody was found to be as effective as lexatumumab (FIG. 1G, 9C). Similar loss of cytotoxicity was observed when BaCa-2 antibody was engineered into NBaCa-2 antibody (FIGS. 9D-9F).

Figure 9J:
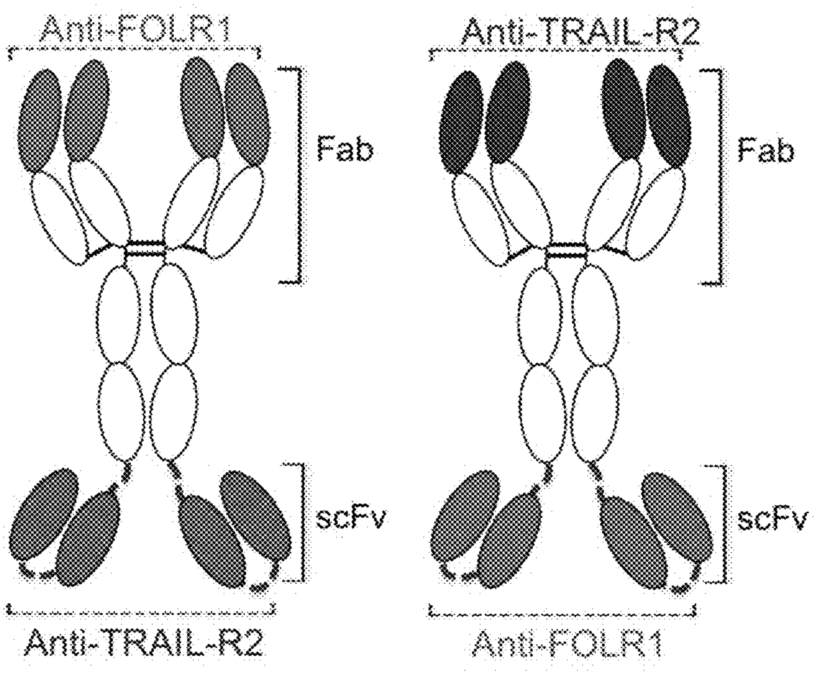
Figure 9K:
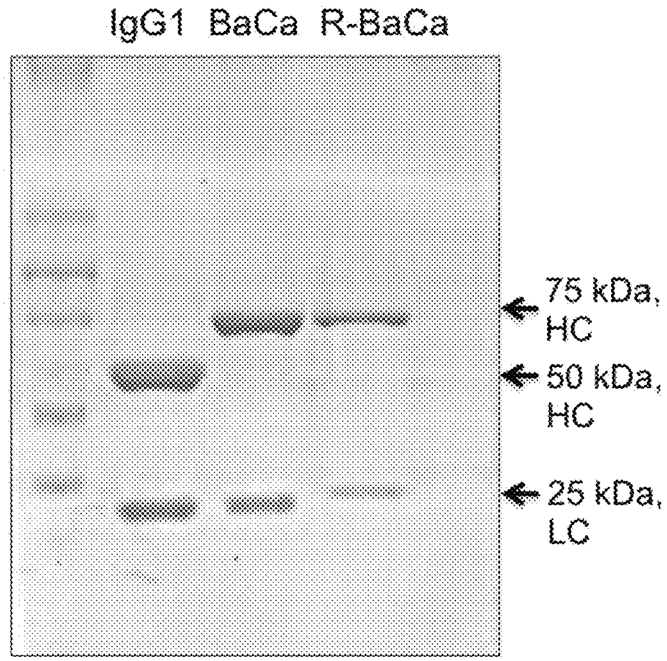
Figure 9L:
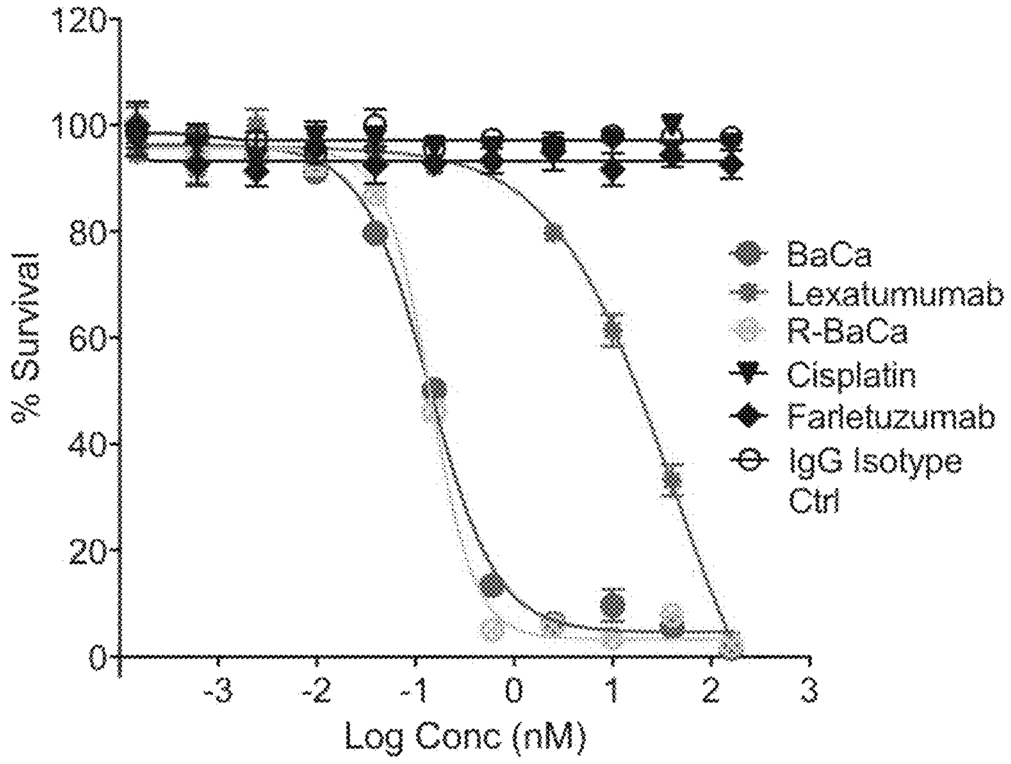

Next, we pre-neutralized BaCa antibody (37° C., 1 hr) with rDR5, rFOLR1 or both before treating the cells. The rFOLR1 pre-neutralization reduced the cytotoxicity of BaCa to lexatumumab, while pre-blocking with rDR5 or loss of rDR5 binding domain abolished the activity (FIGS. 2A, 9G-9I). In comparison to lexatumumab, BaCa treated lysates also showed significantly higher levels of DR5 clustering (in large molecular weight complexes) and cleaved caspase-3 levels (FIG. 2B, C). Next, we tested if the lead BaCa antibody will be effective against FOLR1 anchor enriched OvCa cells independent of DR5 binding being oriented as a Fab or scFv. To this end, we engineered reverse-BaCa (R-BaCa) antibody where anti-FOLR1 affinity is scFv, while anti-DR5 affinity is a Fab. Both BaCa and R-BaCa were equally effective over lexatumumab (FIGS. 9J-9L). Taken together, these sets of findings establish that higher order DR5 receptor clustering, signaling and activity by BaCa antibody is critically dependent on the DR5 co-engagement with the tumor-enriched anchor receptor (FOLR1).

Next, we asked if BaCa antibody would also positively shift the kinetics of apoptotic activation along with the overall superior cytotoxicity. Since both antibodies effectively kill >99% of cells at 100 nM in 48 hr (FIG. 2D), the early time course analysis at 100 nM dose will reflect time dependent apoptotic activation function of DR5 signaling. As shown, BaCa antibody induced DR5 trimerization (120 kDa) and caspase-3 activation within 30 min and 2 hr, while lexatumumab needed 3 hr to do the same (FIG. 2E). In support, BaCa antibody eliminated 50% of the OVCAR-3 cells within 6 hr, while lexatumumab needed ~12 hr (FIG. 2F). Similar kinetic results were obtained in flow cytometry studies (FIG. 2G, H). Importantly, the NBaCa antibody abolished the gained apoptotic kinetics as evident by equal level of 7-AAD+ staining. These findings strengthen that receptor co-engagement by BaCa antibody instigates both kinetically faster and cytotoxically superior DR5 clustering and signaling.

Figure 3A:
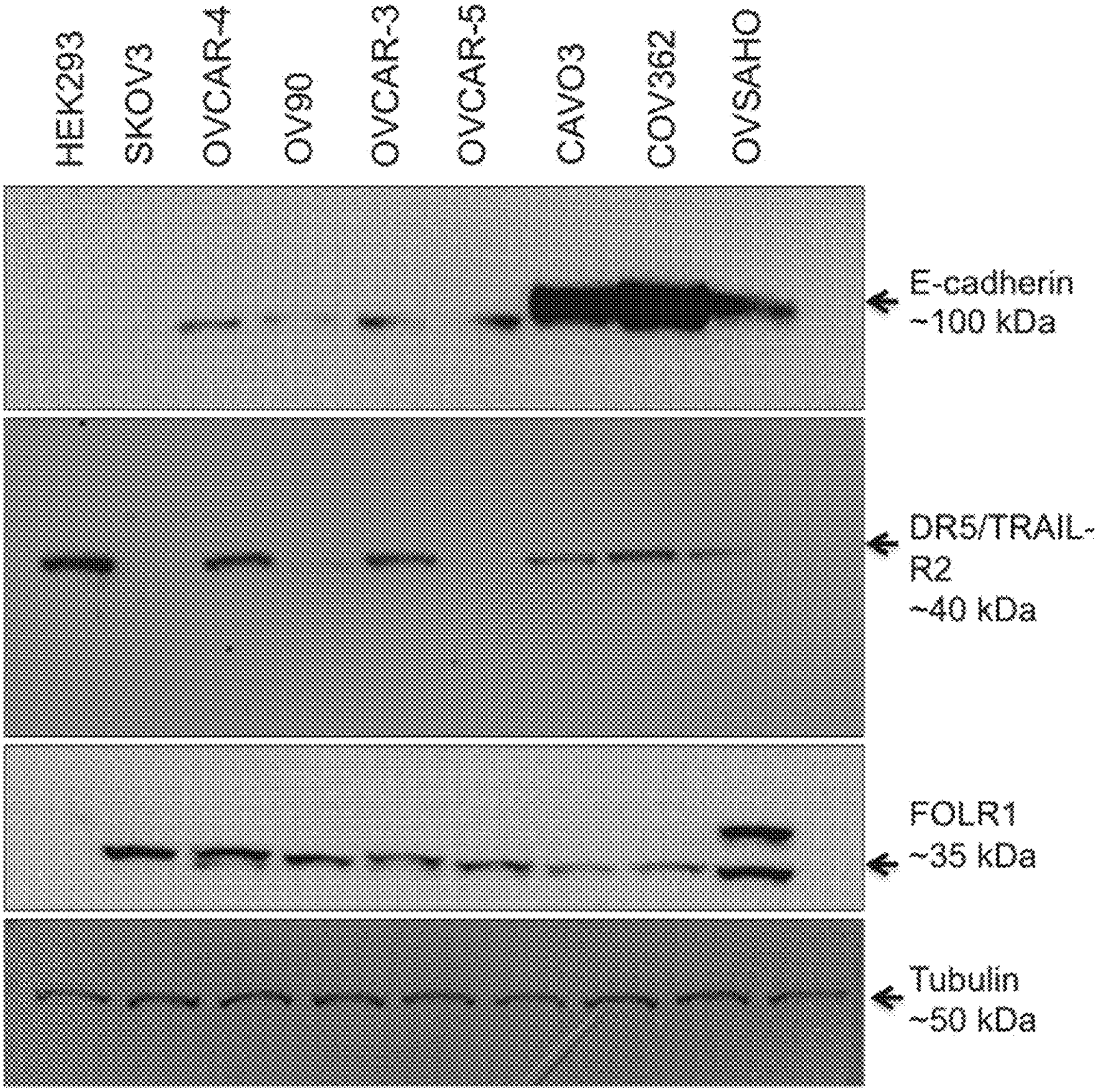
Figure 3B:
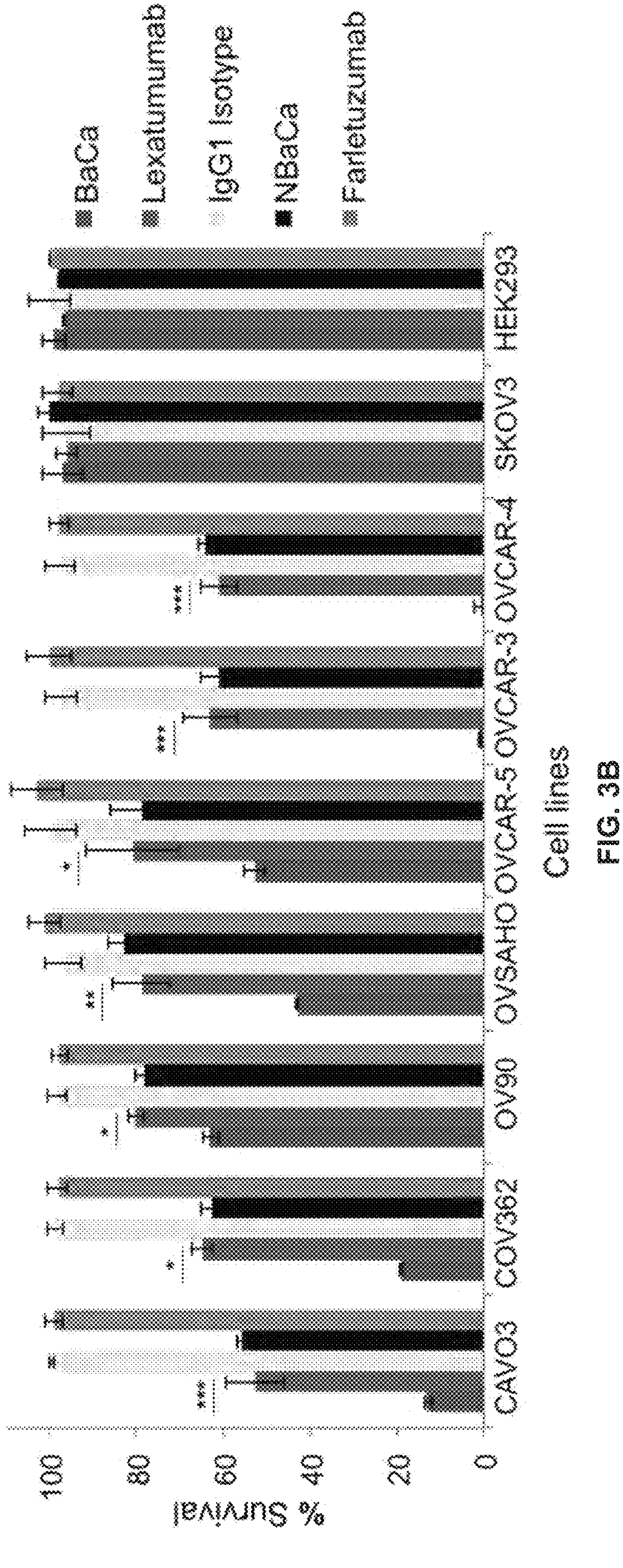

BaCa Antibody is Broadly Effective and is Superior to the Described Cooperativity Next we extended the BaCa activity in various other likely high-grade serous ovarian carcinoma (HGSOC) cells (Domcke et al., 2013). As expected, almost all tested lines expressed high levels of FOLR1 (FIG. 3A). BaCa antibody consistently instigated significantly higher cytotoxicity than lexatumumab in most of the OvCa lines and against heterogeneous patient derived OvCa cells (FIGS. 3B, 10A, 10B). The only OvCa cell line described as non-HGSOC in literature, SKOV3 (Domcke et al., 2013), did not respond to agonist DR5 therapy. Although comparable at transcript levels, the DR5 protein was significantly reduced in SKOV3 cells (FIGS. 3A, 10C). This prompted us to investigate if additional factors regulating DR5 stability might be differentially expressed in SKOV3 cells (Wagner et al., 2007). When tested, expression of key glycosylation regulators, N-acetylgalactosaminyltransferase-3 (GALNT3) was undetectable both at RT-PCR and qPCR levels in SKOV3 cells (FIGS. 10D, 10E). These observations indicate that loss of DR5 O-linked glycosylation in SKOV3 cells limits their sensitivity to DR5 therapy. Therefore, the method may be more effective when DR5 is O-linked glycosylated.

Figure 3C:
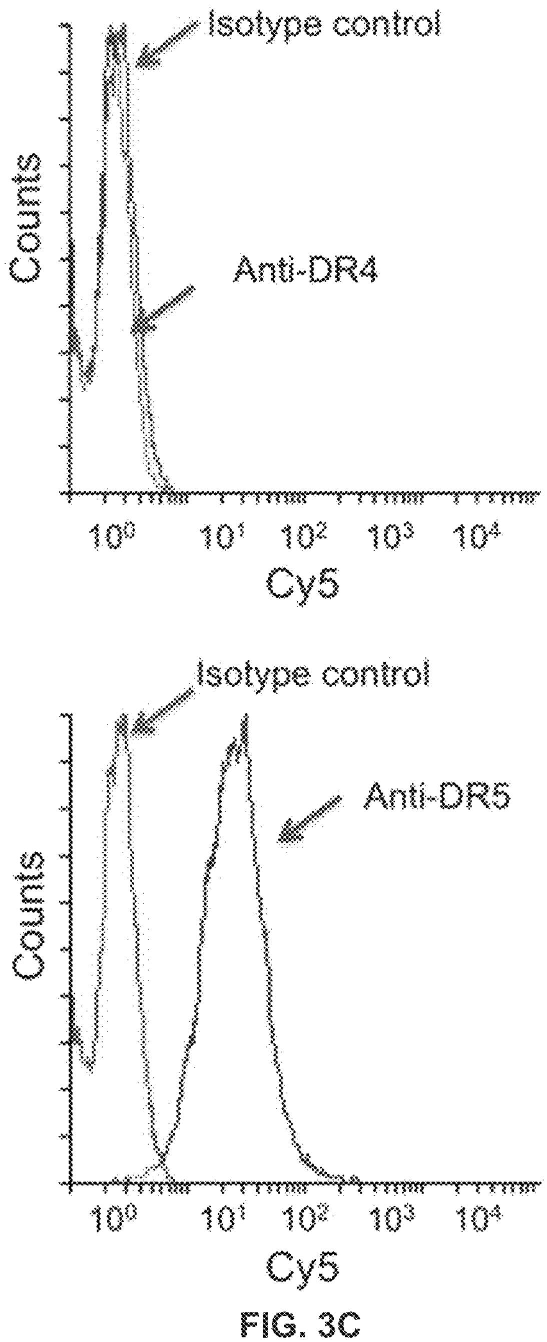
Figure 3D:
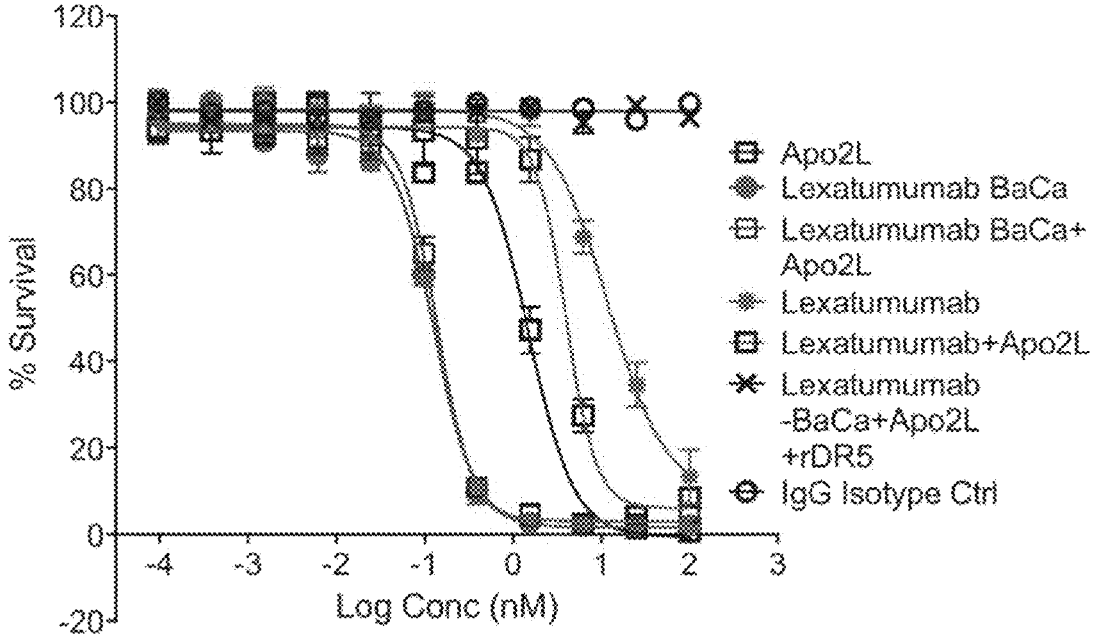

Co-treatment of Apo2L ligand and DR5 agonist antibody AMG-655 has been shown to enhance apoptotic cooperativity (Graves et al., 2014). As Apo2L ligand can induce cytotoxicity via engaging both DR4 (TRAIL-R1) and DR5 receptors, we first confirmed that OVCAR-3 cells only expressed DR5 (FIGS. 3C, 10F, 10G). Apo2L was generated in our lab and tested along with commercial Apo2L (FIG. 10H). Next, we compared the cell-killing activity of BaCa antibodies (generated either with lexatumumab or AMG-655)±Apo2L ligand. The co-treatment of Apo2L ligand was insufficient to enhance the activity of BaCa antibodies (FIG. 3D, E) indicating that higher order DR5 clustering by BaCa antibody is highly superior independent of Apo2L ligand being present. In support, we observed no change in caspase-3 activation by BaCa antibody regardless of Apo2L ligand (FIG. 3F).

Figure 3E:
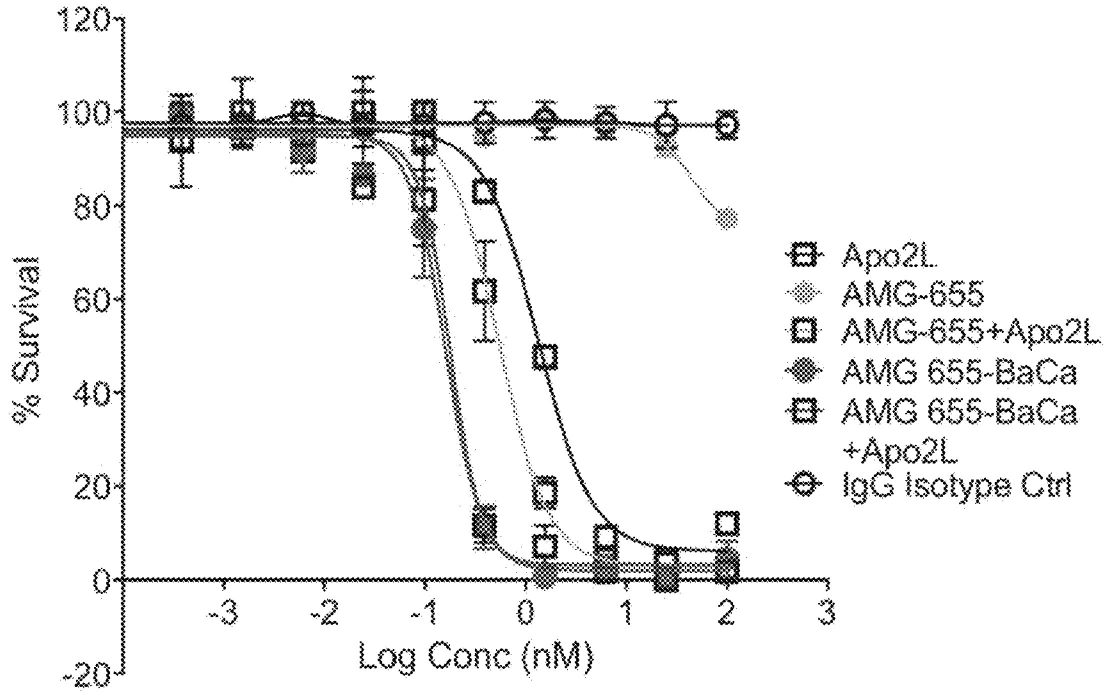
Figure 3F:
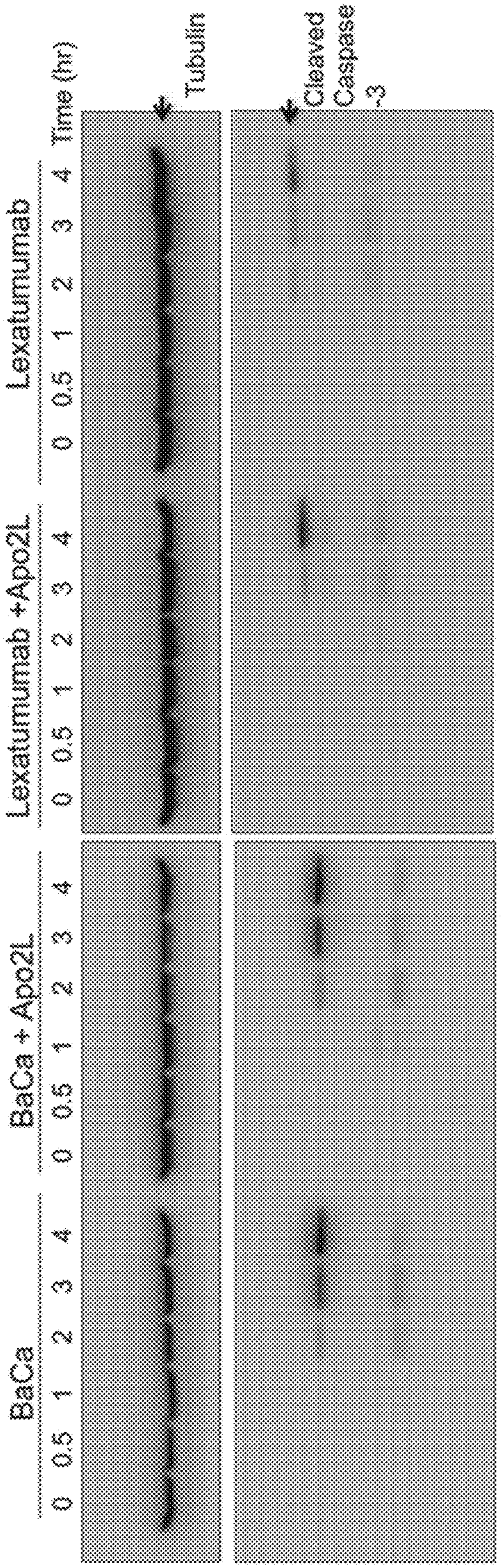
Figure 3G:
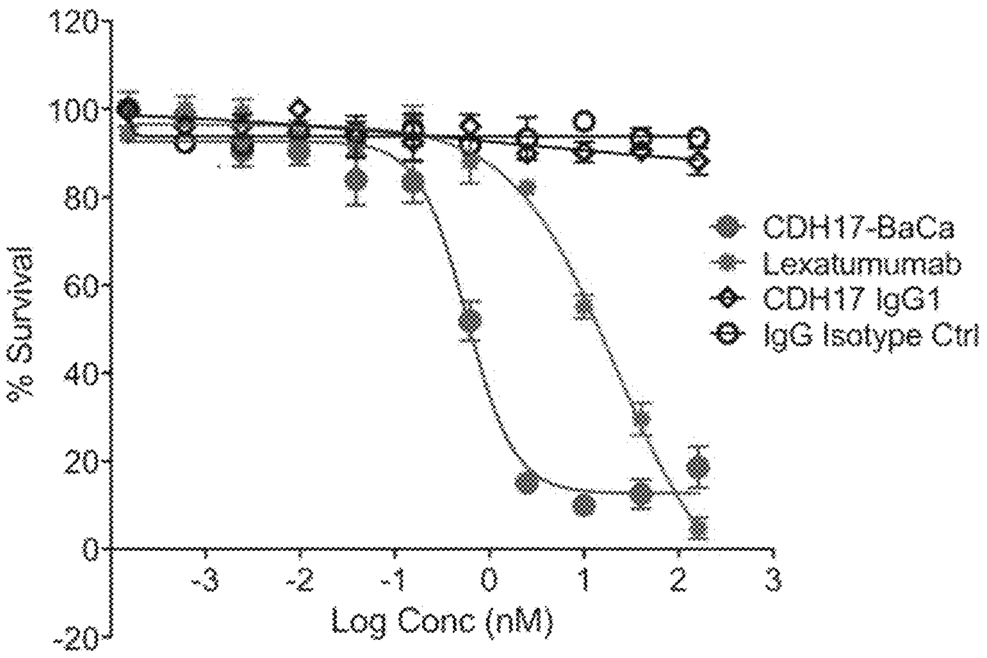

Similar to previous reports, we also observed apoptotic cooperativity due to Apo2L and AMG-655 (FIG. 3E). Interestingly, co-treatment of Apo2L and lexatumumab was not effectively cooperative (FIG. 3D, F). It should also be noted that unlike lexatumumab, AMG-655 was very limitedly effective in inducing loss of OvCa cell viability, which point toward the differences in their working mechanisms. Next, we extended the BaCa targeting strategy by swapping anti-FOLR1 affinity with another cancer-enriched receptor (CDH17) targeting A4 antibody. CDH17 is commonly overexpressed in intestinal and colorectal cancers (Chen et al., 2012). A4-BaCa showed multiple fold higher cytotoxicity against Colo-205 cells over lexatumumab suggesting the reproducible potential of BaCa targeting to other cancers (FIG. 3G).

BaCa Antibody is Highly Selective Towards FOLR1 Positive OvCa Cells.

Selective therapeutic targeting remains a critical concern considering the minimal number of drug approvals by FDA, mostly due to non-specific accumulation and toxicity in clinical trials (Printz, 2011; Vincenzi et al., 2016). Therefore, we next compared the selective BaCa gain of function with anti-Fc crosslinking, a nonspecific way to induce DR5 receptor clustering (Wilson et al., 2011). To this end, we incubated OVCAR-3 cells with a dose titration of lexatumumab or AMG-655, either alone or together with anti-human Fc crosslinking agent (1 μg/ml). Despite non-specific crosslinking of DR5 agonists, single agent BaCa antibodies were multiple folds more effective (FIG. 4A, B).

An ideal anti-cancer therapeutic antibody such as BaCa should have reduced toxicity towards none or low FOLR1 expressing cells. Thus, we next compared the BaCa activity in high and low FOLR1 expressing cells. The colorectal cancer cell line Colo-205 expresses ~5 fold less FOLR1 than does OVCAR-4 ovarian cancer cells but equal levels of the DR5 and GALNT3 transcripts (FIGS. 4C, 10C-10E). Indeed, IC50 of lexatumumab was not significantly different in Colo-205 and OVCAR-4 cells (FIG. 4D). However, the BaCa antibody was ~70 fold more effective in killing OVCAR-4 cells over Colo-205 cells. This reasonably supports the dependence of gain in cytotoxicity on the increased expression of tumor specific FOLR1 anchor antigen.

Next, we asked if this cytotoxic gain would be selective to OvCa cells by co-culturing Colo-205 cells stably expressing GFP with OVCAR-4 (FIG. 4E). When treated with 0.1 nM BaCa antibody for 24-36 hr, we observed selective elimination of □OVCAR-4 cells (FIGS. 4F, 11A). Lexatumumab was completely ineffective at the same dose. Since DR5 expression was similar in both the cell types (FIG. 4C), these findings indicate that at a low dose BaCa antibody is highly selective to FOLR1 anchor enriched tumor cells and prefers to engage DR5 to instigate cell death in "cis". Similar results were obtained when BaCa antibody was generated with AMG-655 (FIG. 11B).

Figure 4G:
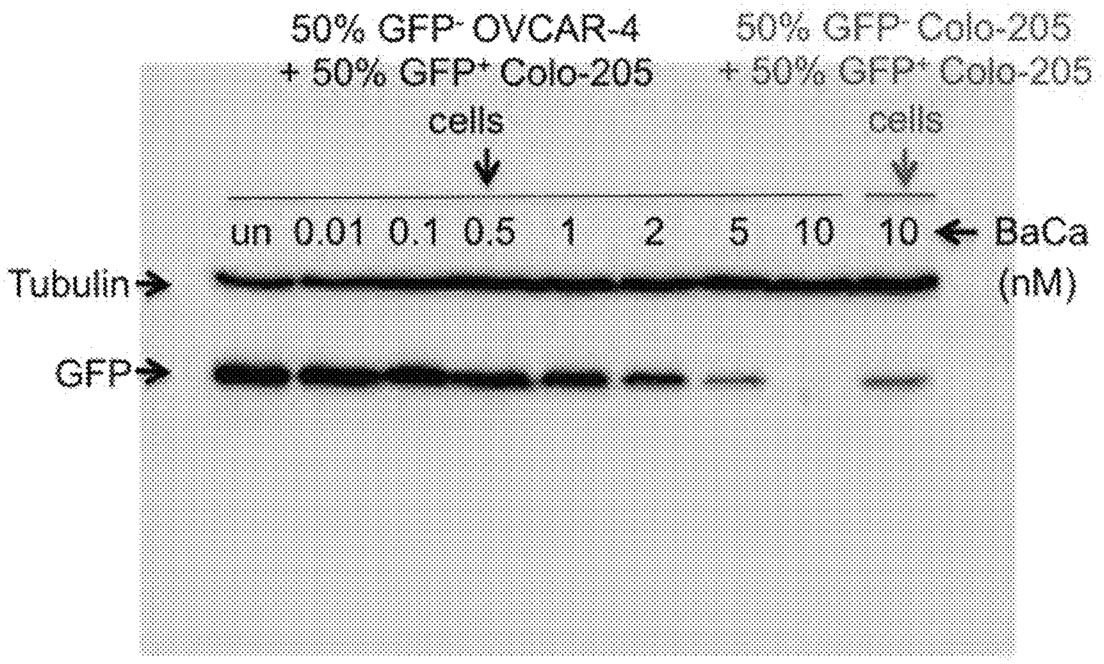
Figure 4H:
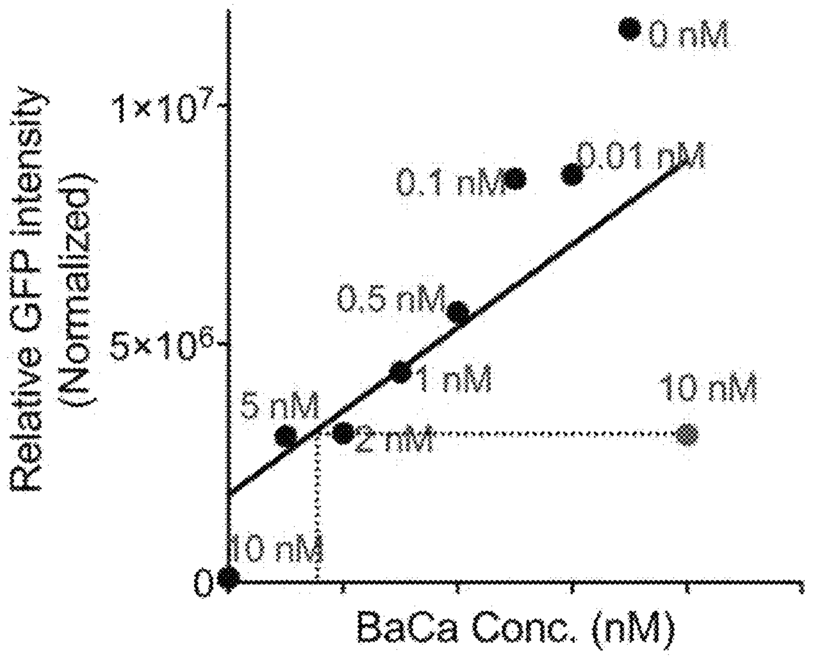
Figure 4I:
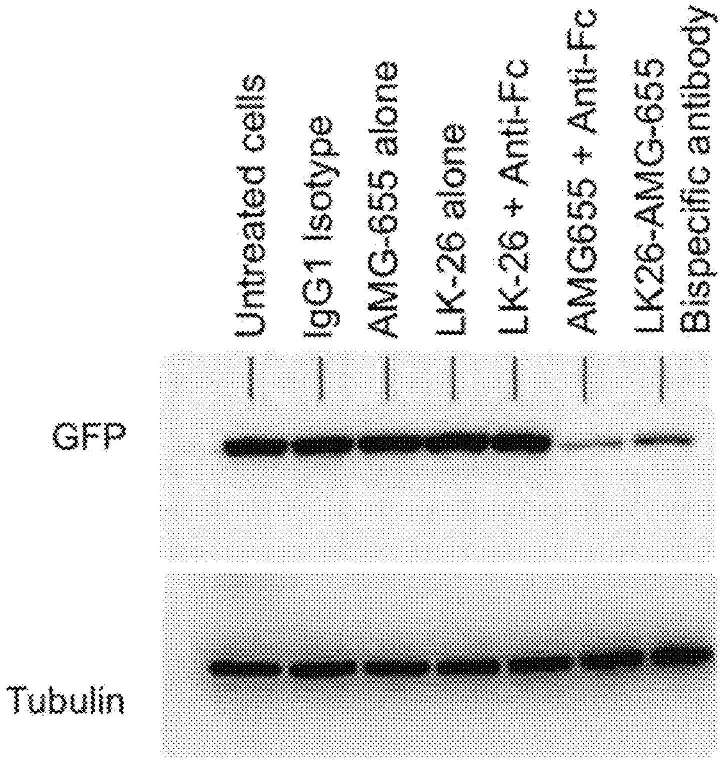
Figure 11C:
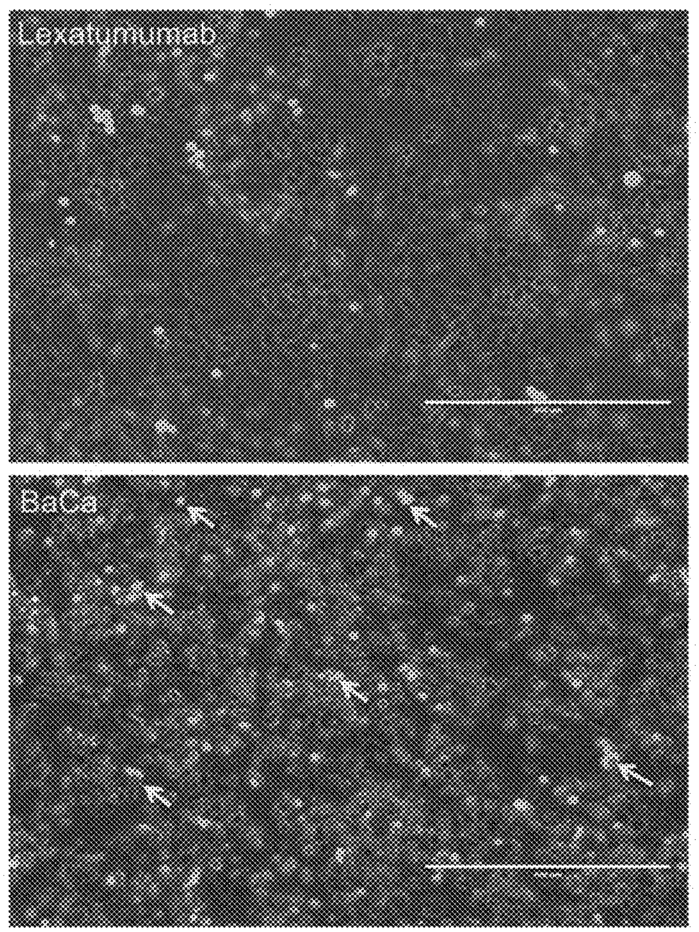
Figure 11D:
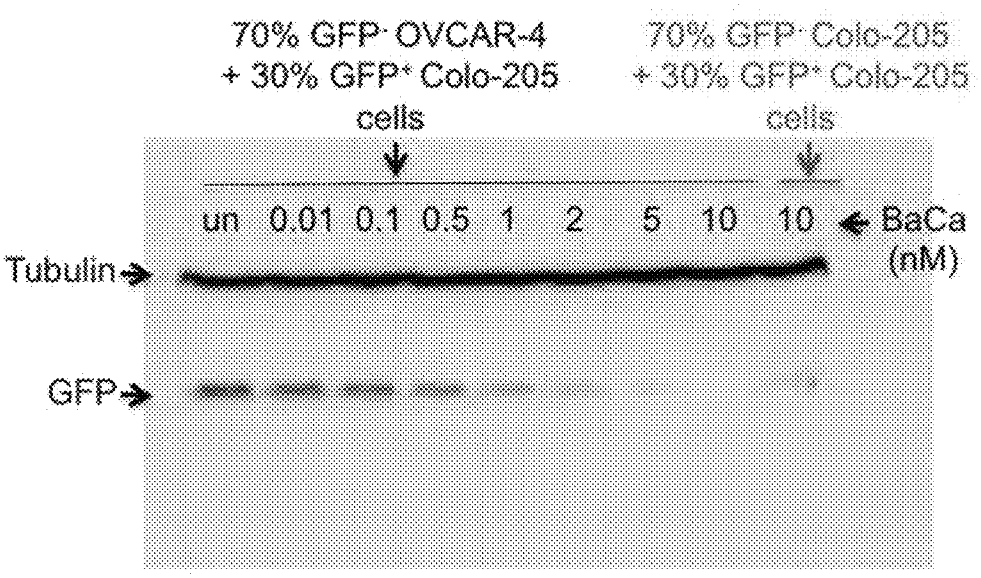
Figure 11E:
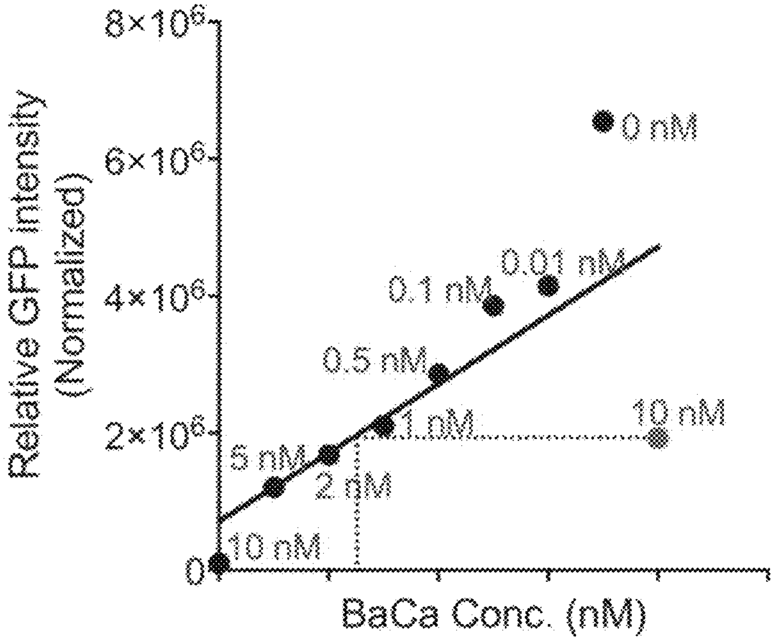

When co-cultures were incubated at >20 fold higher concentrations (2 nM), we observed BaCa cytotoxicity towards both high anchor (OVCAR-4) and low anchor (Colo-205) expressing cells (FIG. 11C). We consistently detected >95% cell death of Colo-205 cells in co-cultures and since the 2 nM concentrations of BaCa antibody were below its IC50 value (3.07 nM) against Colo-205 cells, these findings were highly suggestive of "trans" activation by BaCa antibody at higher concentrations. To reconfirm, we incubated co-cultured cells (50% GFP− OVCAR-4 and 50% GFP+ Colo-205) with the increased concentration of BaCa antibody and evaluated the loss of GFP signal as an indicator for activity in "trans". As a control, we also co-cultured 50% GFP− Colo-205 with 50% GFP+ Colo-205 cells. At higher doses, BaCa antibody was significantly more effective (>5 fold) in killing GFP+ Colo-205 cells that were co-cultured with GFP− OVCAR-4 cells in comparison to those co-cultured with GFP− Colo-205 cell only (FIG. 4G, H). Similar results were seen when co-cultured conditions had 70% GFP− OVCAR-4 and 30% GFP+ Colo-205 cells (FIGS. 11D, 11E).

Figure 4J:
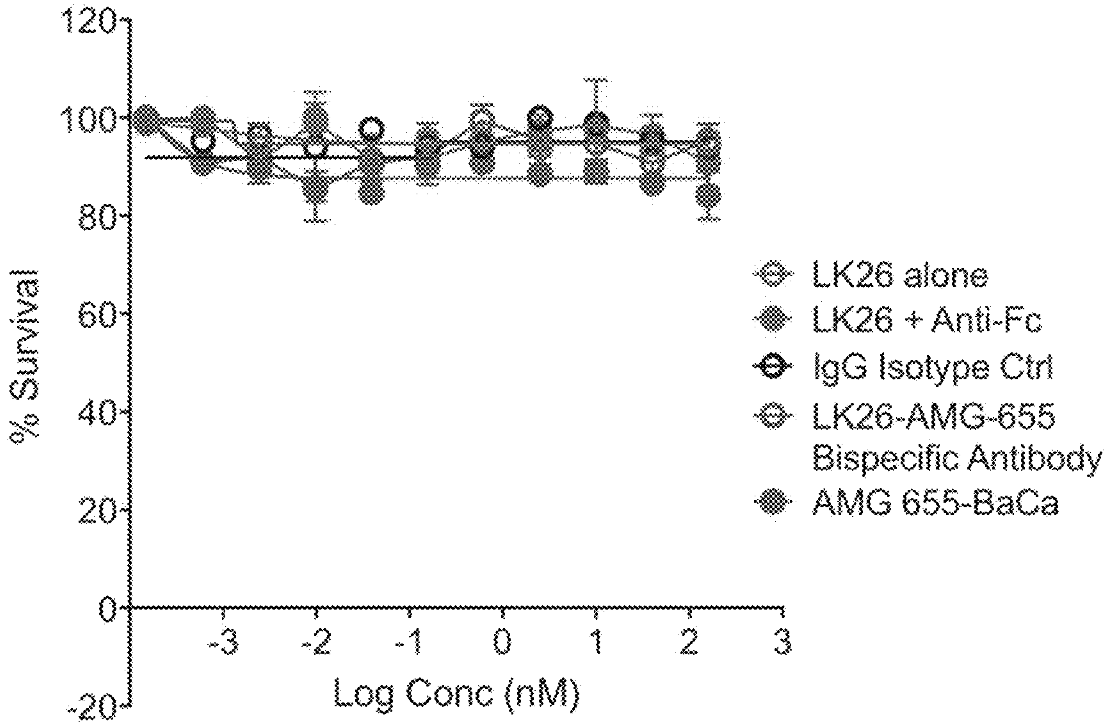
Figure 4K:
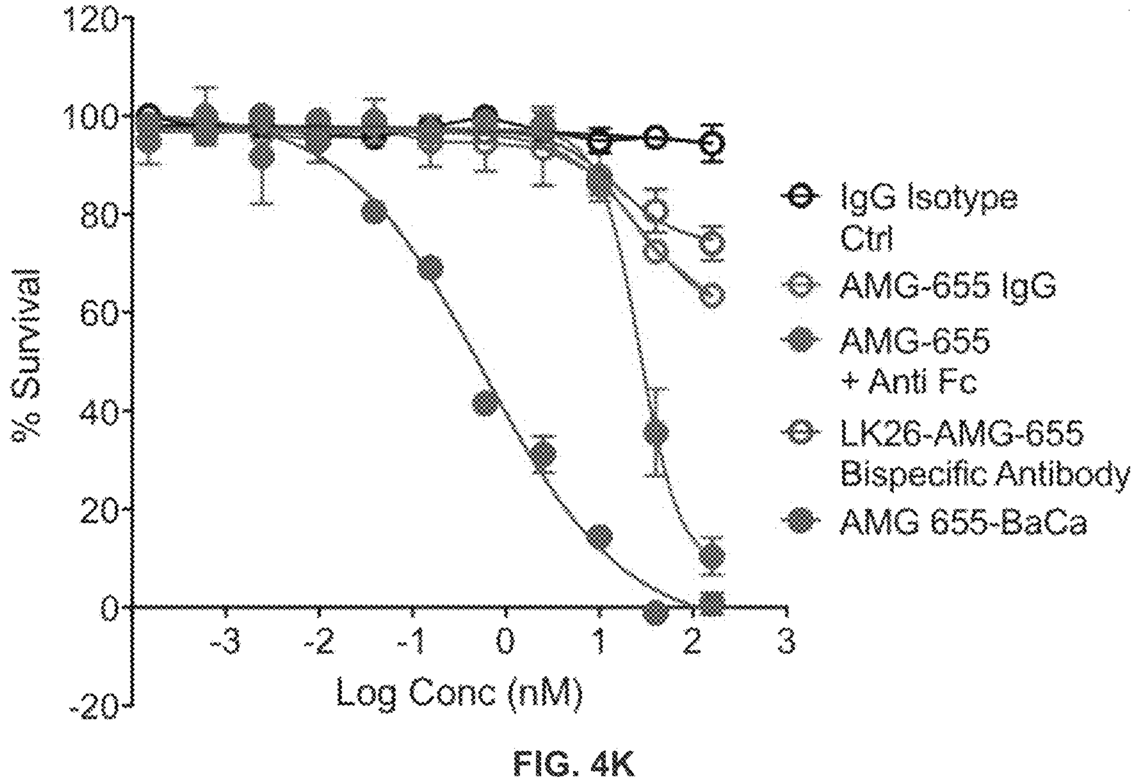
Figure 4L:
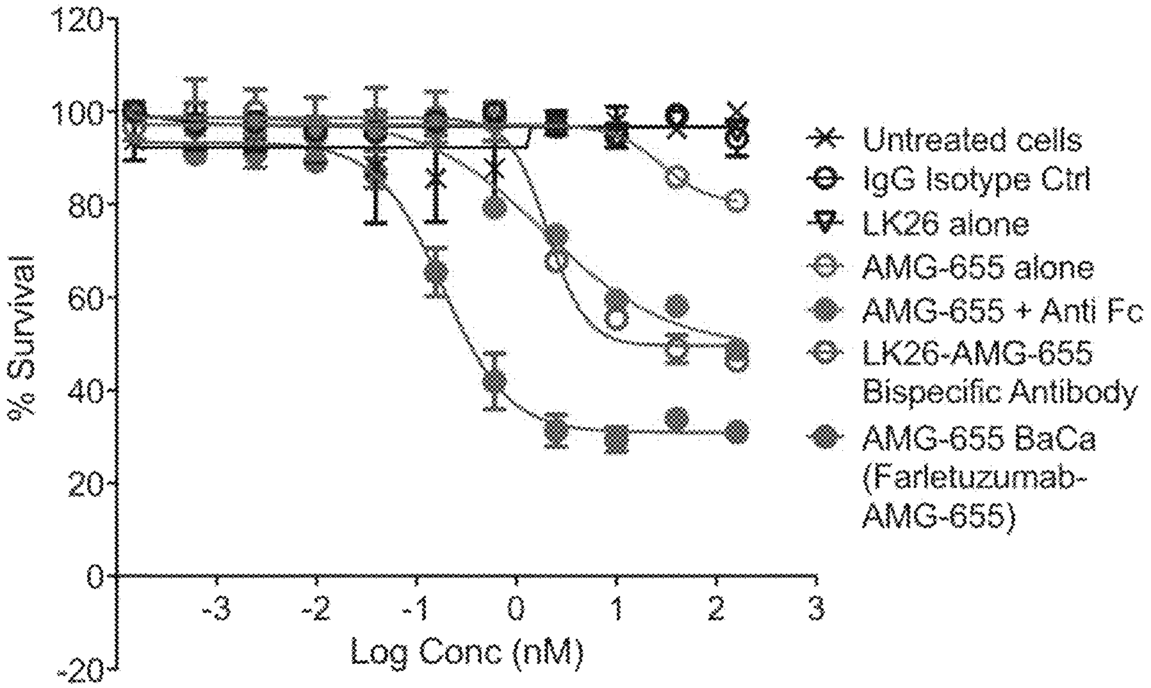
Figure 11F:
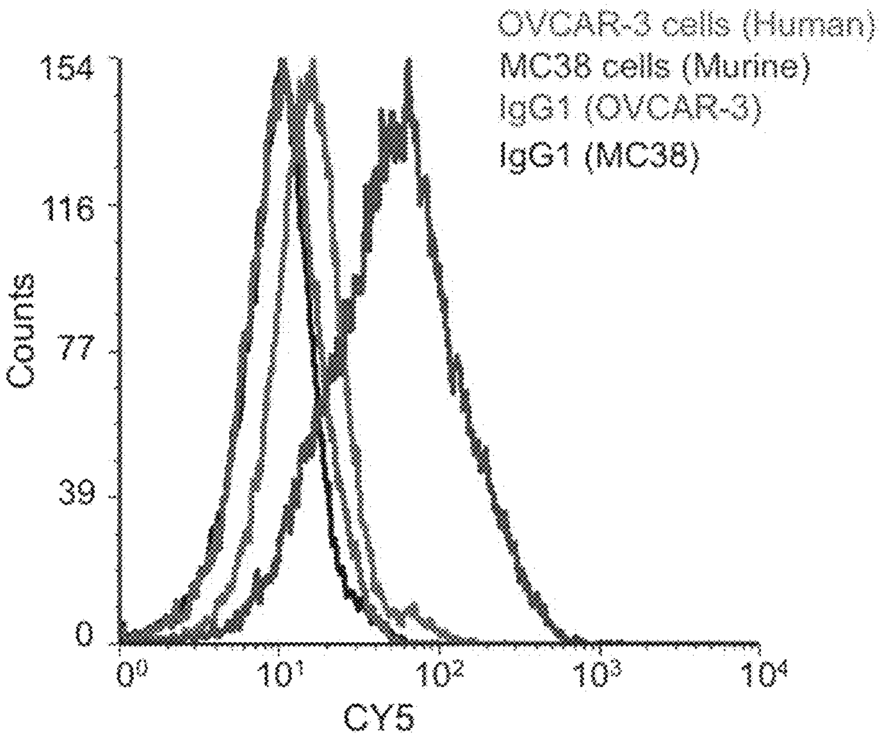
Figure 11G:
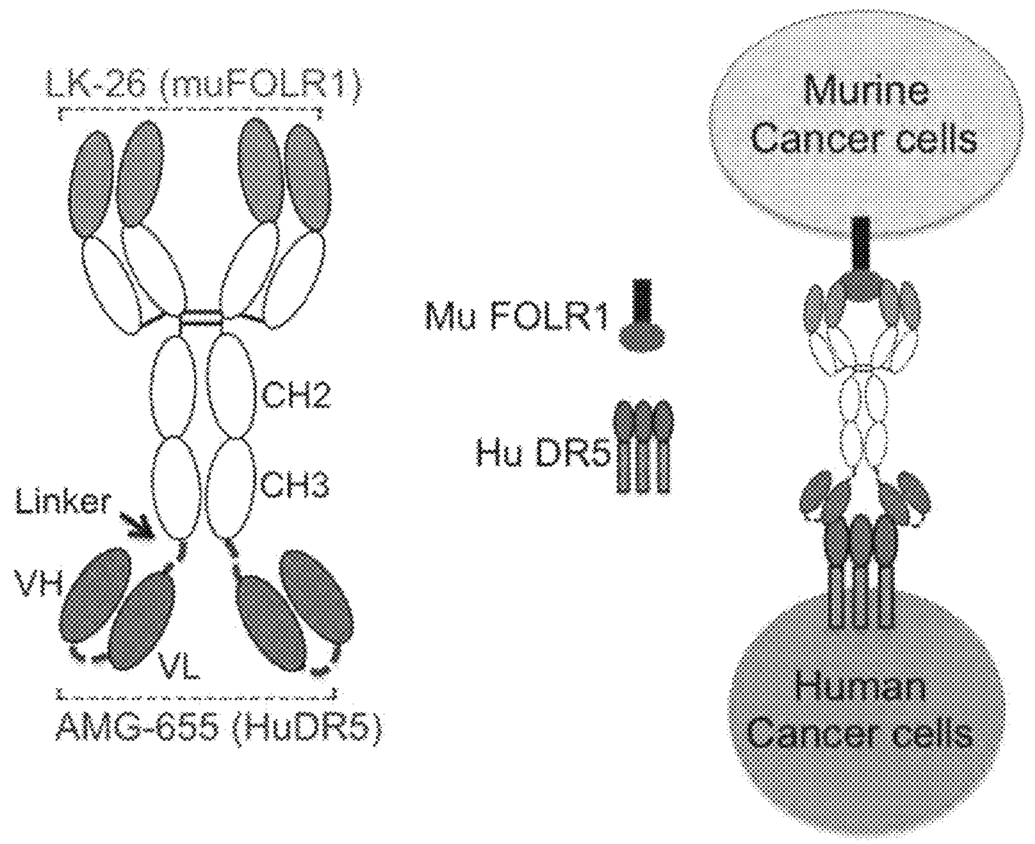
Figure 11H:
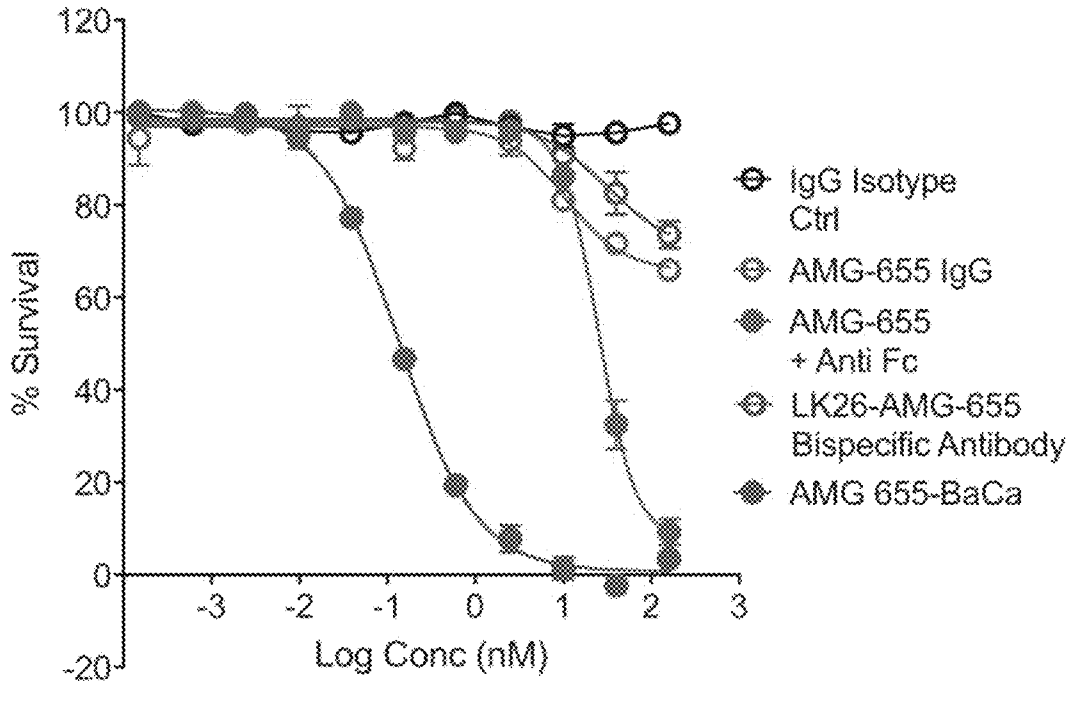
Figure 11I:
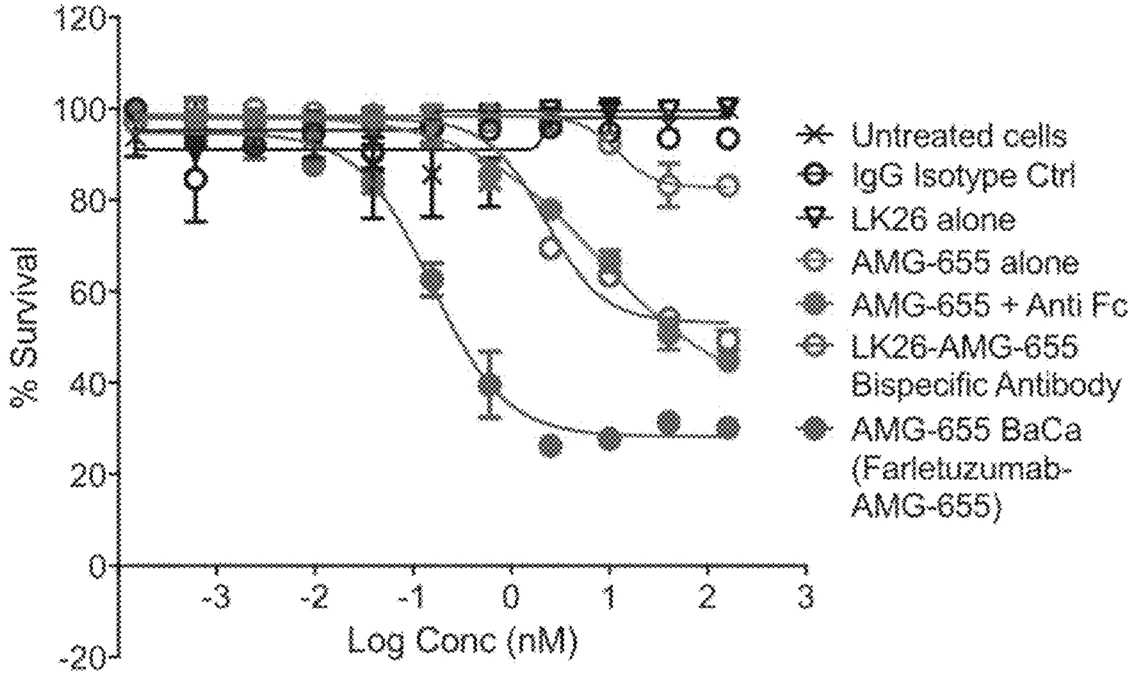

Next, we made use of anchor antigen− cells to compare trans-engaging and DR5 activating bispecific antibody with the BaCa strategy. To this end, we engineered murine FOLR1 (muFOLR1) specific LK-26 antibody and huDR5 specific AMG-655 into a bispecific antibody (FIGS. 11F, 11G). Next we co-cultured GFP+ Colo-205 cells with murine MC38 cells and treated with 50 nM LK26-AMG-655 bispecific antibody. The loss of GFP in FIG. 4I (most right lane) confirms bispecific antibody functioning to engage muFOLR1 to "trans" activate huDR5, similar to described for RG7386 (Brunker et al., 2016). Next, we compared the activity of trans-engaging DR5 bispecific antibody against the BaCa strategy using serial dilutions. BaCa antibody (Farletuzumab-AMG-655) induced cell killing of co-cultured OVCAR-3 at a much lower concentration than the LK26-AMG-655 bispecific antibody (FIG. 4J-L). Notably, unlike BaCa, the trans-engaging bispecific antibody was totally dependent on MC38 cells (FIG. 4K vs L). Similar results were obtained with OVCAR-4 cells (FIGS. 11H, 11I). The inability of cell killing assay to achieve 100% (FIGS. 4L, 11I) is due to presence of AMG-655 non-binding MC38 cells in the co-cultures. These findings strongly substantiate that unlike described for RG7386 that requires two different cell-types (stromal and tumor cells) to induce "trans-only" cytotoxicity, BaCa antibody has built-in function to activate both "cis" and "trans" cytotoxicity by making use of a single anchor antigen expressing cancer cell. Importantly, unlike the "trans-only" activating bispecific antibody, BaCa antibody required a significantly lower dose to achieve highly superior cytotoxicity.

Tumor Specificity of BaCa Antibody

Figure 12E:
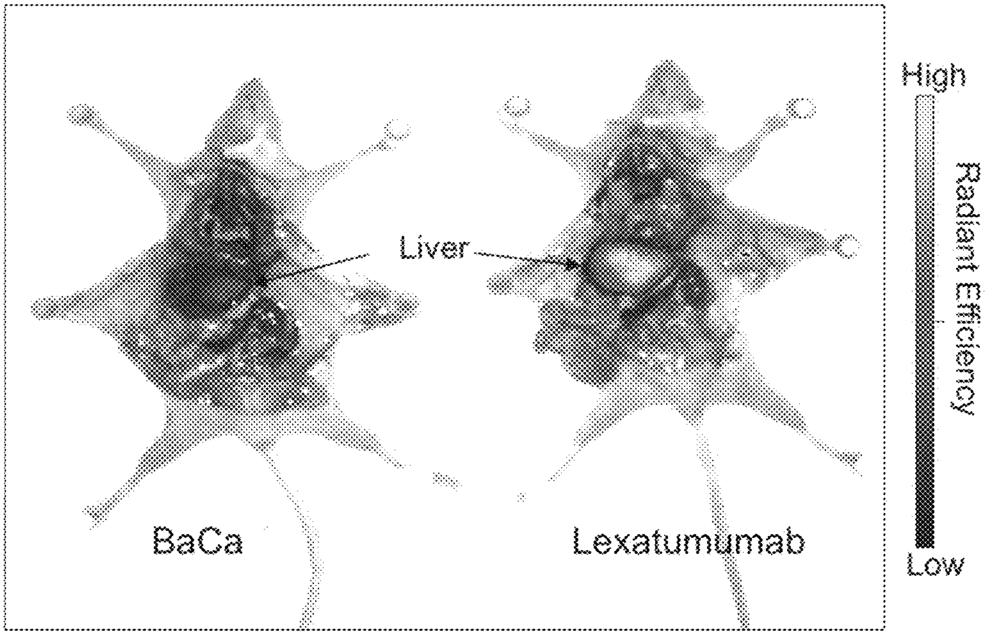
Figure 12F:
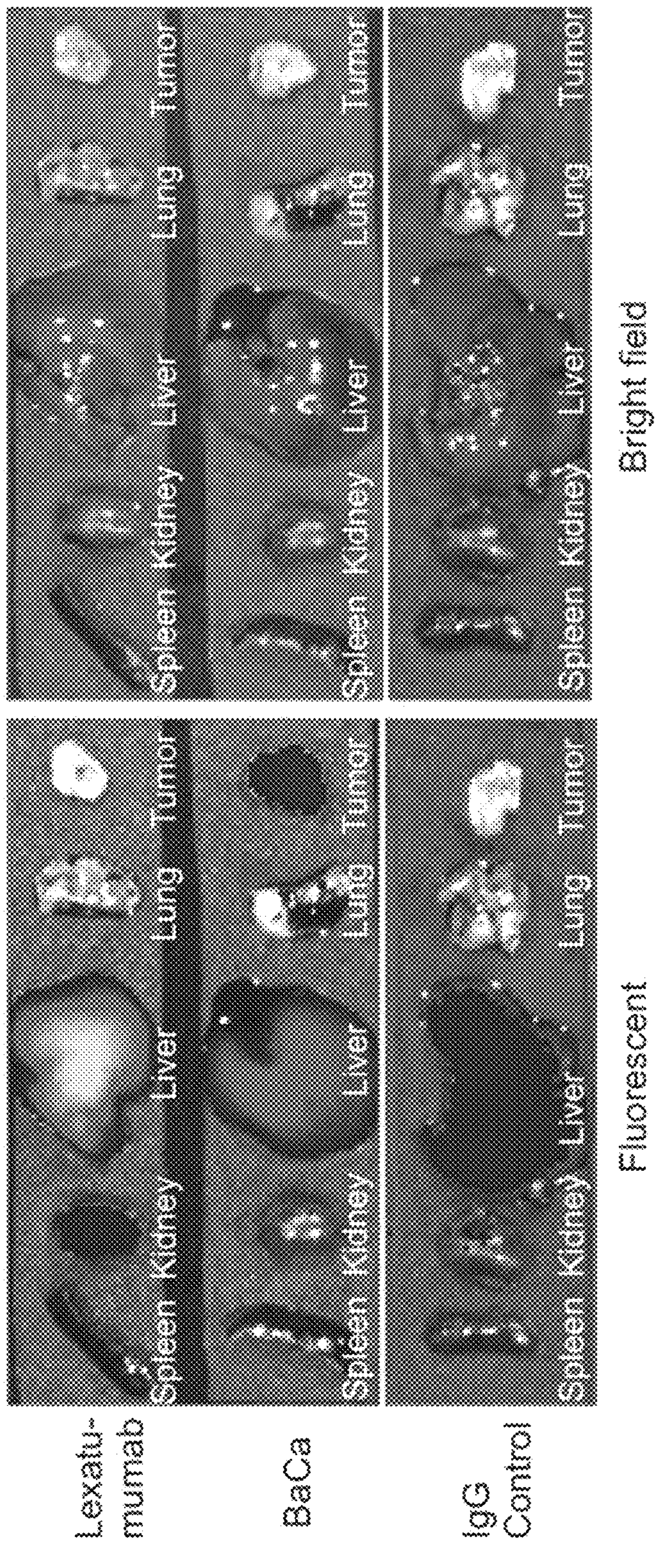

Before moving to in vivo, we tested BaCa antibody for in vitro stability (FIG. 12A). For in vivo stability, we carried out serum half-life analysis as described earlier (Hutt et al., 2012). Lead BaCa antibody showed high in vivo stability with a t½ of ~15 days (FIGS. 12B, 12C). To test the tumor selectivity of BaCa antibody, we intravenously (IV) injected infrared dye IR800-labeled antibodies (25 μg) into the tumor bearing mice to monitor tissue localization as described (FIG. 5A) (Lin et al., 2013). It was also confirmed that IR800 labeling did not change the affinities against the respective receptors (FIG. 12D). BaCa antibody selectively accumulated in the grafted tumors within 24 hr, while lexatumumab showed significant more localization in the liver than tumor (FIG. 5B, 12E, 12F). As predicted, the tumor specific enrichment of BaCa antibody was completely lost if it was neutralized with rFOLR1 before IV injection (FIG. 5C). Interestingly, we observed BaCa antibody accumulation in mice liver upon FOLR1 pre-neutralization. Lexatumumab remained localized consistently in the animal liver in addition to tumors±rFOLR1 neutralization (FIG. 5D).

The differential accumulation of lexatumumab was confirmed using liver specific ELISA. We observed a consistent >5 fold more accumulation of lexatumumab antibody in mice liver than BaCa antibody (FIG. 5E). These results indicate that non-specific accumulation of lexatumumab in tissues (such as liver) could be responsible for its limited clinical efficacy and points to the added safety of BaCa approach due to avidity optimized retention in tumors. Next, we tested the activation of DR5 signaling in grafted OVCAR-3 tumors and also compared to Colo-205 tumors. A single IV dose of BaCa antibody produced >10 fold more cleaved caspase-3 levels in OVCAR-3 tumors and pre-blocking of BaCa antibody with rFOLR1 reduced the gain in caspase activity and DR5 oligomerization (FIG. 5F-J).

Figure 12G:
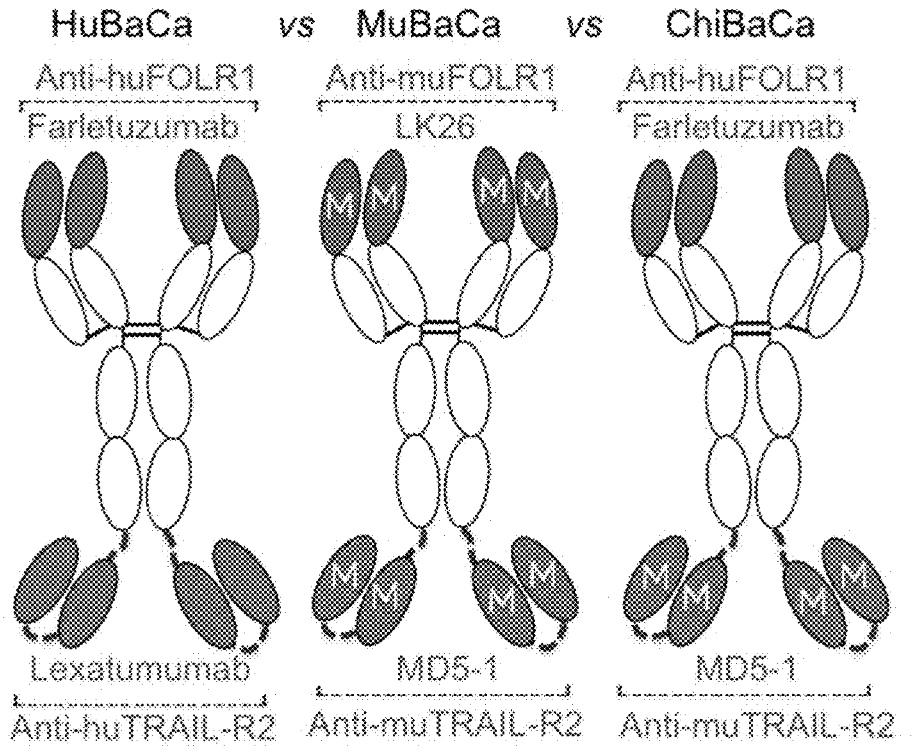
Figure 12H:
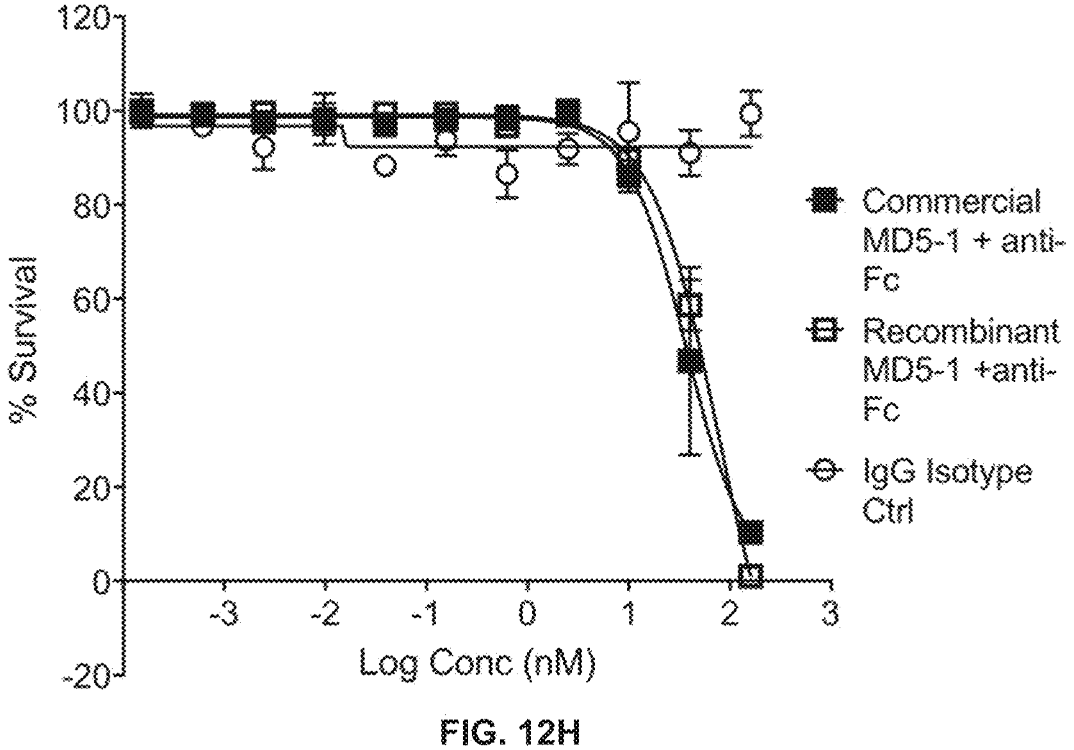
Figure 12I:
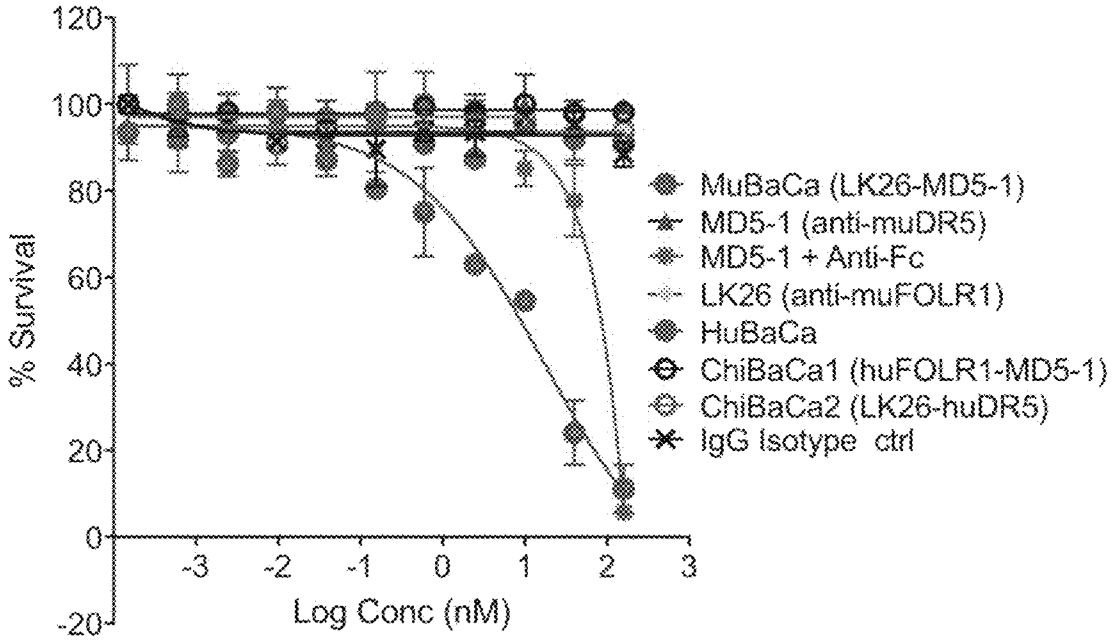
Figure 12J:
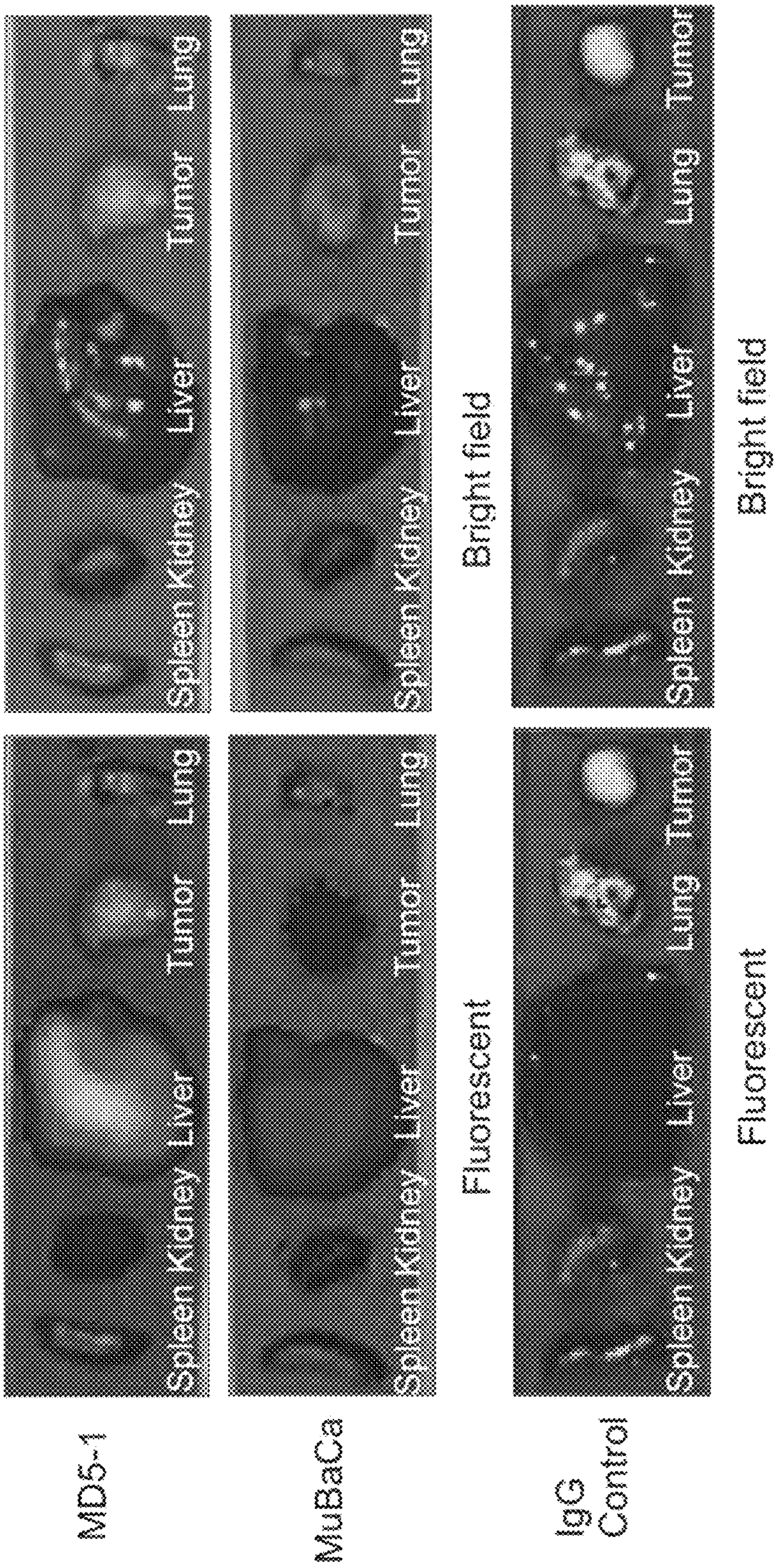

To investigate if accumulated DR5 agonist antibody in liver would result in hepatotoxicity, we engineered a murine cross-reactive BaCa (MuBaCa) antibody consisting of LK26 and MD5-1 (FIGS. 5K, 12G). MD5-1 IgG1 generated in our lab was tested and confirmed along with commercial MD5-1 antibody (FIG. 12H). MuBaCa, but not huBaCa, selectively eliminated murine MC38 cells without any crosslinking agent (FIG. 12I). Since MC38 cells expressed >6 fold more muFOLR1 than mice ovarian ID8 cells (data not shown), we made use of MC38 cells for surrogate studies. Similar to huBaCa, C57BL/6 mice grafted with MC38 tumors showed significantly higher localization of muBaCa compared to MD5-1 antibody (FIG. 5L). We also carried out detailed tissue distribution of muBaCa and MD5-1 using C57BL/6 mice necropsies. Significantly more muBaCa and MD5-1 signal was evident in tumors and livers respectively (FIGS. 5M, 5N 12J). MD5-1 also resulted in elevated serum AST and ALT levels, both of which are indicators of hepatotoxicity (FIG. 5O). H&E stained liver sections from all 3 mice treated with MD5-1 showed a focal lobular hepatitis as evident with the infiltrating neutrophils near portal vein and sinusoids, while only 1 out of 4 muBaCa treated mice showed significantly minor presence of neutrophils (FIGS. 13A, 13B). These findings in surrogate animals further strengthen the selective anchor receptor (FOLR1) mediated retention, safety and activity of BaCa antibody in the grafted tumors.

Anti-Tumor Activity of BaCa Antibody

Figure 14A:
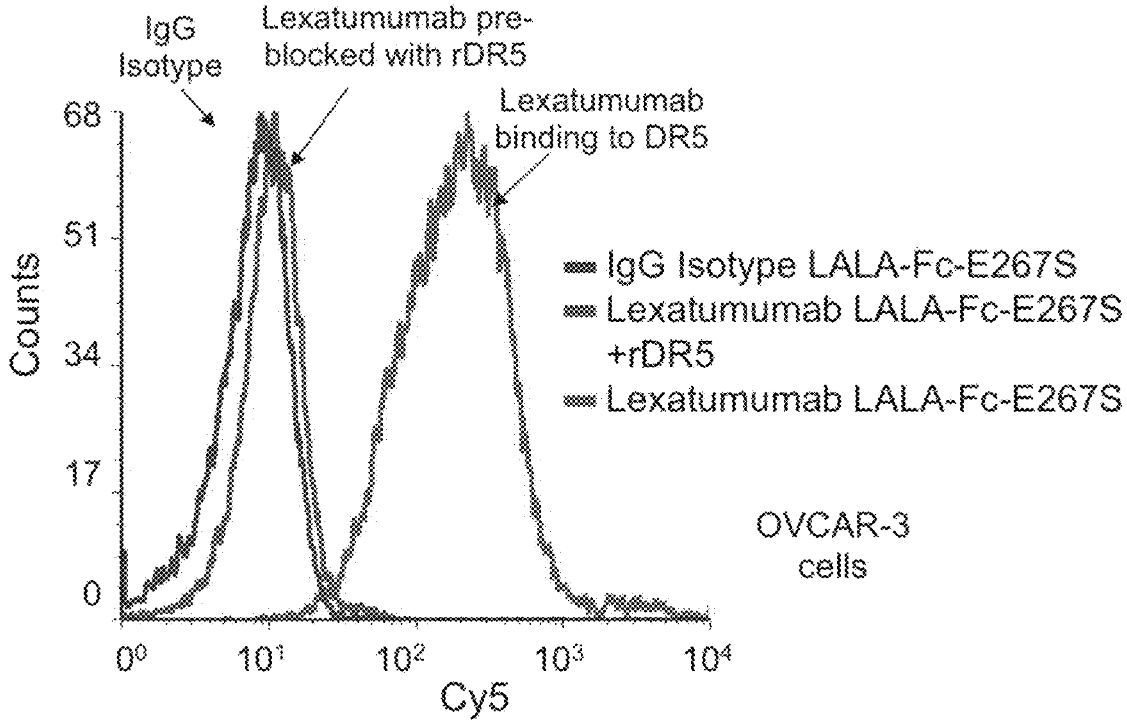
Figure 14B:
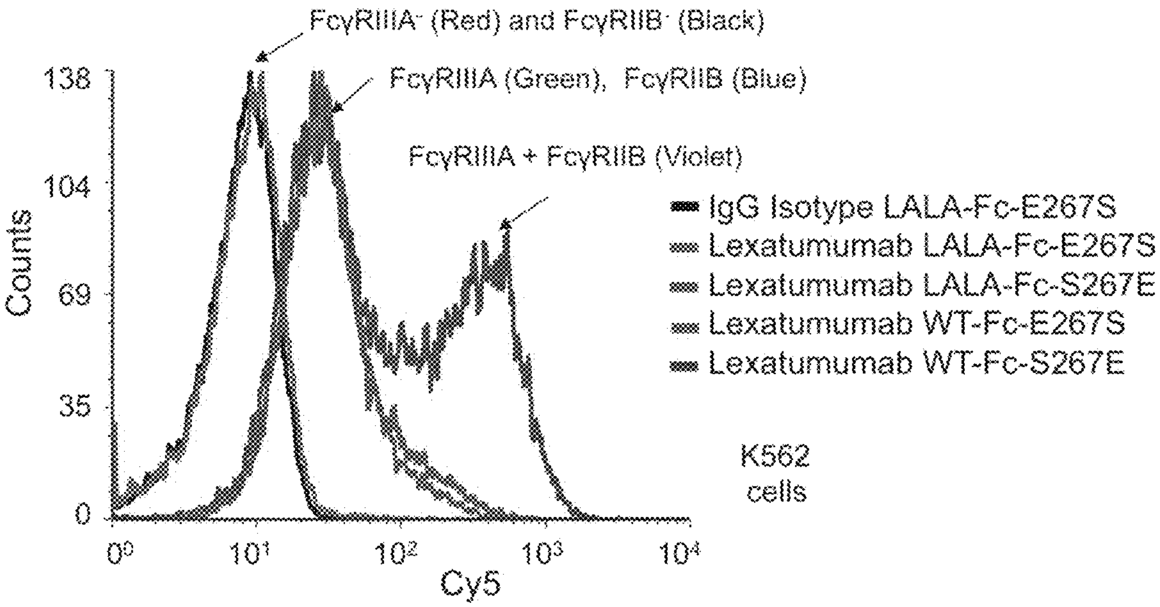
Figure 14C:
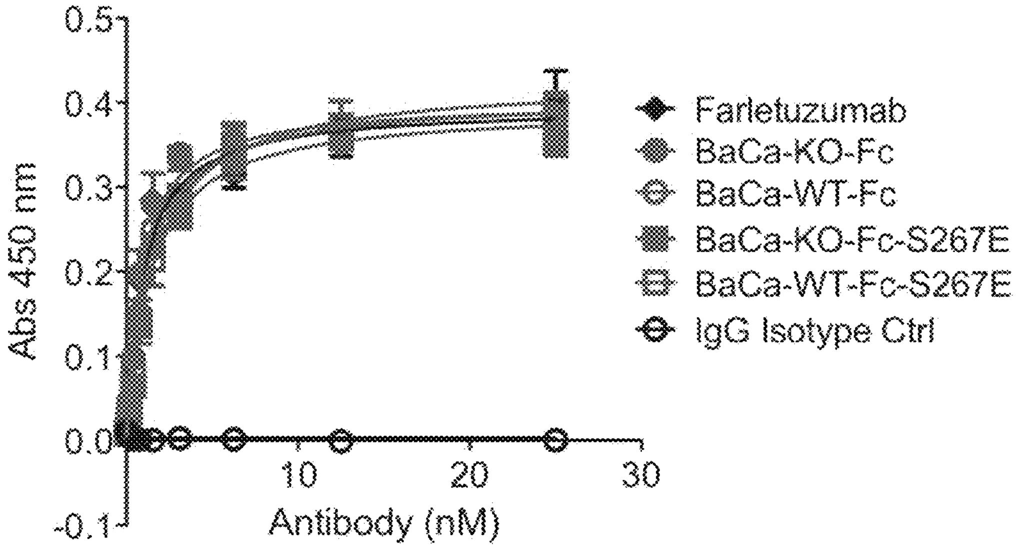
Figure 14D:
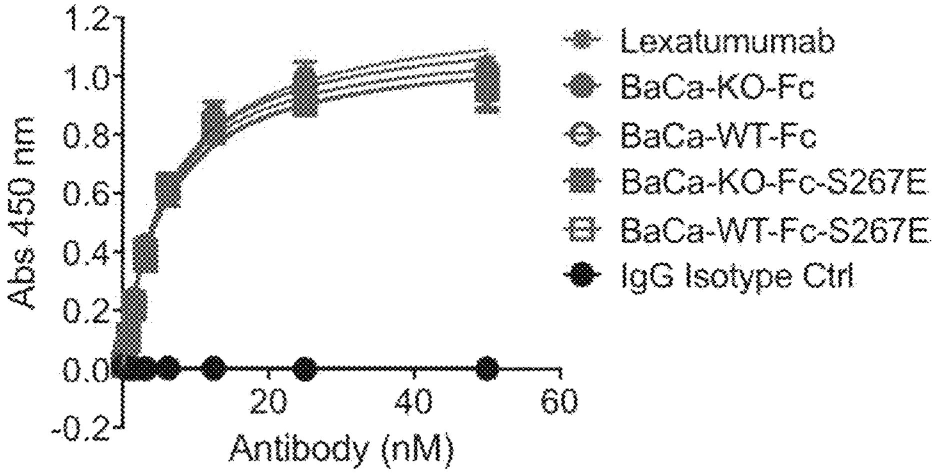
Figure 14E:
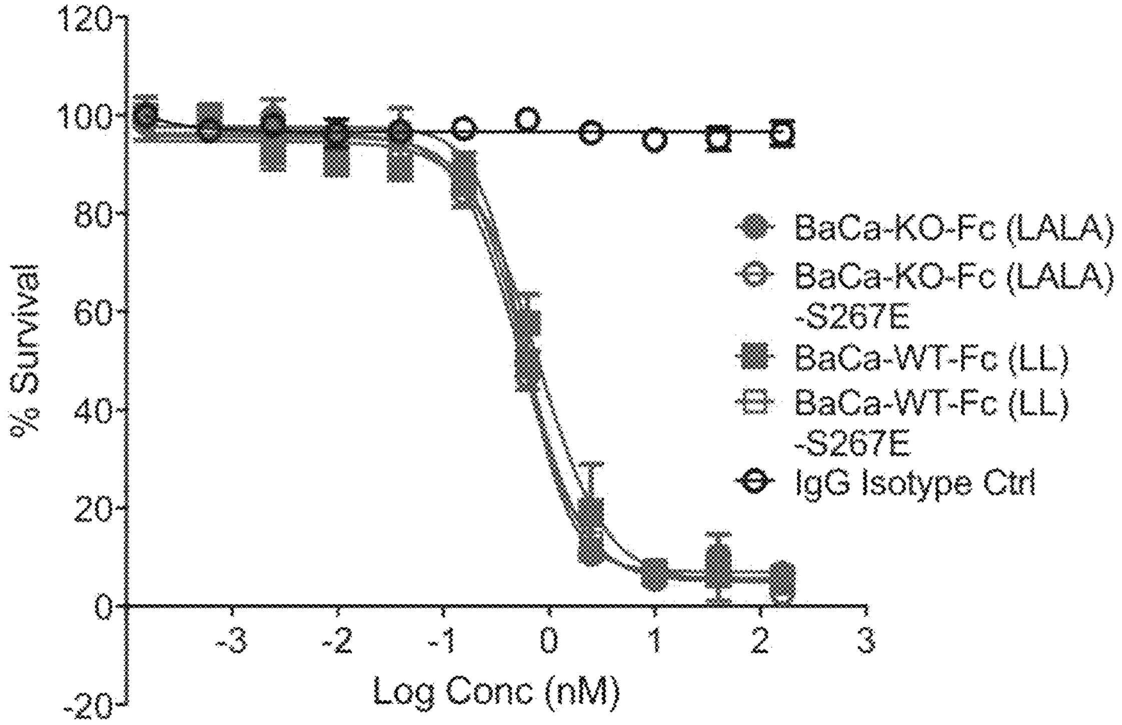
Figure 14F:
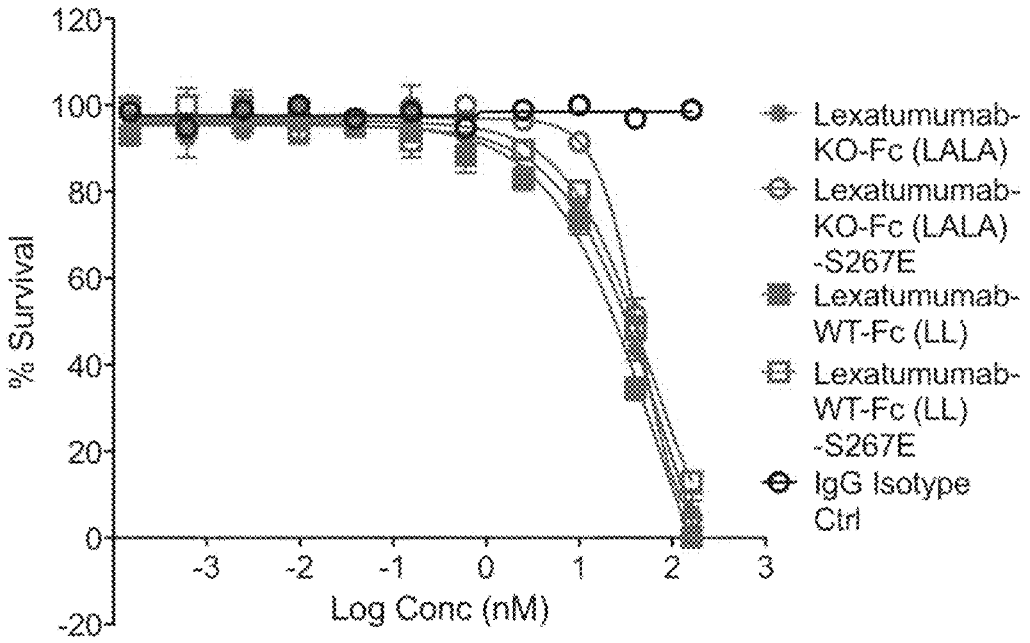

To impair FcγRIIIA binding and ADCC activity, we engineered lexatumumab, farletuzumab, and BaCa antibodies with LALA-Fc (L234A-L235A) mutations in the CH2 domain (Leabman et al., 2013). LALA mutant antibody did not exhibit measurable binding to human FcγRIIIA (FIGS. 14A, 14B). The binding affinities and activities of antibodies also remained unchanged after LALA mutations (FIGS.

14C-14F). Next, randomly selected nude mice bearing OVCAR-3 tumors (>100 mm3) were injected intraperitoneally (IP) every third day with 25 μg dose of antibodies as indicated (FIG. 6A). BaCa antibody completely regressed the tumor growth within 4 doses while lexatumumab only stabilized them. When followed for additional 4 weeks, none of the 6 BaCa injected mice showed tumor re-growth. Similar efficacy of BaCa antibody was observed in tumors generated with OVCAR-4 cells (FIG. 6B). Since LALA mutant antibodies don't engage NK cells (impaired FcγRIIIA binding), the efficacy data (FIG. 6A, B) is independent of ADCC function. Next, we compared ADCC-activating farletuzumab antibody with BaCa antibody in nude animals having active NK cells and innate immunity. To this end, WT-Fc (LL234-235) containing BaCa and farletuzumab antibodies were IP injected at 25 μg dose in the mice. Farletuzumab (WT-Fc) was only limitedly effective compared to BaCa antibodies (FIG. 6C). When dosed at 150 μg, farletuzumab (WT-Fc) also regressed the grafted tumors (data not shown). Both BaCa antibodies (LALA-Fc or WT-Fc) were equally effective±ADCC activating function and the data was not statistically significant (n=6). These findings indicate that BaCa antibody potentially will be highly effective even in the immune deficient ovarian tumor microenvironment.

Figure 6D:
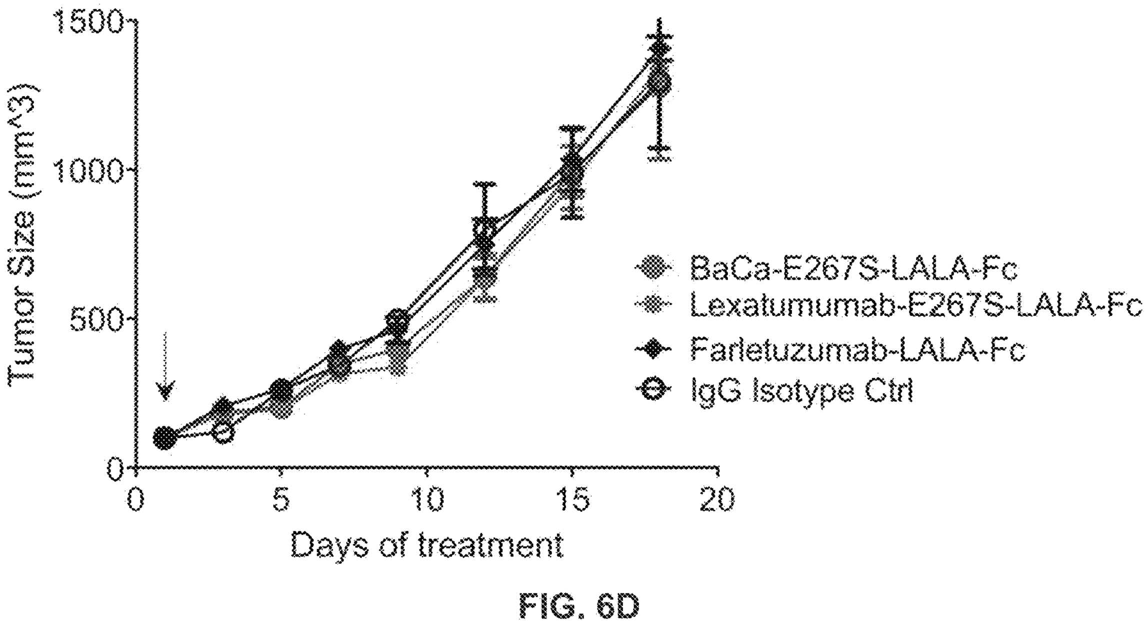
Figure 6E:
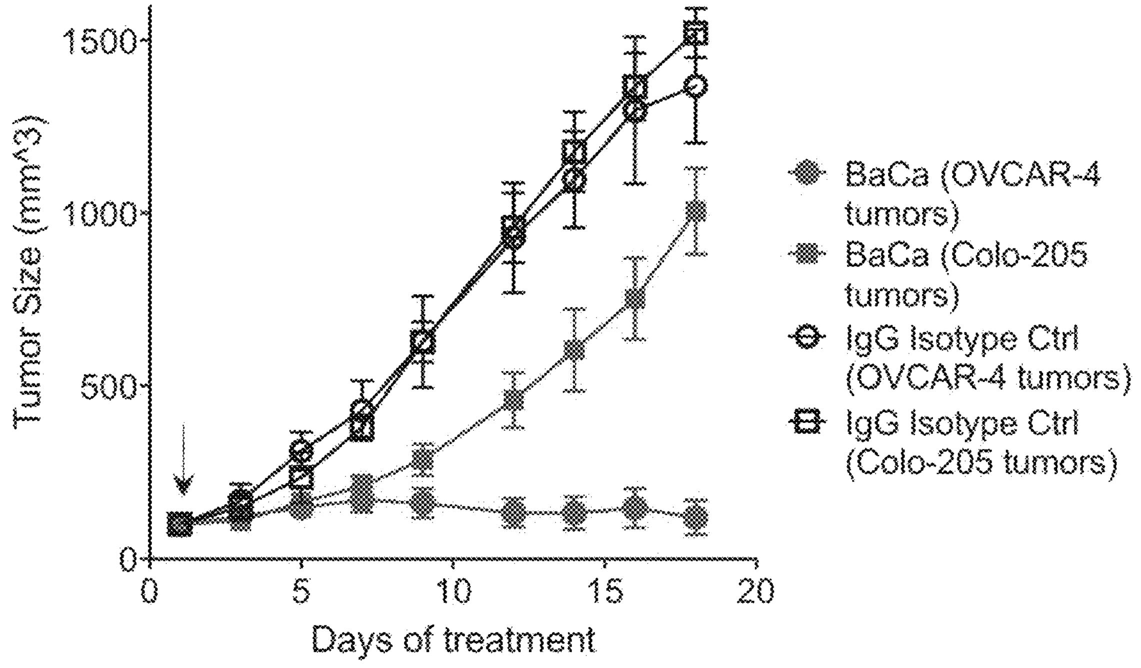
Figure 6F:
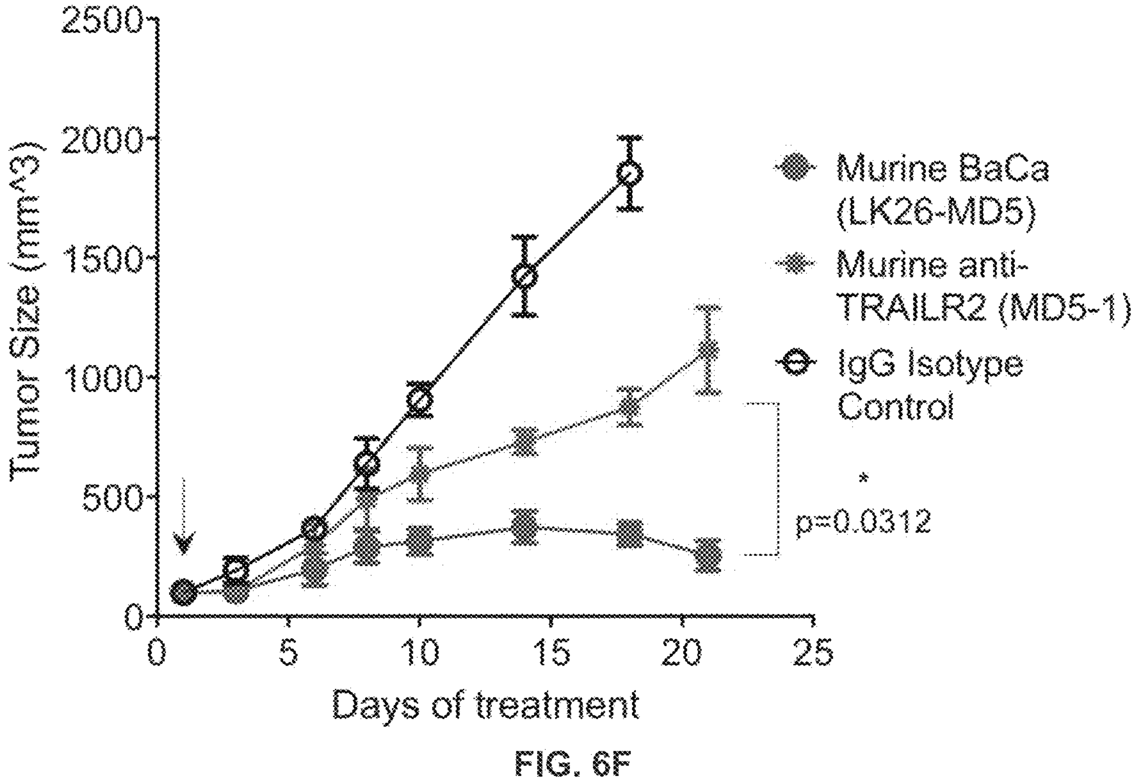
Figure 6G:
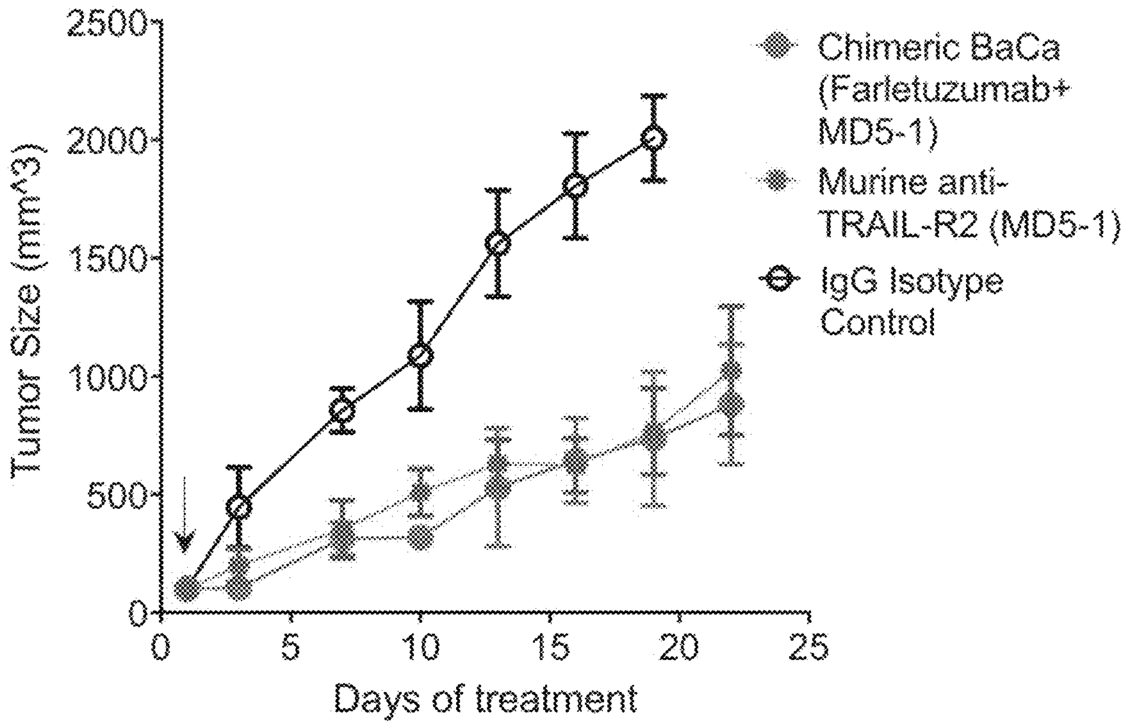
Figure 6H:
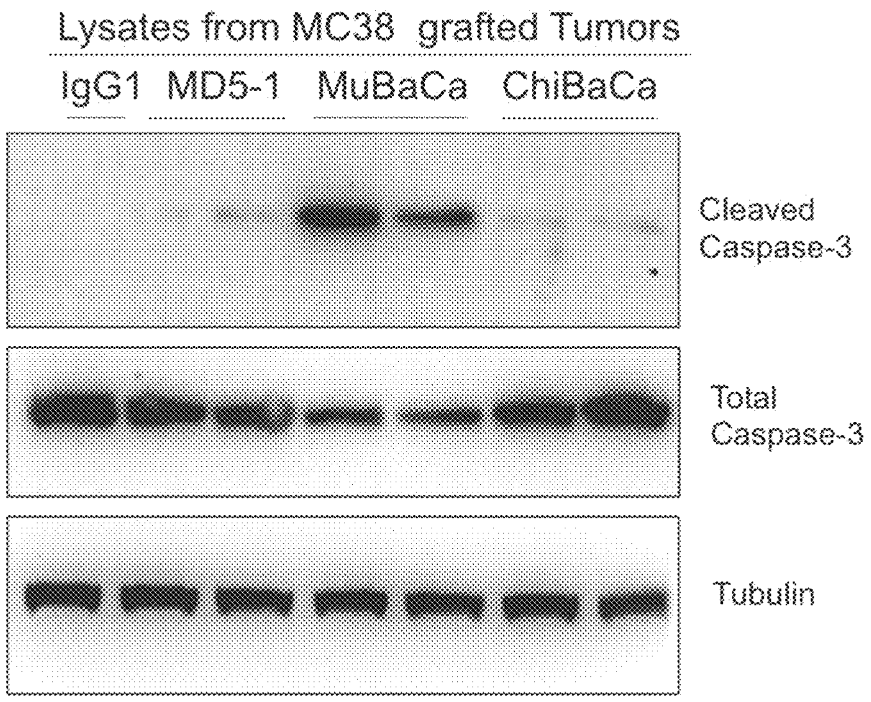
Figure 6I:
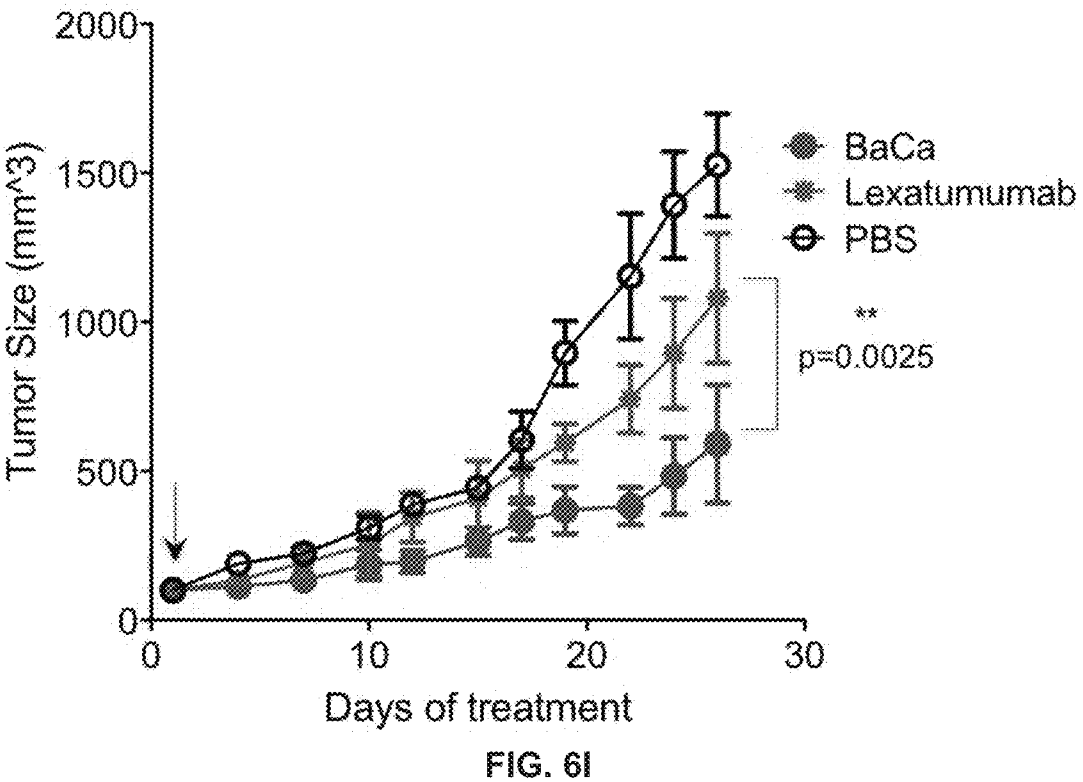

In support with previous reports (Li and Ravetch, 2012), antibodies engineered with E267S mutations (impaired binding to human FcγRIIB) exhibited no anti-tumor activity (FIG. 6D). When tested against high vs low FOLR1 anchor expressing tumors, BaCa antibody (25 μg) completely regressed OVCAR-4 tumors while it remained limitedly effective against Colo-205 tumors at the same dose (FIG. 6E). Similar caspase-3 activation results were reflected at molecular levels (FIG. 5). Comparable efficacy was also observed in immunocompetent mice studies with muBaCa (FIG. 6F). Since farletuzumab did not bind to muFOLR1, we made use of chiBaCa antibody (FIGS. 12G, 12H) having farletuzumab and MD5-1 domains for antigen-tumor regression analysis. When tested against MC38 tumors, chiBaCa was equally effective to MD5-1 (FIG. 6G). These sets of investigations and caspase-3 activity (FIG. 6H) strongly support anchor specific in vivo activity of BaCa targeting strategy. Since treatment failure in OvCa patients is mainly due to emergence of cisplatin resistance, we next compared the in vivo efficacy of BaCa antibody with lexatumumab using patent derived platinum resistant xenografts (PDX) models. As evident, in comparison to lexatumumab, BaCa antibody stabilized platinum resistant tumors (FIG. 6I).

Discussion

Clinical data suggest that insufficient interactions between DR5 agonist antibodies and FcγRIIB receptor potentially limit DR5 receptor clustering, signaling, and associated anti-tumor response (Li and Ravetch, 2012; Wilson et al., 2011). A dual specificity antibody capable of engaging DR5 on tumor cells and fibroblast activating protein (FAP) receptor on stromal cells has been shown to improve DR5 activity (Brunker et al., 2016). Since FAP is also over-expressed in the disease-associated stroma of wound healing tissues and multi-potent bone marrow stem cells, FAP targeting does not give specificity to the tumor. Therefore, toxicities due to non-selective activity are inevitable (Bauer et al., 2006; Tran et al., 2013). Likewise, co-administration of Apo2L and AMG-655 has been reported to enhance DR5 activity (Graves et al., 2014). Thus, reported studies require either combinatorial cell types or combinatorial agents to improve efficacy and therefore have some limitations in terms of tumor selectivity and therapeutic applicability.

To overcome these limitations, we hypothesized that a highly superior and OvCa specific death signaling could be achieved if the initial FcγRIIB crosslinking of DR5 could be supported by BaCa antibody that also co-engages FOLR1 on the same cancer cells (FIG. 7). Consistent with previous reports, our findings support the importance of bivalency and flexible distance requirement for optimal DR5 activity (Jakob et al., 2013; Spiess et al., 2015). We repeatedly found that BaCa antibodies generated with either AMG-655, lexatumumab or MD5-1 were capable of inducing in vitro cytotoxicity >100 fold higher than their parental counterparts. In agreement with previous reports, BaCa antibody activity was dependent on DR5 activity regulators such as GALNT3 (Wagner et al., 2007), p53 (Ashkenazi and Herbst, 2008) and FcγRIIB (Wilson et al., 2011). However, despite high FcγRIIB affinity mutation in lexatumumab and MD5-1, FcγRIIB had its limitations to activate DR5 signaling beyond a certain threshold. On the contrary, at the same therapeutic dose, BaCa antibody was highly effective in enhancing the apoptotic threshold to significantly higher levels than the activating limit of FcγRIIB. How FOLR1 anchor co-engagement by DR5 antibodies achieves a stronger anti-tumor response could be due to multiple reasons: 1) it maintains FcγRIIB crosslinking, 2) it improves FcγRIIB affinity and stability, and 3) it is a combination of these two or other unknown events. Regardless, our findings with BaCa strategy make us believe that despite optimal expression of FcγRIIB, DR5, and other regulators in the tumor, if the DR5 agonist antibody will produce clinically applicable results will largely depend whether it has potential to induce limited (below tumor clearance threshold) or superior (above tumor clearance threshold) apoptotic signals. As reviewed elegantly, the lower DR5 activation threshold against clinical tumors by agonist antibodies accounted for the discrepancy between preclinical and clinical results (Ashkenazi, 2015). If gain in apoptotic threshold by BaCa antibody will potentially result into clinically effective outcome need to be tested?

When tested in vitro, lexatumumab instigated superior apoptotic signals while AMG-655 and MD5-1 did not, unless cross-linked. The differential patterns of apoptotic cooperativity were also observed between Apo2L+AMG-655 and Apo2L+lexatumumab. The disparity reflects a potentially differential threshold for DR5 activation due to their independent working mechanism. One such mechanism could be distinct contact residue on DR5 receptor by these antibodies, as described for AMG-655-DR5-Apo2L ternary complex (Graves et al., 2014). However unlike AMG-655, whether lexatumumab binding to DR5 effects the conformation of DR5-Apo2L complex needs to be investigated in crystallographic studies. Regardless when engineered with FOLR1 anchor binding domain, all tested DR5 agonist antibodies pushed the apoptotic threshold multiple fold beyond the agonist antibody or ligand plus antibody. Moreover, Apo2L was inefficient to enhance the cytotoxicity when added with BaCa antibodies.

These findings reveal that a ternary complex (FOLR1-BaCa-DR5) generated by a tumor anchored receptor either has already pushed the apoptotic threshold beyond the limit of Apo2L potency or has preferred cell death activation kinetics independent of Apo2L presence. The latter is also supported by the fact that in a co-culture of low and high anchor (FOLR1) expressing cells, low FOLR1 expressing Colo-205 cells survived due to lack of formation of a higher ordered anchored ternary complex compared to OVCAR-4 cells. Similar results were evident in vivo with BaCa antibody's inability to regress Colo-205 tumors. At higher BaCa concentration, cancer cells expressing higher levels of FOLR1 helped override the apoptotic threshold in a neighboring cancer cells expressing lower FOLR1 levels potentially being engaged to form anchored complex in "trans". These findings are in line to a hypothetical biochemical reaction where DR5 expressed in "trans" on Colo-205 cells represent a relatively lower affinity substrate for BaCa antibody while DR5 expressed in "cis" on OVCAR-4 cells represent a relatively higher affinity substrate due to avidity-optimized interactions mediated by high availability of FOLR1. Therefore, to achieve a higher enzymatic activity (Apoptosis) for a low affinity substrate, a higher enzyme (BaCa) antibody concentration is essential to increase the rate of reaction.

Since stromal cell engaging antibodies such as RG7386 primarily works in "trans", our results with LK26-AMG-655 bispecific antibody rationally indicate the higher therapeutic dose requirement for trans-engaging antibodies to achieve effective cytotoxic response as compared to BaCa antibody (Brunker et al., 2016). If a higher therapeutic dose will have a higher probability of toxicity and acquired resistance compared to a lower effective dose, need to be seen in clinical trials (Day and Read, 2016; Zuch de Zafra et al., 2016). Importantly, since intratumoral heterogeneity is one key driver of drug resistance (Saunders et al., 2012), by instigating both "cis" and "trans" signaling, BaCa antibody is ideally suited to achieve effective anti-tumor response against an OvCa having heterogeneous low and high anchor (FOLR1) expressing cancer cells. The latter is also supported by BaCa antibody's superior ability to eliminate heterogeneous patient derived cells (in vitro) and heterogeneous cisplatin resistance PDX implants (in vitro) as compared to lexatumumab.

Besides efficacy, BaCa mediated high affinity anchored ternary complex also provides critical insights for safety, tumor selectivity and therapeutic antibody retention. The liver specific ELISA and detailed tissue distribution studies in mouse models support high specificity of BaCa approach toward the grafted tumors. The observed elevated AST/ALT levels and lobular hepatitis in MD5-1 treated animal are in agreement with previous reported MD5-1 hepatotoxicity in C57BL/6 mice (Takeda et al., 2008). Although most DR5 agonist antibodies are well tolerated at a dose of 10 mg/kg, dose limiting toxicities (DLTs) have been observed with lexatumumab >12 mg/kg (Merchant et al., 2012; Wakelee et al., 2010). If anchored lexatumumab or AMG-655 (as in BaCa) will not have DLTs at a dose higher than 10 mg/kg due to their property of avidity optimized tumor retention need to be seen in clinical trials.

Disappointingly, the cellular resistance due to Bcl-2 upregulation, Bax mutations (LeBlanc et al., 2002), NF-κB activation (Godwin et al., 2013), and loss of surface DR5 (Jin et al., 2004) has been reported against many DR5 agonists (Wang et al., 2014). If BaCa antibody will encounter same degree of resistance and discrepancy between preclinical and clinical results, it is difficult to predict (Ashkenazi, 2015). However, because of its anchored binding properties, BaCa antibody exhibited superior activity, a higher ordered DR5 activation function to induce "cis" and "trans" signaling, differential tissue distribution in animals, and significantly faster apoptotic kinetics. If the described gain of constructive functions would potentially limit the required time for cellular resistance compared to antibodies having slower apoptotic kinetics and random tissue distribution need to be seen in clinical trials. The in vivo efficacy differences in nude and surrogate animals, between anchor antigen positive and negative tumors supports a favorable cytotoxicity index of BaCa strategy. In addition, the selective >10 fold activation of cleaved caspase-3 levels in anchor (FOLR1) expressing tumors without focal hepatitis underscores the clinical safety of BaCa therapy. This also supports the idea that along with increased efficacy by BaCa antibody in clinics, a therapeutic safety window is highly achievable in patients experiencing potential toxicity by administration of an extracellular fragment of anchor antigen similar to idarucizumab, a selective reversal agent against PRADAXA® (Glund et al., 2016).

In summary, we have identified a tumor cell specific anchor based DR5 activation mechanism that is highly superior over clinically tested DR5 agonist antibodies and other described strategies. The central role of anchor in retaining and maintaining tumor-restricted activity of BaCa antibody provides insights with implications to improve clinical safety that can be broadly applied. Our findings are highly relevant to clinical investigations and offer a promising path to revive the death receptor agonism field beyond phase-II trials in ovarian and other solid cancers.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Albanesi, M., and Daeron, M. (2012). The interactions of therapeutic antibodies with Fc receptors. Immunol Lett 143, 20-27.
2. Armstrong, D. K., White, A. J., Weil, S. C., Phillips, M., and Coleman, R. L. (2013). Farletuzumab (a monoclonal antibody against folate receptor alpha) in relapsed platinum-sensitive ovarian cancer. Gynecol Oncol 129, 452-458.
3. Ashkenazi, A. (2008). Directing cancer cells to self-destruct with pro-apoptotic receptor agonists. Nat Rev Drug Discov 7, 1001-1012.
4. Ashkenazi, A. (2015). Targeting the extrinsic apoptotic pathway in cancer: lessons learned and future directions. J Clin Invest 125, 487-489.
5. Ashkenazi, A., and Herbst, R. S. (2008). To kill a tumor cell: the potential of proapoptotic receptor agonists. J Clin Invest 118, 1979-1990.
6. Bauer, S., Jendro, M. C., Wadle, A., Kleber, S., Stenner, F., Dinser, R., Reich, A., Faccin, E., Godde, S., Dinges, H., et al. (2006). Fibroblast activation protein is expressed by rheumatoid myofibroblast-like synoviocytes. Arthritis Res Ther 8, R171.
7. Berek, J., Taylor, P., McGuire, W., Smith, L. M., Schultes, B., and Nicodemus, C. F. (2009). Oregovomab maintenance monoimmunotherapy does not improve outcomes in advanced ovarian cancer. J Clin Oncol 27, 418-425.
8. Brinkmann, U., and Kontermann, R. E. (2017). The making of bispecific antibodies. MAbs 9, 182-212.
9. Brunker, P., Wartha, K., Friess, T., Grau-Richards, S., Waldhauer, I., Koller, C. F., Weiser, B., Majety, M., Runza, V., Niu, H., et al. (2016). RG7386, a Novel Tetravalent FAP-DR5 Antibody, Effectively Triggers FAP-Dependent, Avidity-Driven DR5 Hyperclustering and Tumor Cell Apoptosis. Mol Cancer Ther 15, 946-957.
10. Chen, R. Y., Cao, J. J., Chen, J., Yang, J. P., Liu, X. B., Zhao, G. Q., and Zhang, Y. F. (2012). Single nucleotide polymorphisms in the CDH17 gene of colorectal carcinoma. World J Gastroenterol 18, 7251-7261.
11. Day, T., and Read, A. F. (2016). Does High-Dose Antimicrobial Chemotherapy Prevent the Evolution of Resistance? PLoS Comput Biol 12, e1004689.
12. Domcke, S., Sinha, R., Levine, D. A., Sander, C., and Schultz, N. (2013). Evaluating cell lines as tumour models by comparison of genomic profiles. Nat Commun 4, 2126.
13. Durocher, Y., and Butler, M. (2009). Expression systems for therapeutic glycoprotein production. Curr Opin Biotechnol 20, 700-707.
14. Glund, S., Stangier, J., van Ryn, J., Schmohl, M., Moschetti, V., Haazen, W., De Smet, M., Gansser, D., Norris, S., Lang, B., et al. (2016). Restarting Dabigatran Etexilate 24 h After Reversal With Idarucizumab and Redosing Idarucizumab in Healthy Volunteers. J Am Coll Cardiol 67, 1654-1656.
15. Godwin, P., Baird, A. M., Heavey, S., Barr, M. P., O'Byrne, K. J., and Gately, K. (2013). Targeting nuclear factor-kappa B to overcome resistance to chemotherapy. Front Oncol 3, 120.
16. Graves, J. D., Kordich, J. J., Huang, T. H., Piasecki, J., Bush, T. L., Sullivan, T., Foltz, I. N., Chang, W., Douangpanya, H., Dang, T., et al. (2014). Apo2L/TRAIL and the death receptor 5 agonist antibody AMG 655 cooperate to promote receptor clustering and antitumor activity. Cancer Cell 26, 177-189.
17. Gu, J., and Ghayur, T. (2012). Generation of dual-variable-domain immunoglobulin molecules for dual-specific targeting. Methods Enzymol 502, 25-41.
18. Hutt, M., Farber-Schwarz, A., Unverdorben, F., Richter, F., and Kontermann, R. E. (2012). Plasma half-life extension of small recombinant antibodies by fusion to immunoglobulin-binding domains. J Biol Chem 287, 4462-4469.
19. Jakob, C. G., Edalji, R., Judge, R. A., DiGiammarino, E., Li, Y., Gu, J., and Ghayur, T. (2013). Structure reveals function of the dual variable domain immunoglobulin (DVD-Ig) molecule. MAbs 5, 358-363.
20. Jin, Z., McDonald, E. R., 3rd, Dicker, D. T., and El-Deiry, W. S. (2004). Deficient tumor necrosis factor-related apoptosis-inducing ligand (TRAIL) death receptor transport to the cell surface in human colon cancer cells selected for resistance to TRAIL-induced apoptosis. J Biol Chem 279, 35829-35839.
21. Kline, J. B., Kennedy, R. P., Albone, E., Chao, Q., Fernando, S., McDonough, J. M., Rybinski, K., Wang, W., Somers, E. B., Schweizer, C., et al. (2017). Tumor antigen CA125 suppresses antibody-dependent cellular cytotoxicity (ADCC) via direct antibody binding and suppressed Fc-gamma receptor engagement. Oncotarget 8, 52045-52060.
22. Leabman, M. K., Meng, Y. G., Kelley, R. F., DeForge, L. E., Cowan, K. J., and Iyer, S. (2013). Effects of altered FcgammaR binding on antibody pharmacokinetics in cynomolgus monkeys. MAbs 5, 896-903.
23. LeBlanc, H., Lawrence, D., Varfolomeev, E., Totpal, K., Morlan, J., Schow, P., Fong, S., Schwall, R., Sinicropi, D., and Ashkenazi, A. (2002). Tumor-cell resistance to death receptor-induced apoptosis through mutational inactivation of the proapoptotic Bcl-2 homolog Bax. Nat Med 8, 274-281.
24. Levett, P. N., Sonnenberg, K., Sidaway, F., Shead, S., Niedrig, M., Steinhagen, K., Horsman, G. B., and Drebot, M. A. (2005). Use of immunoglobulin G avidity assays for differentiation of primary from previous infections with West Nile virus. J Clin Microbiol 43, 5873-5875.
25. Li, F., and Ravetch, J. V. (2012). Apoptotic and antitumor activity of death receptor antibodies require inhibitory Fcgamma receptor engagement. Proc Natl Acad Sci USA 109, 10966-10971.
26. Lin, J., Spidel, J. L., Maddage, C. J., Rybinski, K. A., Kennedy, R. P., Krauthauser, C. L., Park, Y. C., Albone, E. F., Jacob, S., Goserud, M. T., et al. (2013). The antitumor activity of the human FOLR1-specific monoclonal antibody, farletuzumab, in an ovarian cancer mouse model is mediated by antibody-dependent cellular cytotoxicity. Cancer Biol Ther 14, 1032-1038.
27. Merchant, M. S., Geller, J. I., Baird, K., Chou, A. J., Galli, S., Charles, A., Amaoko, M., Rhee, E. H., Price, A., Wexler, L. H., et al. (2012). Phase I trial and pharmacokinetic study of lexatumumab in pediatric patients with solid tumors. J Clin Oncol 30, 4141-4147.
28. Mongkolsapaya, J., Grimes, J. M., Chen, N., Xu, X. N., Stuart, D. I., Jones, E. Y., and Screaton, G. R. (1999). Structure of the TRAIL-DR5 complex reveals mechanisms conferring specificity in apoptotic initiation. Nat Struct Biol 6, 1048-1053.
29. Niyazi, M., Marini, P., Daniel, P. T., Humphreys, R., Jendrossek, V., and Belka, C. (2009). Efficacy of triple therapies including ionising radiation, agonistic TRAIL antibodies and cisplatin. Oncol Rep 21, 1455-1460.
30. Paz-Ares, L., Balint, B., de Boer, R. H., van Meerbeeck, J. P., Wierzbicki, R., De Souza, P., Galimi, F., Haddad, V., Sabin, T., Hei, Y. J., et al. (2013). A randomized phase 2 study of paclitaxel and carboplatin with or without conatumumab for first-line treatment of advanced non-small-cell lung cancer. J Thorac Oncol 8, 329-337.
31. Printz, C. (2011). Cancer drug safety presents challenges: oncologists, researchers, and government balance risks with benefits. Cancer 117, 5023-5025.
32. Ridgway, J. B., Presta, L. G., and Carter, P. (1996). 'Knobs-into-holes' engineering of antibody CH3 domains for heavy chain heterodimerization. Protein Eng 9, 617-621.
33. Sasaki, Y., Miwa, K., Yamashita, K., Sunakawa, Y., Shimada, K., Ishida, H., Hasegawa, K., Fujiwara, K., Kodaira, M., Fujiwara, Y., et al. (2015). A phase I study of farletuzumab, a humanized anti-folate receptor alpha monoclonal antibody, in patients with solid tumors. Invest New Drugs 33, 332-340.
34. Saunders, N. A., Simpson, F., Thompson, E. W., Hill, M. M., Endo-Munoz, L., Leggatt, G., Minchin, R. F., and Guminski, A. (2012). Role of intratumoural heterogeneity in cancer drug resistance: molecular and clinical perspectives. EMBO Mol Med 4, 675-684.
35. Schaefer, G., Haber, L., Crocker, L. M., Shia, S., Shao, L., Dowbenko, D., Totpal, K., Wong, A., Lee, C. V., Stawicki, S., et al. (2011). A two-in-one antibody against HER3 and EGFR has superior inhibitory activity compared with monospecific antibodies. Cancer Cell 20, 472-486.
36. Soria, J. C., Smit, E., Khayat, D., Besse, B., Yang, X., Hsu, C. P., Reese, D., Wiezorek, J., and Blackhall, F. (2010). Phase 1b study of dulanermin (recombinant human Apo2L/TRAIL) in combination with paclitaxel, carboplatin, and bevacizumab in patients with advanced non-squamous non-small-cell lung cancer. J Clin Oncol 28, 1527-1533.

37. Spiess, C., Zhai, Q., and Carter, P. J. (2015). Alternative molecular formats and therapeutic applications for bispecific antibodies. Mol Immunol 67, 95-106.
38. Takeda, K., Kojima, Y., Ikejima, K., Harada, K., Yamashina, S., Okumura, K., Aoyama, T., Frese, S., Ikeda, H., Haynes, N. M., et al. (2008). Death receptor 5 mediated-apoptosis contributes to cholestatic liver disease. Proc Natl Acad Sci USA 105, 10895-10900.
39. Teleb, M., Salire, K., Wardi, M., Alkhateeb, H., Said, S., and Mukherjee, D. (2016). Idarucizumab: Clinical Role of a Novel Reversal Agent for Dabigatran. Cardiovasc Hematol Disord Drug Targets 16, 25-29.
40. Tran, E., Chinnasamy, D., Yu, Z., Morgan, R. A., Lee, C. C., Restifo, N. P., and Rosenberg, S. A. (2013). Immune targeting of fibroblast activation protein triggers recognition of multipotent bone marrow stromal cells and cachexia. J Exp Med 210, 1125-1135.
41. Tushir-Singh, J. (2017). Antibody-siRNA conjugates: drugging the undruggable for anti-leukemic therapy. Expert Opin Biol Ther 17, 325-338.
42. Vergote, I., Armstrong, D., Scambia, G., Teneriello, M., Sehouli, J., Schweizer, C., Weil, S. C., Bamias, A., Fujiwara, K., Ochiai, K., et al. (2016). A Randomized, Double-Blind, Placebo-Controlled, Phase III Study to Assess Efficacy and Safety of Weekly Farletuzumab in Combination With Carboplatin and Taxane in Patients With Ovarian Cancer in First Platinum-Sensitive Relapse. J Clin Oncol 34, 2271-2278.
43. Vincenzi, B., Armento, G., Spalato Ceruso, M., Catania, G., Leakos, M., Santini, D., Minotti, G., and Tonini, G. (2016). Drug-induced hepatotoxicity in cancer patients—implication for treatment. Expert Opin Drug Saf 15, 1219-1238.
44. Wagner, K. W., Punnoose, E. A., Januario, T., Lawrence, D. A., Pitti, R. M., Lancaster, K., Lee, D., von Goetz, M., Yee, S. F., Totpal, K., et al. (2007). Death-receptor O-glycosylation controls tumor-cell sensitivity to the proapoptotic ligand Apo2L/TRAIL. Nat Med 13, 1070-1077.
45. Wakelee, H. A., Patnaik, A., Sikic, B. I., Mita, M., Fox, N. L., Miceli, R., Ullrich, S. J., Fisher, G. A., and Tolcher, A. W. (2010). Phase I and pharmacokinetic study of lexatumumab (HGS-ETR2) given every 2 weeks in patients with advanced solid tumors. Ann Oncol 21, 376-381.
46. Wang, F., Lin, J., and Xu, R. (2014). The molecular mechanisms of TRAIL resistance in cancer cells: help in designing new drugs. Curr Pharm Des 20, 6714-6722.
47. Wilson, N. S., Yang, B., Yang, A., Loeser, S., Marsters, S., Lawrence, D., Li, Y., Pitti, R., Totpal, K., Yee, S., et al. (2011). An Fcgamma receptor-dependent mechanism drives antibody-mediated target-receptor signaling in cancer cells. Cancer Cell 19, 101-113.
48. Zhang, X., Zhang, L., Tong, H., Peng, B., Rames, M. J., Zhang, S., and Ren, G. (2015). 3D Structural Fluctuation of IgG1 Antibody Revealed by Individual Particle Electron Tomography. Sci Rep 5, 9803.
49. Zuch de Zafra, C. L., Ashkenazi, A., Darbonne, W. C., Cheu, M., Totpal, K., Ortega, S., Flores, H., Walker, M. D., Kabakoff, B., Lum, B. L., et al. (2016). Antitherapeutic antibody-mediated hepatotoxicity of recombinant human Apo2L/TRAIL in the cynomolgus monkey. Cell Death Dis 7, e2338.
50. U.S. patent application Ser. No. 13/880,320.
51. U.S. patent application Ser. No. 14/549,176.

What is claimed is:

1. A bispecific antibody that binds to death receptor 5 (DR5) and folate receptor alpha-1 (FOLR1), wherein said bispecific antibody comprises a first antigen binding site that is specific for said DR5 and a second antigen binding site that is specific for said FOLR1, and wherein the bispecific antibody comprises:

(i) a heavy chain amino acid sequence comprising SEQ ID NO:1 and a light chain amino acid sequence comprising SEQ ID NO:2;

(ii) a heavy chain amino acid sequence comprising SEQ ID NO:11 and a light chain amino acid sequence comprising SEQ ID NO:2;

(ii) a heavy chain amino acid sequence comprising SEQ ID NO:5 and a light chain amino acid sequence comprising SEQ ID NO:6; or (iv) an scFv fragment comprising a knob-into-hole structure comprising SEQ ID NOs: 3 and 4.

2. The bispecific antibody of claim 1, wherein said antigen binding site specific for said DR5 is linked to the carboxy terminus of the CH3 constant region, wherein the CH3 constant region is of the heavy chain.

3. The bispecific antibody of claim 1, wherein the binding affinity of said DR5 to the antigen binding site specific for DR5 and the binding affinity of said FOLR1 to the antigen binding site specific for FOLR1 are unchanged in the bispecific antibody relative to binding affinities for these antigens when the antigen binding site specific for DR5 and the antigen binding site specific for FOLR1 are present as monospecific antibodies.

4. The bispecific antibody of claim 1, wherein the bispecific antibody is Bispecific-Anchored Cytotoxicity-Activator-1 (BaCa-1), said antibody comprising the heavy chain of SEQ ID NO:1 and the light chain of SEQ ID NO:2.

5. The bispecific antibody of claim 1, wherein the antibody is humanized.

6. The bispecific antibody of claim 1, wherein the bispecific antibody is BaCa-2, said antibody comprising a knob-into-hole structure comprising SEQ ID NO:3 and SEQ ID NO:4, wherein SEQ ID NO:3 and SEQ ID NO: 4 together form the knob-into-hole structure.

7. The bispecific antibody of claim 1, wherein the bispecific antibody is BaCa-3, said antibody comprising the heavy chain comprising SEQ ID NO:5 and the light chain comprising SEQ ID NO:6.

8. The bispecific antibody of claim 1, wherein the bispecific antibody is Chimeric BaCa (ChiBaCa), said antibody comprising the heavy chain comprising SEQ ID NO: 11 and the light chain comprising SEQ ID NO: 2.

9. A pharmaceutical composition comprising a pharmaceutically acceptable carrier and the bispecific antibody of claim 1.

10. The pharmaceutical composition of claim 9, wherein the bispecific antibody is BaCa-1, and wherein BaCa-1 comprises the heavy chain of SEQ ID NO: 1 and the light chain of SEQ ID NO:2.

11. A method for treating cancer, said method comprising administering to a subject in need thereof a therapeutically effective amount of a pharmaceutical composition of claim 9, thereby treating said cancer.

12. The method of claim 11, wherein said cancer comprises:

a) cancer cells expressing FOLR1 and DR5; or b) cancer cells expressing FOLR1, but not DR5, and adjacent stromal cells expressing DR5 or other cells adjacent to said cancer cells expressing DR5; or c) cancer cells expressing FOLR1 and DR5 and adjacent stromal cells expressing DR5 or other cells adjacent to said cancer cells expressing DR5.

13. The method of claim 12, wherein said cancer cells express high levels of FOLR1.

14. The method of claim 11, wherein said cancer is ovarian cancer.

15. The method of claim 14, wherein said ovarian cancer is serous ovarian cancer.

16. The method of claim 15, wherein said serous ovarian cancer is high-grade serous carcinoma.

17. The method of claim 11, wherein said cancer is endometrioid adenocarcinoma.

18. The method of claim 17, wherein said endometrioid adenocarcinoma is high-grade endometrioid adenocarcinoma.

19. The method of claim 11, wherein the bispecific antibody restricts DR5-mediated apoptotic activation toward FOLR1 positive cancer cells.

20. The method of claim 11, wherein said method eliminates antibody-dependent cellular cytotoxicity (ADCC).

21. The method of claim 11, wherein the bispecific antibody is BaCa-1, the bispecific antibody comprising a heavy chain of SEQ ID NO: 1 and a light chain of SEQ ID NO:2, or biologically active fragments thereof.

22. The method of claim 11, wherein said method induces DR5 oligomerization.

23. The method of claim 11, wherein said method inhibits tumor growth.

24. The method of claim 11, wherein said pharmaceutical composition is administered parenterally, intravenously, or intraperitoneally.

25. The method of claim 24, wherein said method stimulates tumor regression.

26. The method of claim 11, wherein the bispecific antibody binds to DR5 and FOLR1 polypeptides present on a single cell to stimulate cis cytotoxicity in said cancer.

27. The method of claim 11, wherein the bispecific antibody binds to DR5 and FOLR1 polypeptides present on different cells to stimulate trans cytotoxicity in said cancer.

28. The method of claim 11, wherein the bispecific antibody binds to death receptor 5 (DR5) and folate receptor alpha-1 (FOLR1) on the same cancer cell.

29. The method of claim 11, wherein the antigen binding site specific for said DR5 binds to said DR5 and the antigen binding site specific for said FOLR1 binds to said FOLR1 on the same cancer cell.

30. The method of claim 11, wherein the antigen binding site specific for said DR5 binds to DR5 on a first cancer cell and the antigen binding site specific for said FOLR1 binds to FOLR1 on a second cancer cell.

31. The method of claim 11, wherein binding of said antigen binding site specific for said DR5 to said DR5 and binding of said binding site specific for said FOLR1 to FOLR1 induces apoptosis of a cancer cell.

32. The method of claim 11, wherein the bispecific antibody is administered at a dose ranging from about 0.1 to about 20.0 mg/kg body weight.

33. The method of claim 32, wherein said dose is selected from the group consisting of 0.1, 0.5, 0.75, 0.83, 1.0, 1.25, 1.5, 2.0, 2.5, 3.0, 3.5, 4.0, 4.5, 5.0, 5.5, 6.0, 6,5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, and 20.0 mg/kg body weight.

34. The method of claim 33, wherein said dose is selected from the group consisting of 0.83, 1.0, 1.25, and 5.0 mg/kg body weight.

35. The method of claim 11, wherein an additional therapeutic agent is administered.

* * * * *